US011053215B2

(12) United States Patent
Vechorkin et al.

(10) Patent No.: US 11,053,215 B2
(45) Date of Patent: *Jul. 6, 2021

(54) HETEROCYCLIC COMPOUNDS USEFUL AS PIM KINASE INHIBITORS

(71) Applicant: Incyte Corporation, Wilmington, DE (US)

(72) Inventors: Oleg Vechorkin, Wilmington, DE (US); Yun-Long Li, Chadds Ford, PA (US); Alexander Sokolsky, Philadelphia, PA (US); Anlai Wang, Wilmington, DE (US); Wenyu Zhu, Media, PA (US); Jincong Zhuo, Garnet Valley, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,229

(22) Filed: Sep. 9, 2019

(65) Prior Publication Data

US 2020/0002309 A1 Jan. 2, 2020

Related U.S. Application Data

(60) Continuation of application No. 15/879,999, filed on Jan. 25, 2018, now Pat. No. 10,450,296, which is a division of application No. 15/281,679, filed on Sep. 30, 2016, now Pat. No. 9,920,032.

(60) Provisional application No. 62/325,778, filed on Apr. 21, 2016, provisional application No. 62/236,259, filed on Oct. 2, 2015.

(51) Int. Cl.
| *C07D 401/12* | (2006.01) |
| *C07D 401/14* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 491/048* | (2006.01) |
| *C07D 497/08* | (2006.01) |
| *C07D 403/12* | (2006.01) |
| *C07D 471/08* | (2006.01) |
| *C07D 498/08* | (2006.01) |
| *A61P 35/00* | (2006.01) |

(52) U.S. Cl.
CPC .......... *C07D 401/12* (2013.01); *A61P 35/00* (2018.01); *C07D 401/14* (2013.01); *C07D 403/12* (2013.01); *C07D 405/14* (2013.01); *C07D 413/14* (2013.01); *C07D 417/14* (2013.01); *C07D 471/04* (2013.01); *C07D 471/08* (2013.01); *C07D 487/04* (2013.01); *C07D 491/048* (2013.01); *C07D 498/08* (2013.01)

(58) Field of Classification Search
CPC .. C07D 401/12; C07D 401/14; C07D 403/12; C07D 405/14; C07D 413/14; C07D 417/14; C07D 471/04; C07D 471/08; C07D 487/04; C07D 491/048; C07D 498/08; A61P 35/00
See application file for complete search history.

(56) References Cited

U.S. PATENT DOCUMENTS

| 6,987,116 | B2 | 1/2006 | Boschelli et al. |
| 8,168,794 | B2 | 5/2012 | Burger et al. |
| 8,329,732 | B2 | 12/2012 | Burger et al. |
| 9,200,004 | B2 | 12/2015 | Xue |
| 9,278,950 | B2 | 3/2016 | Li et al. |
| 9,340,546 | B2 | 5/2016 | Ahmad |
| 9,540,347 | B2 | 1/2017 | Vechorkin et al. |
| 9,550,765 | B2 | 1/2017 | Xue et al. |
| 9,556,197 | B2 | 1/2017 | Li et al. |
| 9,580,418 | B2 | 2/2017 | Sun et al. |
| 9,676,750 | B2 | 6/2017 | Li et al. |
| 9,802,918 | B2 | 10/2017 | Vechorkin et al. |
| 9,822,124 | B2 | 11/2017 | Vechorkin et al. |
| 9,849,120 | B2 | 12/2017 | Xue et al. |
| 9,862,705 | B2 | 1/2018 | Jia et al. |
| 9,920,032 | B2 | 3/2018 | Vechorkin et al. |
| 10,000,507 | B2 | 6/2018 | Li et al. |
| 10,265,307 | B2 | 4/2019 | Xue et al. |
| 10,336,728 | B2 | 7/2019 | Jia et al. |
| 10,450,296 | B2 | 10/2019 | Vechorkin et al. |
| 10,517,858 | B2 | 12/2019 | Xue et al. |
| 2011/0059961 | A1 | 3/2011 | Wang et al. |
| 2011/0130418 | A1 | 6/2011 | Poncelet et al. |
| 2012/0114663 | A1 | 5/2012 | Gelfand et al. |
| 2012/0225062 | A1 | 9/2012 | Burger et al. |
| 2013/0057956 | A1 | 3/2013 | Iwasa |

(Continued)

FOREIGN PATENT DOCUMENTS

| CA | 2668255 | 5/2008 |
| CN | 101568527 | 10/2009 |

(Continued)

OTHER PUBLICATIONS

Amson et al., "The human protooncogene product p33pim is expressed during fetal hematopoiesis and in diverse leukemias," Proc. Nat. Acad. Sci., USA, 1989, 86:8857-61.

(Continued)

*Primary Examiner* — Savitha M Rao
(74) *Attorney, Agent, or Firm* — Fish & Richardson P.C.

(57) ABSTRACT

The present application is concerned with heterocyclic compounds that inhibit the activity of Pim kinases and are useful in the treatment of diseases related to the activity of Pim kinases including, e.g., cancers and other diseases.

12 Claims, No Drawings

(56) References Cited

U.S. PATENT DOCUMENTS

| | | | |
|---|---|---|---|
| 2014/0086941 A1 | 3/2014 | Reddy et al. |
| 2014/0088117 A1 | 3/2014 | Burch et al. |
| 2014/0163000 A1 | 6/2014 | Ahmad |
| 2014/0200216 A1 | 7/2014 | Li et al. |
| 2014/0200227 A1 | 7/2014 | Xue et al. |
| 2015/0057265 A1 | 2/2015 | Li et al. |
| 2015/0329534 A1 | 11/2015 | Xue et al. |
| 2016/0009714 A1 | 1/2016 | Sun et al. |
| 2016/0009726 A1 | 1/2016 | Vechorkin et al. |
| 2016/0137626 A1 | 5/2016 | Li et al. |
| 2016/0347735 A1 | 12/2016 | Vechorkin et al. |
| 2017/0096411 A1 | 4/2017 | Vechorkin et al. |
| 2017/0121310 A1 | 5/2017 | Jia et al. |
| 2017/0158670 A1 | 6/2017 | Vechorkin et al. |
| 2017/0182017 A1 | 6/2017 | Xue et al. |
| 2017/0190716 A1 | 7/2017 | Li et al. |
| 2017/0253587 A1 | 9/2017 | Sun et al. |
| 2018/0170907 A1 | 6/2018 | Jia et al. |
| 2018/0193323 A1 | 7/2018 | Xue et al. |
| 2018/0282302 A1 | 10/2018 | Vechorkin et al. |
| 2019/0209537 A1 | 7/2019 | Xue et al. |
| 2019/0270725 A1 | 9/2019 | Jia et al. |
| 2020/0155527 A1 | 5/2020 | Xue et al. |

FOREIGN PATENT DOCUMENTS

| | | |
|---|---|---|
| CN | 102985426 | 3/2013 |
| CN | 103664878 | 3/2014 |
| EP | 2637650 | 9/2013 |
| EP | 2743269 | 6/2014 |
| JP | 2010508278 | 3/2010 |
| JP | 2010533716 | 10/2010 |
| JP | 2010535201 | 11/2010 |
| JP | 2012524085 | 10/2012 |
| JP | 2014527959 | 10/2014 |
| WO | WO 2002/000196 | 1/2002 |
| WO | WO 2002/055489 | 7/2002 |
| WO | WO 2002/093173 | 11/2002 |
| WO | WO 2003/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/020370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |

(56) References Cited

FOREIGN PATENT DOCUMENTS

| | | |
|---|---|---|
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/113388 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2015/021153 | 2/2015 |
| WO | WO 2015/027124 | 2/2015 |
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Arunesh et al., "Small molecule inhibitors of PIM1 kinase: Jul. 2009 to Feb. 2013 patent update," Expert Opin Ther Pat, Jan. 2014, 24(1): 5-17.
Asano et al., "The serine/threonine kinase Pim-2 is a novel anti-apoptotic mediator in myeloma cells," Leukemia, 2011, 25: 1182-1188.
Bamborough, "Assessment of Chemical Coverage of Kinome Space and Its Implications for Kinase Drug Discovery," J. Med. Chem., 2008, 51: 7898-7914.
Baron et al., "PIM1 gene cooperates with human BCL6 gene to promote the development of lymphomas," PNAS, Apr. 2012, 109(15): 5735-5739.
Berge et al., "Pharmaceutical Salts," J. Pharm. Sci., 1977, 66(1):1-19.
Blanco-Aparicio, Biochemical Pharmacology, vol. 85, pp. 629-643, 2013.
Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump At Column Dilution Configuration for Preparative Liquid Chromatography—Mass Spectrometry," J. Comb. Chem., 2002, 4:295-301.
Brault et al., "PIM kinases are progression markers and emerging therapeutic targets in diffuse large B-cell lymphoma," British Journal of Cancer, 2012, 107: 491-500.
Burger et al. "Structure Guided Optimization, in Vitro Activity, and in Vivo Activity of Pan-PIM Kinase Inhibitors," ACS Med Chem Lett., 2013, 4:1193-1197.
Caira, "Crystalline Polymorphism of Organic Compounds," Topics in Current Chemistry, Jan. 1998, 198: 163-208.
Cancer [online], [retrieved on Jul. 6, 2007] Retrieved from the Internet, URL: http://www.nlm.nih.gov/medlineplus/cancer.html.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chilean Office Action, Patent Application No. 1985-2015, dated Jul. 7, 2016, 22 pages (English Translation).
Chinese Office Action in Chinese Application No. 201480012783.3. dated Sep. 6, 2016, 16 pages (English Translation).
Claudio et al., "A molecular compendium of genes expressed in multiple myeloma," Blood, 2002, 100:2175-86.
Colombian Office Action in Colombian Application No. 15-168.544, dated Aug. 10, 2016, 10 pages.
Coperet, "A simple and efficient method for the preparation of pyridine N-Oxides," The Journal of Organic Chemistry, Jan. 1998, 63: 1740-1741.
Damia "Contemporary pre-clinical development of anticancer agents—What are the optimal preclinical models?" European Journal of Cancer, 2009, 45, 2768-2781.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface p. 1-15.
Eurasian Office Action in Eurasian Application No. 201690458/28, dated Jan. 25, 2017, 11 pages (with English translation).
Eurasian Office Action in Eurasian Application No. 201890663/28, dated Dec. 10, 2018, 8 pages (with English translation).
Freshney, Culture of Animal Cells, A Manual of Basic Technique, Alan R. Liss, Inc., 1983, New York, p. 4.
Fujii et al., "Aberrant expression of serine-threonine kinase Pim-3 in hepatocellular carcinoma development and its role in the proliferation of human hepatoma cell lines," Int. J. Canc., 2005, 114:209-18.

(56) References Cited

OTHER PUBLICATIONS

Georg Pilz, "Modern multiple sclerosis treatment—what is approved, what is on the horizon" Drug Discovery Today Dec. 2008, vol. 13, Nos. 23/24 1013-1025.
Golub et al., "Molecular Classification of Cancer: Class Discovery and Class Prediction by Gene Expression Monitoring," Science, 1999, 286: 531-537.
Gomez-Abad et al., "PIM2 inhibition as a rational therapeutic approach in B-cell lymphoma," Blood, 2011, 118:5517-27.
Gozgit et al., "Effects of the JAK2 Inhibitor, AZ960, on Pim/BAD/BCL-xL, Survival Signaling in the Human JAK2 V617F Cell Line SET-2," Journal of Biological Chemistry, Nov. 2008, 283(47): 32334-32343.
Gu and Li, "A concise synthesis of (2S,4R)- and (2S,4S)-4-methylglutamic acid," Tetrahedron Lett., 2003, 44:3203-3205.
Guo et al., "Overexpression of Pim-1 in bladder cancer," J. Experimental & Clinical Cancer Research, 2010, 29: 161-167.
Hammerman et al., "Lymphocyte Transformation by Pim-2 Is Dependent on Nuclear Factor-kB Activation," Cancer Research, Nov. 2004, 64: 8341-8348.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.
Hsu et al., "Pim-1 knockdown potentiates paclitaxel-induced apoptosis in human hormone-refractory prostate cancers through inhibition of NHEJ DNA repair," Cancer Lett., 2012, 319:214-222.
Hu et al., "PIM-1-specific mAb suppresses human and mouse tumor growth by decreasing PIM-1 levels, reducing Akt phosphorylation and activating apoptosis," J. Clinical Investigation, Feb. 2009, 119(2):362-375.
Huang et al., "Structure-based design and optimization of 2-aminothiazole-4-carboxamide as a new class of CHK1 inhibitors," Bioorganic Med Chem Lett., Mar. 2013, 23(9):2590-2594.
International Preliminary Report on Patentability in International Application No. PCT/US2014/011486, dated Jul. 21, 2015, 7 pages.
International Preliminary Report on Patentability in International Application No. PCT/US2014/011487, dated Jul. 23, 2015, 6 pages.
International Preliminary Report on Patentability in International Application No. PCT/US2014/052214, dated Feb. 23, 2016, 7 pages.
International Preliminary Report on Patentability in International Application No. PCT/US2015/040146, dated Jan. 17, 2017, 8 pages.
International Preliminary Report on Patentability in International Application No. PCT/US2016/034520, dated Dec. 14, 2017, 7 pages.
International Preliminary Report on Patentability in International Application No. PCT/US2016/050925, dated Mar. 22, 2018, 8 pages.
International Search Report and Written Opinion in International Application No. PCT/US2014/011486, dated Mar. 17, 2014, 12 pages.
International Search Report and Written Opinion in International Application No. PCT/US2014/011487, dated Apr. 4, 2014, 11 pages.
International Search Report and Written Opinion in International Application No. PCT/US2014/052214, dated Oct. 28, 2014, 13 pages.
International Search Report and Written Opinion in International Application No. PCT/US2015/040146, dated Oct. 5, 2015, 12 pages.
International Search Report and Written Opinion in International Application No. PCT/US2016/034520, dated Jul. 12, 2016, 11 pages.
International Search Report and Written Opinion in International Application No. PCT/US2016/050925, dated Oct. 21, 2016, 13 pages.
International Search Report and Written Opinion in International Application No. PCT/US2016/054779, dated Dec. 9, 2016, 12 pages.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Israeli Office Action in Israel Application No. 244,224, dated May 18, 2018, 8 pages (English Translation).
Jiang et al., "3,5-Disubstituted quinolines as novel c-Jun N-terminal kinase inhibitors," Bioorganic & Medicinal Chemistry Letters, 2007, 17: 6378-6382.
Jin et al., "Expressions of Osteopontin (OPN), anb3 an Pim-1 Associated with Poor Prognosis in Non-small Cell Lung Cancer (NSCLC)," Chin J. Cancer Res, 2012, 24(2): 103-108.
Johnson et al., "Relationship between drug activity in NCI preclinical in vitro and in vivo models and early clinical trials" British Journal of Cancer, 2001, 84, 1424-1437.
Katano et al., "Synthesis and biological activity of (cyclopentenopyridinium)thiomethylcephalosporins," The Journal of Antibiotics, Jan. 1990, 43(9): 1150-1159.
Kelly et al., "Targeting PIM kinase activity significantly augments the efficacy of cytarabine," British Journal of Haematology, 2011, 156: 129-152.
Kirschner, "PIM Kinase Inhibitor AZD1208 for Treatment of MYC-Driven Prostate Cancer," JNCI J Natl Cancer Inst, 2015. 107(2): 1-11.
Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Lala et al., "Role of nitric oxide in tumor progression: Lessons from experimental tumors," Cancer and Metastasis Reviews, 1998, 17: 91-106.
Lam et al., "New aryl/heteroaryl C N bond cross-coupling reactions via arylboronic acid/cupric acetate arylation," Tetrahedron Letters, May 1998, 39(19): 2941-2944.
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Lin et al., "A small molecule inhibitor of Pim protein kinases blocks the growth of precursor T-cell lymphoblastic leukemia/lymphoma," Blood, Jan. 2010, 115(4): 824-833.
Liu et al., "Overexpression of Pim-1 is associated with poor prognosis in patients with esophageal squamous cell carcinoma," J. Surg. Oncol., 2010,102:683-88.
Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16:2590-2594.
Lu et al., "Pim2 is required for maintaining multiple myeloma cell growth through modulating TSC2 phosphorylation," Blood, Aug. 2013, 122(9): 1610-1620.
Mahalingam et al., "Targeting PIM kinase enhances the activity of sunitinib in renal cell carcinoma," British J. Cancer, Oct. 2011, 105: 1563-1573.
Magnuson, "Why target PIM1 for cancer diagnosis and treatment?" Future Oncol., Sep. 2010. 6(9): 1461-1478.
Martin-Sanchez et al., "HDAC inhibitors induce cell cycle arrest, activate the apoptotic extrinsic pathway and synergize with a novel PIM inhibitor in Hodgkin lymphoma-derived cell lines," British. J. Haematology, 2010, 152:347-362.
Merkel et al., "PIM1 kinase as a target for cancer therapy," Exp. Opin. Investig. Drugs, 2012, 21:425-38.
Michelotti et al., "Two classes of p38a MAP kinase inhibitors having a common diphenylether core but exhbiting divergent binding modes," 2005, 15: 5274-5279.
Mikkers et al., "High-throughput retroviral tagging to identify components of specific signaling pathways in cancer," Nature Genet., 2002, 32:153-159.
Mikkers et al., "Mice deficient for all PIM kinases display reduced body size and impaired responses to hematopoietic growth factors," Mol. Cell. Biol., 2004, 24:6104-15.

(56) References Cited

OTHER PUBLICATIONS

Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.
Mizuki et al., "Suppression of myeloid transcription factors and induction of STAT response genes by AML-specific Flt3 mutations," Blood, 2003, 101:3164-73.
Morwick, "Pim kinase inhibitors: a survey of the patent literature," Exp. Opin. Ther. Patents, 2010, 20(2):193-212.
Mukaida et al., "Roles of Pim-3, a novel survival kinase, in tumorgenesis," Cancer Science, Aug. 2011, 102(8):1437-1442.
Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.
Ocana, A. "Preclinical development of molecular targeted agents for cancer" Nat. Rev. Clin. Oncol. 2011, 8, 200-209.
Ogawa et al., "Insights from Pim1 structure for anti-cancer drug design," Expert Opin Drug Discov, Dec. 2012, 7(12): 1177-92.
Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297-1303.
Ravin, "Preformulation," Remington's Pharmaceutical Sciences, $17^{th}$ Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol., 2012, 188:119.9.
Schatz, et al., "Targeting cap-dependent translation blocks converging survival signals by AKT and PIM kinases in lymphoma," J. Exp. Med., 2011, 208:1799-1807.
Schwemmers et al., "JAK2$^{V617F}$-negative ET Patients do not display constitutively active JAK/STAT signaling," Exp. Hematol., Nov. 2007, 35(11): 1695-1703.
Search Report, dated Jul. 2, 2014, 6 pages.
Search Report, dated Jul. 3, 2014, 4 pages.
Search Report, dated Jul. 8, 2014, 4 pages.
Sharma "Cell line-based platforms to evaluate the therapeutic efficacy of candidate anticancer agents" Nature Reviews Cancer Apr. 2010, vol. 10, 241-253.
Shen et al., "Inhibition of Pim-1 kinase ameliorates dextran sodium sulfate-induced colitis in mice," Dig. Dis. Sci., 2012, 57:1822-31.
Shinto et al., "Moloney murine leukemia virus infection accelerates lymphomagenesis in Eμ-bcl-2 transfenic mice," Oncogene, 1995, 11:1729-36.
Simone, Oncology: Introduction, Cecil Textbook of Medicine, 20th Edition, 1996 vol. 1, pp. 1004-1010.
Swords et al., "The Pim kinases: new targets for drug development," Curr. Drug Targets, 2011, 12(14):2059-66.
United States Office Action in U.S. Appl. No. 14/155,134, dated Jul. 27, 2015, 12 pages.
Venkatesh et al., "Role of the Development Scientist in Compound Lead Selection and Optimization," J. Pharm. Sci., 2000, 89:145-54.
Wang et al., "Inhibition of Pim1 kinase prevents peanut allergy by enhancing Runx3 expression and suppressing T(H)2 and T(H)17 T-cell differentiation," J. All. Clin. Immunol., 2012, 130:932-44.
www.leukaemia.org' [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.
Yan et al., "Clinical and therapeutic relevance of PIM1 kinase in gastric cancer," Gastric Cancer, 2012, 15:188-197.
Yang et al., "Proviral integration site 2 is required for interleukin-6 expression induced by interleukin-1, tumour necrosis factor-α and lipopolysaccharide," Immunol., 2010, 131:174-182.

Zippo, et al., "PIM1-dependent phosphorylation of histone H3 at serine 10 is required for MYC-dependent transcriptional activation and oncogenic transformation," Nature Cell Biol., 2007, 9:932-44.
Argentina Office Action in Argentina Application No. P140100129, dated Nov. 27, 2019, 10 pages (English Translation).
Australian Office Action in Australian Application No. 2014207691, dated Aug. 17, 2017, 4 pages.
Australian Office Action in Australian Application No. 2018217210, dated Feb. 22, 2019, 4 pages.
Brazilian Office Action in Brazilian Application No. BR112015016793-4, dated Sep. 19,. 2019, 5 pages.
Chinese Office Action in Chinese Application No. 201480057613.7, dated Apr. 5, 2017, 15 pages (English Translation).
Chilean Office Action in Chilean Application No. 1985-2015, dated Mar. 23, 2017, 13 pages (English Translation).
Chilean Office Action in Chilean Application No. 201600398, dated Jul. 27, 2017, 16 pages (English Translation).
Chilean Office Action in Chilean Application No. 611-2018. dated May 16, 2019, 21 pages (English Translation).
Colombian Office Action in Colombian Application No. 16-070.957, dated Sep. 13, 2017, 7 pages (English Translation).
Costa Rican Office Action in Costa Rican Application No. 2015-0412 dated Jul. 12, 2019, 14 pages (English Translation).
Eurasian Office Action in Eurasian Application No. 201591339, dated Nov. 5, 2019, 2 pages (English Translation).
Eurasian Office Action in Eurasian Application No. 201591339, dated Mar. 26, 2019, 4 pages (English Translation).
European Office Action in European Application No. 14702389.9-1109, dated Jun. 11, 2018.
Israeli Office Action in Israeli Application No. 239,886, dated Apr. 2, 2019, 4 pages (English Translation).
Israeli Office Action in Israeli Application No. 239,886, dated Dec. 16, 2019, 9 pages (English Translation).
Indian Office Action in Indian Application No. 201627008738, dated May 16, 2019, 6 pages.
Japanese Office Action in Japanese Application No. 2015-552896, dated Nov. 28, 2017, 8 pages (English Translation).
Japanese Office Action in Japanese Application No. 2016-536470, dated Apr. 24, 2018, 4 pages (English Translation).
Malaysian Office Action in Malaysian Application No. PI 2015001776, dated Jul. 22, 2019, 2 pages.
Mexican Office Action in Mexican Application No. MX/a/2015/009057, dated Dec. 9, 2019, 3 pages (English Translation).
New Zealand Office Action in New Zealand Application No. 749911, dated Jul. 19, 2019, 4 pages.
New Zealand Office Action in New Zealand Application No. 749911, dated Oct. 7, 2019, 2 pages.
Peruvian Office Action in Peruvian Application No. 1345.15, dated Mar. 21, 2019, 18 pages (English Translation).
Philippine Office Action in Philippine Office Application No. 1/2015/501567, dated Jan. 13, 2020, 2 pages (English Translation).
Taiwanese Office Action in Taiwanese Application No. 103101314, dated Dec. 28, 2017, 18 pages (English Translation).
Ukraine Office Action in Ukraine Application No. a 201508119, dated Jul. 15, 2019, 8 pages (English Translation).
Ukraine Grant in Ukraine Application No. a201508119, dated Nov. 21, 2019, 6 pages (English Translation).
Vietnamese Office Action in Vietnamese Application No. 48930/SHTT-SC, dated Dec. 28, 2018, 2 pages (English Translation).
Bastin et al., "Salt Selection and Optimisation Procedures for Pharmaceutical New Chemical Entities," Org Proc Res Dev., Jul. 19, 2000, 4(5):427-435.
Morissette et al., "High-Throughput Crystallization: polymorphs, salts, co-crystals and solvates of pharmaceutical solids," Advanced Drug Delivery Reviews, Feb. 23, 2004, 56:375-300.
Canadian Office Action in Canadian Application No. 2897200, dated Feb. 14, 2020, 4 pages.
Canadian Office Action in Canadian Application No. 2897200, dated Sep. 16, 2020, 3 pages.
Chilean Office Action in Chilean Application No. 2079-2019, dated May 15, 2020, 28 pages.
Chinese Office Action in Chinese Office Application No. 201680057727.0, dated Aug. 18, 2020, 13 pages.

(56) References Cited

OTHER PUBLICATIONS

Colombian Office Action in Colombian Application No. NC2018/0003739, dated Apr. 1, 2020, 27 pages.
Japanese Office Action in Japanese Application No. 2018-512592, dated Aug. 25, 2020, 14 pages.
Korean Office Action in Korean Application No. 10-2015-7022084, dated Jul. 30, 2020, 15 pages.
Indonesian Office Action in Indonesian Application No. P00201807826, dated Apr. 17, 2020, 10 pages.
Indonesian Office Action in Indonesian Application No. PID201802590, dated Mar. 27, 2020, 6 pages.
Takashi Kojima, "Iyakuhin Kaihatu niokeru kesyosei sentaku no kourituka wo mezasite (documents indicating well-known arts) for the purpose of improving the selection of a crystalline selection in the development of small or pharmaceutical drug and pharmaceutical drug development," Medicine, Sep. 1, 2008, 68(5):344-349.
Noriaki Hirayama, "Handbook for organic compound crystal preparation—Principle and know-how," Marzen Co. Ltd., Jul. 25, 2008, p. 57-84.
Teruzo Asahara, "Solvent Handbook," Incorporated Company Kodansha, 1985, p. 47-51.

HETEROCYCLIC COMPOUNDS USEFUL AS PIM KINASE INHIBITORS

FIELD OF THE INVENTION

The present application is concerned with pharmaceutically active compounds. The disclosure provides compounds as well as their compositions and methods of use. The compounds inhibit the activity of Pim kinases and are useful in the treatment of diseases related to the activity of Pim kinases including, e.g., cancers and other diseases.

BACKGROUND OF THE INVENTION

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J. Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., *Blood*, 2002, 100, 2175-86; Amson et al., *Proc. Nat. Acad. Sci., USA,* 1989, 86, 8857-61; Mizuki et al., *Blood*, 2003, 101, 3164-73; Li et al., *Canc. Res.,* 2006, 66, 6741-7; Fujii et al., *Int. J. Canc.,* 2005, 114, 209-18. Pim1 overexpression is associated with poor prognosis in mantle cell lymphoma, esophageal and head and neck cancers. Hsi et al., *Leuk. Lymph.,* 2008, 49, 2081-90; Liu et al., *J. Surg. Oncol.,* 2010, 102, 683-88; Peltola et al., *Neoplasia,* 2009, 11, 629-36. Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood,* 2009, 114, 4150-57; Isaac et al., *Drug Resis. Updates,* 2011, 14, 203-11; Hsu et al., *Cancer Lett.,* 2012, 319, 214; Peltola et al., *Neoplasia,* 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.,* 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.,* 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J. Immunol.,* 2012, 188, 119.9) and rheumatoid arthritis (Yang et al., *Immunol.* 2010, 131, 174-182) and other immunological and inflammatory disorders.

The Pim kinases have therefore been identified as useful targets for drug development efforts. Swords et al., *Curr. Drug Targets,* 2011, 12(14), 2059-66; Merkel et al., *Exp. Opin. Investig. Drugs,* 2012, 21, 425-38; Morwick et al., *Exp. Opin. Ther. Patents,* 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of Formula (I):

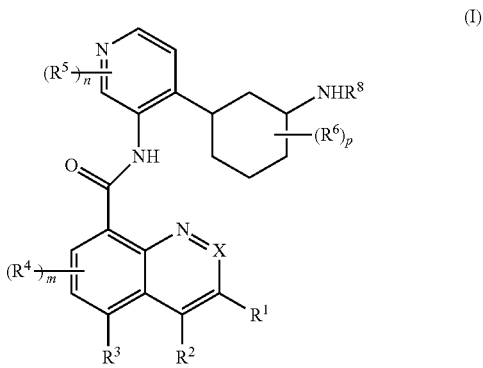

or a pharmaceutically acceptable salt or a stereoisomer thereof, wherein constituent variables are defined herein.

The present invention further provides pharmaceutical composition comprising a compound of the invention, or a pharmaceutically acceptable salt or a stereoisomer thereof, and at least one pharmaceutically acceptable carrier.

The present invention further provides methods of inhibiting Pim kinases comprising contacting a Pim kinase with a compound of the invention, or a pharmaceutically acceptable salt or a stereoisomer thereof.

The present invention further provides methods of treating disease in a patient comprising administering a therapeutically effective amount of a compound of the invention, or a pharmaceutically acceptable salt or a stereoisomer thereof, to the patient.

DETAILED DESCRIPTION

I. Compounds

The present invention provides Pim kinase-inhibition compounds such as a compound of Formula (I):

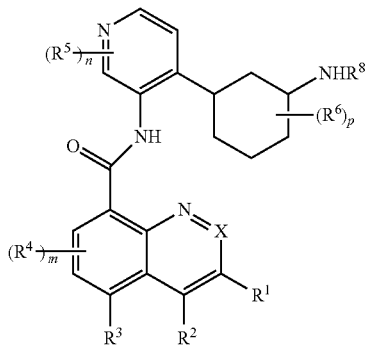

or a pharmaceutically acceptable salt or a stereoisomer thereof, wherein:

$R^1$ is selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$-aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^1$ are each optionally substituted with 1, 2, 3, or 4 $R^b$ substituents;

each $R^b$ substituent is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^b$ are each optionally substituted with 1-3 independently selected $R^d$ substituents;

or two adjacent $R^b$ substituents on the $C_{6-10}$ aryl, $C_{3-10}$ cycloalkyl, 5-10 membered heteroaryl or 4-10 membered heterocycloalkyl ring of $R^1$, taken together with the atoms to which they are attached, form a fused phenyl ring, a fused 5- or 6-membered heterocycloalkyl ring, a fused 5- or 6-membered heteroaryl ring, or a fused $C_{5-6}$ cycloalkyl ring, wherein the fused 5- or 6-membered heterocycloalkyl ring and fused 5- or 6-membered heteroaryl ring each have 1-4 heteroatoms as ring members selected from N, O and S and wherein the fused phenyl ring, fused 5- or 6-membered heterocycloalkyl ring, fused 5- or 6-membered heteroaryl ring, and fused $C_{5-6}$ cycloalkyl are each optionally substituted with 1 or 2 independently selected $R^r$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-4}$ alkyl, $C_{1-4}$ haloalkyl, halo, $C_{3-10}$ cycloalkyl, 4-10 membered heterocycloalkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-4}$ alkyl, $C_{3-10}$ cycloalkyl and 4-10 membered heterocycloalkyl of $R^d$ are each further optionally substituted with 1-3 independently selected $R^r$ substituents;

each $R^e$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^e$ are each optionally substituted with 1, 2, 3, 4, or 5 $R^f$ substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o)NR^oC(=NR^oNR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1-3 independently selected $R^p$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents independently selected from $C_{1-6}$ alkyl, $C_{3-10}$ cycloalkyl, 4-7 membered heterocycloalkyl, $C_{6-10}$ aryl, 5-6 membered heteroaryl, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR'S(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, and 5-6 membered heteroaryl of $R^h$ are each further optionally substituted by 1, 2, or 3 substituents independently selected from $C_{3-6}$ cycloalkyl, $C_{6-10}$ aryl, 5- or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$; or two $R^h$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^e$, $R^i$, $R^k$, $R^o$ or $R^p$ is independently selected from H, $C_{1-4}$ alkyl, $C_{3-6}$ cycloalkyl, $C_{6-10}$ aryl, 5- or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5- or 6-membered heteroaryl, $C_{2-4}$ alkenyl, and $C_{2-4}$ alkynyl of $R^e$, $R^i$, $R^k$, $R^o$ or $R^p$ are each optionally substituted with 1, 2 or 3 $R^r$ substituents;

each $R^r$ is independently selected from OH, CN, amino, halo, $C_{1-4}$ alkyl, $C_{1-4}$ alkoxy, $C_{1-4}$ alkylthio, $C_{3-6}$ cycloalkyl, $NHR^9$, $NR^9R^9$, and $C_{1-4}$ haloalkoxy, wherein the $C_{1-4}$ alkyl of $R^r$ is optionally substituted with OH, CN, $NH_2$, $C_{1-4}$ alkoxy, $C_{3-10}$ cycloalkyl, and 4-10 membered heterocycloalkyl, wherein each $R^9$ is independently H or $C_{1-6}$ alkyl;

$R^2$ is H, OH, $OR^a$, $NHR^a$ or $NR^aR^a$;

$R^3$ is H, halo or CN;

each $R^4$ is independently selected from H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$ alkynyl and cyclopropyl, wherein the $C_{1-4}$ alkyl and $C_{1-4}$ alkoxy are each optionally substituted with CN or $CH_3O$—;

each $R^5$ is independently selected from H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$ alkynyl, $C_{3-6}$ cycloalkyl, $C_{6-10}$ aryl, and 5- or 6-membered heteroaryl, wherein the $C_{1-4}$ alkyl and $C_{1-4}$ alkoxy are each optionally substituted with CN or $CH_3O$—;

each $R^6$ is independently selected from H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$ alkynyl, $C_{3-6}$ cycloalkyl, $C_{6-10}$ aryl, and 5- or 6-membered heteroaryl, wherein the $C_{1-4}$ alkyl, $C_{1-4}$ alkoxy, $C_{3-6}$ cycloalkyl, $C_{6-10}$ aryl, and 5- or 6-membered heteroaryl are each optionally substituted with OH, CN or $CH_3O$—;

or any two $R^6$ substituents attached to the same carbon atom, taken together with the carbon atom to which they are attached, form $C_{3-10}$ cycloalkyl or a 4-, 5-, or 6-membered heterocycloalkyl, wherein the $C_{3-10}$ cycloalkyl and 4-, 5-, or 6-membered heterocycloalkyl are each optionally substituted with 1-3 independently selected $R^p$ substituents;

$R^8$ is H, $C_{1-4}$ alkyl, $C_{3-6}$ cycloalkyl, $C_{3-6}$ cycloalkyl-$C_{1-4}$ alkyl-, wherein the $C_{1-4}$ alkyl, $C_{3-6}$ cycloalkyl and $C_{3-6}$ cycloalkyl-$C_{1-4}$ alkyl are each optionally substituted with OH, CN or $CH_3O$—;

X is N or $CR^7$, wherein $R^7$ is H, halo, $NH_2$, $C_{1-4}$ alkoxy, $C_{1-4}$ alkyl-NH— or $(C_{1-4}$ alkyl$)_2$N—;

the subscript m is an integer of 1 or 2;

the subscript n is an integer of 1, 2 or 3; and the subscript p is an integer of 1, 2 or 3.

In some embodiments, the present invention provides a compound having Formula (II):

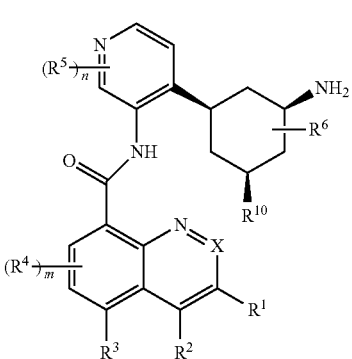

(II)

or a pharmaceutically acceptable salt or a stereoisomer thereof, wherein $R^{10}$ is halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$ alkynyl or $C_{3-6}$ cycloalkyl, $C_{6-10}$ aryl, 5 or 6-membered heteroaryl, wherein $C_{1-4}$ alkyl and $C_{1-4}$ alkoxy, $C_{3-6}$ cycloalkyl, $C_{6-10}$ aryl, 5 or 6-membered hetero aryl are each optionally substituted with OH, CN or $CH_3O—$.

In some embodiments, the present invention provides a compound having formula (III):

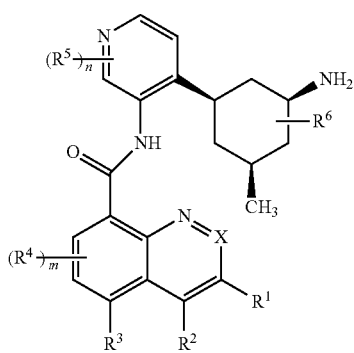

(III)

or a pharmaceutically acceptable salt or a stereoisomer thereof.

In some embodiments, the present invention provides a compound having formula (IV):

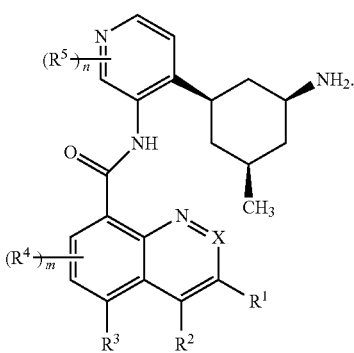

(IV)

In some embodiments, the present invention provides a compound having formula (V):

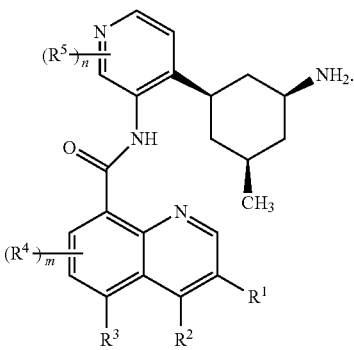

(V)

In some embodiments, the present invention provides a compound having formula (VI):

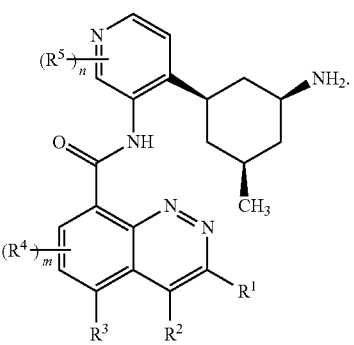

(VI)

In some embodiments, $R^1$ is H, halo, $C_{1-6}$ alkyl, $C_{2-6}$ alkynyl, $C_{6-10}$ aryl, $C_{3-6}$ cycloalkyl, 5-14 membered heteroaryl, 4-10 membered heterocycloalkyl, $OR^a$, $NHR^a$, $NR^aR^a$, wherein the $C_{1-6}$ alkyl, $C_{2-6}$ alkynyl, $C_{6-10}$ aryl, $C_{3-10}$ cycloalkyl, 5-14 membered heteroaryl and 4-10 membered heterocycloalkyl of $R^1$ are each optionally substituted with 1, 2, 3, or 4 $R^b$ substituents;

or two adjacent $R^b$ substituents on the $C_{6-10}$ aryl, $C_{3-10}$ cycloalkyl, 5-10 membered heteroaryl or 4-10 membered heterocycloalkyl ring of R', taken together with the atoms to which they are attached, form a fused phenyl ring, a fused 5- or 6-membered heterocycloalkyl ring, a fused 5- or 6-membered heteroaryl ring or a fused $C_{5-6}$ cycloalkyl ring, wherein the fused 5- or 6-membered heterocycloalkyl ring and fused 5- or 6-membered heteroaryl ring each have 1-4 heteroatoms as ring members selected from N, O and S and wherein the fused phenyl ring, fused 5- or 6-membered heterocycloalkyl ring, fused 5- or 6-membered heteroaryl ring and fused $C_{5-6}$ cycloalkyl are each optionally substituted with 1 or 2 independently selected $R^r$ substituents.

In some embodiments, $R^1$ is H, halo, $C_{1-6}$ alkyl, $C_{6-10}$ aryl, $C_{3-6}$ cycloalkyl, 5-14 membered heteroaryl, 4-10 membered heterocycloalkyl, $OR^a$, $NHR^a$, $NR^aR^a$, wherein the $C_{1-6}$ alkyl, $C_{6-10}$ aryl, $C_{3-10}$ cycloalkyl, 5-14 membered heteroaryl and 4-10 membered heterocycloalkyl of $R^1$ are each optionally substituted with 1, 2, 3, or 4 $R^b$ substituents;

or two adjacent $R^b$ substituents on the $C_{6-10}$ aryl, $C_{3-10}$ cycloalkyl, 5-10 membered heteroaryl or 4-10 membered heterocycloalkyl ring of $R^1$, taken together with the atoms to which they are attached, form a fused phenyl ring, a fused 5- or 6-membered heterocycloalkyl ring, a fused 5- or 6-membered heteroaryl ring or a fused $C_{5-6}$ cycloalkyl ring, wherein the fused 5- or 6-membered heterocycloalkyl ring and fused 5- or 6-membered heteroaryl ring each have 1-4 heteroatoms as ring members selected from N, O and S and wherein the fused phenyl ring, fused 5- or 6-membered heterocycloalkyl ring, fused 5- or 6-membered heteroaryl ring and fused $C_{5-6}$ cycloalkyl are each optionally substituted with 1 or 2 independently selected $R^r$ substituents.

In some embodiments, $R^1$ is selected from $C_{1-6}$ alkyl, $C_{2-6}$ alkynyl, $C_{6-10}$ aryl, $C_{3-10}$ cycloalkyl, 5-14 membered heteroaryl, 4-10 membered heterocycloalkyl, $NHR^a$, and $NR^aR^a$, wherein the $C_{1-6}$ alkyl, $C_{2-6}$ alkynyl, $C_{6-10}$ aryl, $C_{3-10}$ cycloalkyl, 5-14 membered heteroaryl, and 4-10 membered heterocycloalkyl, of $R^1$ are each optionally substituted with 1, 2, 3, or 4 $R^b$ substituents.

In some embodiments, $R^1$ is selected from ethyl, ethynyl, phenyl, cyclopropyl, pyrazolyl, pyridyl, quinolinyl, azetidinyl, pyrrolidinyl, piperidinyl, piperazinyl, azepanyl, morpholino, thiomorpholino, indolinyl, 3-oxa-8-azabicyclo[3.2.1]octan-8-yl, 2-oxo-5-azabicyclo[2.2.1]heptan-5-yl, 6-oxo-3-azabicyclo[3.1.1]heptan-3-yl, 2.5-diazabicyclo[2.2.1]heptan-2-yl, $NHR^a$, $NR^aR^a$, tetrahydropyranyl, 4-oxodihydro-1H-pyrido[1,2-a]pyrazin-2 (6H,7H, 8H,9H, 9aH)-yl), oxazepanyl, 2-azaspiro[3.3]heptan-2-yl, 3-oxa-9-azabicyclo[3.3.1]nonan-9-yl, 1,2-oxazinan-2-yl, dihydro-1H-furo[3,4-c]pyrrol-5(3H,6H,6aH)-yl, 6,7-dihydro-2H-pyrazolo[4,3-c]pyridin-5(4H)-yl, 2H-benzo[b][1,4]oxazin-4(3H)-yl, 7-oxa-2-azaspiro[3.5]nonan-2-yl, diazepanyl, 4,5-dihydro-1H-pyrazolo[3,4-c]pyridin-6(7H)-yl, 1,1-dioxido-1,2,6-thiadiazinan-2-yl, 1,2,3,4-tetrahydroquinolinyl, 5,6-dihydro-[1,2,4]triazolo[4,3-a]pyrazin-7(8H)-yl, 7-azabicyclo[2.2.1]heptan-7-yl, 1,1-dioxidoisothiazolidin-2-yl, 3-oxopiperazin-1-yl, 2-oxopyrrolidin-1-yl, 6-oxohexahydropyrrolo[1,2-a]pyrazin-2 (1H)-yl, 5-oxopiperazin-1-yl, and 3-oxo-1,4-diazepan-1-yl, wherein the ethyl, ethynyl, phenyl, cyclopropyl, pyrazolyl, pyridyl, quinolinyl, azetidinyl, pyrrolidinyl, piperidinyl, piperazinyl, azepanyl, morpholino, thiomorpholino, indolinyl, 3-oxa-8-azabicyclo[3.2.1]octan-8-yl, 2-oxo-5-azabicyclo[2.2.1]heptan-5-yl, 6-oxo-3-azabicyclo[3.1.1]heptan-3-yl, 2.5-diazabicyclo[2.2.1]heptan-2-yl, $NHR^a$, $NR^aR^a$, tetrahydropyranyl, 4-oxodihydro-1H-pyrido[1,2-a]pyrazin-2 (6H,7H,8H,9H, 9aH)-yl), oxazepanyl, 2-azaspiro[3.3]heptan-2-yl, 3-oxa-9-azabicyclo[3.3.1]nonan-9-yl, 1,2-oxazinan-2-yl, dihydro-1H-furo[3,4-c]pyrrol-5(3H,6H,6aH)-yl, 6,7-dihydro-2H-pyrazolo[4,3-c]pyridin-5(4H)-yl, 2H-benzo[b][1,4]oxazin-4(3H)-yl, 7-oxa-2-azaspiro[3.5]nonan-2-yl, diazepanyl, 4,5-dihydro-1H-pyrazolo[3,4-c]pyridin-6 (711)-yl, 1,1-dioxido-1,2,6-thiadiazinan-2-yl, 1,2,3,4-tetrahydroquinolinyl, 5,6-dihydro-[1,2,4]triazolo[4,3-a]pyrazin-7(8H)-yl, 7-azabicyclo[2.2.1]heptan-7-yl, 1,1-dioxidoisothiazolidin-2-yl, 3-oxopiperazin-1-yl, 2-oxopyrrolidin-1-yl, 6-oxohexahydropyrrolo[1,2-a]pyrazin-2 (1H)-yl, 5-oxopiperazin-1-yl, and 3-oxo-1,4-diazepan-1-yl of $R^1$ are each optionally substituted with 1, 2, 3, or 4 $R^b$ substituents.

In some embodiments, $R^1$ is selected from ethyl, ethynyl, phenyl, cyclopropyl, pyrazolyl, pyridyl, quinolinyl, azetidinyl, pyrrolidinyl, piperidinyl, piperazinyl, azepanyl, morpholino, thiomorpholino, indolinyl, 3-oxa-8-azabicyclo[3.2.1]octan-8-yl, 2-oxo-5-azabicyclo[2.2.1]heptan-5-yl, 6-oxo-3-azabicyclo[3.1.1]heptan-3-yl, 2.5-diazabicyclo[2.2.1]heptan-2-yl, $NHR^a$, and $NR^aR^a$, wherein the ethyl, ethynyl, phenyl, cyclopropyl, pyrazolyl, pyridyl, quinolinyl, azetidinyl, pyrrolidinyl, piperidinyl, piperazinyl, azepanyl, morpholino, thiomorpholino, indolinyl, 3-oxa-8-azabicyclo[3.2.1]octan-8-yl, 2-oxo-5-azabicyclo[2.2.1]heptan-5-yl, 6-oxo-3-azabicyclo[3.1.1]heptan-3-yl, 2.5-diazabicyclo[2.2.1]heptan-2-yl, of $R^1$ are each optionally substituted with 1, 2, 3, or 4 $R^b$ substituents.

In some embodiments, $R^1$ is selected from 2-azabicyclo[2.2.1]heptan-2-yl, 8-azabicyclo[3.2.1]octan-8-yl, 5-oxopiperazin-1-yl, (R)-4-oxodihydro-1H-pyrido[1,2-a]pyrazin-2(6H,7H,8H,9H,9aH)-yl, azepan-1-yl, 1,4-oxazepan-4-yl, 2-azaspiro[3.3]heptan-2-yl, piperidin-1-yl, 3-oxa-9-azabicyclo[3.3.1]nonan-9-yl, tetrahydro-2H-1,2-oxazin-2-yl (also know as 1,2-oxazinan-2-yl), dihydro-1H-furo[3,4-c]pyrrol-5(3H,6H,6aH)-yl, azetidin-1-yl, 3-oxopiperazin-1-yl, 6,7-dihydro-2H-pyrazolo[4,3-c]pyridin-5(4H)-yl, 2H-benzo[b][1,4]oxazin-4(3H)-yl, 7-oxa-2-azaspiro[3.5]nonan-2-yl, 1,4-diazepan-1-yl, 4,5-dihydro-1H-pyrazolo[3,4-c]pyridin-6 (7H)-yl, 1,1-dioxido-1,2,6-thiadiazinan-2-yl, 3,4-dihydro-2H-quinolin-4-yl, 4-morpholinyl, 3-oxopiperazin-1-yl, 5,6-dihydro-[1,2,4]triazolo[4,3-a]pyrazin-7(8H)-yl, 3-oxo-1,4-diazepan-1-yl, 7-azabicyclo[2.2.1]heptan-7-yl, 1,1-dioxidoisothiazolidin-2-yl, pyridin-2-yl, pyridin-3-yl, pyrrolidin-1-yl, 1,4-piperizin-4-yl, $NHR^a$, and $NR^aR^a$, wherein the 2-azabicyclo[2.2.1]heptan-2-yl, 8-azabicyclo[3.2.1]octan-8-yl, 5-oxopiperazin-1-yl, (R)-4-oxodihydro-1H-pyrido[1,2-a]pyrazin-2(6H,7H,8H,9H,9aH)-yl, azepan-1-yl, 1,4-oxazepan-4-yl, 2-azaspiro[3.3]heptan-2-yl, piperidin-1-yl, 3-oxa-9-azabicyclo[3.3.1]nonan-9-yl, tetrahydro-2H-1,2-oxazin-2-yl (also know as 1,2-oxazinan-2-yl), dihydro-1H-furo[3,4-c]pyrrol-5(3H,6H,6aH)-yl, azetidin-1-yl, 3-oxopiperazin-1-yl, 6,7-dihydro-2H-pyrazolo[4,3-c]pyridin-5(4H)-yl, 2H-benzo[b][1,4]oxazin-4(3H)-yl, 7-oxa-2-azaspiro[3.5]nonan-2-yl, 1,4-diazepan-1-yl, 4,5-dihydro-1H-pyrazolo[3,4-c]pyridin-6(7H)-yl, 1,1-dioxido-1,2,6-thiadiazinan-2-yl, 3,4-dihydro-2H-quinolin-4-yl, 4-morpholinyl, 3-oxopiperazin-1-yl, 5,6-dihydro-[1,2,4]triazolo[4,3-a]pyrazin-7(8H)-yl, 3-oxo-1,4-diazepan-1-yl, 7-azabicyclo[2.2.1]heptan-7-yl, 1,1-dioxidoisothiazolidin-2-yl, pyridin-2-yl, pyridin-3-yl, pyrrolidin-1-yl, 1,4-piperizin-4-yl, of $R^1$ are each optionally substituted with 1, 2, 3, or 4 $R^b$ substituents.

In some embodiments, each $R^b$ substituent is independently selected from halo, $C_{1-4}$ alkyl, $C_{1-4}$ haloalkyl, $C_{3-10}$ cycloalkyl, CN, OH, $OR^c$, $C(O)NR^cR^c$, $C(O)OR^c$, $S(O)_2R^c$ and $S(O)_2NR^cR^c$; wherein the $C_{1-4}$ alkyl, $C_{1-4}$ haloalkyl, and $C_{3-10}$ cycloalkyl of $R^b$ are each optionally substituted with 1-3 independently selected $R^d$ substituents;

or two adjacent $R^b$ substituents on the $C_{6-10}$ aryl, $C_{3-10}$ cycloalkyl, 5-10 membered heteroaryl or 4-10 membered heterocycloalkyl ring of $R^1$, taken together with the atoms to which they are attached, form a fused phenyl ring, a fused 5- or 6-membered heterocycloalkyl ring, a fused 5- or 6-membered heteroaryl ring, or a fused $C_{5-6}$ cycloalkyl ring, wherein the fused 5- or 6-membered heterocycloalkyl ring and fused 5- or 6-membered heteroaryl ring each have 1-4 heteroatoms as ring members selected from N, O and S and wherein the fused phenyl ring, fused 5- or 6-membered heterocycloalkyl ring, fused 5- or 6-membered heteroaryl ring, and fused $C_{5-6}$ cycloalkyl are each optionally substituted with 1 or 2 independently selected $R^r$ substituents.

In some embodiments, $R^1$ is selected from ethyl, isopropyl, 3-methoxypropyl, Br, I, cyclopropyl, cyclobutyl, cyclopentyl, cyclohexy, 2-fluorophenyl, phenyl, 3,5-difluorophenyl, 2-cyanophenyl, 2-cyano-6-fluorophenyl, 2-methoxyphenyl, 2-trifluomethoxyphenyl, 2,6-difluoro-4-hydroxyphenyl, 2,6-difluoro-4-methoxyphenyl, 2,6-difluoro-4-dimethylaminomethylphenyl, 2,6-difluoro-4-hydroxymethylphenyl, 2-methylsulfonylphenyl, 2-chloro-6-methoxyphenyl, 2-carbamoyl-6-methoxyphenyl, 3-fluoro-4-methylcarbamoylphenyl, 3-fluoro-2-pyridyl, 2-methyoxy-5- pyridyl, 3-fluoropyridyl, 1-pyrrolidinyl, 1-azetidinyl, 3-fluoropyrrolidin-1-yl, 3-cyanopyrroolidin-1-yl, 3-fluoroazetidin-1-yl, morpholin-4-yl, 3-methoxy-piperidin-1-yl, 3-cyclopropyl-ethynyl, ethyl(methyl)amino, cyclopropyl(methyl)amino, methyl(2,2,2,trifluoroethyl)amino, 2-fluoroethyl(methyl)amino, methyl(tetrahydrofuran-3-yl)amino, cyclobutyl(methyl)amino, dimethylamino, 2-fluoroethylamino, 2,2-difluoroethylamino, 3,3-difluoropiperdin-1-yl, 3-fluoro-4-hydroxypiperidin-1-yl, 4-methylpiperazin-1-yl, tetrahydro-2H-pyran-4-yl, 3-methylmorpholino, 2-methylmorpholino, 2-methylpyrrolidin-1-yl, 2,5-dimethylmorpholino, 2,5-dimethylpyrrolidin-1-yl, 2,6-dimethylmorpholino, 4,4-difluoropiperidin-1-yl, 4-hydroxy-4-methylpiperidin-1-yl, 2-methylpiperidin-1-yl, 4-hydroxypiperidin-1-yl, 4-cyanopiperidin-1-yl, 4-methylpiperidin-1-yl, 3-methoxypyrrolidin-1-yl, (2-methoxyethyl)(methyl)amino, 2-(methoxymethyl)pyrrolidin-1-yl, 1-cyclopropylethylamino, 3-methylbutan-2-ylamino, methyl(propyl)amino, isopropyl(methyl)amino, 2-ethylpiperidin-1-yl, 2-difluoromethylpiperidin-1-yl, 6-fluoroquinolin-8-yl, 5-fluoroquinolin-8-yl, 6-trifluoromethylpyridin-3-yl, 1-ethyl-1-H-pyrazol-4-yl, 1,3-dimethyl-1-H-pyrazol-4-yl, 1-methyl-1-H-pyrazol-4-yl, 3-methyl-1-H-pyrazol-4-yl, 1-H-pyrazol-4-yl, 2,2-difluoroethyl(methyl)amino, thiomorpholino, 4-(dimethylsulfamoyl)piperazin-1-yl, 4-methyl-3-oxopiperazin-1-yl, azepan-1-yl, 3-oxa-8-azabicyclo[3.2.1]octan-8-yl, 2-oxo-pyrrolidin-1-yl, indolin-1-yl, 2-oxa-5-azabicyclo[2.2.1]heptan-5-yl, 6-oxa-3-azabicyclo[3.1.1]heptan-3-yl, 4-(dimethylcarbamoyl)piperidin-1-yl, (methyl)(phenyl)amino, 6-oxohexahydropyrrolo[1,2-a]pyrazin-2(1H)-yl, 2-methyl-4-(methylsulfonyl)piperazin-1-yl, 2-methyl-4-(methylcarboxy)piperazin-1-yl, 2-(methylcarboxy)-2,5-diazabicyclo[2.2.1]heptan-5-yl, 2-azabicyclo[2.2.1]heptan-2-yl, (2-fluorophenyl)(methyl)amino, 3-hydroxy-8-azabicyclo[3.2.1]octan-8-yl, (R)-2,4-dimethyl-5-oxopiperazin-1-yl, (R)-4-oxodihydro-1H-pyrido[1,2-a]pyrazin-2(6H,7H,8H,9H,9aH)-yl, 4-methoxyazepan-1-yl, 1,4-oxazepan-4-yl, 6-hydroxy-2-azaspiro[3.3]heptan-2-yl, 4-hydroxyazepan-1-yl, (R)-3-methylpiperidin-1-yl, 3-oxa-9-azabicyclo[3.3.1]nonan-9-yl, 2-azaspiro[3.3]heptan-2-yl, tetrahydro-2H-1,2-oxazin-2-yl (also know as 1,2-oxazinan-2-yl), dihydro-1H-furo[3,4-c]pyrrol-5(3H,6H,6aH)-yl, 3-methylazetidin-1-yl, (S)-2,4-dimethyl-3-oxopiperazin-1-yl, (S)-3-methylpiperidin-1-yl, 4-cyclopropyl-3-oxopiperazin-1-yl, 4-isopropyl-3-oxopiperazin-1-yl, 3,3-dimethylazetidin-1-yl, 4-isobutyl-3-oxopiperazin-1-yl, 3-methoxy-3-methylazetidin-1-yl, 2-methyl-6,7-dihydro-2H-pyrazolo[4,3-c]pyridin-5(4H)-yl, 5-fluoro-2H-benzo[b][1,4]oxazin-4(3H)-yl, 7-oxa-2-azaspiro[3.5]nonan-2-yl, 3-ethoxyazetidin-1-yl, (S)-2-(hydroxymethyl)azetidin-1-yl, 4-(methylsulfonyl)-1,4-diazepan-1-yl, 2-fluorophenylamino, 1-carbomethoxy-1,4-diazepan-4-yl, 1-methyl-4,5-dihydro-1H-pyrazolo[3,4-c]pyridin-6(7H)-yl, 6-methyl-1,1-dioxido-1,2,6-thiadiazinan-2-yl, 2-cyanophenylamino, 3,4-dihydro-2H-quinolin-4-yl, 4-methoxypiperidin-1-yl, 2-(hydroxymethyl)morpholino, 4-(2-methoxyethyl)-3-oxopiperazin-1-yl, 5,6-dihydro-[1,2,4]triazolo[4,3-a]pyrazin-7(8H)-yl, 4-methyl-3-oxo-1,4-diazepan-1-yl, 7-azabicyclo[2.2.1]heptan-7-yl, 8-fluoro-3,4-dihydro-2H-quinolin-4-yl, 1,1-dioxidoisothiazolidin-2-yl, (3-(difluoromethoxy)pyridin-2-yl)(methyl)amino, (2-cyanocyclopentyl)(methyl)amino, (2,6-dimethylpyridin-3-yl)(methyl)amino, (3-fluoropyridin-2-yl)(methyl)amino, (4-(trifluoromethyl)pyridin-3-yl)(methyl)amino, (6-methoxy-2-methylpyridin-3-yl)(methyl)amino, (3-fluoropyridin-4-yl)(methyl)amino, (4-methylpyridin-3-yl)(methyl)amino, (2-methylcyclobutyl)(methyl)amino, (4-methoxyphenyl)(methyl)amino, (3-methylpyrazin-2-yl)(methyl)amino, (4-methoxypyridin-3-yl)(methyl)amino, (methyl)(tetrahydro-2H-pyran-3-yl)amino, (2-methoxyphenyl)(methyl)amino, (imidazo[1,2-a]pyridin-6-yl)(methyl)amino, (methyl)((R)-tetrahydrofuran-3-yl)amino, (2S,4R)-4-methoxy-2-methylpyrrolidin-1-yl, (2R,4R)-4-methoxy-2-methylpyrrolidin-1-yl, (2S,4S)-4-methoxy-2-methylpyrrolidin-1-yl, (2R,4S)-4-methoxy-2-methylpyrrolidin-1-yl, (2R,4S)-4-methoxy-2-methylpiperidin-1-yl, (2S,4R)-4-methoxy-2-methylpiperidin-1-yl, (2R,4R)-4-methoxy-2-methylpiperidin-1-yl, (3R,4R)-3-fluoro-4-methoxypiperidin-1-yl, (3S,4S)-3-fluoro-4-(2-methoxyethoxy)piperidin-1-yl, (2R,4S)-4-hydroxy-2-methylpyrrolidin-1-yl, (2S,4S)-4-hydroxy-2-methylpyrrolidin-1-yl, (S)-2-methylazetidin-1-yl, (R)-2-methylazetidin-1-yl, 1-carboethoxy-1,4-piperizin-4-yl, (R)-2-methylpiperidin-1-yl and (S)-2-methylpiperidin-1-yl.

In some embodiments, $R^1$ is selected from ethyl, isopropyl, 3-methoxypropyl, Br, I, cyclopropyl, cyclobutyl, cyclopentyl, cyclohexy, 2-fluorophenyl, phenyl, 3,5-difluorophenyl, 2-cyanophenyl, 2-cyano-6-fluorophenyl, 2-methoxyphenyl, 2-trifluomethoxyphenyl, 2,6-difluoro-4-hydroxyphenyl, 2,6-difluoro-4-methoxyphenyl, 2,6-difluoro-4-dimethylaminomethylphenyl, 2,6-difluoro-4-hydroxymethylphenyl, 2-methylsulfonylphenyl, 2-chloro-6-methoxyphenyl, 2-carbamoyl-6-methoxyphenyl, 3-fluoro-4-methylcarbamoylphenyl, 3-fluoro-2-pyridyl, 2-methyoxy-5-pyridyl, 3-fluoropyridyl, 1-pyrrolidinyl, 1-azetidinyl, 3-fluoropyrrolidin-1-yl, 3-cyanopyrroolidin-1-yl, 3-fluoroazetidin-1-yl, morpholin-4-yl, 3-methoxy-piperidin-1-yl, 3-cyclopropyl-ethynyl, ethyl(methyl)amino, cyclopropyl(methyl)amino, methyl(2,2,2,trifluoroethyl)amino, 2-fluoroethyl(methyl)amino, methyl(tetrahydrofuran-3-yl)amino, cyclobutyl(methyl)amino, dimethylamino, 2-fluoroethylamino, 2,2-difluoroethylamino, 3,3-difluoropiperdin-1-yl, 3-fluoro-4-hydroxypiperidin-1-yl, 4-methylpiperazin-1-yl, tetrahydro-2H-pyran-4-yl, 3-methylmorpholino, 2-methylmorpholino, 2-methylpyrrolidin-1-yl, 2,5-dimethylmorpholino, 2,5-dimethylpyrrolidin-1-yl, 2,6-dimethylmorpholino, 4,4-difluoropiperidin-1-yl, 4-hydroxy-4-methylpiperidin-1-yl, 2-methylpiperidin-1-yl, 4-hydroxypiperidin-1-yl, 4-cyanopiperidin-1-yl, 4-methylpiperidin-1-yl, 3-methoxypyrrolidin-1-yl, (2-methoxyethyl)(methyl)amino, 2-(methoxymethyl)pyrrolidin-1-yl, 1-cyclopropylethylamino, 3-methylbutan-2-ylamino, methyl(propyl)amino, isopropyl(methyl)amino, 2-ethylpiperidin-1-yl, 2-difluoromethylpiperidin-1-yl, 6-fluoroquinolin-8-yl, 5-fluoroquinolin-8-yl, 6-trifluoromethylpyridin-3-yl, 1-ethyl-1-H-pyrazol-4-yl, 1,3-dimethyl-1-H-pyrazol-4-yl, 1-methyl-1-H-pyrazol-4-yl, 3-methyl-1-H-pyrazol-4-yl, 1-H-pyrazol-4-yl, 2,2-difluoroethyl(methyl)amino, thiomorpholino, 4-(dimethylsulfamoyl)piperazin-1-yl, 4-methyl-3-oxopiperazin-1-yl, azepan-1-yl, 3-oxa-8-azabicyclo[3.2.1]octan-8-yl, 2-oxo-pyrrolidin-1-yl, indolin-1-yl, 2-oxa-5-azabicyclo[2.2.1]heptan-5-yl, 6-oxa-3-azabicyclo[3.1.1]heptan-3-yl, 4-(dimethylcarbamoyl)piperidin-1-yl, (methyl)(phenyl)amino, 6-oxohexahydropyrrolo[1,2-a]pyrazin-2(1H)-yl, 2-methyl-4-(methylsulfonyl)piperazin-1-yl, 2-methyl-4-(methylcarboxy)piperazin-1-yl, and 2-(methylcarboxy)-2,5-diazabicyclo[2.2.1]heptan-5-yl, or stereoisomers thereof.

In some embodiments, $R^1$ is selected from 2-azabicyclo[2.2.1]heptan-2-yl, (2-fluorophenyl)(methyl)amino, 3-hydroxy-8-azabicyclo[3.2.1]octan-8-yl, (R)-2,4-dimethyl-5-oxopiperazin-1-yl, (R)-4-oxodihydro-1H-pyrido[1,2-a]pyrazin-2(6H,7H,8H,9H,9aH)-yl, 4-methoxyazepan-1-yl, 1,4-oxazepan-4-yl, 6-hydroxy-2-azaspiro[3.3]heptan-2-yl, 4-hydroxyazepan-1-yl, (R)-3-methylpiperidin-1-yl, 3-oxa-9-azabicyclo[3.3.1]nonan-9-yl, 2-azaspiro[3.3]heptan-2-yl, 3-fluoro-4-hydroxypiperidin-1-yl, tetrahydro-2H-1,2-oxazin-2-yl (also know as 1,2-oxazinan-2-yl), dihydro-1H-furo[3,4-c]pyrrol-5(3H,6H,6aH)-yl, 3-methyl azetidin-1-yl, (S)-2,4-dimethyl-3-oxopiperazin-1-yl, (S)-3-methylpiperidin-1-yl, 4-cyclopropyl-3-oxopiperazin-1-yl, 4-isopropyl-3-oxopiperazin-1-yl, 3,3-dimethylazetidin-1-yl, 4-isobutyl-3-oxopiperazin-1-yl, 3-methoxy-3-methylazetidin-1-yl, 2-methyl-6,7-dihydro-2H-pyrazolo[4,3-c]pyridin-5(4H)-yl, 5-fluoro-2H-benzo[b][1,4]oxazin-4(3H)-yl, 7-oxa-2-azaspiro[3.5]nonan-2-yl, 3-ethoxyazetidin-1-yl, (S)-2-(hydroxymethyl)azetidin-1-yl, 4-(methylsulfonyl)-1,4-diazepan-1-yl, 2-fluorophenylamino, 1-carbomethoxy-1,4-diazepan-4-yl, 1-methyl-4,5-dihydro-1H-pyrazolo[3,4-c]pyridin-6(7H)-yl, 6-methyl-1,1-dioxido-1,2,6-thiadiazinan-2-yl, 2-cyanophenylamino, 3,4-dihydro-2H-quinolin-4-yl, 4-methoxypiperidin-1-yl, 2-(hydroxymethyl)morpholino, 4-morpholinyl, 4-(2-methoxyethyl)-3-oxopiperazin-1-yl, 5,6-dihydro-[1,2,4]triazolo[4,3-a]pyrazin-7(8H)-yl, 4-methyl-3-oxo-1,4-diazepan-1-yl, 7-azabicyclo[2.2.1]heptan-7-yl, 8-fluoro-3,4-dihydro-2H-quinolin-4-yl, 1,1-(3-(difluoromethoxy)pyridin-2-yl)(methyl)amino, (2-cyanocyclopentyl)(methyl)amino, (2,6-dimethylpyridin-3-yl)(methyl)amino, (3-fluoropyridin-2-yl)(methyl)amino, (4-(trifluoromethyl)pyridin-3-yl)(methyl)amino, (6-methoxy-2-methylpyridin-3-yl)(methyl)amino, (3-fluoropyridin-4-yl)(methyl)amino, (4-methylpyridin-3-yl)(methyl)amino, (2-methylcyclobutyl)(methyl)amino, (4-methoxyphenyl)(methyl)amino, (3-methylpyrazin-2-yl)(methyl)amino, (4-methoxypyridin-3-yl)(methyl)amino, (methyl)(tetrahydro-2H-pyran-3-yl)amino, (2-methoxyphenyl)(methyl)amino, (imidazo[1,2-a]pyridin-6-yl)(methyl)amino, (methyl)((R)-tetrahydrofuran-3-yl)amino, (2S,4R)-4-methoxy-2-methylpyrrolidin-1-yl, (2R,4R)-4-methoxy-2-methylpyrrolidin-1-yl, (2S,4S)-4-methoxy-2-methylpyrrolidin-1-yl, (2R,4S)-4-methoxy-2-methylpyrrolidin-1-yl, (2R,4S)-4-methoxy-2-methylpiperidin-1-yl, (2S,4R)-4-methoxy-2-methylpiperidin-1-yl, (2R,4R)-4-methoxy-2-methylpiperidin-1-yl, (3R,4R)-3-fluoro-4-methoxypiperidin-1-yl, (3S,4S)-3-fluoro-4-(2-methoxyethoxy)piperidin-1-yl, (2R,4S)-4-hydroxy-2-methylpyrrolidin-1-yl, (2S,4S)-4-hydroxy-2-methylpyrrolidin-1-yl, (S)-2-methylazetidin-1-yl, (R)-2-methylazetidin-1-yl, 1-carboethoxy-1,4-piperizin-4-yl, (R)-2-methylpiperidin-1-yl and (S)-2-methylpiperidin-1-yl.

In some embodiments, each $R^a$ is independently selected from H, $C_{1-6}$ alkyl, $C_{1-4}$ haloalkyl, $C_{6-10}$ aryl, $C_{3-10}$ cycloalkyl, 4-10 membered heterocycloalkyl, and $C_{3-10}$ cycloalkyl-$C_{1-4}$ alkyl-, wherein the $C_{1-6}$ alkyl, $C_{6-10}$ aryl, $C_{3-10}$ cycloalkyl, and 4-10 membered heterocycloalkyl of $R^a$ are each optionally substituted with 1, 2, 3, 4, or 5 $R^d$ substituents.

In some embodiments, each $R^a$ is independently selected from H, methyl, ethyl, n-propyl, isopropyl, —$CH_2CF_3$, —$CH_2CHF_2$, —$CH_2CH_2F$, —$CH_2CH_2OCH_3$, cyclopropyl, cyclobutyl, tetrahydrofuranyl (e.g., (R)-tetrahydrofuran-3-yl), phenyl, 1-cyclopropylethyl, 3-methylbutan-2-yl, 2-fluorophenyl, 3-(difluoromethoxy)pyridin-2-yl, 2-cyanocyclopentyl, 2,6-dimethylpyridin-3-yl, 3-fluoropyridin-2-yl, 4-(trifluoromethyl)pyridin-3-yl, 6-methoxy-2-methylpyridin-3-yl, 3-fluoropyridin-4-yl, 4-methylpyridin-3-yl, 2-methylcyclobutyl, 4-methoxyphenyl, 3-methylpyrazin-2-yl, 4-methoxypyridin-3-yl, tetrahydropyranyl (e.g., tetrahydro-2H-pyran-3-yl), 2-methoxyphenyl, imidazo[1,2-a]pyridin-6-yl, cyclopropylmethyl, 2-methoxyethyl, 2-cyanophenyl, and (2-cyanocyclopentyl)methyl.

In some embodiments, each $R^a$ is independently selected from H, methyl, ethyl, n-propyl, isopropyl, —$CH_2CF_3$, —$CH_2CHF_2$, —$CH_2CH_2F$, —$CH_2CH_2OCH_3$, cyclopropyl, cyclobutyl, tetrahydrofuranyl, phenyl, 1-cyclopropylethyl, 3-methylbutan-2-yl, cyclopropylmethyl, and 2-methoxyethyl.

In some embodiments, each $R^a$ is independently selected from H, methyl, ethyl, n-propyl, isopropyl, —$CH_2CF_3$, —$CH_2CHF_2$, —$CH_2CH_2F$, —$CH_2CH_2OCH_3$, cyclopropyl, cyclobutyl, tetrahydrofuranyl, phenyl, 1-cyclopropylethyl, and 3-methylbutan-2-yl.

In some embodiments, each $R^a$ is independently selected from H, methyl, 2-fluorophenyl, 3-(difluoromethoxy)pyridin-2-yl, 2-cyanocyclopentyl, 2,6-dimethylpyridin-3-yl, 3-fluoropyridin-2-yl, 4-(trifluoromethyl)pyridin-3-yl, 6-methoxy-2-methylpyridin-3-yl, 3-fluoropyridin-4-yl, 4-methylpyridin-3-yl, 2-methylcyclobutyl, 4-methoxyphenyl, 3-methylpyrazin-2-yl, 4-methoxypyridin-3-yl, tetrahydro-2H-pyran-3-yl, 2-methoxyphenyl, imidazo[1,2-a]pyridin-6-yl, (R)-tetrahydrofuran-3-yl, 2-cyanophenyl, and (2-cyanocyclopentyl)methyl.

In some embodiments, each $R^a$ is independently selected from methyl, ethyl, n-propyl, isopropyl, —$CH_2CF_3$, —$CH_2CHF_2$, —$CH_2CH_2F$, —$CH_2CH_2OCH_3$, cyclopropyl, cyclobutyl, tetrahydrofuranyl, phenyl, 1-cyclopropylethyl, and 3-methylbutan-2-yl.

In some embodiments, $R^2$ is H, OH, $OR^a$, $NHR^a$ or $NR^aR^a$.

In some embodiments, $R^2$ is H, OH, $OR^a$, or $NHR^a$.

In some embodiments, $R^2$ is H.

In some embodiments, $R^2$ is methoxy, 2,5-difluorophenoxy, 2-fluorophenoxy, propylamino, isopropylamino, 2,2-difluoroamino, 2-methoxyethylamino, hydroxyl, 2,2,2-trifluoroethylamino, cyclopropylamino, cyclopropylmethylamino, 3-methoxypropylamino, 2,5-difluorophenylamino, cyclobutymethylamino, 3-fluorocyclobutylamino, methylamino, oxazol-4-ylmethylamino, 2-butylamino, cyanomethylamino, ethyl(methyl)amino, methyl(2-methoxyethyl)amino, 2-fluoroethyl(methyl)amino, cyclopropyl(methyl)amino or dimethylamino.

In some embodiments, $R^3$ is H, F, $NH_2$, —$N(C_{1-4}$ alkyl$)_2$ or —$OC_{1-6}$ alkyl.

In some embodiments, $R^3$ is H or halo.

In some embodiments, $R^3$ is H or F.

In some embodiments, $R^4$ is H, F, $NH_2$, —$N(C_{1-4}$ alkyl$)_2$ or —$OC_{1-6}$ alkyl.

In some embodiments, $R^4$ is H, F, $NH_2$, —$N(CH_3)_2$ or —$C_{1-4}$ alkoxy.

In some embodiments, $R^4$ is H.

In some embodiments, $R^5$ is H, F, $NH_2$, —$N(CH_3)_2$ or —$C_{1-4}$ alkoxy.

In some embodiments, $R^5$ is H.

In some embodiments, $R^6$ is H.

In some embodiments, X is N or CH.

In some embodiments, X is $CR^7$.

In some embodiments, $CR^7$ is CH.

In some embodiments, $R^7$ is H or isopropylamino.

In some embodiments, X is N.

In some embodiments, $R^8$ is H.

In some embodiments, the disclosure provides intermediates useful for the synthesis of the compounds as described herein, wherein the intermediates have Formula (VII):

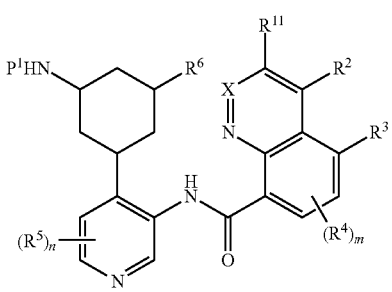

(VII)

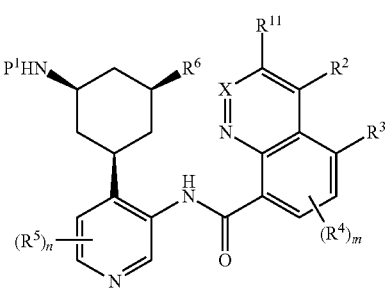

(VIII)

P¹ is an amino protecting group. $R^{11}$ is halo. The other variables $R^2, R^3, R^4, R^5, R^6, R^7$, X, m and n in Formula (VII) are as defined herein.

In some embodiments of compounds of Formula (VII), X is N or $CR^7$, wherein $R^7$ is H, halo, $NH_2$, $C_{1-4}$alkoxy, $C_{1-4}$alkyl-NH— or $(C_{1-4}alkyl)_2N$—;

$R^6$ is H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$alkynyl or $C_{3-6}$ cycloalkyl, $C_{6-10}$ aryl, 5 or 6-membered heteroaryl, wherein $C_{1-4}$ alkyl and $C_{1-4}$ alkoxy, $C_{3-6}$ cycloalkyl, $C_{6-10}$ aryl, 5 or 6-membered heteroaryl are each optionally substituted with OH, CN or $CH_3O$;

$R^{11}$ is halo;

$R^2$ is H, OH, $OR^p$, $NHR^p$ or $NR^pR^p$, wherein each $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^p$ are each optionally substituted with 1, 2 or 3 $R^r$ substituents independently selected from OH, CN, amino, halo, $C_{1-4}$ alkyl, $C_{1-4}$ alkoxy, $C_{1-4}$ alkylthio, $C_{3-6}$ cycloalkyl, $NHR^9$, $NR^9R^9$, and $C_{1-4}$ haloalkoxy, wherein the $C_{1-4}$ alkyl of W is optionally substituted with OH, CN, $NH_2$, $C_{1-4}$ alkoxy, $C_{3-10}$ cycloalkyl and 4-10 membered heterocycloalkyl and each $R^9$ is independently H or $C_{1-6}$ alkyl;

$R^3$ is H, halo or CN;

$R^4$ is H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$alkynyl or cyclopropyl, wherein $C_{1-4}$ alkyl and $C_{1-4}$ alkoxy are each optionally substituted with CN or $CH_3O$;

$R^5$ is H, halo, CN, OH, $NH_2$, $NHCH_3$, $N(CH_3)_2$, $C_{1-4}$ alkyl, $C_{1-4}$ alkoxy, $C_{1-2}$ haloalkyl, $C_{1-2}$ haloalkoxy, ethenyl, $C_{2-4}$alkynyl or $C_{3-6}$ cycloalkyl, $C_{6-10}$ aryl, 5 or 6-membered heteroaryl, wherein $C_{1-4}$ alkyl and $C_{1-4}$ alkoxy are each optionally substituted with CN or $CH_3O$;

the subscript m is an integer of 1 or 2; and the subscript n is an integer of 1, 2 or 3.

In some embodiments, the disclosure provides intermediates having Formula (VIII):

wherein the variables $R^2, R^3, R^4, R^5, R^6, R^7, R^{11}$, $P^1$, X, m and n in Formula (VII) are as defined herein.

In some embodiments of compounds of Formula (VII) or (VIII), $P^1$ is t-butoxycarbonyl. $R^2$ is H. $R^4$ is H. $R^5$ is H.

In some embodiments of compounds of Formula (VII) or (VIII), $R^6$ is methyl.

In some embodiments of compounds of Formula (VII) or (VIII), $R^3$ is F.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")_n-includes both —NR(CR'R")_n— and —(CR'R")_nNR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]thiazolyl, purinyl, imidazopyridinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, 3-oxa-8-azabicyclo[3.2.1]octanyl, 2-oxo-5-azabicyclo[2.2.1]heptanyl, 6-oxo-3-azabicyclo[3.1.1]heptanyl, 2.5-diazabicyclo[2.2.1]heptanyl, oxazepanyl, piperidinyl, piperazinyl, oxopiperazinyl, pyranyl, pyrrolidinyl, quinuclidinyl, indolinyl, tetrahydrofuranyl, tetrahydropyranyl, 1,2,3,4-tetrahydroquinolinyl, 4-oxodihydro-1H-pyrido[1,2-a]pyrazin-2(6H,7H,8H,9H,9aH)-yl, 2-azaspiro[3.3]heptanyl, 3-oxa-9-azabicyclo[3.3.1]nonanyl oxazinanyl, dihydro-1H-furo[3,4-c]pyrrol-5(3H,6H,6aH)-yl, dihydro-2H-pyrazolo[4,3-c]pyridin-5(4H)-yl, 2H-benzo[b][1,4]oxazin-4(3H)-yl, oxaazaspiro[3.5]nonanyl, diazepanyl, dihydro-1H-pyrazolo[3,4-c]pyridin-6 (711)-yl, dioxido-1,2,6-thiadiazinanyl, dihydro-[1,2,4]triazolo[4,3-a]pyrazin-7(8H)-yl, 7-azabicyclo[2.2.1]heptanyl, dioxidoisothiazolidinyl, oxopyrrolidinyl, oxohexahydropyrrolo[1,2-a]pyrazin-2(1H)-yl, oxodiazepanyl, tropanyl, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The term "protecting group" refers to a grouping of atoms that when attached to a reactive group in a molecule masks, reduces or prevents that reactivity. Examples of protecting groups can be found in T. W. Greene and P. G. Wuts, Protective Groups in Organic Synthesis, (Wiley, 4th ed. 2006), Beaucage and Iyer, Tetrahedron 48:2223-23 1 1 (1992), and Harrison and Harrison et al, Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2$=$CHCH_2$—, and the like, groups of the formula —C(O)R', wherein R' is, for example, methyl, phenyl, trifluoromethyl, and the like, groups of the formula —$SO_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula (I) can be prepared, e.g., using a process as illustrated in Scheme 1. In the process depicted in Scheme 1, a suitable aromatic amine of formula 1-1 is reacted with an acid of formula 1-2 under conditions suitable for forming an amide bond to provide the compound of formula 1-3. Compounds of formula 1-1 can be prepared in accordance with the protocols described in PCT publication WO 2012/120428, which is incorporated herein by reference for all purposes. Suitable combinations for forming the amide bond include, e.g., the methods used to form amide bonds in peptides as described, e.g., in Jones, *Amino Acid and Peptide Synthesis*, 2nd Ed., Oxford University Press, 2002; and Jones, *The Chemical Synthesis of Peptides (International Series of Monographs on Chemistry)* (Oxford University Press, 1994). An example of a suitable coupling agent is HATU/DIPEA. The halogen substituent in compounds of formula 1-3 can be converted into $R^1$ via a number of different cross-coupling reactions, including Suzuki, Sonogashira, Negishi, Buchwald-Hartwig amination and others, to give the desired compounds of formula (I)

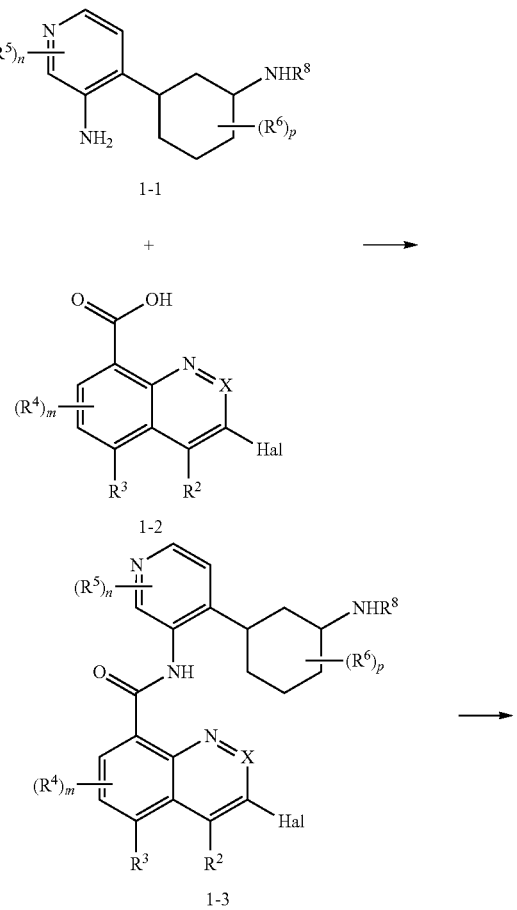

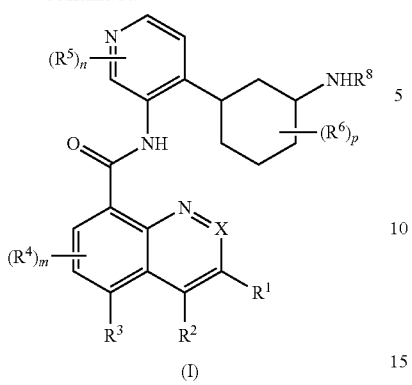

(I)

Compounds of formula 1-2 (or synthetic equivalents thereof) may be prepared, e.g., as shown in Scheme 2. Substituted bromo-quinolines of general formula 2-1 can be converted to the ester-quinolines of formula 2-2 via palladium catalyzed carbonylation reaction. These compounds can be further halogenated with one of the halogenated agents to form compounds of formula 2-3. Finally, ester hydrolysis under basic conditions results in the formation of compounds of formula 1-2.

Scheme 2

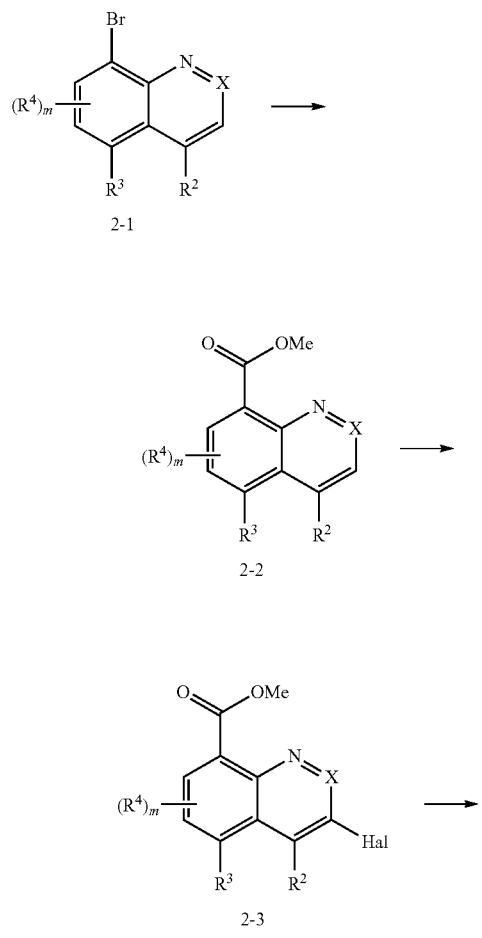

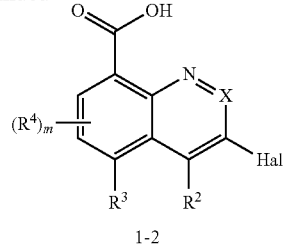

1-2

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of the invention, or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a Pim kinase-associated disease or disorder. Also provided is the use of a compound of the invention, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or Bcl2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (A ML), chronic lymphocytic leukemia (CLL), chronic myelogenous leukemia (C ML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitis (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

In some embodiments Pim inhibitors of the invention can be combined with inhibitors selective for JAK1 and/or JAK2 (e.g., ruxolitinib, baricitinib, momelotinib, filgotinib, pacritinib, INCB039110, INCB052793, INCB054707, CYT387, ABT494, AZD1480, XL019, CEP-33779, AZ 960, TG101209, and gandotinib). In some embodiments Pim inhibitors of the invention can be combined with inhibitors selective for JAK1 (e.g. INCB039110, INCB052793, INCB054707, and ABT494) such as those disclosed in e.g., WO 2010/135650, WO 2011/028685, WO 2011/112662, WO 2012/068450, WO 2012/068440, WO 2012/177606, WO 2013/036611, WO 2013/026025, WO 2014/138168, WO 2013/173720, WO 2015/021153, WO 2014/071031, WO 2014/106706, WO 2015/131031, WO 2015/168246, and WO 2015/184305. In some embodiments Pim inhibitors of the invention can be combined with inhibitors selective for JAK2 (e.g., pacritinib, AZD1480, XL019, CEP-33779, AZ 960, TG101209, and gandotinib).

In some embodiments Pim inhibitors of the invention can be combined with inhibitors selective for PI3K delta (e.g., idelalisib, INCB040093, INCB050465, and TGR 1202) such as those disclosed in e.g., WO 2011/0008487, WO 2011/075643, WO 2011/075630, WO 2011/163195, WO 2011/130342, WO 2012/087881, WO 2012/125629, WO 2012/135009, WO 2013/033569, WO2013/151930, WO 2014/134426, WO 2015/191677, and WO 2015/157257.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments Pim inhibitors of the invention can be combined with cytarabine.

Other anti-cancer agent(s) include antibody therapeutics such as trastuzumab (Herceptin), antibodies to costimulatory molecules such as CTLA-4, 4-1BB, PD-1 and PD-L1, or antibodies to cytokines (IL-10, TGF-β, etc.).

The Pim inhibitors of the present invention can further be used in combination with one or more anti-inflammatory agents, steroids, immunosuppressants or therapeutic antibodies.

The Pim inhibitors of the present invention can be used in combination with one or more immune check point inhibitors. Exemplary immune checkpoint inhibitors include inhibitors against immune checkpoint molecules such as CD27, CD28, CD40, CD122, CD96, CD73, CD47, OX40, GITR, CSF1R, JAK (e.g., JAK1 and/or JAK2), PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, immune checkpoint inhibitors include inhibitors against immune checkpoint molecules such as JAK1 and/or JAK2.

In some embodiments, immune checkpoint inhibitors include inhibitors against immune checkpoint molecules such as CD96.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166. In some embodiments, the anti-GITR antibody is INCAGN01876.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383. In some embodiments, the anti-OX40 antibody is INCAGN01949.

In some embodiments, the inhibitor of an immune checkpoint molecule is an inhibitor of TIM3, e.g., an anti-TIM3 antibody.

In some embodiments Pim inhibitors of the invention can be combined with TIGIT inhibitors.

The Pim inhibitors of the present invention can be used in combination with one or more other anti-cancer agents including BET inhibitors (e.g., INCB054329, OTX015, and CPI-0610), LSD1 inhibitors (e.g., GSK2979552 and INCB059872), HDAC inhibitors (e.g., panobinostat, vorinostat, and entinostat), DNA methyl transferase inhibitors (e.g., azacitidine and decitabine), and other epigenetic modulators.

In some embodiments Pim inhibitors of the invention can be combined with BET inhibitors. In some embodiments Pim inhibitors of the invention can be combined with LSD1 inhibitors. In some embodiments Pim inhibitors of the invention can be combined with HDAC inhibitors. In some embodiments Pim inhibitors of the invention can be combined with DNA methyl transferase inhibitors.

The Pim inhibitors of the present invention can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™) In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-substituted compounds of the invention. An "isotopically-substituted" compound is a compound of the invention where one or more atoms are replaced or substituted by an atom having an atomic mass or mass number different from the atomic mass or mass number typically found in nature (i.e., naturally occurring). It is to be understood that a "radio-labeled" is a compound that has incorporated at least one isotope that is radioactive (e.g., radionuclide). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro Pim kinase labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful. In some embodiments the radionuclide is selected from the group consisting of $^{3}H$ $^{14}C$ $^{125}I$, $^{35}S$ and $^{82}Br$. Synthetic methods for incorporating radioisotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Intermediate 1 tert-Butyl (1S,3R,5S)-3-(3-(5-fluoro-3-iodoquinoline-8-carboxamido)pyridin-4-yl)-5-methylcyclohexylcarbamate

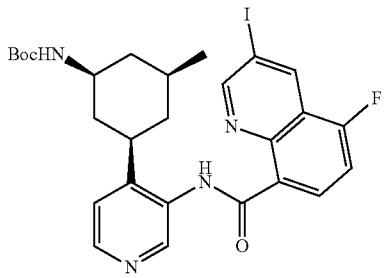 [SMILES: C[C@@H]1C[C@H](NC(=O)OC(C)(C)C)C[C@H](c2ccncc2NC(=O)c2ccc(F)c3cc(I)cnc23)C1]

Step 1. 5-Methyl-3-oxocyclohex-1-en-1-yl trifluoromethanesulfonate

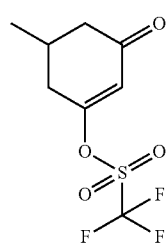 [SMILES: CC1CC(=O)C=C(OS(=O)(=O)C(F)(F)F)C1]

To a solution of 5-methylcyclohexane-1,3-dione (50.1 g, 397 mmol) in dichloromethane (DCM) (700 mL) was added sodium carbonate (46.3 g, 437 mmol) and the resulting mixture was cooled to 0° C. A solution of trifluoromethanesulfonic anhydride (66.8 mL, 397 mmol) in DCM (600 mL) was added to the reaction flask dropwise over 1 h at 0° C. The reaction mixture was stirred at room temperature for 2 h. The solution was filtered and the filtrate was quenched by careful addition of saturated NaHCO$_3$ (aq) to reach pH=7. The organic layer was washed with water, brine, then dried over Na$_2$SO$_4$ and concentrated to give product as a light yellow oil which was used in the next step without purification. LCMS calculated for C$_8$H$_{10}$F$_3$O$_4$S (M+H)$^+$: m/z=259.0; Found: 259.1.

Step 2. 5-Methyl-3-(4,4,5,5-tetramethyl-1,3,2-dioxaborolan-2-yl)cyclohex-2-en-1-one

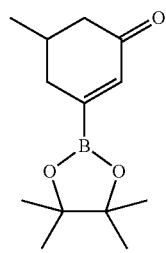 [SMILES: CC1CC(=O)C=C(B2OC(C)(C)C(C)(C)O2)C1]

A mixture of 4,4,5,5,4',4',5',5'-octamethyl-[2,2']bi[[1,3,2]dioxaborolanyl] (77.6 g, 306 mmol), potassium acetate (77.1 g, 785 mmol), and [1,1'-bis(diphenylphosphino)ferrocene]-dichloropalladium(II) complexed with dichloromethane (1:1) (8.6 g, 10.0 mmol) under N$_2$ was combined with a solution of 5-methyl-3-oxocyclohex-1-en-1-yl trifluoromethanesulfonate (67.6 g, 262 mmol) in 1,4-dioxane (420 mL). The reaction mixture was degassed with nitrogen and stirred at 80° C. overnight. After cooling to room temperature, the mixture was filtered through a pad of celite (eluted with EtOAc). The filtrate was concentrated in vacuo, and the residue was used in next step without purification.

Step 3. 5-Methyl-3-(3-nitropyridin-4-yl)cyclohex-2-en-1-one

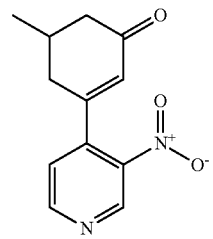 [SMILES: CC1CC(=O)C=C(c2ccncc2[N+](=O)[O-])C1]

To a solution of 5-methyl-3-(4,4,5,5-tetramethyl-1,3,2-dioxaborolan-2-yl)cyclohex-2-en-1-one (20.0 g, 84.7 mmol) in 1,4-dioxane (120 mL) was added 4-chloro-3-nitropyridine (10.0 g, 63.1 mmol), 2.0 M sodium carbonate in water (63.1 mL, 126 mmol), and [1,1'-bis(diphenylphosphino)ferrocene]dichloropalladium(II) complexed with dichloromethane (1:1) (2.58 g, 3.15 mmol). The mixture was refluxed under nitrogen atmosphere for 1 h. The reaction mixture was diluted with ethyl acetate and water, then filtered through a pad of celite, and washed with EtOAc. The separated aqueous layer was extracted with EtOAc (2×). The combined organic phases were washed with water, brine and dried over $Na_2SO_4$. The crude was purified by flash chromatography (eluting with a gradient 0-60% ethyl acetate in hexanes) to give the desired product as an orange oil (6.6 g, 45%). LCMS calculated for $C_{12}H_{13}N_2O_3$ $(M+H)^+$: m/z=233.1; Found: 233.1.

Step 4. cis-(+/−)-5-Methyl-3-(3-nitropyridin-4-yl) cyclohex-2-en-1-ol

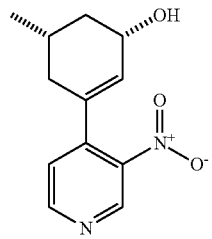 [SMILES: C[C@H]1CC(c2ccncc2[N+](=O)[O-])=C[C@@H](O)C1]

To a solution of 5-methyl-3-(3-nitropyridin-4-yl)cyclohex-2-en-1-one (6.6 g, 28 mmol) in ethanol (93 mL) was added cerium (III) chloride heptahydrate (12.7 g, 34.1 mmol). The resulting mixture was cooled to 0° C. and sodium tetrahydroborate (1.29 g, 34.1 mmol) was added portionwise. After stirring at 0° C. for 1 h, the reaction was quenched with water, concentrated to remove most of the ethanol. The residue was extracted with ethyl acetate. The separated organic layer was washed with brine, dried over $Na_2SO_4$, filtered and concentrated. The crude was purified by flash chromatography (eluting with a gradient of 20-90% ethyl acetate in hexanes) to give the desired product as a racemic mixture (6.4 g, 96%). LCMS calculated for $C_{12}H_{15}N_2O_3$ $(M+H)^+$: m/z=235.1; Found: 235.1.

Step 5. 4-(3-(tert-Butyldimethylsilyloxy)-5-methyl-cyclohex-1-enyl)-3-nitropyridine

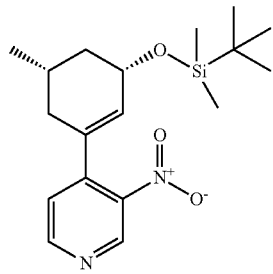 [SMILES: C[C@H]1CC(c2ccncc2[N+](=O)[O-])=C[C@@H](O[Si](C)(C)C(C)(C)C)C1]

A solution of cis(+/−)-5-methyl-3-(3-nitropyridin-4-yl) cyclohex-2-en-1-ol (6.4 g, 27 mmol) in DMF (51 mL) was combined with 1H-imidazole (3.7 g, 55 mmol) and tert-butyldimethylsilyl chloride (5.8 g, 38 mmol). The mixture was stirred at room temperature overnight. The reaction solution was diluted with water and extracted with ethyl acetate. The organic layer was washed with water (2×), brine, dried over $Na_2SO_4$ and concentrated to give the crude product as an orange oil. LCMS calculated for $C_{18}H_{29}N_2O_3Si$ $(M+H)^+$: m/z=349.2; Found: 349.2.

Step 6. 4-(3-(tert-Butyldimethylsilyloxy)-5-methyl-cyclohex-1-enyl)pyridin-3-amine

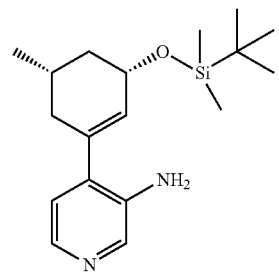

The mixture of 4-(3-(tert-butyldimethylsilyloxy)-5-methylcyclohex-1-enyl)-3-nitropyridine (9.3 g, 27 mmol), iron powder (8.9 g, 160 mmol) and acetic acid (67 mL) was stirred at room temperature for 2 h. The reaction mixture was filtered through a pad of Celite. The pad was rinsed with methanol. The combined filtrate was concentrated. The resulting residue was dissolved in EtOAc, washed with saturated $Na_2CO_3$ (aq), and brine. The organic layer was dried over $Na_2SO_4$, filtered and concentrated to give the desired product as a yellow oil (7.7 g, 90%). LCMS calculated for $C_{18}H_{31}N_2OSi$ $(M+H)^+$: m/z=319.2; Found: 319.2.

Step 7. 4-(3-(tert-Butyldimethylsilyloxy)-5-methyl-cyclohexyl)pyridin-3-amine

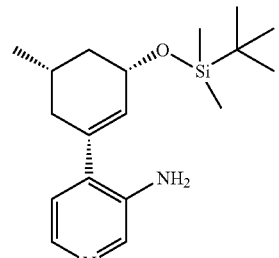

To a suspension of 4-(3-(tert-butyldimethylsilyloxy)-5-methylcyclohex-1-enyl)pyridin-3-amine (7.7 g, 24 mmol) in methanol (203 mL) under $N_2$ was added 10% palladium on carbon (2.64 g, 2.48 mmol). The mixture was purged with $H_2$ and stirred under $H_2$ balloon for 3 h. The mixture was filtered through a pad of Celite which was further eluted with MeOH. The filtrate was concentrated to give the crude product as an off-white foamy solid (7.3 g, 93%) which was used directly in the next step without further purification. LCMS calculated for $C_{18}H_{33}N_2OSi$ $(M+H)^+$: m/z=321.2; Found: 321.3.

Step 8. cis-(+/−)-Benzyl 4-(3-(tert-butyldimethylsilyloxy)-5-methylcyclohexyl)pyridin-3-yl carbamate

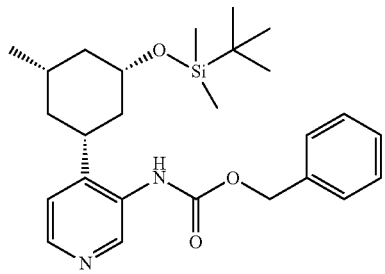 [SMILES: C[C@@H]1C[C@H](O[Si](C)(C)C(C)(C)C)C[C@H](c2ccncc2NC(=O)OCc2ccccc2)C1]

To a solution of 4-(3-(tert-butyldimethylsilyloxy)-5-methylcyclohexyl)pyridin-3-amine (7.3 g, 23 mmol) in dichloromethane (DCM, 50 mL) was added N-(benzyloxycarbonyloxy)succinimide (6.5 g, 26 mmol) and 4-dimethylaminopyridine (0.14 g, 1.2 mmol). The mixture was stirred at room temperature for 16 h. Then another portion of N-(benzyloxycarbonyloxy)succinimide (3.1 g, 12 mmol) was added, followed by 4-dimethylaminopyridine. The reaction mixture was stirred for additional 16 h. The reaction solution was partitioned between ethyl acetate and sat. $Na_2CO_3$ (aq) solution. The separated organic layer was washed with sat. $Na_2CO_3$ solution and brine, dried over $Na_2SO_4$, filtered and concentrated. The residue was purified by flash chromatography (eluting with a gradient of 0-40% ethyl acetate in hexanes) to give the desired product as brown oil. LCMS calculated for $C_{26}H_{39}N_2O_3Si$ $(M+H)^+$: m/z=455.3; Found: 455.2.

Step 9. cis-(+/−)-Benzyl 4-(3-hydroxy-5-methylcyclohexyl)pyridin-3-yl carbamate

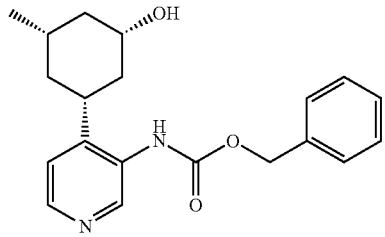 [SMILES: C[C@@H]1C[C@H](O)C[C@H](c2ccncc2NC(=O)OCc2ccccc2)C1]

To a solution of cis (+/−) benzyl 4-(3-(tert-butyldimethylsilyloxy)-5-methylcyclohexyl)pyridin-3-yl carbamate (7.0 g, 15 mmol) in methanol (100 mL) was added 6.0 M hydrogen chloride in water (50.0 mL, 300. mmol). The resulting mixture was stirred at room temperature for 6 h. The pH was then adjusted to pH=7 by addition of 6 N NaOH and the volatiles were removed in vacuo. The resulting aqueous was extracted with EtOAc and the organic was washed with brine, dried over $MgSO_4$, filtered and concentrated to give the crude product which was used in next step without further purification (4.8 g, 92%). LCMS calculated for $C_{20}H_{25}N_2O_3$ $(M+H)^+$: m/z=341.2; Found: 341.1.

Step 10. cis-(+/−)-Benzyl 4-(3-methyl-5-oxocyclohexyl)pyridin-3-ylcarbamate

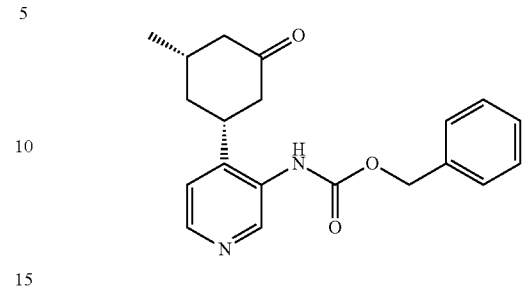

A solution of cis-(+/−)-benzyl 4-(3-hydroxy-5-methylcyclohexyl)pyridin-3-yl carbamate (4.8 g, 14 mmol) in DCM (90. mL) was added Dess-Martin periodinane (8.97 g, 21.2 mmol). The reaction mixture was stirred at room temperature for 2 h. The reaction mixture was diluted with ether and saturated $NaHCO_3$ (aq) solution and stirred for 30 min. The organic layer was separated and washed with brine, dried over $Na_2SO_4$, filtered and concentrated. The crude was purified with flash chromatography (eluting with a gradient of 0-50% ethyl acetate in hexanes) to give the desired product (2.5 g, 52%). LCMS calculated for $C_{20}H_{23}N_2O_3$ $(M+H)^+$: m/z=339.2; Found: 339.1.

Step 11. cis-(+/−)-Benzyl 4-(3-(benzylamino)-5-methylcyclohexyl)pyridin-3-ylcarbamate

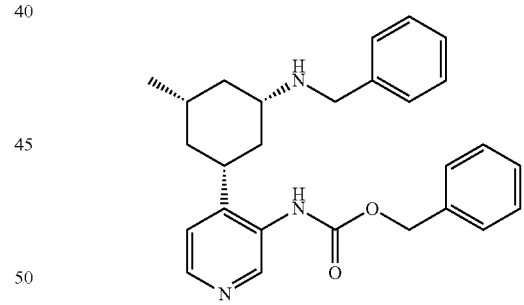

To a solution of cis-(+/−)-benzyl 4-(3-methyl-5-oxocyclohexyl)pyridin-3-ylcarbamate (2.50 g, 7.39 mmol) in methanol (30. mL) was added benzylamine (2.42 mL, 22.2 mmol). The resulting mixture was stirred at room temperature for 2 h. After cooling to −78° C., the reaction was treated with 2.0 M lithium tetrahydroborate in THF (4.1 mL, 8.1 mmol). The mixture was allowed to warm to room temperature and stirred overnight. The solution was partitioned between EtOAc and sat. $NaHCO_3$ (aq). The organic layer was separated, washed further with sat. $NaHCO_3$ (aq) and brine, dried over $MgSO_4$, filtered and concentrated. The crude was used in the next step without further purification (3.1 g, 98%). LCMS calculated for $C_{27}H_{32}N_3O_2$ $(M+H)^+$: m/z=430.2; Found: 430.2.

Step 12. tert-Butyl [(1S,3R,5S)-3-(3-aminopyridin-4-yl)-5-methylcyclohexyl]carbamate (Peak 2) and tert-Butyl [(1R,3S,5R)-3-(3-aminopyridin-4-yl)-5-methylcyclohexyl]carbamate (Peak 1

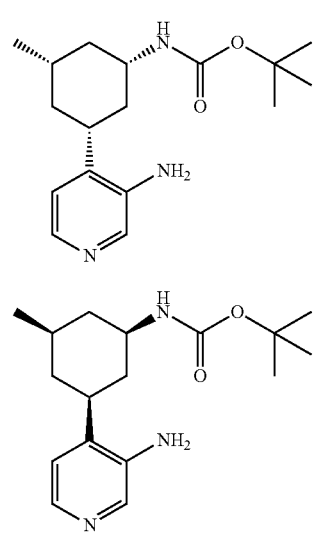

Peak 2

Peak 1

To a solution of cis-(+/−)-benzyl 4-(3-(benzylamino)-5-methylcyclohexyl)pyridin-3-ylcarbamate (3.10 g, 7.22 mmol) in methanol (100 mL) was added 20% palladium hydroxide (1.0 g, 1.4 mmol). The resultant heterogeneous solution was put under an atmosphere of hydrogen and was stirred for 14 h. At this time the reaction was purged with $N_2$, then di-tert-butyldicarbonate (1.6 g, 7.2 mmol) was added and the solution was stirred for 7 h. Additional di-tert-butyldicarbonate (1.6 g, 7.2 mmol) was added and the solution was stirred overnight. The solvent was removed in vacuo and the residue was purified with flash chromatography (eluting with a gradient of 20-100% ethyl acetate in hexanes) to give the racemic product. The racemic mixture was separated by chiral column (CHIRALPAK IA Col, 15% ethanol/85% hexanes, 12 mL/min) to give two peaks. Peak 1: RT 8.2-9.5 min; Peak 2: RT 10.6-12.4 min. LCMS calculated for $C_{17}H_{28}N_3O_2$ (M+H)$^+$: m/z=306.2; Found: 306.2.

Step 13. Methyl 5-fluoroquinoline-8-carboxylate

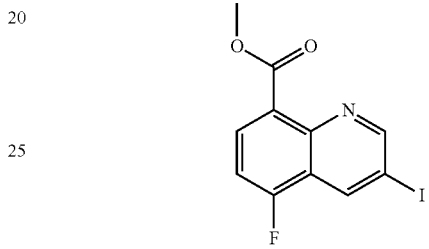

A mixture of 8-bromo-5-fluoroquinoline (6.0 g, 26 mmol, Combi-Blocks) and [1,1'-bis(diphenylphosphino)ferrocene]dichloropalladium(II) complexed with dichloromethane (1:1) (2.2 g, 2.6 mmol, Combi-Blocks) was placed in a flask with a septum. The flask was then evacuated and backfilled with nitrogen three times. After addition of methanol (100 mL) and triethylamine (7.4 mL, 53 mmol) the flask was evacuated and backfilled with carbon monoxide gas three times. Then a balloon with carbon monoxide gas was connected to the reaction flask and reaction mixture was heated at 85° C. overnight. After cooling down to r.t., the reaction mixture was filtered through Celite and concentrated under reduced pressure. Crude material was purified by Biotage Isolera™ (flash purification system with hexane/ethyl acetate at a ratio from 0 to 100%) to give the desired product (4.64 g, 87%). LCMS calculated for $C_{11}H_9FNO_2$ (M+H)$^+$ m/z=206.1; found: 206.0.

Step 14. Methyl 5-fluoro-3-iodoquinoline-8-carboxylate

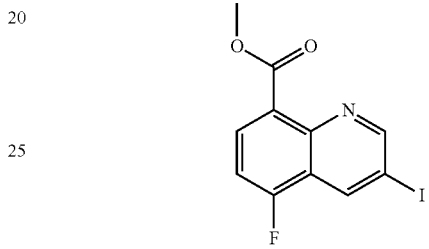

N-Iodosuccinimide (3.0 g, 13 mmol) was slowly added to a solution of 5-fluoroquinoline-8-carboxylate (1.3 g, 6.3 mmol) in acetic acid (8.0 mL) at r.t. After stirring at 50° C. overnight, the reaction was concentrated at reduced pressure and crude product was redissolved in ethyl acetate. Then pH was adjusted to 8 by the addition of saturated solution of sodium bicarbonate. The product was extracted with ethyl acetate. The organic phase was washed with brine and saturated solution of sodium thiosulfate, dried over sodium sulfate and solvent was evaporated under reduced pressure. Crude material was purified by Biotage Isolera™ (flash purification system with hexane/ethyl acetate at a ratio from 0 to 100%) to give the desired compound (1.92 g, 92%). LCMS calculated for $C_{11}H_8FINO_2$ (M+H)$^+$ m/z=332.0; found: 332.0.

Step 15. 5-Fluoro-3-iodoquinoline-8-carboxylic acid

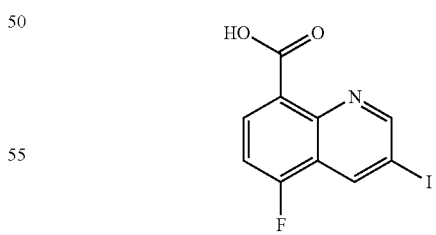

A 1 M solution of sodium hydroxide in water (10 mL, 10 mmol) was added to a solution of methyl 5-fluoro-3-iodoquinoline-8-carboxylate (1.5 g, 4.5 mmol) in tetrahydrofuran (10 mL) and methanol (6 mL). After stirring at r.t. for 2 h, pH was adjusted to 5 by the addition of a 1 M solution of HCl. The product was then extracted with ethyl acetate and the organic phase was washed with brine. The organic phase was dried over sodium sulfate and the solvent was evaporated under reduced pressure. The obtained solid product was used in the next step without further purification (1.35 g, 95%). LCMS calculated for $C_{10}H_6FINO_2$ (M+H)$^+$ m/z=317.9; found 317.9.

Step 16. tert-Butyl (1S,3R,5S)-3-(3-(5-fluoro-3-iodoquinoline-8-carboxamido)pyridin-4-yl)-5-methylcyclohexylcarbamate

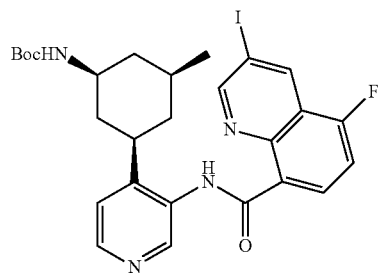 [SMILES: C[C@@H]1C[C@H](NC(=O)OC(C)(C)C)C[C@H](c2ccncc2NC(=O)c2ccc(F)c3cc(I)cnc23)C1]

To a solution of tert-butyl (1S,3R,5S)-3-(3-aminopyridin-4-yl)-5-methylcyclohexylcarbamate (400 mg, 1.3 mmol; Peak 2 of Step 12) and 5-fluoro-3-iodoquinoline-8-carboxylic acid (494 mg, 1.56 mmol) in N,N-dimethylformamide (10 mL) were added N,N-diisopropylethylamine (480 µL, 2.7 mmol) and N,N,N',N'-tetramethyl-O-(7-azabenzotriazol-1-yl)uronium hexafluorophosphate (780 mg, 2.1 mmol). After the reaction mixture was stirred at r.t. for 2 hours, it was quenched by the addition of water. The precipitate was collected by filtration and washed with water twice. Then it was redissolved in ethyl acetate to give a solution which was washed with brine and dried over sodium sulfate. After the solvent was evaporated, the crude product was purified by Biotage Isolera™ (flash purification system with hexane/ethyl acetate at a ratio from 0 to 100%) to give the desired compound (595 mg, 76%). LCMS calculated for $C_{27}H_{31}FIN_4O_3$ (M+H)$^+$ m/z=605.1; found 605.1.

Intermediate 2 tert-Butyl [(1S,3R,5S)-3-(3-{[(3-bromoquinolin-8-yl)carbonyl]amino}pyridin-4-yl)-5-methylcyclohexyl]carbamate

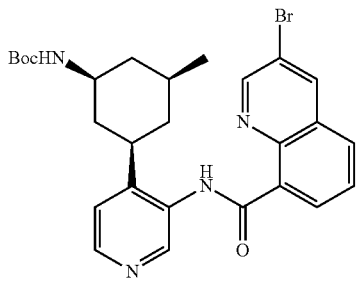 [SMILES: C[C@@H]1C[C@H](NC(=O)OC(C)(C)C)C[C@H](c2ccncc2NC(=O)c2cccc3cc(Br)cnc23)C1]

To a solution of tert-butyl (1S,3R,5S)-3-(3-aminopyridin-4-yl)-5-methylcyclohexylcarbamate (200 mg, 0.65 mmol) and 3-bromoquinoline-8-carboxylic acid (200 mg, 0.79 mmol) in N,N-dimethylformamide (5 mL) were added N,N-diisopropylethylamine (240 µL, 1.35 mmol) and N,N,N',N'-tetramethyl-O-(7-azabenzotriazol-1-yl)uronium hexafluorophosphate (390 mg, 1.05 mmol). After the reaction mixture was stirred at r.t. for 2 hours, it was quenched by the addition of water. The precipitate was collected by filtration and washed with water twice. Then it was redissolved in ethyl acetate to give a solution which was washed with brine and dried over sodium sulfate. After the solvent was evaporated, the crude product was purified by Biotage Isolera™ (flash purification system with hexane/ethyl acetate at a ratio from 0 to 100%) to give the desired compound (290 mg, 83%). LCMS calculated for $C_{27}H_{32}BrN_4O_3$ (M+H)$^+$ m/z=539.2; found 539.1.

Example 1

N-{4-[(1R,3S,5S)-3-Amino-5-methylcyclohexyl] pyridin-3-yl}-3-ethyl-5-fluoroquinoline-8-carboxamide

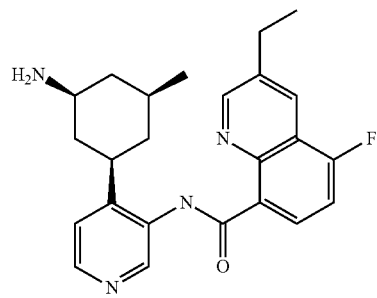

Step 1. Methyl 5-fluoroquinoline-8-carboxylate

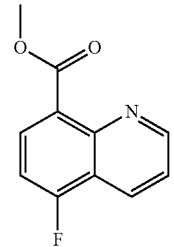

A mixture of 8-bromo-5-fluoroquinoline (8.00 g, 35.4 mmol) (from Combi-Block), [1,1'-bis(diphenylphosphino)ferrocene]dichloropalladium(II) complexed with dichloromethane (1:1) (2.9 g, 3.5 mmol) and triethylamine (9.9 mL, 71 mmol) in methanol (100 mL) was degassed, bubbled with CO for 1 minute, and refluxed under a balloon of CO for 2 h. The reaction mixture was filtered through a pad of Celite which was further rinsed with EtOAc. The filtrate was concentrated and the residue was purified by flash chromatography (eluting with a gradient of 0-50% EtOAc in hexanes) to give the desired product as a brown oil (7.0 g, 96%). LCMS calculated for $C_{11}H_9FNO_2$ (M+H)$^+$: m/z=206.1; Found: 206.1. $C_{11}H_8FNO_2$.

Step 2. Methyl 3-bromo-5-fluoroquinoline-8-carboxylate

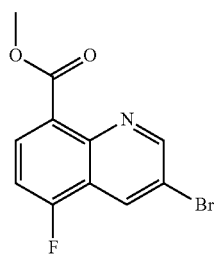 [SMILES: COC(=O)c1ccc(F)c2cc(Br)cnc12]

To a mixture of methyl 5-fluoroquinoline-8-carboxylate (11.0 g, 53.6 mmol) in acetic acid (60 mL) was added N-bromosuccinimide (10.0 g, 56.3 mmol). The reaction was stirred at room temperature for 1 h. The solvent was removed in vacuo, and the residue was diluted with ethyl acetate and saturated NaHCO₃ solution. The separated aqueous layer was extracted with EtOAc (2×) and the combined organic phases were washed with water, brine, dried over Na₂SO₄ and filtered. The filtrate was concentrated under reduced pressure, and the residue was purified by flash chromatography (eluting with a gradient of 0-30% EtOAc in hexanes) to give the desired product white solid (4.3 g, 28%). LCMS calculated for $C_{11}H_8BrFNO_2$ $(M+H)^+$: m/z=284.0, 286.0; Found: 284.0, 286.0.

Step 3. 3-Bromo-5-fluoroquinoline-8-carboxylic acid

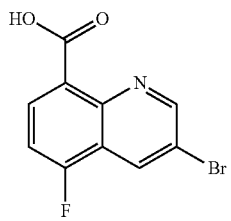 [SMILES: O=C(O)c1ccc(F)c2cc(Br)cnc12]

A mixture of methyl 3-bromo-5-fluoroquinoline-8-carboxylate (450 mg, 1.6 mmol), THF (9 mL) and 1.0 M sodium hydroxide in water (9.5 mL, 9.5 mmol) was stirred at room temperature for 1 h. The pH of the solution was adjusted to 3 with 1 M solution of HCl (aq). The aqueous layer was extracted with ethyl acetate (2×). The organic layers were dried over Na₂SO₄, filtered and concentrated to give the desired product as a white solid (410 mg, 96%). LCMS calculated for $C_{10}H_6BrFNO_2$ $(M+H)^+$: m/z=270.0, 272.0; Found: 270.0, 272.0.

Step 4. tert-Butyl [(1S,3R,5S)-3-(3-{[(3-bromo-5-fluoroquinolin-8-yl)carbonyl]amino}pyridin-4-yl)-5-methylcyclohexyl]carbamate

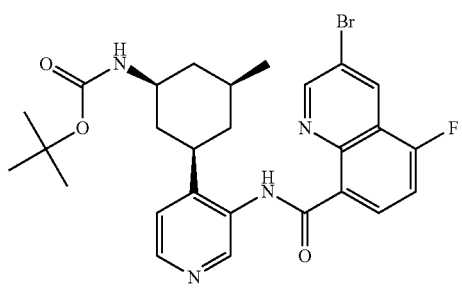 [SMILES: C[C@@H]1C[C@H](NC(=O)OC(C)(C)C)C[C@H](c2ccncc2NC(=O)c2ccc(F)c3cc(Br)cnc23)C1]

To a solution of 3-bromo-5-fluoroquinoline-8-carboxylic acid (196 mg, 0.726 mmol) and tert-butyl [(1S,3R,5S)-3-(3-aminopyridin-4-yl)-5-methylcyclohexyl]carbamate (185 mg, 0.605 mmol, Intermediate 1, Step 12) in DMF (1 mL) were added N,N,N',N'-tetramethyl-O-(7-azabenzotriazol-1-yl)uronium hexafluorophosphate (335 mg, 0.880 mmol) and N,N-diisopropylethylamine (320 μL, 1.8 mmol). The reaction mixture was stirred at room temperature overnight. The reaction mixture was diluted with DCM and water, and the separated aqueous layer was extracted with DCM once. The combined organic layers were washed with water, brine, dried over Na₂SO₄, filtered and concentrated in vacuo. The residue was purified with flash chromatography (eluting with a gradient of 0-100% EtOAc in hexanes) to give the desired product as a white solid (285 mg, 85%). LCMS calculated for $C_{27}H_{31}BrFN_4O_3$ $(M+H)^+$: m/z=557.2, 559.2; Found: 557.1, 559.1.

Step 5. tert-Butyl [(1S,3R,5S)-3-(3-{[(5-fluoro-3-vinylquinolin-8-yl)carbonyl]amino}pyridin-4-yl)-5-methylcyclohexyl]carbamate

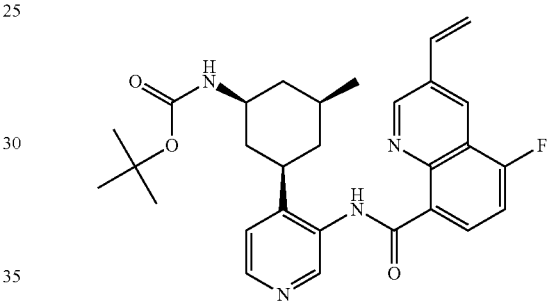

A microwave vial was charged with tert-butyl [(1S,3R,5S)-3-(3{[(3-bromo-5-fluoroquinolin-8-yl)carbonyl]amino}pyridin-4-yl)-5-methylcyclohexyl]carbamate (27.8 mg, 0.0499 mmol), dicyclohexyl(2',4',6'-triisopropylbiphenyl-2-yl)phosphine-(2'-aminobiphenyl-2-yl)(chloro)palladium (1:1) (3.4 mg, 0.0044 mmol) and tripotassium phosphate hydrate (25.3 mg, 0.110 mmol). The vial was sealed and evacuated under high vacuum and backfilled with nitrogen (repeated three times). 1,4-Dioxane (0.54 mL) and water (0.18 mL) were added, followed by 4,4,5,5-tetramethyl-2-vinyl-1,3,2-dioxaborolane (12.3 mg, 0.0798 mmol). The mixture was stirred at 70° C. for 1 h. After cooling to room temperature, the mixture was diluted with water and DCM. The organic layer was concentrated and purified with flash chromatography (eluting with a gradient of 0-100% EtOAc in hexanes) to give the desired product as a yellow oil (13 mg, 52%). LCMS calculated for $C_{29}H_{34}FN_4O_3$ $(M+H)^+$: m/z=505.3; Found: 505.3.

Step 6. N-{4-[(1R,3S,5S)-3-Amino-5-methylcyclohexyl]pyridin-3-yl}-3-ethyl-5-fluoroquinoline-8-carboxamide To a solution of tert-butyl [(1S,3R,5S)-3-(3{[(5-fluoro-3-vinylquinolin-8-yl)carbonyl]amino}pyridin-4-yl)-5-methylcyclohexyl]carbamate (13 mg, 0.026 mmol) in methanol (1 mL) was added 10% palladium on carbon (3 mg). The resulting mixture was stirred under H₂ balloon for 2 h. The mixture was filtered and the filtrate was concentrated. The residue was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as white solid (6.5 mg, 50%). LCMS calculated for $C_{24}H_{28}FN_4O$ $(M+H)^+$: m/z=407.2; Found: 407.2.

Example 2. N-{4-[(1R,3S,5S)-3-Amino-5-methylcyclohexyl]pyridin-3-yl}-5-fluoro-3-[(3,R)-3-fluoropiperidin-1-yl]quinoline-8-carboxamide

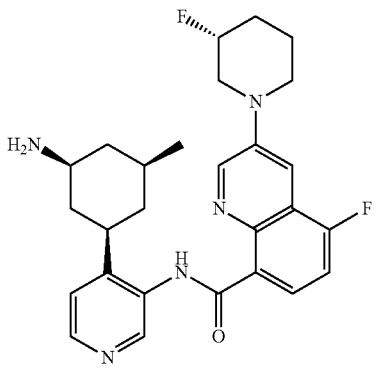 [SMILES: C[C@@H]1C[C@H](N)C[C@H](c2ccncc2NC(=O)c2ccc(F)c3cc(N4CCC[C@@H](F)C4)cnc23)C1]

Step 1. tert-Butyl ((1S,3R,5S)-3-{3-[({5-fluoro-3-[(3R)-3-fluoropiperidin-1-yl]quinolin-8-yl}carbonyl)amino]pyridin-4-yl}-5-methylcyclohexyl)carbamate

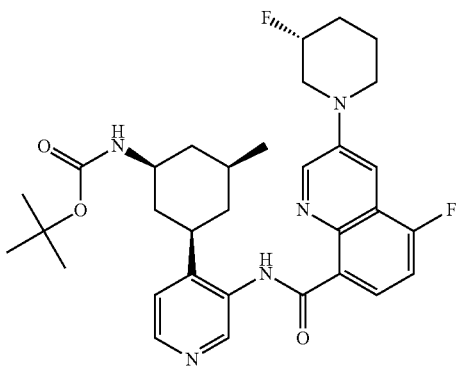 [SMILES: C[C@@H]1C[C@H](NC(=O)OC(C)(C)C)C[C@H](c2ccncc2NC(=O)c2ccc(F)c3cc(N4CCC[C@@H](F)C4)cnc23)C1]

A vial was charged with tert-butyl [(1S,3R,5S)-3-(3{[(3-bromo-5-fluoroquinolin-8-yl)carbonyl]amino}pyridin-4-yl)-5-methylcyclohexyl]carbamate (30.0 mg, 0.0538 mmol), (3R)-3-fluoropiperidine hydrochloride (16.5 mg, 0.118 mmol), dicyclohexyl-(2',6'-diisopropoxybiphenyl-2-yl)phosphine-(2'-aminobiphenyl-2-yl)(chloro)palladium (1:1) (6.3 mg, 0.0081 mmol) and cesium carbonate (71.9 mg, 0.221 mmol). The vial was sealed with a teflon screw-cap, evacuated and backfilled with nitrogen (this process was repeated a total of three times). Anhydrous tert-butyl alcohol (0.4 mL) was added. The mixture was heated to 90° C. for 5 h. The reaction mixture was diluted with water and DCM, the organic layer was separated and concentrated. The crude was purified with flash chromatography (eluting with a gradient of 0-100% ethyl acetate in hexanes) to give the desired product as yellow foam. LCMS calculated for $C_{32}H_{40}F_2N_5O_3$ $(M+H)^+$: m/z=580.3; Found: 580.3.

Step 2. N-{4-[(1R,3S,5S)-3-Amino-5-methylcyclohexyl]pyridin-3-yl}-5-fluoro-3-[(3R)-3-fluoropiperidin-1-yl]quinoline-8-carboxamide The product from above step was treated with 1:1 DCM/TFA (2 mL) for 1 h. The volatile was removed in vacuo and the residue was dissolved in methanol and purified with purified with prep-LCMS (XBridge C18 column, eluting with a gradient of acetonitrile/water containing 0.1% ammonium hydroxide, at flow rate of 60 mL/min) to give the desired product as yellow solid (6.6 mg, 26% two steps). LCMS calculated for $C_{27}H_{32}F_2N_5O$ $(M+H)^+$: m/z=480.3; Found: 480.2. $^1$H NMR (600 MHz, DMSO-d$_6$) δ 13.10 (d, J=3.9 Hz, 1H), 9.24 (d, J=7.8 Hz, 1H), 9.06 (m, 1H), 8.54 (d, J=5.4 Hz, 1H), 8.43 (dd, J=8.3, 6.2 Hz, 1H), 8.02 (s, 2H), 7.76 (d, J=3.0 Hz, 1H), 7.59 (m, 1H), 7.54 (m, 1H), 4.95 (m, 1H), 3.85 (m, 1H), 3.72-3.57 (m, 2H), 3.40-3.33 (m, 1H), 3.26-3.19 (m, 2H), 2.13 (m, 1H), 1.99 (m, 2H), 1.92 (m, 3H), 1.74 (m, 1H), 1.67 (m, 1H), 1.55 (q, J=12.0 Hz, 1H), 1.14 (m, 1H), 1.08 (m, 1H), 1.00 (t, J=6.4 Hz, 3H) ppm.

Example 3. N-{4-[(1R,3S,5S)-3-Amino-5-methylcyclohexyl]pyridin-3-yl}-5-fluoro-3-pyrrolidin-1-ylquinoline-8-carboxamide

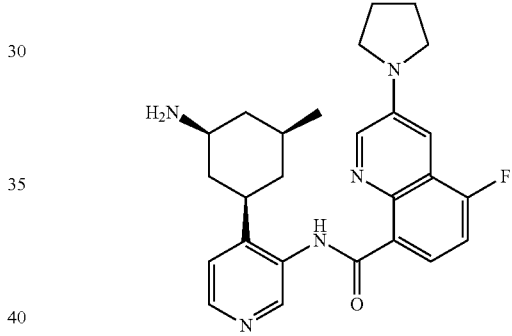

This compound was prepared according to the procedure described in Example 2, using pyrrolidine instead of (3R)-3-fluoropiperidine hydrochloride as starting material. LCMS calculated for $C_{26}H_{31}FN_5O$ $(M+H)^+$: m/z=448.2; Found: 448.3.

Example 4. N-{4-[(1R,3S,5S)-3-Amino-5-methylcyclohexyl]pyridin-3-yl}-3-azetidin-1-yl-5-fluoroquinoline-8-carboxamide

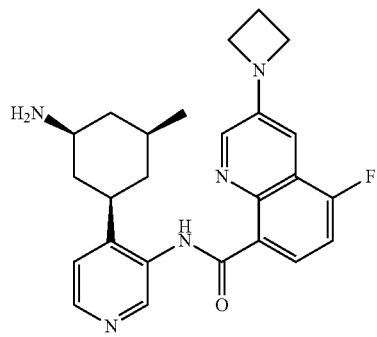 [SMILES: C[C@@H]1C[C@H](N)C[C@H](c2ccncc2NC(=O)c2ccc(F)c3cc(N4CCC4)cnc23)C1]

This compound was prepared according to the procedure described in Example 2, using azetidine instead of (3R)-3-fluoropiperidine hydrochloride as starting material. LCMS calculated for $C_{25}H_{29}FN_5O$ (M+H)$^+$: m/z=434.2; Found: 434.3.

Example 5. N-{4-[(1R,3S,5S)-3-Amino-5-methylcyclohexyl]pyridin-3-yl}-5-fluoro-3-[(3S)-3-fluoropyrrolidin-1-yl]quinoline-8-carboxamide

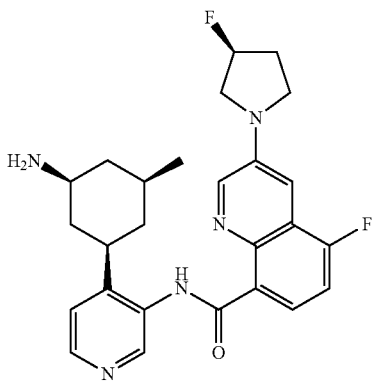 [SMILES: C[C@@H]1C[C@H](N)C[C@H](c2ccncc2NC(=O)c2ccc(F)c3cc(N4CC[C@H](F)C4)cnc23)C1]

This compound was prepared according to the procedure described in Example 2, using (3S)-3-fluoropyrrolidine hydrochloride instead of (3R)-3-fluoropiperidine hydrochloride as starting material. LCMS calculated for $C_{26}H_{30}F_2N_5O$ (M+H)$^+$: m/z=466.2; Found: 466.3.

Example 6. N-{4-[(1R,3S,5S)-3-Amino-5-methylcyclohexyl]pyridin-3-yl}-5-fluoro-3-[(3R)-3-fluoropyrrolidin-1-yl]quinoline-8-carboxamide

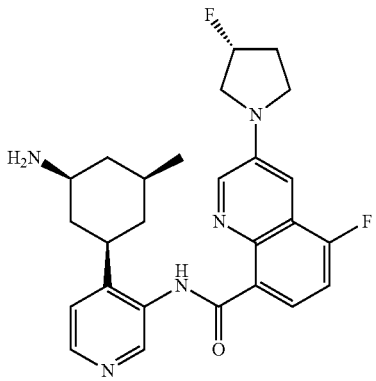 [SMILES: C[C@@H]1C[C@H](N)C[C@H](c2ccncc2NC(=O)c2ccc(F)c3cc(N4CC[C@@H](F)C4)cnc23)C1]

This compound was prepared according to the procedure described in Example 2, using (3R)-3-fluoropyrrolidine hydrochloride instead of (3R)-3-fluoropiperidine hydrochloride as starting material. LCMS calculated for $C_{26}H_{30}F_2N_5O$ (M+H)$^+$: m/z=466.2; Found: 466.3.

Example 7. N-{4-[(1R,3S,5S)-3-Amino-5-methylcyclohexyl]pyridin-3-yl}-3-[(3S)-3-cyanopyrrolidin-1-yl]-5-fluoroquinoline-8-carboxamide

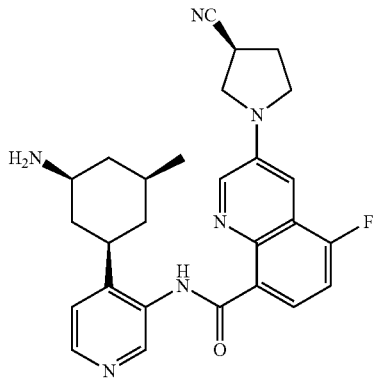 [SMILES: C[C@@H]1C[C@H](N)C[C@H](c2ccncc2NC(=O)c2ccc(F)c3cc(N4CC[C@H](C#N)C4)cnc23)C1]

This compound was prepared according to the procedure described in Example 2, using (3S)-pyrrolidine-3-carbonitrile hydrochloride instead of (3R)-3-fluoropiperidine hydrochloride as starting material. LCMS calculated for $C_{27}H_{30}FN_6O$ (M+H)$^+$: m/z=473.2; Found: 473.3.

Example 8. N-{4-[(1R,3S,5S)-3-Amino-5-methylcyclohexyl]pyridin-3-yl}-3-[(3R)-3-cyanopyrrolidin-1-yl]-5-fluoroquinoline-8-carboxamide

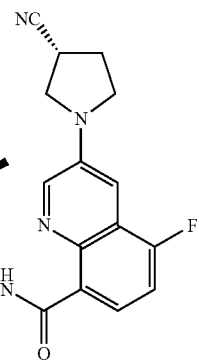

This compound was prepared according to the procedure described in Example 2, using (3R)-pyrrolidine-3-carbonitrile hydrochloride instead of (3R)-3-fluoropiperidine hydrochloride as starting material. LCMS calculated for $C_{27}H_{30}FN_6O$ (M+H)$^+$: m/z=473.2; Found: 473.3.

Example 9. N-{4-[(1R,3S,5S)-3-Amino-5-methylcyclohexyl]pyridin-3-yl}-5-fluoro-3-(3-fluoroazetidin-1-yl)quinoline-8-carboxamide

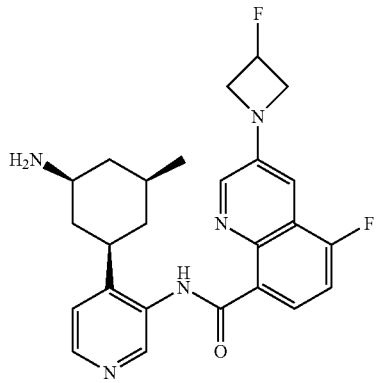 [SMILES: C[C@@H]1C[C@H](N)C[C@H](c2ccncc2NC(=O)c2ccc(F)c3cc(N4CC(F)C4)cnc23)C1]

This compound was prepared according to the procedure described in Example 2, using 3-fluoroazetidine hydrochloride instead of (3R)-3-fluoropiperidine hydrochloride as starting material. LCMS calculated for $C_{25}H_{28}F_2N_5O$ (M+H)$^+$: m/z=452.2; Found: 452.3.

Example 10. N-{4-[(1R,3S,5S)-3-Amino-5-methylcyclohexyl]pyridin-3-yl}-5-fluoro-3-morpholin-4-ylquinoline-8-carboxamide

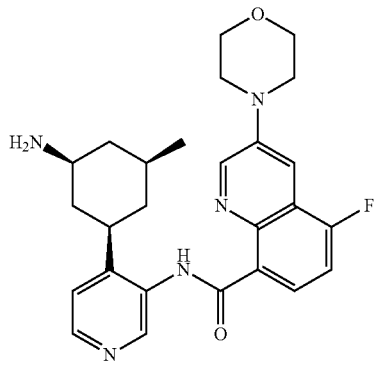 [SMILES: C[C@@H]1C[C@H](N)C[C@H](c2ccncc2NC(=O)c2ccc(F)c3cc(N4CCOCC4)cnc23)C1]

This compound was prepared according to the procedure described in Example 2, using morpholine instead of (3R)-3-fluoropiperidine hydrochloride as starting material. LCMS calculated for $C_{26}H_{31}FN_5O_2$ (M+H)$^+$: m/z=464.2; Found: 464.3.

Example 11. N-{4-[(1R,3S,5S)-3-Amino-5-methylcyclohexyl]pyridin-3-yl}-5-fluoro-3-[(3S)-3-methoxypiperidin-1-yl]quinoline-8-carboxamide

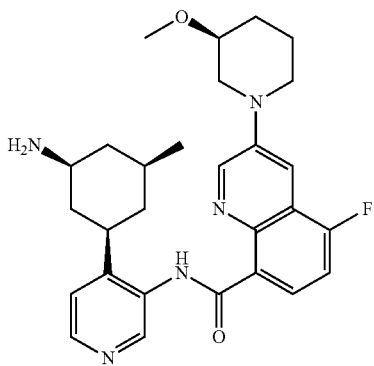 [SMILES: CO[C@H]1CCCN(c2cnc3c(C(=O)Nc4cnccc4[C@@H]4C[C@H](C)C[C@H](N)C4)ccc(F)c3c2)C1]

This compound was prepared according to the procedure described in Example 2, using (3S)-3-methoxypiperidine hydrochloride instead of (3R)-3-fluoropiperidine hydrochloride as starting material. LCMS calculated for $C_{28}H_{35}FN_5O_2$ (M+H)$^+$: m/z=492.3; Found: 492.3.

Example 12. N-{4-[(1R,3S,5S)-3-Amino-5-methylcyclohexyl]pyridin-3-yl}-5-fluoro-3-[(3S)-3-methoxypiperidin-1-yl]quinoline-8-carboxamide

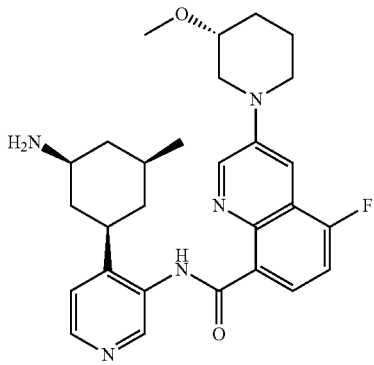 [SMILES: CO[C@@H]1CCCN(c2cnc3c(C(=O)Nc4cnccc4[C@@H]4C[C@H](C)C[C@H](N)C4)ccc(F)c3c2)C1]

This compound was prepared according to the procedure described in Example 2, using (3R)-3-methoxypiperidine hydrochloride instead of (3R)-3-fluoropiperidine hydrochloride as starting material. LCMS calculated for $C_{28}H_{35}FN_5O_2$ (M+H)$^+$: m/z=492.3; Found: 492.3.

Example 13. N-{4-[(1R,3S,5S)-3-Amino-5-methyl-cyclohexyl]pyridin-3-yl}-3-cyclopropyl-5-fluoroquinoline-8-carboxamide

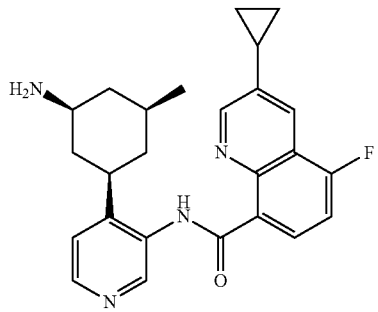 [SMILES: C[C@@H]1C[C@H](N)C[C@H](c2ccncc2NC(=O)c2ccc(F)c3cc(C4CC4)cnc23)C1]

Step 1. tert-Butyl [(1S,3R,5S)-3-(3-{[(3-cyclopropyl-5-fluoroquinolin-8-yl)carbonyl]amino}pyridin-4-yl)-5-methylcyclohexyl]carbamate

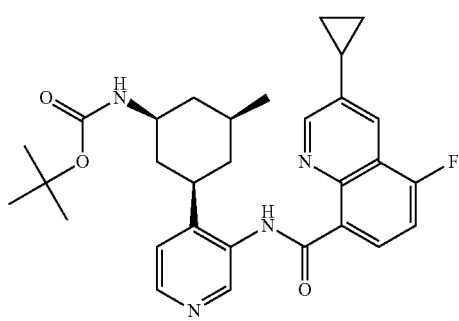 [SMILES: C[C@@H]1C[C@H](NC(=O)OC(C)(C)C)C[C@H](c2ccncc2NC(=O)c2ccc(F)c3cc(C4CC4)cnc23)C1]

To a microwave vial was added tert-butyl [(1S,3R,5S)-3-(3{[(3-bromo-5-fluoroquinolin-8-yl)carbonyl]amino}pyridin-4-yl)-5-methylcyclohexyl]carbamate (30.3 mg, 0.0544 mmol), potassium cyclopropyltrifluoroborate (9.6 mg, 0.065 mmol), cesium carbonate (53.1 mg, 0.163 mmol), palladium acetate (1.2 mg, 0.0054 mmol) and di-1-adamantyl(butyl)phosphine (2.9 mg, 0.0082 mmol). The vial was seal and evacuated then backfilled with $N_2$ (this procedure was repeated three times), then toluene (0.25 mL) and water (0.025 mL) were added. The reaction mixture was heated at 100° C. for 16 h. After cooling to room temperature, the reaction mixture was diluted with water and ethyl acetate. The aqueous layer was extracted with ethyl acetate once. The combined organic layers were dried over $Na_2SO_4$, filtered and concentrated. The residue was purified with flash chromatography (eluting with a gradient of 0-100% ethyl acetate in hexanes) to give the desired product as yellow foam. LCMS calculated for $C_{30}H_{36}FN_4O_3$ $(M+H)^+$: m/z=519.3; Found: 519.2.

Step 2. N-{4-[(1R,3S,5S)-3-Amino-5-methylcyclohexyl]pyridin-3-yl}-3-cyclopropyl-5-fluoroquinoline-8-carboxamide The product from the previous step was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as a white solid (8.6 mg, 38% for two steps). LCMS calculated for $C_{25}H_{28}FN_4O$ $(M+H)^+$: m/z=419.2; Found: 419.2.

Example 14. N-{4-[(1R,3S,5S)-3-Amino-5-methyl-cyclohexyl]pyridin-3-yl}-3-(cyclopropylethynyl)-5-fluoroquinoline-8-carboxamide

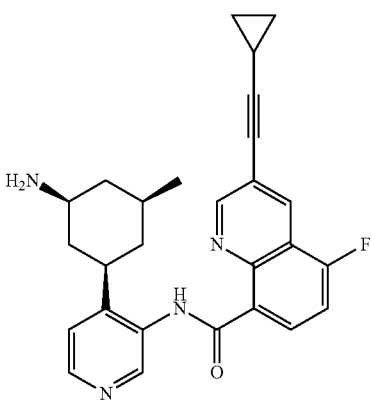 [SMILES: C[C@@H]1C[C@H](N)C[C@H](c2ccncc2NC(=O)c2ccc(F)c3cc(C#CC4CC4)cnc23)C1]

Step 1. tert-Butyl {(1S,3R,5S)-3-[3-({[3-(cyclopropylethynyl)-5-fluoroquinolin-8-yl]carbonyl}amino)pyridin-4-yl]-5-methylcyclohexyl}carbamate

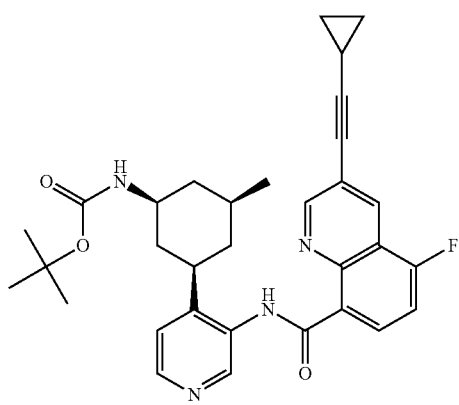 [SMILES: C[C@@H]1C[C@H](NC(=O)OC(C)(C)C)C[C@H](c2ccncc2NC(=O)c2ccc(F)c3cc(C#CC4CC4)cnc23)C1]

A microwave vial was charged with tert-butyl [(1S,3R,5S)-3-(3-{[(3-bromo-5-fluoroquinolin-8-yl)carbonyl]amino}pyridin-4-yl)-5-methylcyclohexyl]carbamate (32.5 mg, 0.0583 mmol), copper(I) iodide (1.38 mg, 0.00723 mmol) and dichloro[bis(triphenylphosphonio)]palladium (3.37 mg, 0.00481 mmol). The vial was sealed and evacuated then backfilled with $N_2$ (this procedure was repeated three times), then DMF (0.50 mL) and triethylamine (24.4 µL, 0.175 mmol) were added, followed by ethynylcyclopropane (14.8 µL, 0.175 mmol). The reaction mixture was stirred at 60° C. for 3 h. After cooling to rt, the reaction mixture was quenched with water and aqueous layer was extracted with EtOAc, the organic layer was washed with brine, dried over $Na_2SO_4$, and filtered. The filtrate was concentrated in vacuo and the residue was purified with flash chromatography (eluting with a gradient of 0-100% ethyl acetate in hexanes) to give the desired product as a yellow foam. LCMS calculated for $C_{32}H_{36}FN_4O_3$ $(M+H)^+$: m/z=543.3; Found: 543.2.

Step 2. N-{4-[(1R,3S,5S)-3-Amino-5-methylcyclohexyl]pyridin-3-yl}-3-(cyclopropylethynyl)-5-fluoroquinoline-8-carboxamide tris(trifluoroacetate The product from the previous step was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.05% TFA, at flow rate of 60 mL/min) to give the desired product as a TFA salt (white solid, 12.5 mg, 27% for two steps). LCMS calculated for $C_{27}H_{28}FN_4O$ $(M+H)^+$: m/z=443.2; Found: 443.1.

Example 15. N-{4-[(1R,3S,5S)-3-Amino-5-methylcyclohexyl]pyridin-3-yl}-3-(2-cyano-6-fluorophenyl)-5-fluoroquinoline-8-carboxamide

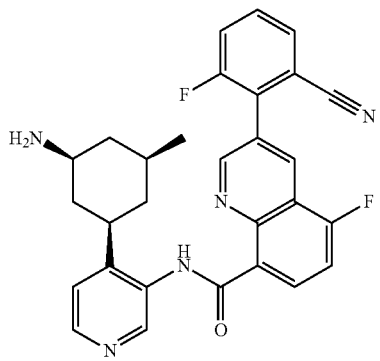 [SMILES: C[C@@H]1C[C@H](N)C[C@H](c2ccncc2NC(=O)c2ccc(F)c3cc(-c4c(F)cccc4C#N)cnc23)C1]

Step 1. tert-Butyl ((1S,3R,5S)-3-{3-[({3-[2-(aminocarbonyl)-6-fluorophenyl]-5-fluoroquinolin-8-yl}carbonyl)amino]pyridin-4-yl}-5-methylcyclohexyl)carbamate

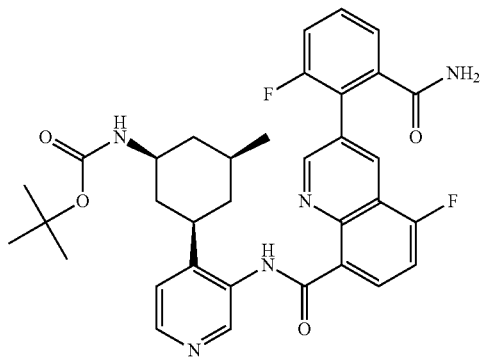 [SMILES: C[C@@H]1C[C@H](NC(=O)OC(C)(C)C)C[C@H](c2ccncc2NC(=O)c2ccc(F)c3cc(-c4c(F)cccc4C(N)=O)cnc23)C1]

To a microwave vial was added tert-butyl [(1S,3R,5S)-3-(3-{[(3-bromo-5-fluoroquinolin-8-yl)carbonyl]amino}pyridin-4-yl)-5-methylcyclohexyl]carbamate (33.4 mg, 0.0599 mmol), (2-cyano-6-fluorophenyl)boronic acid (15.8 mg, 0.0958 mmol), dicyclohexyl-(2',4',6'-triisopropylbiphenyl-2-yl)phosphine-(2'-aminobiphenyl-2-yl)(chloro)palladium (1:1) (3.4 mg, 0.0044 mmol) and tripotassium phosphate hydrate (25.3 mg, 0.110 mmol). The vial was sealed and evacuated under high vacuum and backfilled with nitrogen (repeated three times). 1,4-Dioxane (0.54 mL) and water (0.18 mL) were added. The mixture was stirred at 70° C. for 1 h. After cooling to room temperature, the mixture was diluted with water and DCM. The organic layer was concentrated and purified with flash chromatography (eluting with a gradient of 0-100% EtOAc in hexanes) to give the desired product as a yellow oil (26 mg, 70%). LCMS calculated for $C_{34}H_{36}F_2N_5O_4$ $(M+H)^+$: m/z=616.3; Found: 616.3.

Step 2. N-{4-[(1R,3S,5S)-3-Amino-5-methylcyclohexyl]pyridin-3-yl}-3-(2-cyano-6-fluorophenyl)-5-fluoroquinoline-8-carboxamide To a solution of tert-butyl ((1S,3R,5S)-3-{3-[({3-[2-(aminocarbonyl)-6-fluorophenyl]-5-fluoroquinolin-8-yl}-carbonyl)amino]pyridin-4-yl}-5-methylcyclohexyl)carbamate (26 mg, 0.042 mmol) in DCM (1 mL) was added trichloroacetyl chloride (13 µl, 0.12 mmol) and pyridine (14.5 µl, 0.18 mmol). After stirring at room temperature for 2 h, the volatiles were removed in vacuo. The residue was treated with 1:1 DCM/TFA (2 mL) for 1 h. The volatiles were removed in vacuo and the residue was dissolved in methanol and purified with prep-LCMS (XBridge C18 column, eluting with a gradient of acetonitrile/water containing 0.1% ammonium hydroxide, at flow rate of 60 mL/min) to give the desired product as a white solid (16 mg, 46%). LCMS calculated for $C_{29}H_{26}F_2N_5O$ $(M+H)^+$: m/z=498.2; Found: 498.1. $^1$H NMR (600 MHz, DMSO-$d_6$) δ 12.57 (s, 1H), 9.37 (m, 1H), 9.08 (m, 2H), 8.81 (dd, J=8.4, 6.3 Hz, 1H), 8.39 (d, J=5.1 Hz, 1H), 8.01 (dd, J=7.7, 1.0 Hz, 1H), 7.89 (m, 1H), 7.81 (m, 2H), 7.38 (d, J=5.1 Hz, 1H), 3.16 (m 1H), 2.95 (m 1H), 2.04 (d, J=11.9 Hz, 1H), 1.84 (m, 2H), 1.67 (m, 1H), 1.30 (q, J=12.0 Hz, 1H), 1.12 (q, J=12.1 Hz, 1H), 1.00 (d, J=6.3 Hz, 3H), 0.92 (m, 1H) ppm.

Example 16. tert-Butyl {(1S,3R,5S)-3-[3-({[3-(2,6-difluorophenyl)-5-fluoroquinolin-8-yl]carbonyl}amino)pyridin-4-yl]-5-methylcyclohexyl}carbamate

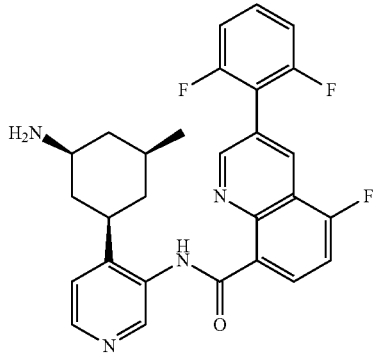 [SMILES: C[C@@H]1C[C@H](N)C[C@H](c2ccncc2NC(=O)c2ccc(F)c3cc(-c4c(F)cccc4F)cnc23)C1]

Step 1. tert-Butyl {(1S,3R,5S)-3-[3-({[3-(2,6-difluorophenyl)-5-fluoroquinolin-8-yl]carbonyl}amino)pyridin-4-yl]-5-methylcyclohexyl}carbamate

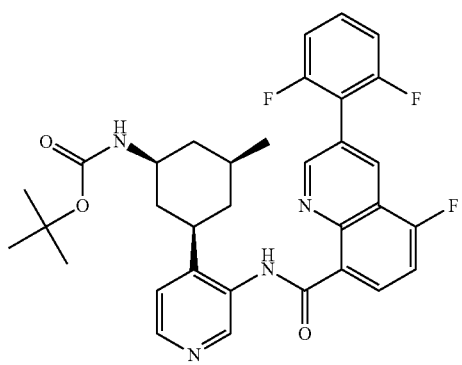

This compound was prepared according to the procedure described in Example 1, Step 5, using 2-(2,6-difluorophenyl)-4,4,5,5-tetramethyl-1,3,2-dioxaborolane instead of 4,4,5,5-tetramethyl-2-vinyl-1,3,2-dioxaborolane as starting material. LCMS calculated for $C_{33}H_{34}F_3N_4O_3$ (M+H)$^+$: m/z=591.3; Found: 591.3.

Step 2. tert-Butyl {(1S,3R,5S)-3-[3-({[3-(2,6-difluorophenyl)-5-fluoroquinolin-8-yl]carbonyl}amino)pyridin-4-yl]-5-methylcyclohexyl}carbamate The product from the previous step was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as a white solid. LCMS calculated for $C_{28}H_{26}F_3N_4O$ (M+H)$^+$: m/z=491.2; Found: 491.2.

Example 17. N-{4-[(1R,3S,5S)-3-Amino-5-methylcyclohexyl]pyridin-3-yl}-3-(2-cyanophenyl)-5-fluoroquinoline-8-carboxamide

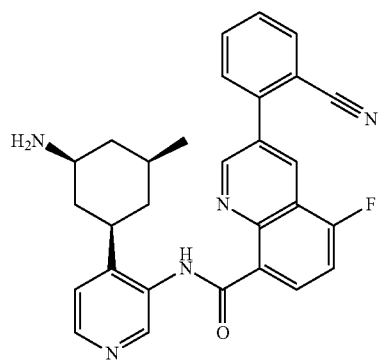 [SMILES: C[C@@H]1C[C@H](N)C[C@H](c2ccncc2NC(=O)c2ccc(F)c3cc(-c4ccccc4C#N)cnc23)C1]

This compound was prepared according to the procedure described in Example 16, using (2-cyanophenyl)boronic acid instead of 2-(2,6-difluorophenyl)-4,4,5,5-tetramethyl-1,3,2-dioxaborolane as starting material. LCMS calculated for $C_{29}H_{27}FN_5O$ (M+H)$^+$: m/z=480.2; Found: 480.2.

Example 18. N-{4-[(1R,3S,5S)-3-Amino-5-methylcyclohexyl]pyridin-3-yl}-3-(2,6-difluoro-4-hydroxyphenyl)-5-fluoroquinoline-8-carboxamide

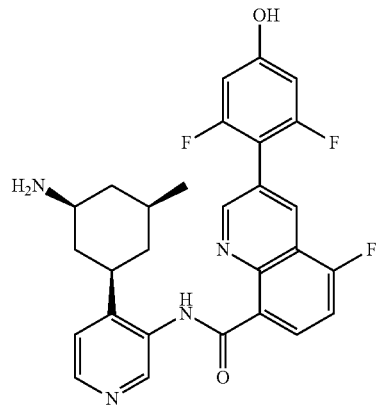 [SMILES: C[C@@H]1C[C@H](N)C[C@H](c2ccncc2NC(=O)c2ccc(F)c3cc(-c4c(F)cc(O)cc4F)cnc23)C1]

This compound was prepared according to the procedure described in Example 16, using (2,6-difluoro-4-hydroxyphenyl)boronic acid instead of 2-(2,6-difluorophenyl)-4,4,5,5-tetramethyl-1,3,2-dioxaborolane as starting material. LCMS calculated for $C_{28}H_{26}F_3N_4O_2$ (M+H)$^+$: m/z=507.2; Found: 507.2.

Example 19. N-{4-[(1R,3S,5S)-3-Amino-5-methylcyclohexyl]pyridin-3-yl}-3-[(cyclopropylmethyl)(methyl)amino]-5-fluoroquinoline-8-carboxamide

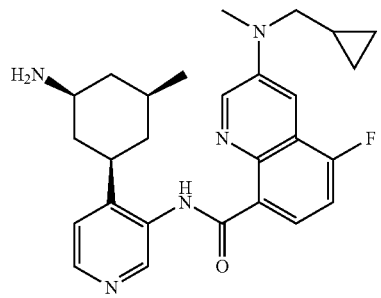 [SMILES: C[C@@H]1C[C@H](N)C[C@H](c2ccncc2NC(=O)c2ccc(F)c3cc(N(C)CC4CC4)cnc23)C1]

This compound was prepared according to the procedure described in Example 2, using 1-cyclopropyl-N-methylmethanamine hydrochloride instead of (3R)-3-fluoropiperidine hydrochloride as starting material. LCMS calculated for $C_{27}H_{33}FN_5O$ (M+H)$^+$: m/z=462.3; Found: 462.3.

Example 20. N-(4-((1R,3S,5S)-3-Amino-5-methylcyclohexyl)pyridin-3-yl)-3-(ethyl(methyl)amino)-5-fluoroquinoline-8-carboxamide

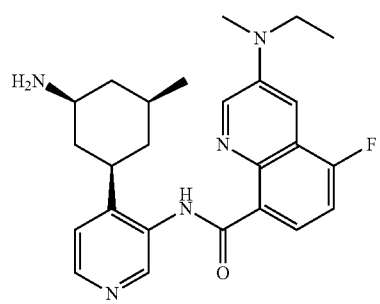 [SMILES: CCN(C)c1cnc2c(C(=O)Nc3cnccc3[C@@H]3C[C@H](C)C[C@H](N)C3)ccc(F)c2c1]

This compound was prepared according to the procedure described in Example 2, using N-methyl-ethanamine, instead of (3R)-3-fluoropiperidine hydrochloride as starting material. LCMS calculated for $C_{25}H_{31}FN_5O$ (M+H)$^+$: m/z=436.2; Found: 436.2.

Example 21. N-{4-[(1R,3S,5S)-3-Amino-5-methyl-cyclohexyl]pyridin-3-yl}-5-fluoro-3-[methyl(2,2,2-trifluoroethyl)amino]quinoline-8-carboxamide

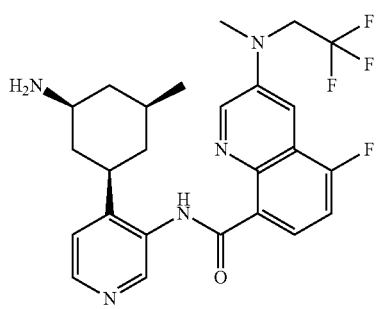 [SMILES: C[C@@H]1C[C@H](N)C[C@H](c2ccncc2NC(=O)c2ccc(F)c3cc(N(C)CC(F)(F)F)cnc23)C1]

This compound was prepared according to the procedure described in Example 2, using 2,2,2-trifluoro-N-methyl-ethanamine hydrochloride, instead of (3R)-3-fluoropiperidine hydrochloride as starting material. LCMS calculated for $C_{25}H_{28}F_4N_5O$ (M+H)$^+$: m/z=490.2; Found: 490.2.

Example 22. N-{4-[(1R,3S,5S)-3-Amino-5-methyl-cyclohexyl]pyridin-3-yl}-5-fluoro-3-[(2-fluoroethyl)(methyl)amino]quinoline-8-carboxamide

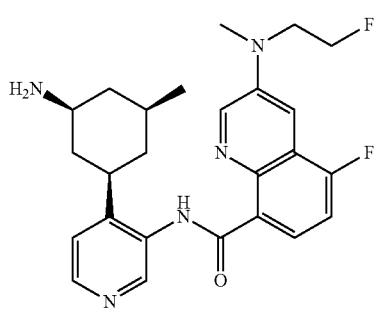 [SMILES: C[C@@H]1C[C@H](N)C[C@H](c2ccncc2NC(=O)c2ccc(F)c3cc(N(C)CCF)cnc23)C1]

This compound was prepared according to the procedure described in Example 2, using 2-fluoro-N-methyl-ethanamine hydrochloride, instead of (3R)-3-fluoropiperidine hydrochloride as starting material. LCMS calculated for $C_{25}H_{30}F_2N_5O$ (M+H)$^+$: m/z=454.2; Found: 454.3.

Example 23. N-{4-[(1R,3S,5S)-3-Amino-5-methyl-cyclohexyl]pyridin-3-yl}-5-fluoro-3-[methyl(tetrahydrofuran-3-yl)amino]quinoline-8-carboxamide

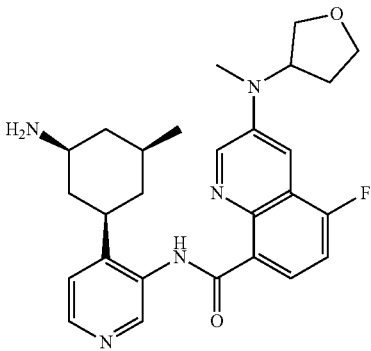 [SMILES: C[C@@H]1C[C@H](N)C[C@H](c2ccncc2NC(=O)c2ccc(F)c3cc(N(C)C4CCOC4)cnc23)C1]

This compound was prepared according to the procedure described in Example 2, using N-methyltetrahydrofuran-3-amine, instead of (3R)-3-fluoropiperidine hydrochloride as starting material. LCMS calculated for $C_{27}H_{33}FN_5O_2$ (M+H)$^+$: m/z=478.3; Found: 478.3.

Example 24. N-{4-[(1R,3S,5S)-3-Amino-5-methyl-cyclohexyl]pyridin-3-yl}-3-[cyclobutyl(methyl)amino]-5-fluoroquinoline-8-carboxamide

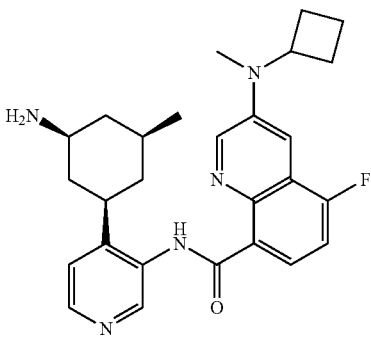 [SMILES: C[C@@H]1C[C@H](N)C[C@H](c2ccncc2NC(=O)c2ccc(F)c3cc(N(C)C4CCC4)cnc23)C1]

This compound was prepared according to the procedure described in Example 2, using N-methylcyclobutanamine, instead of (3R)-3-fluoropiperidine hydrochloride as starting material. LCMS calculated for $C_{27}H_{33}FN_5O$ (M+H)$^+$: m/z=462.3; Found: 462.3.

Example 25. N-{4-[(1R,3S,5S)-3-Amino-5-methyl-cyclohexyl]pyridin-3-yl}-3-(dimethylamino)-5-fluoroquinoline-8-carboxamide

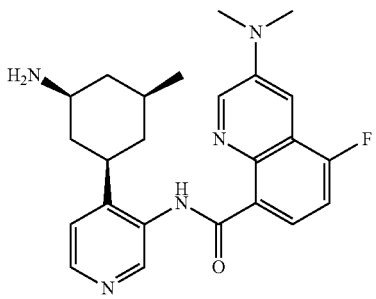

This compound was prepared according to the procedure described in Example 2, using dimethylamine hydrochloride, instead of (3R)-3-fluoropiperidine hydrochloride as starting material. LCMS calculated for $C_{24}H_{29}FN_5O$ $(M+H)^+$: m/z=422.2; Found: 422.3.

Example 26. N-{4-[(1R,3S,5S)-3-Amino-5-methyl-cyclohexyl]pyridin-3-yl}-5-fluoro-3-[(2-fluoroethyl)amino]quinoline-8-carboxamide

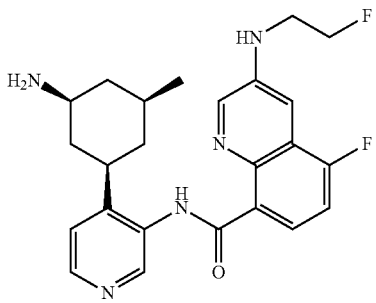 [SMILES: C[C@@H]1C[C@H](N)C[C@H](c2ccncc2NC(=O)c2ccc(F)c3cc(NCCF)cnc23)C1]

Step 1. tert-Butyl ((1S,3R,5S)-3-{3-[({5-fluoro-3-[(2-fluoroethyl)amino]quinolin-8-yl}carbonyl)amino]pyridin-4-yl}-5-methylcyclohexyl)carbamate

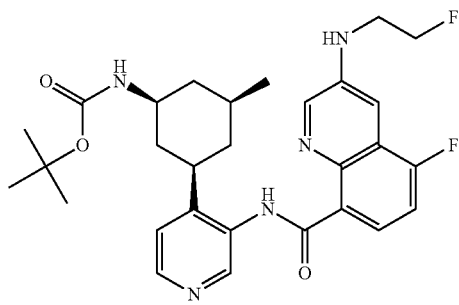 [SMILES: C[C@@H]1C[C@H](NC(=O)OC(C)(C)C)C[C@H](c2ccncc2NC(=O)c2ccc(F)c3cc(NCCF)cnc23)C1]

To a microwave vial was added tert-butyl [(1S,3R,5S)-3-(3{[(3-bromo-5-fluoroquinolin-8-yl)carbonyl]amino}pyridin-4-yl)-5-methylcyclohexyl]carbamate (34.6 mg, 0.0621 mmol), dicyclohexyl-(2',4',6'-triisopropyl-3,6-dimethoxybiphenyl-2-yl)phosphine-[2-(2-aminoethyl)phenyl](chloro)palladium (1:1) (7.4 mg, 0.0093 mmol), 2-fluoroethanamine hydrochloride and cesium carbonate (82.9 mg, 0.254 mmol). The vial was sealed with a teflon screw-cap, evacuated and backfilled with nitrogen (this process was repeated a total of three times). To the reaction vial was added anhydrous tert-butyl alcohol (0.44 mL). The resulting mixture was heated at 90° C. for 5 h. After cooling to room temperature, the reaction mixture was diluted with water and DCM, the organic layer was separated and concentrated. The crude was purified with flash chromatography (eluting with a gradient of 0-100% ethyl acetate in hexanes) to give the desired product as a yellow foam. LCMS calculated for $C_{29}H_{36}F_2N_5O_3$ $(M+H)^+$: m/z=540.3; Found: 540.3.

Step 2. N-{4-[(1R,3S,5S)-3-Amino-5-methylcyclohexyl]pyridin-3-yl}-5-fluoro-3-[(2-fluoroethyl)amino]quinoline-8-carboxamide The product from the previous step was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as a yellow solid (7.5 mg, 30% two steps). LCMS calculated for $C_{24}H_{28}F_2N_5O$ $(M+H)^+$: m/z=440.3; Found: 440.3.

Example 27. N-{4-[(1R,3S,5S)-3-Amino-5-methyl-cyclohexyl]pyridin-3-yl}-3[(2,2-difluoroethyl)amino]-5-fluoroquinoline-8-carboxamide

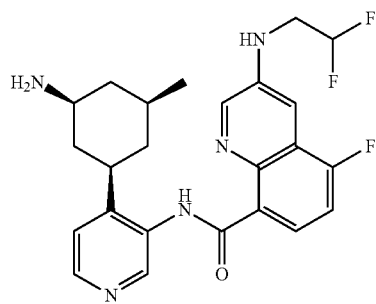 [SMILES: C[C@@H]1C[C@H](N)C[C@H](c2ccncc2NC(=O)c2ccc(F)c3cc(NCC(F)F)cnc23)C1]

This compound was prepared according to the procedure described in Example 26, using 2,2-difluoroethanamine, instead of 2-fluoroethanamine hydrochloride as starting material. LCMS calculated for $C_{24}H_{27}F_3N_5O$ $(M+H)^+$: m/z=458.2; Found: 458.3.

Example 28. N-{4-[(1R,3S,5S)-3-Amino-5-methyl-cyclohexyl]pyridin-3-yl}-3-(3,3-difluoropiperidin-1-yl)-5-fluoroquinoline-8-carboxamide

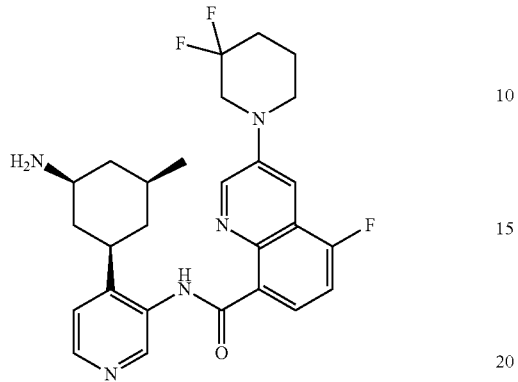

This compound was prepared according to the procedure described in Example 2, using 3,3-difluoropiperidine hydrochloride, instead of (3R)-3-fluoropiperidine hydrochloride as starting material. LCMS calculated for $C_{27}H_{31}F_3N_5O$ (M+H)$^+$: m/z=498.2; Found: 498.2.

Example 29. N-{4-[(1R,3S,5S)-3-Amino-5-methyl-cyclohexyl]pyridin-3-yl}-5-fluoro-3-[(3S,4S)-3-fluoro-4-hydroxypiperidin-1-yl]quinoline-8-carboxamide

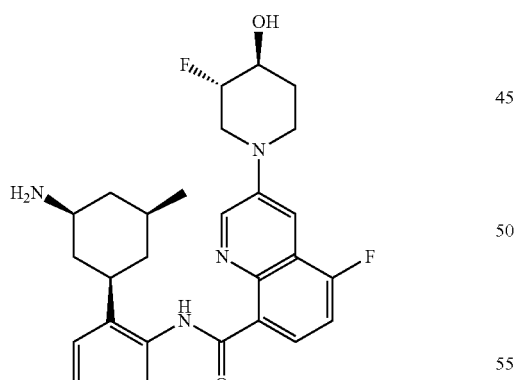

This compound was prepared according to the procedure described in Example 2, using (3S,4S)-3-fluoropiperidin-4-ol hydrochloride, instead of (3R)-3-fluoropiperidine hydrochloride as starting material. LCMS calculated for $C_{27}H_{32}F_2N_5O_2$ (M+H)$^+$: m/z=496.2; Found: 496.3.

Example 30. N-{4-[(1R,3S,5S)-3-Amino-5-methyl-cyclohexyl]pyridin-3-yl}-5-fluoro-3-(4-methylpiperazin-1-yl)quinoline-8-carboxamide

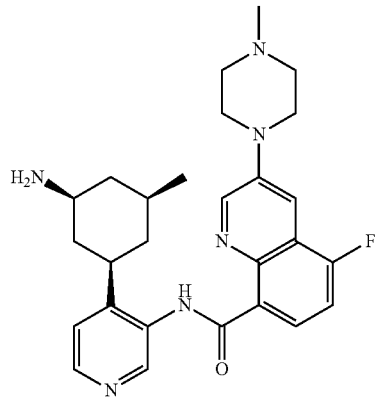 [SMILES: C[C@@H]1C[C@H](N)C[C@H](c2ccncc2NC(=O)c2ccc(F)c3cc(N4CCN(C)CC4)cnc23)C1]

This compound was prepared according to the procedure described in Example 2, using 1-methyl-piperazine, instead of (3R)-3-fluoropiperidine hydrochloride as starting material. LCMS calculated for $C_{27}H_{34}FN_6O$ (M+H)$^+$: m/z=477.3; Found: 477.3.

Example 31. N-{4-[(1R,3S,5S)-3-Amino-5-methyl-cyclohexyl]pyridin-3-yl}-5-fluoro-3-(tetrahydro-2H-pyran-4-yl)quinoline-8-carboxamide

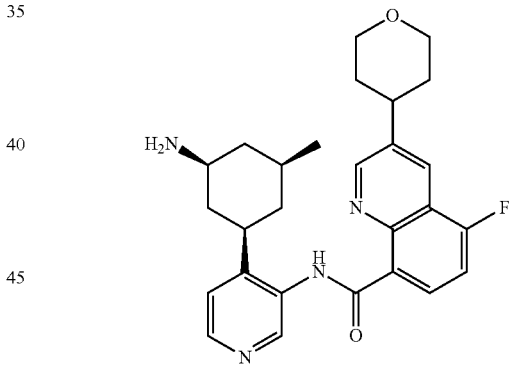

Step 1. Methyl 3-(3,6-dihydro-2H-pyran-4-yl)-5-fluoroquinoline-8-carboxylate

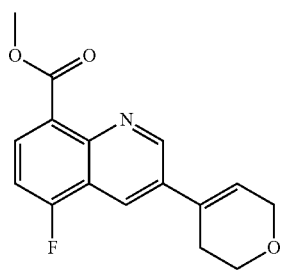 [SMILES: COC(=O)c1ccc(F)c2cc(C3=CCOCC3)cnc12]

To a microwave vial was added methyl 3-bromo-5-fluoroquinoline-8-carboxylate (0.300 g, 1.06 mmol), 4-(4,4,5,5-tetramethyl-1,3,2-dioxaborolan-2-yl)-3,6-dihydro-2H-pyran (0.288 g, 1.37 mmol), K$_3$PO$_4$ (0.448 g, 2.11 mmol) and dicyclohexyl-(2',4',6'-triisopropylbiphenyl-2-yl)phosphine-(2'-aminobiphenyl-2-yl)(chloro)palladium (1:1) (0.083 g, 0.10 mmol). The vial was sealed with a Teflon screw-cap, evacuated and backfilled with nitrogen (this process was repeated a total of three times). To the vial was added 1,4-dioxane (4 mL) and water (0.9 mL), and the mixture was heated at 75° C. for 6 h. After cooling to room temperature, the reaction mixture was filtered through a pad of Celite which was further rinsed with EtOAc. The aqueous layer was extracted with EtOAc (2×). The combined organic phases were washed with water, brine and dried over Na$_2$SO$_4$, and then filtered. The filtrate was concentrated, and the residue was purified by flash chromatography (eluting with a gradient of 0-40% EtOAc in hexanes) to give the desired product as white solid (0.29 g, 97%). LCMS calculated for C$_{16}$H$_{15}$FNO$_3$ (M+H)$^+$: m/z=288.1; Found: 288.1.

Step 2. Methyl 5-fluoro-3-(tetrahydro-2H-pyran-4-yl)quinoline-8-carboxylate

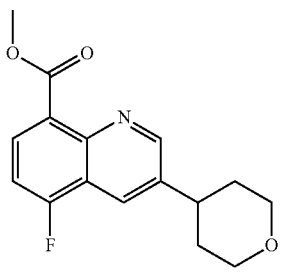 [SMILES: COC(=O)c1ccc(F)c2cc(C3CCOCC3)cnc12]

A mixture of methyl 3-(3,6-dihydro-2H-pyran-4-yl)-5-fluoroquinoline-8-carboxylate (290.0 mg, 1.009 mmol) and 10% palladium on carbon (50 mg, 0.023 mmol) in ethyl acetate (10 mL) was stirred under a balloon of H$_2$ for 3 h. The reaction mixture was filtered through a pad of Celite, and rinsed with EtOAc. The filtrate was concentrated to give the desired product as light green oil (0.265 g, 91%). LCMS calculated for C$_{16}$H$_{17}$FNO$_3$ (M+H)$^+$: m/z=290.1; Found: 290.1.

Step 3. 5-Fluoro-3-(tetrahydro-2H-pyran-4-yl)quinoline-8-carboxylic acid

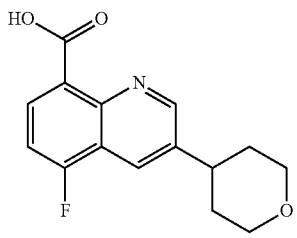 [SMILES: O=C(O)c1ccc(F)c2cc(C3CCOCC3)cnc12]

A mixture of methyl 5-fluoro-3-(tetrahydro-2H-pyran-4-yl)quinoline-8-carboxylate (265.0 mg, 0.9160 mmol), lithium hydroxide (180 mg, 7.3 mmol), THF (4 mL), methanol (4 mL) and water (4 mL) was stirred at room temperature for 1 h. The volatiles were removed in vacuo, the residue was neutralized to pH 4-5 with 1 N HCl solution. The resulting precipitate was filtered, rinsed with water, and dried under vacuum to give the desired product as a tan solid (203 mg, 81%). LCMS calculated for C$_{15}$H$_{15}$FNO$_3$ (M+H)$^+$: m/z=276.1; Found: 276.0.

Step 4. tert-Butyl {(1S,3R,5S)-3-[3-({[5-fluoro-3-(tetrahydro-2H-pyran-4-yl)quinolin-8-yl]carbonyl}amino)pyridin-4-yl]-5-methylcyclohexyl}carbamate

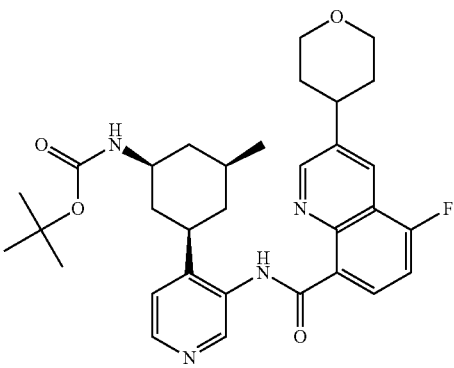 [SMILES: C[C@@H]1C[C@H](NC(=O)OC(C)(C)C)C[C@H](c2ccncc2NC(=O)c2ccc(F)c3cc(C4CCOCC4)cnc23)C1]

To a solution of 5-fluoro-3-(tetrahydro-2H-pyran-4-yl)quinoline-8-carboxylic acid (16.2 mg, 0.0589 mmol) and tert-butyl [(1S,3R,5S)-3-(3-aminopyridin-4-yl)-5-methylcyclohexyl]carbamate (15.0 mg, 0.0491 mmol) in DMF (1 mL) was added N,N,N',N'-tetramethyl-O-(7-azabenzotriazol-1-yl)uronium hexafluorophosphate (26.1 mg, 0.0688 mmol) and N,N-diisopropylethylamine (29 µL, 0.17 mmol). The reaction mixture was stirred at room temperature overnight. The reaction mixture was diluted with water and DCM, and the aqueous layer was extracted with DCM once. The combined organic layers were dried over Na$_2$SO$_4$, filtered and concentrated. The residue was purified by prep-LCMS (XBridge C$_{18}$ column, eluting with a gradient of acetonitrile/water containing 0.05% TFA, at flow rate of 60 mL/min) to give the desired product. LCMS calculated for C$_{32}$H$_{40}$FN$_4$O$_4$ (M+H)$^+$: m/z=563.3; Found: 563.3.

Step 5. N-{4-[(1R,3S,5S)-3-Amino-5-methylcyclohexyl]pyridin-3-yl}-5-fluoro-3-(tetrahydro-2H-pyran-4-yl)quinoline-8-carboxamide The product from the previous step was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as a white solid (5.6 mg, 25% for two steps). LCMS calculated for C$_{27}$H$_{32}$FN$_4$O$_2$ (M+H)$^+$: m/z=463.2; Found: 463.2.

Example 32. N-(4-((1R,3S,5S)-3-Amino-5-methyl-cyclohexyl)pyridin-3-yl)-5-fluoro-3-((R)-3-methyl-morpholino)quinoline-8-carboxamide

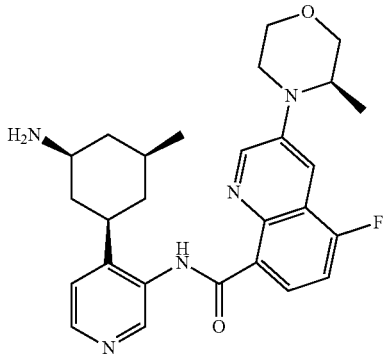 [SMILES: C[C@@H]1C[C@H](N)C[C@H](c2ccncc2NC(=O)c2ccc(F)c3cc(N4CCOC[C@H]4C)cnc23)C1]

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then tert-butyl alcohol (2 mL) and (R)-3-methylmorpholine (6 µL, 0.06 mmol) were added. The reaction was stirred at 65° C. overnight. After this time the reaction was quenched by the addition of water and the product was extracted with ethyl acetate. Combined organic fractions were washed with brine, dried over sodium sulfate and filtered. The filtrate was concentrated under reduced pressure. The resulting residue was treated with trifluoroacetic acid (1 mL) and dichloromethane (1 mL). After stirring at r.t. for 1 h, the reaction mixture was diluted with acetonitrile and neutralized with ammonia solution. The mixture was purified by RP-HPLC (water XBridge C18 column, 30 mm×100 mm, 5 µm particle size, eluting with a gradient of acetonitrile/water containing 0.1% NH$_4$OH, at flow rate of 60 mL/min) to give the desired product. LCMS calculated for C$_{27}$H$_{33}$FN$_5$O$_2$ (M+H)$^+$ m/z=478.3; found: 478.2. $^1$H NMR (600 MHz, DMSO-d6) δ 13.03 (s, 1H), 9.17 (s, 1H), 9.03 (d, J=3.0 Hz, 1H), 8.52 (d, J=5.4 Hz, 1H), 8.44 (dd, J=8.3, 6.2 Hz, 1H), 7.93 (br, 2H), 7.70 (d, J=3.0 Hz, 1H), 7.64-7.53 (m, 2H), 4.34-4.25 (m, 1H), 4.04 (d, J=11.5, 2.9 Hz, 1H), 3.82 (d, J=1.9 Hz, 2H), 3.67 (td, J=11.6, 3.1 Hz, 1H), 3.56 (d, J=12.3 Hz, 1H), 3.28-3.14 (m, 3H), 2.11 (d, J=12.1 Hz, 1H), 1.97 (d, J=12.4 Hz, 1H), 1.92 (d, J=13.1 Hz, 1H), 1.79-1.66 (m, 1H), 1.52 (q, J=12.1 Hz, 1H), 1.19 (d, J=12.4 Hz, 1H), 1.16 (d, J=6.7 Hz, 3H), 1.08 (q, J=12.1 Hz, 1H), 1.01 (d, J=6.6 Hz, 3H) ppm.

Example 33

N-(4-((1R,3S,5S)-3-Amino-5-methylcyclohexyl)pyridin-3-yl)-5-fluoro-3-((S)-3-methylmorpholino)quinoline-8-carboxamide

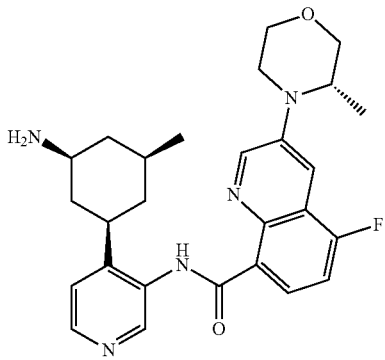 [SMILES: C[C@@H]1C[C@H](N)C[C@H](c2ccncc2NC(=O)c2ccc(F)c3cc(N4CCOC[C@@H]4C)cnc23)C1]

This compound was synthesized as described in Example 32, using (S)-3-methylmorpholine. LCMS calculated for C$_{27}$H$_{33}$FN$_5$O$_2$ (M+H)$^+$ m/z=478.3; found: 478.3. $^1$H NMR (600 MHz, DMSO-d6) δ 13.02 (s, 1H), 9.19 (s, 1H), 9.07 (d, J=3.0 Hz, 1H), 8.50 (d, J=5.3 Hz, 1H), 8.44 (dd, J=8.3, 6.2 Hz, 1H), 7.93 (br, 2H), 7.70 (d, J=3.0 Hz, 1H), 7.59 (dd, J=9.5, 8.4 Hz, 1H), 7.53 (d, J=5.3 Hz, 1H), 4.34-4.27 (m, 1H), 4.05 (dd, J=11.4, 3.2 Hz, 1H), 3.82 (s, 2H), 3.67 (td, J=11.6, 3.1 Hz, 1H), 3.55 (d, J=12.2 Hz, 1H), 3.23 (tt, J=14.5, 8.0 Hz, 3H), 2.13 (d, J=11.8 Hz, 1H), 1.98 (d, J=11.8 Hz, 1H), 1.91 (d, J=12.7 Hz, 1H), 1.72 (br, 1H), 1.62-1.47 (m, 1H), 1.20-1.16 (m, 1H), 1.15 (d, J=6.7 Hz, 3H), 1.08 (q, J=12.1 Hz, 1H), 0.97 (d, J=6.6 Hz, 3H) ppm.

Example 34

N-(4-((1R,3S,5S)-3-Amino-5-methylcyclohexyl)pyridin-3-yl)-5-fluoro-3-((R)-2-methylpyrrolidin-1-yl)quinoline-8-carboxamide

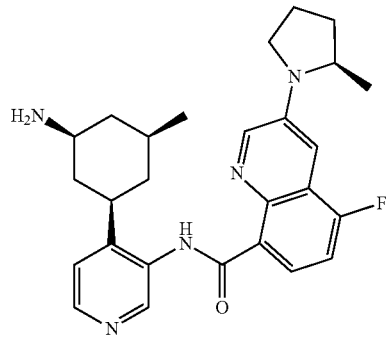 [SMILES: C[C@@H]1C[C@H](N)C[C@H](c2ccncc2NC(=O)c2ccc(F)c3cc(N4CCC[C@H]4C)cnc23)C1]

This compound was synthesized according to the procedures of Example 32, using (R)-2-methylpyrrolidine. LCMS calculated for C$_{27}$H$_{33}$FN$_5$O (M+H)$^+$ m/z=462.3; found: 462.2.

Example 35

N-(4-((1R,3S,5S)-3-Amino-5-methylcyclohexyl)pyridin-3-yl)-3-(2,5-dimethylmorpholino)-5-fluoro-quinoline-8-carboxamide

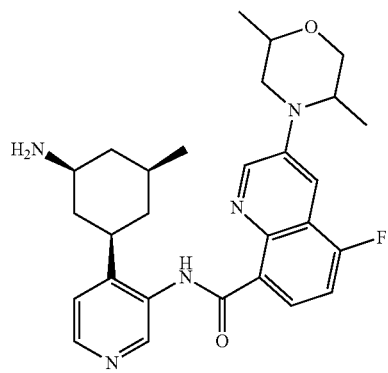 [SMILES: CC1CN(c2cnc3c(C(=O)Nc4cnccc4[C@@H]4C[C@H](C)C[C@H](N)C4)ccc(F)c3c2)C(C)CO1]

This compound was synthesized according to the procedures of Example 32, using 2,5-dimethylmorpholine. LCMS calculated for $C_{28}H_{35}FN_5O_2$ (M+H)$^+$ m/z=492.3; found: 492.2.

Example 36

N-(4-((1R,3S,5S)-3-Amino-5-methylcyclohexyl)pyridin-3-yl)-3-(2,5-dimethylpyrrolidin-1-yl)-5-fluoroquinoline-8-carboxamide

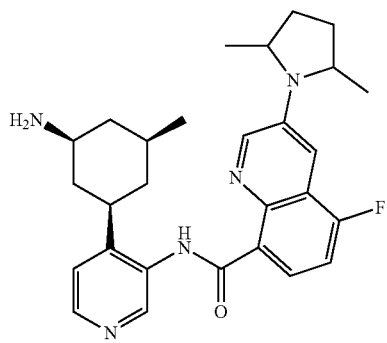 [SMILES: CC1CCC(C)N1c1cnc2c(C(=O)Nc3cnccc3[C@@H]3C[C@H](C)C[C@H](N)C3)ccc(F)c2c1]

This compound was synthesized according to the procedures of Example 32, using 2,5-dimethylpyrrolidine. LCMS calculated for $C_{28}H_{35}FN_5O$ (M+H)$^+$ m/z=476.3; found: 476.3.

Example 37

N-(4-((1R,3S,5S)-3-Amino-5-methylcyclohexyl)pyridin-3-yl)-3-(2,6-dimethylmorpholino)-5-fluoroquinoline-8-carboxamide

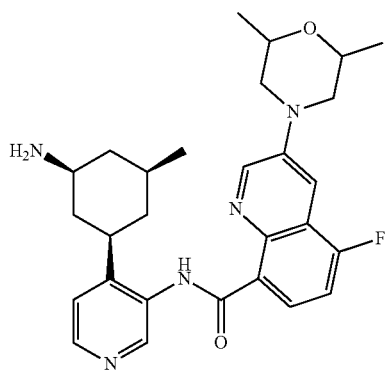 [SMILES: CC1CN(c2cnc3c(C(=O)Nc4cnccc4[C@@H]4C[C@H](C)C[C@H](N)C4)ccc(F)c3c2)CC(C)O1]

This compound was synthesized according to the procedures of Example 32, using 2,6-dimethylmorpholine. LCMS calculated for $C_{28}H_{35}FN_5O_2$ (M+H)$^+$ m/z=492.3; found: 492.3.

Example 38

N-(4-((1R,3S,5S)-3-Amino-5-methylcyclohexyl)pyridin-3-yl)-5-fluoro-3-((S)-2-methylmorpholino)quinoline-8-carboxamide

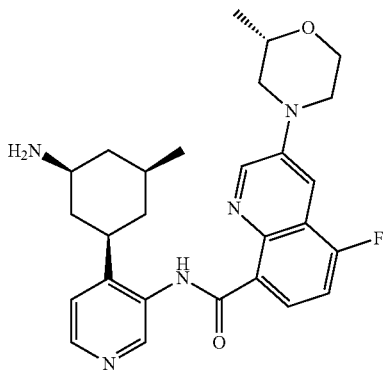 [SMILES: C[C@@H]1C[C@H](N)C[C@H](c2ccncc2NC(=O)c2ccc(F)c3cc(N4CCO[C@@H](C)C4)cnc23)C1]

This compound was synthesized according to the procedures of Example 32, using (S)-2-methylmorpholine. LCMS calculated for $C_{27}H_{33}FN_5O_2$ (M+H)$^+$ m/z=478.3; found: 478.3.

Example 39

N-(4-((1R,3S,5S)-3-Amino-5-methylcyclohexyl)pyridin-3-yl)-5-fluoro-3-((S)-2-methylpyrrolidin-1-yl)quinoline-8-carboxamide

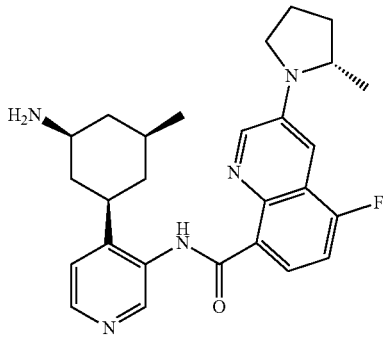 [SMILES: C[C@@H]1C[C@H](N)C[C@H](c2ccncc2NC(=O)c2ccc(F)c3cc(N4CCC[C@@H]4C)cnc23)C1]

This compound was synthesized according to the procedures of Example 32, using (S)-2-methylpyrrolidine. LCMS calculated for $C_{27}H_{33}FN_5O$ (M+H)$^+$ m/z=462.3; found: 462.2.

Example 40

N-(4-((1R,3S,5S)-3-Amino-5-methylcyclohexyl)pyridin-3-yl)-3-(4,4-difluoropiperidin-1-yl)-5-fluoro-quinoline-8-carboxamide

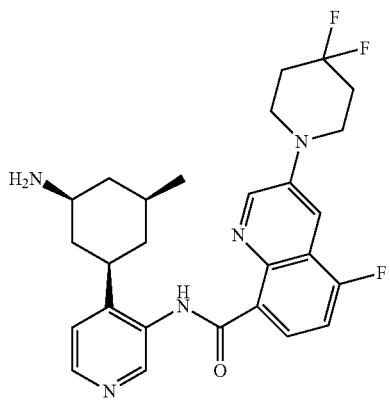 [SMILES: C[C@@H]1C[C@H](N)C[C@H](c2ccncc2NC(=O)c2ccc(F)c3cc(N4CCC(F)(F)CC4)cnc23)C1]

This compound was synthesized according to the procedures of Example 32, using 4,4-difluoropiperidine. LCMS calculated for $C_{27}H_{31}F_3N_5O$ (M+H)$^+$ m/z=498.2; found: 498.2.

Example 41

N-(4-((1R,3S,5S)-3-Amino-5-methylcyclohexyl)pyridin-3-yl)-5-fluoro-3-(4-hydroxy-4-methylpiperidin-1-yl)quinoline-8-carboxamide

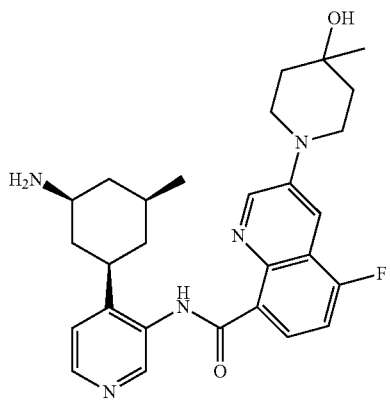 [SMILES: C[C@@H]1C[C@H](N)C[C@H](c2ccncc2NC(=O)c2ccc(F)c3cc(N4CCC(C)(O)CC4)cnc23)C1]

This compound was synthesized according to the procedures of Example 32, using 4-methylpiperidin-4-ol. LCMS calculated for $C_{28}H_{35}FN_5O_2$ (M+H)$^+$ m/z=492.3; found: 492.3.

Example 42

N-(4-((1R,3S,5S)-3-Amino-5-methylcyclohexyl)pyridin-3-yl)-3-((2,2-difluoroethyl)(methyl)amino)-5-fluoroquinoline-8-carboxamide

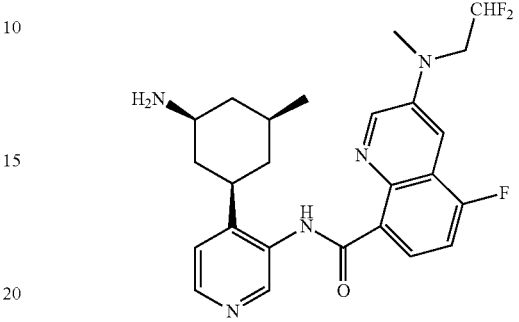

This compound was synthesized according to the procedures of Example 32, using 2,2-difluoro-N-methylethanamine. LCMS calculated for $C_{25}H_{29}F_3N_5O$ (M+H)$^+$ m/z=472.2; found: 472.2.

Example 43

N-(4-((1R,3S,5S)-3-Amino-5-methylcyclohexyl)pyridin-3-yl)-5-fluoro-3-(2-methylpiperidin-1-yl)quinoline-8-carboxamide

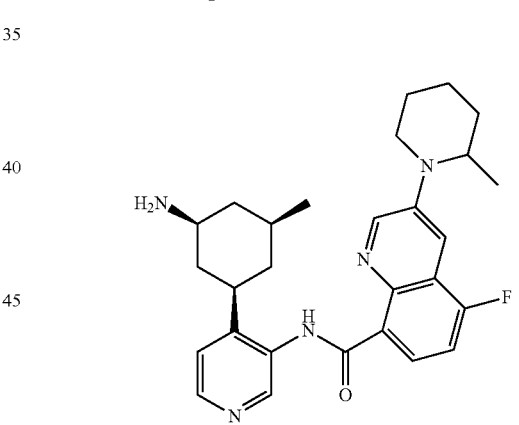

This compound was synthesized according to the procedures of Example 32, using 2-methylpiperidine. LCMS calculated for $C_{28}H_{35}FN_5O$ (M+H)$^+$ m/z=476.3; found: 476.3. $^1$H NMR (600 MHz, DMSO-d6) δ 13.10 (s, 1H), 9.18 (s, 1H), 9.03 (d, J=3.0 Hz, 1H), 8.52 (d, J=5.4 Hz, 1H), 8.41 (dd, J=8.3, 6.2 Hz, 1H), 7.92 (br, 2H), 7.66 (d, J=3.0 Hz, 1H), 7.60-7.52 (m, 2H), 4.53-4.43 (m, 1H), 3.73-3.64 (m, 1H), 3.26-3.16 (m, 1H), 3.08 (td, J=12.2, 3.0 Hz, 1H), 2.10 (d, J=11.8 Hz, 1H), 1.95 (dd, J=22.9, 12.7 Hz, 2H), 1.91-1.82 (m, 2H), 1.77-1.65 (m, 3H), 1.66-1.58 (m, 2H), 1.54 (q, J=12.0 Hz, 1H), 1.18 (q, J=12.2 Hz, 1H), 1.13 (d, J=6.7 Hz, 3H), 1.11-1.05 (m, 1H), 1.01 (d, J=6.6 Hz, 3H) ppm.

Example 44

N-(4-((1R,3S,5S)-3-Amino-5-methylcyclohexyl)pyridin-3-yl)-5-fluoro-3-(4-hydroxypiperidin-1-yl)quinoline-8-carboxamide

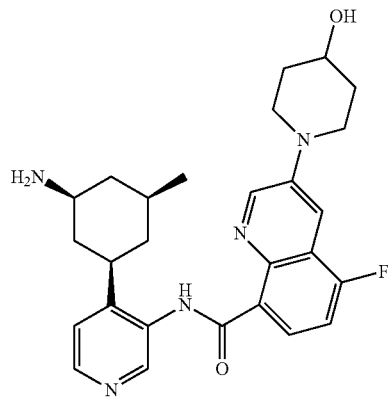 [SMILES: C[C@@H]1C[C@H](N)C[C@H](c2ccncc2NC(=O)c2ccc(F)c3cc(N4CCC(O)CC4)cnc23)C1]

This compound was synthesized according to the procedures of Example 32, using piperidin-4-ol. LCMS calculated for $C_{27}H_{33}FN_5O_2$ (M+H)$^+$ m/z=478.3; found: 478.3.

Example 45

N-(4-((1R,3S,5S)-3-Amino-5-methylcyclohexyl)pyridin-3-yl)-3-(4-cyanopiperidin-1-yl)-5-fluoroquinoline-8-carboxamide

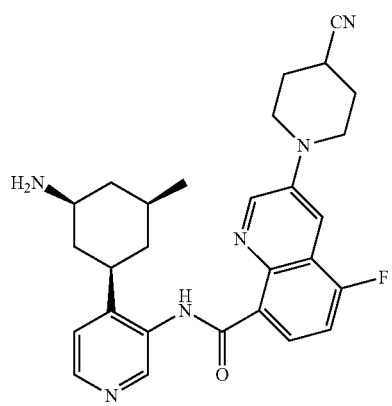 [SMILES: C[C@@H]1C[C@H](N)C[C@H](c2ccncc2NC(=O)c2ccc(F)c3cc(N4CCC(C#N)CC4)cnc23)C1]

This compound was synthesized according to the procedures of Example 32, using piperidine-4-carbonitrile. LCMS calculated for $C_{28}H_{32}FN_6O$ (M+H)$^+$ m/z=487.3; found: 487.2.

Example 46

N-(4-((1R,3S,5S)-3-Amino-5-methylcyclohexyl)pyridin-3-yl)-5-fluoro-3-(4-methylpiperidin-1-yl)quinoline-8-carboxamide

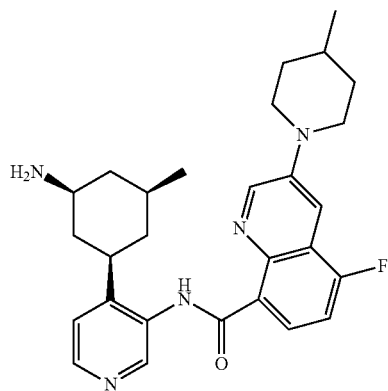 [SMILES: CC1CCN(c2cnc3c(C(=O)Nc4cnccc4[C@@H]4C[C@H](C)C[C@H](N)C4)ccc(F)c3c2)CC1]

This compound was synthesized according to the procedures of Example 32, using 4-methylpiperidine. LCMS calculated for $C_{28}H_{35}FN_5O$ (M+H)$^+$ m/z=476.3; found: 476.3.

Example 47

N-(4-((1R,3S,5S)-3-Amino-5-methylcyclohexyl)pyridin-3-yl)-5-fluoro-3-((R)-2-(methoxymethyl)pyrrolidin-1-yl)quinoline-8-carboxamide

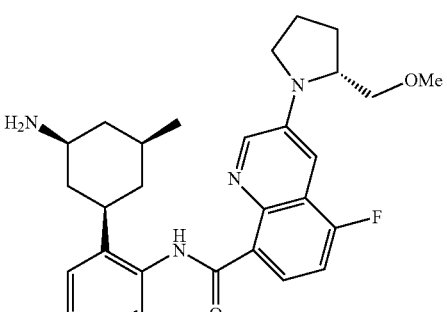

This compound was synthesized according to the procedures of Example 32, using (R)-2-(methoxymethyl)pyrrolidine. LCMS calculated for $C_{28}H_{35}FN_5O_2$ (M+H)$^+$ m/z=492.3; found: 492.3.

Example 48

N-(4-((1R,3S,5S)-3-Amino-5-methylcyclohexyl)pyridin-3-yl)-5-fluoro-3-((S)-2-(methoxymethyl)pyrrolidin-1-yl)quinoline-8-carboxamide

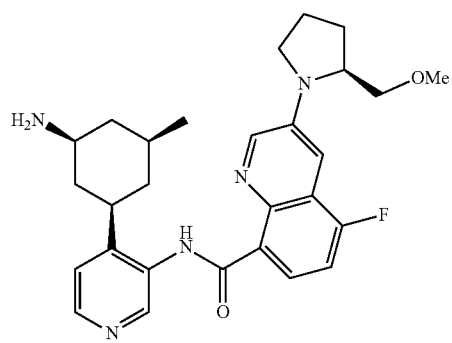 [SMILES: COC[C@@H]1CCCN1c1cnc2c(C(=O)Nc3cnccc3[C@@H]3C[C@H](C)C[C@H](N)C3)ccc(F)c2c1]

This compound was synthesized according to the procedures of Example 32, using (S)-2-(methoxymethyl)pyrrolidine. LCMS calculated for $C_{28}H_{35}FN_5O_2$ $(M+H)^+$ m/z=492.3; found: 492.2.

Example 49

N-(4-((1R,3S,5S)-3-amino-5-methylcyclohexyl)pyridin-3-yl)-5-fluoro-3-((R)-3-methoxypyrrolidin-1-yl)quinoline-8-carboxamide

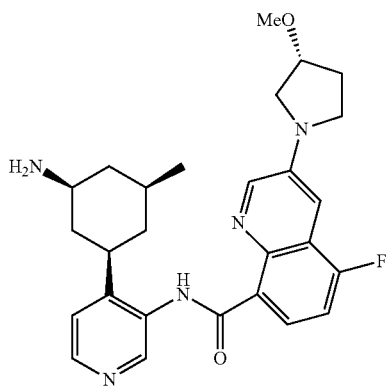 [SMILES: CO[C@@H]1CCN(c2cnc3c(C(=O)Nc4cnccc4[C@@H]4C[C@H](C)C[C@H](N)C4)ccc(F)c3c2)C1]

This compound was synthesized according to the procedures of Example 32, using (R)-3-methoxypyrrolidine. LCMS calculated for $C_{27}H_{33}FN_5O_2$ $(M+H)^+$ m/z=478.3; found: 478.2.

Example 50

N-(4-((1R,3S,5S)-3-Amino-5-methylcyclohexyl)pyridin-3-yl)-5-fluoro-3-((S)-3-methoxypyrrolidin-1-yl)quinoline-8-carboxamide

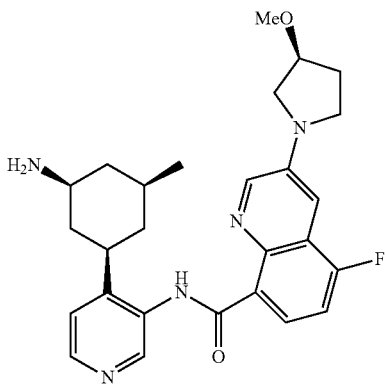 [SMILES: CO[C@H]1CCN(c2cnc3c(C(=O)Nc4cnccc4[C@@H]4C[C@H](C)C[C@H](N)C4)ccc(F)c3c2)C1]

This compound was synthesized according to the procedures of Example 32, using
(S)-3-methoxypyrrolidine. LCMS calculated for $C_{27}H_{33}FN_5O_2$ $(M+H)^+$ m/z=478.3; found: 478.2.

Example 51

N-(4-((1R,3S,5S)-3-Amino-5-methylcyclohexyl)pyridin-3-yl)-5-fluoro-3-((2-methoxyethyl)(methyl)amino)quinoline-8-carboxamide

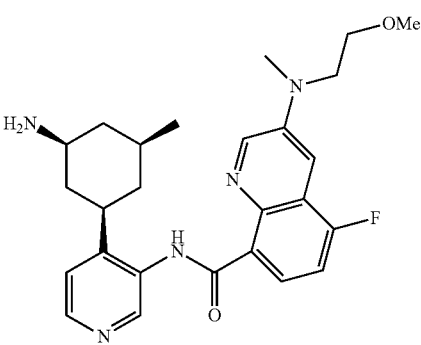 [SMILES: COCCN(C)c1cnc2c(C(=O)Nc3cnccc3[C@@H]3C[C@H](C)C[C@H](N)C3)ccc(F)c2c1]

This compound was synthesized according to the procedures of Example 32, using 2-methoxy-N-methylethanamine. LCMS calculated for $C_{26}H_{33}FN_5O_2$ $(M+H)^+$ m/z=466.3; found: 466.2.

Example 52

N-(4-((1R,3S,5S)-3-Amino-5-methylcyclohexyl)pyridin-3-yl)-3-((S)-1-cyclopropylethylamino)-5-fluoroquinoline-8-carboxamide

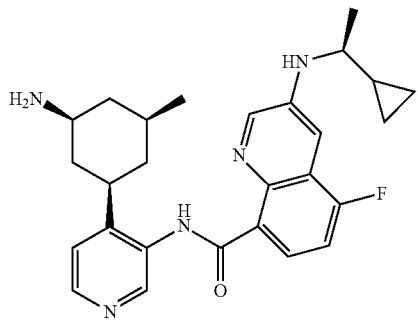 [SMILES: C[C@@H]1C[C@H](N)C[C@H](c2ccncc2NC(=O)c2ccc(F)c3cc(N[C@@H](C)C4CC4)cnc23)C1]

This compound was synthesized according to the procedures of Example 32, using (S)-1-cyclopropylethanamine. LCMS calculated for $C_{27}H_{33}FN_5O$ (M+H)$^+$ m/z=462.3; found: 462.2.

Example 53

N-(4-((1R,3S,5S)-3-Amino-5-methylcyclohexyl)pyridin-3-yl)-5-fluoro-3-((S)-3-methylbutan-2-ylamino)quinoline-8-carboxamide

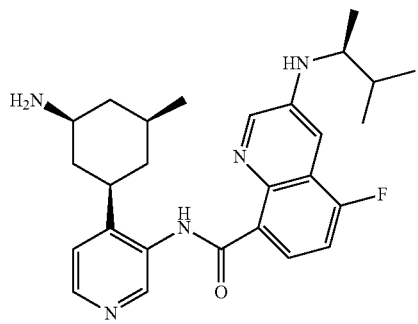 [SMILES: CC(C)[C@H](C)Nc1cnc2c(C(=O)Nc3cnccc3[C@@H]3C[C@H](C)C[C@H](N)C3)ccc(F)c2c1]

This compound was synthesized according to the procedures of Example 32, using (S)-3-methylbutan-2-amine. LCMS calculated for $C_{27}H_{35}FN_5O$ (M+H)$^+$ m/z=464.3; found: 464.3.

Example 54

N-(4-((1R,3S,5S)-3-amino-5-methylcyclohexyl)pyridin-3-yl)-5-fluoro-3-((R)-3-methylbutan-2-ylamino)quinoline-8-carboxamide

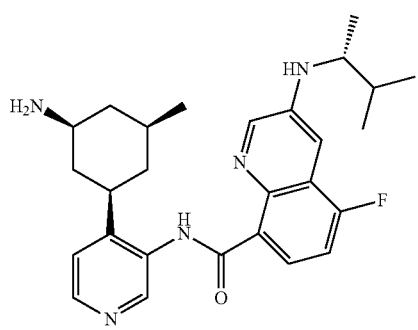 [SMILES: CC(C)[C@@H](C)Nc1cnc2c(C(=O)Nc3cnccc3[C@@H]3C[C@H](C)C[C@H](N)C3)ccc(F)c2c1]

This compound was synthesized according to the procedures of Example 32, using (R)-3-methylbutan-2-amine. LCMS calculated for $C_{27}H_{35}FN_5O$ (M+H)$^+$ m/z=464.3; found: 464.3.

Example 55

N-(4-((1R,3S,5S)-3-Amino-5-methylcyclohexyl)pyridin-3-yl)-5-fluoro-3-(methyl(propyl)amino)quinoline-8-carboxamide

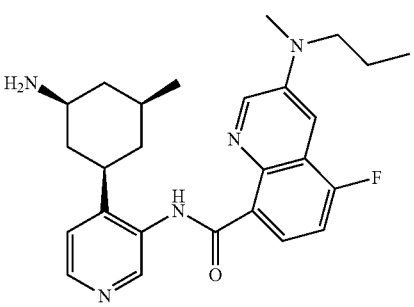 [SMILES: CCCN(C)c1cnc2c(C(=O)Nc3cnccc3[C@@H]3C[C@H](C)C[C@H](N)C3)ccc(F)c2c1]

This compound was synthesized according to the procedures of Example 32, using N-methylpropan-1-amine. LCMS calculated for $C_{26}H_{33}FN_5O$ (M+H)$^+$ m/z=450.3; found: 450.3.

Example 56

N-(4-((1R,3S,5S)-3-Amino-5-methylcyclohexyl)pyridin-3-yl)-5-fluoro-3-(isopropyl(methyl)amino)quinoline-8-carboxamide

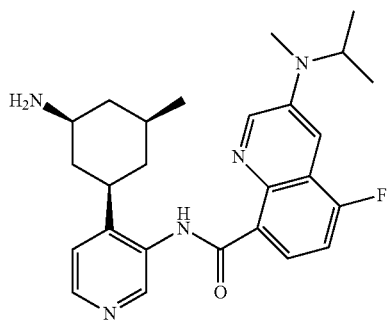 [SMILES: CC(C)N(C)c1cnc2c(C(=O)Nc3cnccc3[C@@H]3C[C@H](C)C[C@H](N)C3)ccc(F)c2c1]

This compound was synthesized according to the procedures of Example 32, using N-methylpropan-2-amine. LCMS calculated for $C_{26}H_{33}FN_5O$ (M+H)$^+$ m/z=450.3; found: 450.3.

Example 57

N-(4-((1R,3S,5S)-3-Amino-5-methylcyclohexyl)pyridin-3-yl)-3-(2-ethylpiperidin-1-yl)-5-fluoroquinoline-8-carboxamide

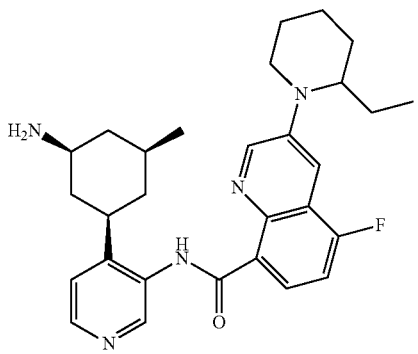 [SMILES: CCC1CCCCN1c1cnc2c(C(=O)Nc3cnccc3[C@@H]3C[C@H](C)C[C@H](N)C3)ccc(F)c2c1]

This compound was synthesized according to the procedures of Example 32, using 2-ethylpiperidine. LCMS calculated for $C_{29}H_{37}FN_5O$ (M+H)$^+$ m/z=490.3; found: 490.3.

Example 58

N-(4-((1R,3S,5S)-3-Amino-5-methylcyclohexyl)pyridin-3-yl)-3-(2-(difluoromethyl)piperidin-1-yl)-5-fluoroquinoline-8-carboxamide

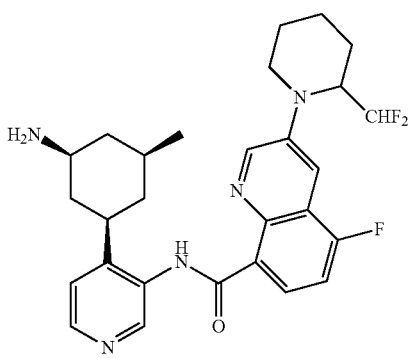 [SMILES: C[C@@H]1C[C@H](N)C[C@H](c2ccncc2NC(=O)c2ccc(F)c3cc(N4CCCCC4C(F)F)cnc23)C1]

This compound was synthesized according to the procedures of Example 32, using 2-(difluoromethyl)piperidine. LCMS calculated for $C_{28}H_{33}F_3N_5O$ (M+H)$^+$ m/z=512.3; found: 512.2.

Example 59. N-(4-((1R,3S,5S)-3-Amino-5-methylcyclohexyl)pyridin-3-yl)-5,6'-difluoro-3,8'-biquinoline-8-carboxamide

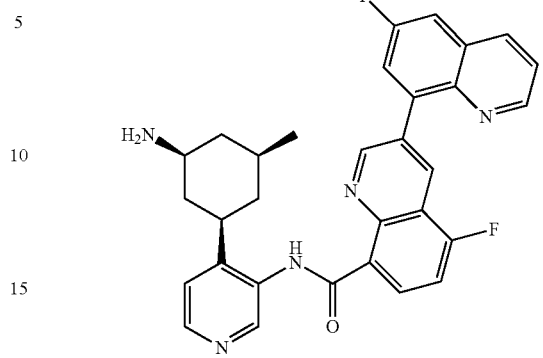

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), 6-fluoroquinolin-8-ylboronic acid (9.4 mg, 0.049 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and a magnet bar were placed in a vial with septum which was then evacuated and backfilled with nitrogen three times. 1,4-Dioxane (2.5 mL) and degassed water (0.3 mL) were added and the reaction mixture was stirred at 65° C. for 1 h. Then the reaction was diluted with ethyl acetate. The resulting solution was washed with brine, dried over sodium sulfate and solvent evaporated. Trifluoroacetic acid (1 mL) and dichloromethane (1 mL) were added to the obtained crude product and the reaction mixture was stirred at r.t. for 1 h. After dilution with acetonitrile and neutralization by the addition of the ammonia solution the desired product was purified by RP-HPLC (water XBridge C18 column, 30 mm×100 mm, 5 μm particle size, eluting with a gradient of acetonitrile/water containing 0.1% NH$_4$OH, at flow rate of 60 mL/min). LCMS calculated for $C_{31}H_{28}F_2N_5O$ (M+H)$^+$ m/z=524.2; found: 524.1.

Example 60

N-(4-((1R,3S,5S)-3-Amino-5-methylcyclohexyl)pyridin-3-yl)-5,5'-difluoro-3,8'-biquinoline-8-carboxamide

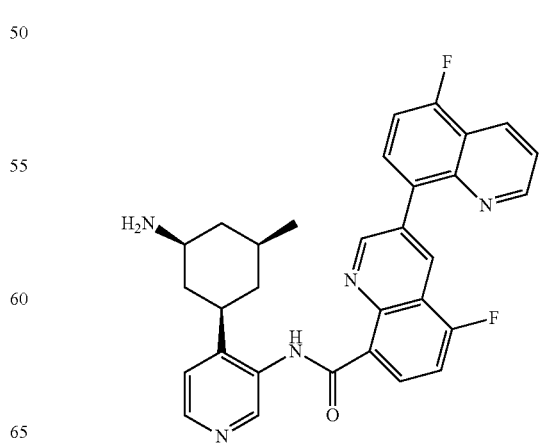

This compound was synthesized according to the procedures of Example 59, using 5-fluoroquinolin-8-ylboronic acid. LCMS calculated for $C_{31}H_{28}F_2N_5O$ $(M+H)^+$ m/z=524.2; found: 524.1.

Example 61

N-(4-((1R,3S,5S)-3-Amino-5-methylcyclohexyl)pyridin-3-yl)-5-fluoro-3-(6-(trifluoromethyl)pyridin-3-yl)quinoline-8-carboxamide

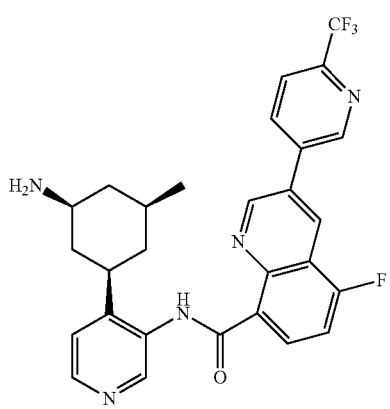 [SMILES: C[C@@H]1C[C@H](N)C[C@H](c2ccncc2NC(=O)c2ccc(F)c3cc(-c4ccc(C(F)(F)F)nc4)cnc23)C1]

This compound was synthesized according to the procedures of Example 59, using 6-(trifluoromethyl)pyridin-3-ylboronic acid. LCMS calculated for $C_{28}H_{26}F_4N_5O$ $(M+H)^+$ m/z=524.2; found: 524.1.

Example 62

N-(4-((1R,3S,5S)-3-Amino-5-methylcyclohexyl)pyridin-3-yl)-3-(1-ethyl-1H-pyrazol-4-yl)-5-fluoro-quinoline-8-carboxamide

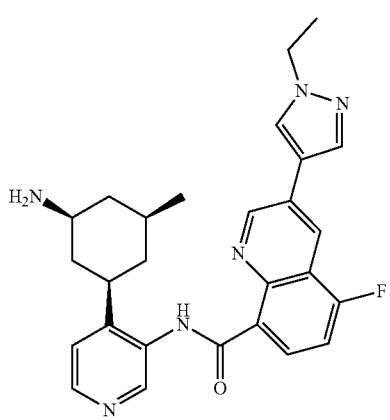 [SMILES: CCn1cc(-c2cnc3c(C(=O)Nc4cnccc4[C@@H]4C[C@H](C)C[C@H](N)C4)ccc(F)c3c2)cn1]

This compound was synthesized according to the procedures of Example 59, using 1-ethyl-4-(4,4,5,5-tetramethyl-1,3,2-dioxaborolan-2-yl)-1H-pyrazole. LCMS calculated for $C_{27}H_{30}FN_6O$ $(M+H)^+$ m/z=473.2; found: 473.2.

Example 63

N-(4-((1R,3S,5S)-3-Amino-5-methylcyclohexyl)pyridin-3-yl)-3-(1,3-dimethyl-1H-pyrazol-4-yl)-5-fluoroquinoline-8-carboxamide

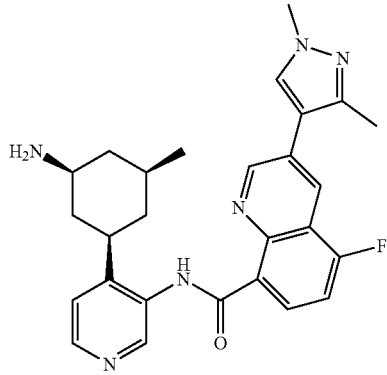 [SMILES: Cc1nn(C)cc1-c1cnc2c(C(=O)Nc3cnccc3[C@@H]3C[C@H](C)C[C@H](N)C3)ccc(F)c2c1]

This compound was synthesized according to the procedures of Example 59, using 1,5-dimethyl-4-(4,4,5,5-tetramethyl-1,3,2-dioxaborolan-2-yl)-1H-pyrazole. LCMS calculated for $C_{27}H_{30}FN_6O$ $(M+H)^+$ m/z=473.2; found: 473.2.

Example 64

N-(4-((1R,3S,5S)-3-Amino-5-methylcyclohexyl)pyridin-3-yl)-5-fluoro-3-(1-methyl-1H-pyrazol-4-yl)quinoline-8-carboxamide

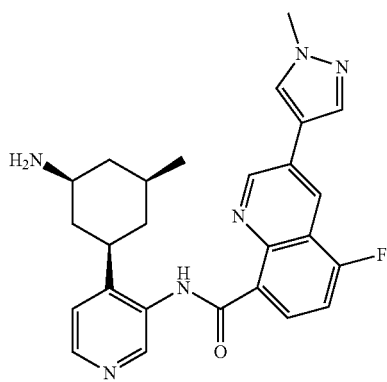 [SMILES: C[C@@H]1C[C@H](N)C[C@H](c2ccncc2NC(=O)c2ccc(F)c3cc(-c4cnn(C)c4)cnc23)C1]

This compound was synthesized according to the procedures of Example 59, using 1-methyl-4-(4,4,5,5-tetramethyl-1,3,2-dioxaborolan-2-yl)-1H-pyrazole. LCMS calculated for $C_{26}H_{28}FN_6O$ $(M+H)^+$ m/z=459.2; found: 459.2.

Example 65

N-(4-((1R,3S,5S)-3-amino-5-methylcyclohexyl)pyridin-3-yl)-5-fluoro-3-(3-methyl-1H-pyrazol-4-yl)quinoline-8-carboxamide

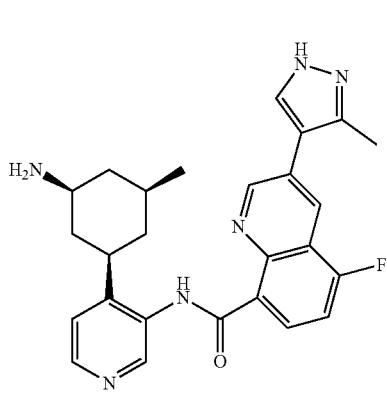 [SMILES: Cc1n[nH]cc1-c1cnc2c(C(=O)Nc3cnccc3[C@@H]3C[C@H](C)C[C@H](N)C3)ccc(F)c2c1]

This compound was synthesized according to the procedures of Example 59, using tert-butyl 5-methyl-4-(4,4,5,5-tetramethyl-1,3,2-dioxaborolan-2-yl)-1H-pyrazole-1-carboxylate. LCMS calculated for $C_{26}H_{28}FN_6O$ (M+H)$^+$ m/z=459.2; found: 459.2.

Example 66

N-(4-((1R,3S,5S)-3-amino-5-methylcyclohexyl)pyridin-3-yl)-5-fluoro-3-(1H-pyrazol-4-yl)quinoline-8-carboxamide

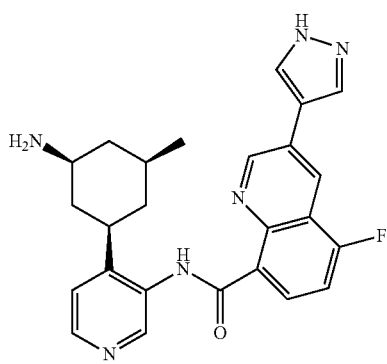 [SMILES: C[C@@H]1C[C@H](N)C[C@H](c2ccncc2NC(=O)c2ccc(F)c3cc(-c4cn[nH]c4)cnc23)C1]

This compound was synthesized according to the procedures of Example 59, using tert-butyl 4-(4,4,5,5-tetramethyl-1,3,2-dioxaborolan-2-yl)-1H-pyrazole-1-carboxylate. LCMS calculated for $C_{25}H_{26}FN_6O$ (M+H)$^+$ m/z=445.2; found: 445.2.

Example 67. N-(4-((1R,3S,5S)-3-Amino-5-methylcyclohexyl)pyridin-3-yl)-3-((R)-3-methylmorpholino)quinoline-8-carboxamide

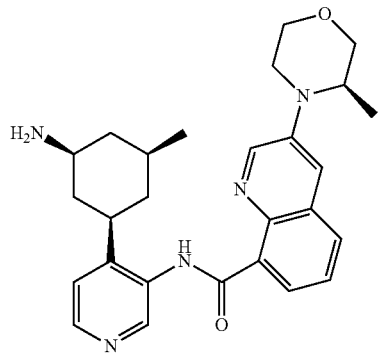 [SMILES: C[C@@H]1C[C@H](N)C[C@H](c2ccncc2NC(=O)c2cccc3cc(N4CCOC[C@H]4C)cnc23)C1]

tert-Butyl (1S,3R,5S)-3-(3-(3-bromoquinoline-8-carboxamido)pyridin-4-yl)-5-methylcyclohexylcarbamate (16 mg, 0.03 mmol, Intermediate 2), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then tert-butyl alcohol (2 mL) and (R)-3-methylmorpholine (6 μL, 0.06 mmol) were added. The reaction mixture was stirred at 65° C. overnight. After this time the reaction was quenched by the addition of water and the product was extracted with ethyl acetate. Combined organic fractions were washed with brine, dried over sodium sulfate and the solvents were evaporated under reduced pressure. Trifluoroacetic acid (1 mL) and dichloromethane (1 mL) were added to the obtained crude product and the reaction mixture was stirred at r.t. for 1 h. After dilution with acetonitrile and neutralization by the addition of ammonia solution, the desired product was purified by RP-HPLC (water XBridge C18 column, 30 mm×100 mm, 5 μm particle size, eluting with a gradient of acetonitrile/water containing 0.1% NH$_4$OH, at flow rate of 60 mL/min). LCMS calculated for $C_{27}H_{34}N_5O_2$ (M+H)$^+$ m/z=460.3; found: 460.2.

Example 68

N-(4-((1R,3S,5S)-3-Amino-5-methylcyclohexyl)pyridin-3-yl)-3-((R)-2-methylpyrrolidin-1-yl)quinoline-8-carboxamide

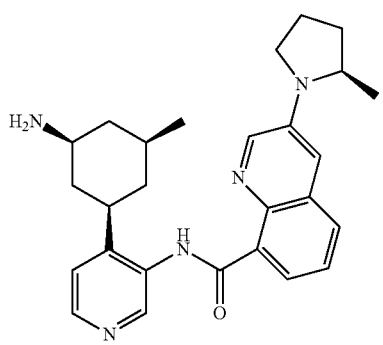 [SMILES: C[C@@H]1C[C@H](N)C[C@H](c2ccncc2NC(=O)c2cccc3cc(N4CCC[C@H]4C)cnc23)C1]

This compound was synthesized according to the procedures of Example 67, using (R)-2-methylpyrrolidine. LCMS calculated for $C_{27}H_{34}N_5O$ (M+H)+ m/z=444.3; found: 444.2.

Example 69

N-(4-((1R,3S,5S)-3-Amino-5-methylcyclohexyl) pyridin-3-yl)-3-((S)-2-methylpyrrolidin-1-yl)quinoline-8-carboxamide

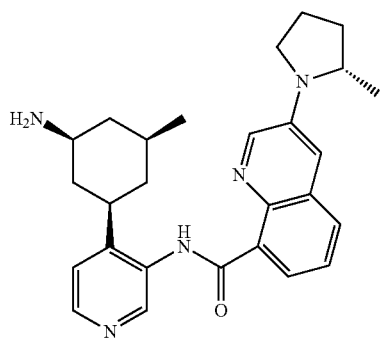 [SMILES: C[C@@H]1C[C@H](N)C[C@H](c2ccncc2NC(=O)c2cccc3cc(N4CCC[C@@H]4C)cnc23)C1]

This compound was synthesized according to the procedures of Example 67, using (S)-2-methylpyrrolidine. LCMS calculated for $C_{27}H_{34}N_5O$ (M+H)+ m/z=444.3; found: 444.3.

Example 70

N-(4-((1R,3S,5S)-3-Amino-5-methylcyclohexyl) pyridin-3-yl)-3-(2-methylpiperidin-1-yl)quinoline-8-carboxamide

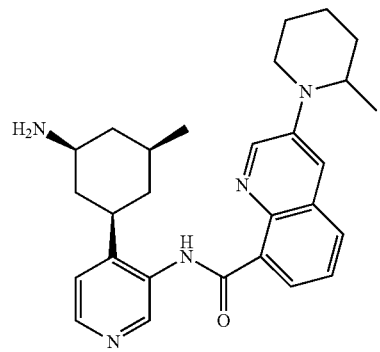 [SMILES: CC1CCCCN1c1cnc2c(C(=O)Nc3cnccc3[C@@H]3C[C@H](C)C[C@H](N)C3)cccc2c1]

This compound was synthesized according to the procedures of Example 67, using 2-methylpiperidine. LCMS calculated for $C_{28}H_{36}N_5O$ (M+H)+ m/z=458.3; found: 458.2.

Example 71

N-(4-((1R,3S,5S)-3-Amino-5-methylcyclohexyl) pyridin-3-yl)-3-(2-(difluoromethyl)piperidin-1-yl) quinoline-8-carboxamide

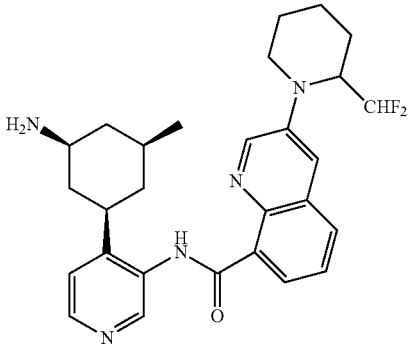 [SMILES: C[C@@H]1C[C@H](N)C[C@H](c2ccncc2NC(=O)c2cccc3cc(N4CCCCC4C(F)F)cnc23)C1]

This compound was synthesized according to the procedures of Example 67, using 2-(difluoromethyl)piperidine. LCMS calculated for $C_{28}H_{34}F_2N_5O$ (M+H)+ m/z=494.3; found: 494.3.

Example 72

N-(4-((1R,3S,5S)-3-Amino-5-methylcyclohexyl) pyridin-3-yl)-3-((2,2-difluoroethyl)(methyl)amino) quinoline-8-carboxamide

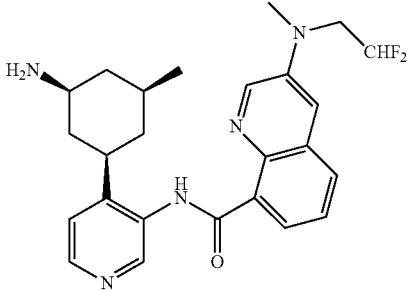 [SMILES: C[C@@H]1C[C@H](N)C[C@H](c2ccncc2NC(=O)c2cccc3cc(N(C)CC(F)F)cnc23)C1]

This compound was synthesized according to the procedures of Example 67, using 2,2-difluoro-N-methylethanamine. LCMS calculated for $C_{25}H_{30}F_2N_5O$ (M+H)+ m/z=454.2; found: 454.2.

Example 73

N-(4-((1R,3S,5S)-3-Amino-5-methylcyclohexyl)pyridin-3-yl)-5-fluoro-3-thiomorpholinoquinoline-8-carboxamide

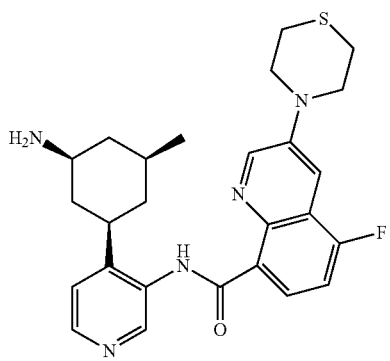 [SMILES: C[C@@H]1C[C@H](N)C[C@H](c2ccncc2NC(=O)c2ccc(F)c3cc(N4CCSCC4)cnc23)C1]

This compound was synthesized according to the procedures of Example 32, using thiomorpholine. LCMS calculated for $C_{26}H_{31}FN_5OS$ (M+H)$^+$ m/z=480.2; found: 480.2.

Example 74

N-(4-((1R,3S,5S)-3-Amino-5-methylcyclohexyl)pyridin-3-yl)-3-(4-(N,N-dimethylsulfamoyl)piperazin-1-yl)-5-fluoroquinoline-8-carboxamide

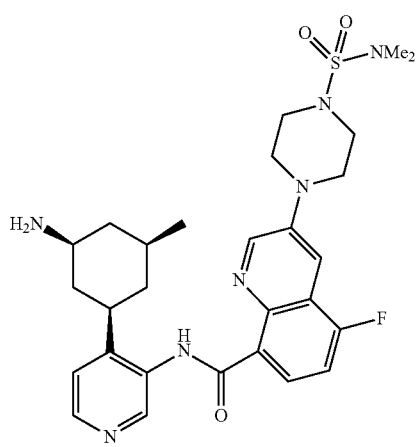 [SMILES: C[C@@H]1C[C@H](N)C[C@H](c2ccncc2NC(=O)c2ccc(F)c3cc(N4CCN(S(=O)(=O)N(C)C)CC4)cnc23)C1]

This compound was synthesized according to the procedures of Example 32, using N,N-dimethylpiperazine-1-sulfonamide. LCMS calculated for $C_{28}H_{37}FN_7O_3S$ (M+H)$^+$ m/z=570.3; found: 570.2.

Example 75

N-(4-((1R,3S,5S)-3-Amino-5-methylcyclohexyl)pyridin-3-yl)-5-fluoro-3-(4-methyl-3-oxopiperazin-1-yl)quinoline-8-carboxamide

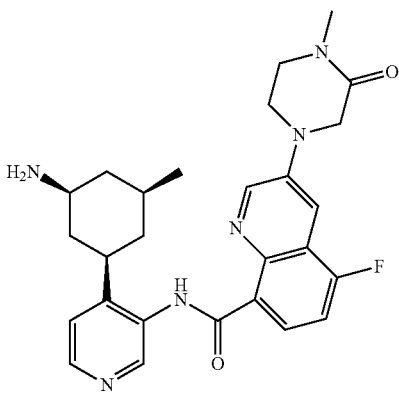 [SMILES: C[C@@H]1C[C@H](N)C[C@H](c2ccncc2NC(=O)c2ccc(F)c3cc(N4CCN(C)C(=O)C4)cnc23)C1]

This compound was synthesized according to the procedures of Example 32, using 1-methylpiperazin-2-one. LCMS calculated for $C_{27}H_{32}FN_6O_2$ (M+H)$^+$ m/z=491.3; found: 491.2.

Example 76

N-(4-((1R,3S,5S)-3-Amino-5-methylcyclohexyl)pyridin-3-yl)-3-(azepan-1-yl)-5-fluoroquinoline-8-carboxamide

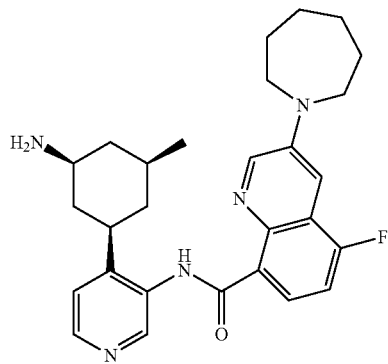 [SMILES: C[C@@H]1C[C@H](N)C[C@H](c2ccncc2NC(=O)c2ccc(F)c3cc(N4CCCCCC4)cnc23)C1]

This compound was synthesized according to the procedures of Example 32, using azepane. LCMS calculated for $C_{28}H_{35}FN_5O$ (M+H)$^+$ m/z=476.3; found: 476.2.

Example 77

N-(4-((1R,3S,5S)-3-Amino-5-methylcyclohexyl)pyridin-3-yl)-3-(3-oxa-8-azabicyclo[3.2.1]octan-8-yl)-5-fluoroquinoline-8-carboxamide

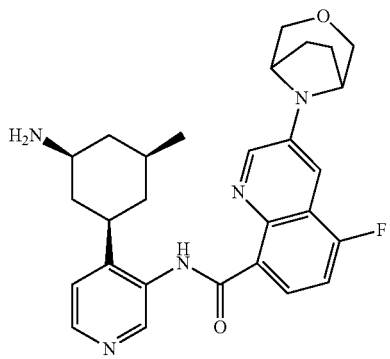 [SMILES: C[C@@H]1C[C@H](N)C[C@H](c2ccncc2NC(=O)c2ccc(F)c3cc(N4C5CCC4COC5)cnc23)C1]

This compound was synthesized according to the procedures of Example 32, using 3-oxa-8-azabicyclo[3.2.1]octane. LCMS calculated for $C_{28}H_{33}FN_5O_2$ $(M+H)^+$ m/z=490.3; found: 490.2.

Example 78

N-(4-((1R,3S,5S)-3-Amino-5-methylcyclohexyl)pyridin-3-yl)-5-fluoro-3-(2-oxopyrrolidin-1-yl)quinoline-8-carboxamide

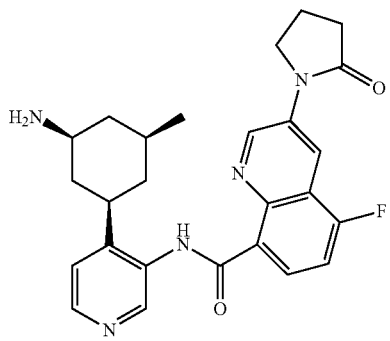 [SMILES: C[C@@H]1C[C@H](N)C[C@H](c2ccncc2NC(=O)c2ccc(F)c3cc(N4CCCC4=O)cnc23)C1]

This compound was synthesized according to the procedures of Example 32, using pyrrolidin-2-one. LCMS calculated for $C_{26}H_{29}FN_5O_2$ $(M+H)^+$ m/z=462.2; found: 462.2.

Example 79

N-(4-((1R,3S,5S)-3-Amino-5-methylcyclohexyl)pyridin-3-yl)-5-fluoro-3-(indolin-1-yl)quinoline-8-carboxamide

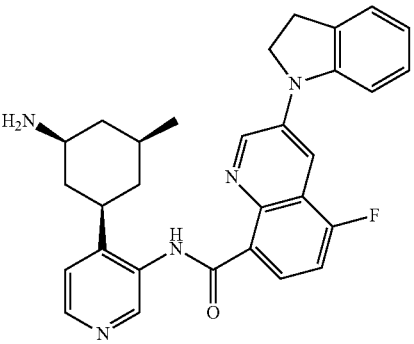 [SMILES: C[C@@H]1C[C@H](N)C[C@H](c2ccncc2NC(=O)c2ccc(F)c3cc(N4CCc5ccccc54)cnc23)C1]

This compound was synthesized according to the procedures of Example 32, using indoline. LCMS calculated for $C_{30}H_{31}FN_5O$ $(M+H)^+$ m/z=496.2; found: 496.2.

Example 80

N-(4-((1R,3S,5S)-3-Amino-5-methylcyclohexyl)pyridin-3-yl)-3-((1R,4R)-2-oxa-5-azabicyclo[2.2.1]heptan-5-yl)-5-fluoroquinoline-8-carboxamide

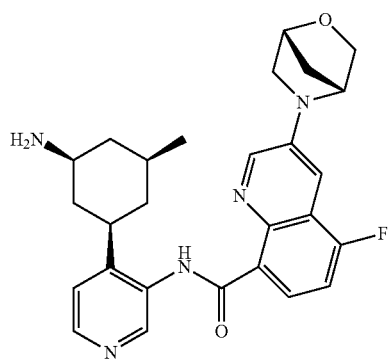 [SMILES: C[C@@H]1C[C@H](N)C[C@H](c2ccncc2NC(=O)c2ccc(F)c3cc(N4C[C@H]5C[C@@H]4CO5)cnc23)C1]

This compound was synthesized according to the procedures of Example 32, using (1R,4R)-2-oxa-5-azabicyclo[2.2.1]heptane. LCMS calculated for $C_{27}H_{31}FN_5O_2$ $(M+H)^+$ m/z=476.2; found: 476.2.

Example 81

N-(4-((1R,3S,5S)-3-Amino-5-methylcyclohexyl)pyridin-3-yl)-3-(6-oxa-3-azabicyclo[3.1.1]heptan-3-yl)-5-fluoroquinoline-8-carboxamide

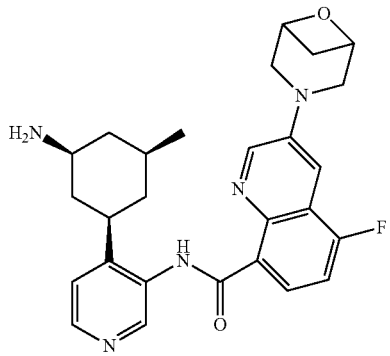 [SMILES: C[C@@H]1C[C@H](N)C[C@H](c2ccncc2NC(=O)c2ccc(F)c3cc(N4CC5CC(C4)O5)cnc23)C1]

This compound was synthesized according to the procedures of Example 32, using 6-oxa-3-azabicyclo[3.1.1]heptane. LCMS calculated for $C_{27}H_{31}FN_5O_2$ $(M+H)^+$ m/z=476.2; found: 476.2.

Example 82

N-(4-((1R,3S,5S)-3-Amino-5-methylcyclohexyl)pyridin-3-yl)-3-(4-(dimethylcarbamoyl)piperazin-1-yl)-5-fluoroquinoline-8-carboxamide

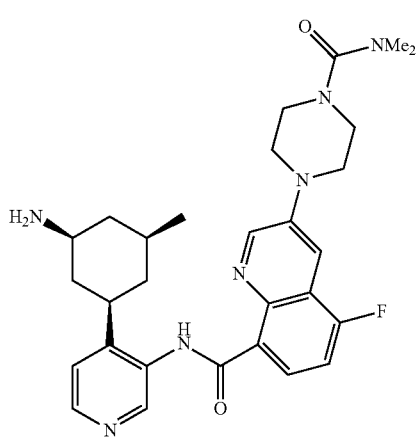 [SMILES: C[C@@H]1C[C@H](N)C[C@H](c2ccncc2NC(=O)c2ccc(F)c3cc(N4CCN(C(=O)N(C)C)CC4)cnc23)C1]

This compound was synthesized according to the procedures of Example 32, using N,N-dimethylpiperazine-1-carboxamide. LCMS calculated for $C_{29}H_{37}FN_7O_2$ $(M+H)^+$ m/z=534.3; found: 534.2.

Example 83

N-(4-((1R,3S,5S)-3-Amino-5-methylcyclohexyl)pyridin-3-yl)-5-fluoro-3-(methyl(phenyl)amino)quinoline-8-carboxamide

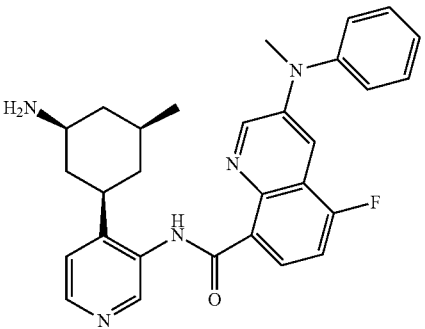 [SMILES: C[C@@H]1C[C@H](N)C[C@H](c2ccncc2NC(=O)c2ccc(F)c3cc(N(C)c4ccccc4)cnc23)C1]

This compound was synthesized according to the procedures of Example 32, using N-methylaniline. LCMS calculated for $C_{29}H_{31}FN_5O$ $(M+H)^+$ m/z=484.2; found: 484.2.

Example 84

N-(4-((1R,3S,5S)-3-Amino-5-methylcyclohexyl)pyridin-3-yl)-5-fluoro-3-(6-oxohexahydropyrrolo[1,2-a]pyrazin-2(1H)-yl)quinoline-8-carboxamide

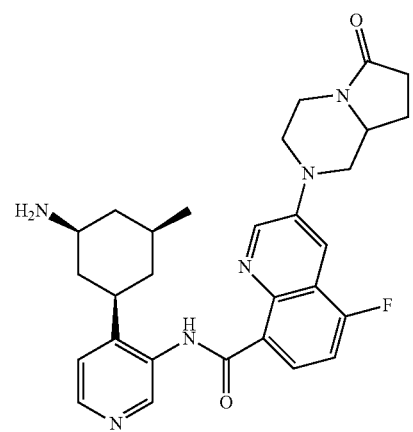 [SMILES: C[C@@H]1C[C@H](N)C[C@H](c2ccncc2NC(=O)c2ccc(F)c3cc(N4CCN5C(=O)CCC5C4)cnc23)C1]

This compound was synthesized according to the procedures of Example 32, using hexahydropyrrolo[1,2-a]pyrazin-6(7H)-one. LCMS calculated for $C_{29}H_{34}FN_6O_2$ $(M+H)^+$ m/z=517.3; found: 517.3.

Intermediate 3.
(S)-3-Methyl-1-(methylsulfonyl)piperazine (HCl Salt

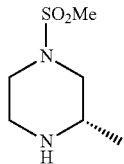

Methanesulfonyl chloride (232 µL, 3.00 mmol) was slowly added at 0° C. to a solution of tert-butyl (2S)-2-methylpiperazine-1-carboxylate (300 mg, 1.5 mmol) and triethylamine (835 µL, 6 mmol) in methylene chloride (6 mL). After stirring at r.t. for 1 h, reaction mixture was carefully quenched by addition of water and the desired product was extracted with ethyl acetate. The organic phase was washed with brine, dried over sodium sulfate, and filtered. The filtrate was concentrated under reduced pressure. The resulting residue was purified by Biotage Isolera™ (flash purification system with hexane/ethyl acetate at a ratio from 0 to 100%) to give tert-butyl (2S)-2-methyl-4-(methylsulfonyl)piperazine-1-carboxylate (404 mg, 97%). LCMS calculated for $C_6H_{15}N_2O_2S$ (M+H-Boc)$^+$ m/z=179.1; found: 179.1.

A 4.0 M solution of hydrogen chloride in dioxane (4 mL, 16 mmol) was added to the tert-butyl (2S)-2-methyl-4-(methylsulfonyl)piperazine-1-carboxylate (404 mg, 1.45 mmol). After stirring at r.t. for 1 h, solvent was evaporated under reduced pressure and the resulting product was dried under vacuum for 1 h. LCMS calculated for $C_6H_{15}N_2O_2S$ (M+H)$^+$ m/z=179.1; found: 179.1.

Example 85

N-(4-((1R,3S,5S)-3-Amino-5-methylcyclohexyl)pyridin-3-yl)-5-fluoro-3-((S)-2-methyl-4-(methylsulfonyl)piperazin-1-yl)quinoline-8-carboxamide

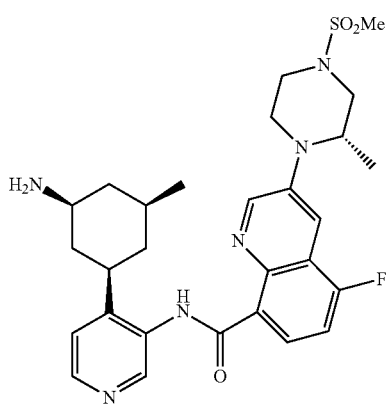 [SMILES: C[C@@H]1C[C@H](N)C[C@H](c2ccncc2NC(=O)c2ccc(F)c3cc(N4CCN(S(C)(=O)=O)C[C@@H]4C)cnc23)C1]

This compound was synthesized according to the procedures of Example 32, using Intermediate 3. LCMS calculated for $C_{28}H_{36}FN_6O_3S$ (M+H)$^+$ m/z=555.3; found: 555.2.

Intermediate 4.
(R)-3-Methyl-1-(methylsulfonyl)piperazine (HCl Salt

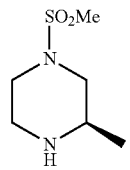

This compound was synthesized by the same way as Intermediate 3, using tert-butyl (2R)-2-methylpiperazine-1-carboxylate. LCMS calculated for $C_6H_{15}N_2O_2S$ (M+H)$^+$ m/z=179.1; found: 179.1.

Example 86

N-(4-((1R,3S,5S)-3-Amino-5-methylcyclohexyl)pyridin-3-yl)-5-fluoro-3-((R)-2-methyl-4-(methylsulfonyl)piperazin-1-yl)quinoline-8-carboxamide

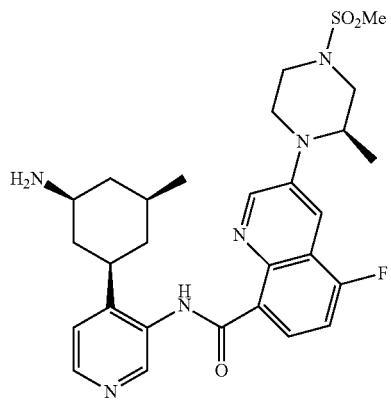 [SMILES: C[C@@H]1C[C@H](N)C[C@H](c2ccncc2NC(=O)c2ccc(F)c3cc(N4CCN(S(C)(=O)=O)C[C@H]4C)cnc23)C1]

This compound was synthesized according to the procedures of Example 32, using Intermediate 4. LCMS calculated for $C_{28}H_{36}FN_6O_3S$ (M+H)$^+$ m/z=555.3; found: 555.2.

Intermediate 5. (1R,4R)-2-(Methylsulfonyl)-2,5-diazabicyclo[2.2.1]heptane (HCl Salt

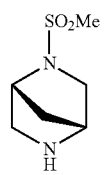 [SMILES: CS(=O)(=O)N1C[C@H]2C[C@@H]1CN2]

This compound was synthesized according to the procedures of Intermediate 3, using (1R,4R)-tert-butyl 2,5-diazabicyclo[2.2.1]heptane-2-carboxylate. LCMS calculated for $C_6H_{13}N_2O_2S$ (M+H)$^+$ m/z=177.1; found: 177.1.

Example 87

N-(4-((1R,3S,5S)-3-Amino-5-methylcyclohexyl)pyridin-3-yl)-5-fluoro-3-((1R,4R)-5-(methylsulfonyl)-2,5-diazabicyclo[2.2.1]heptan-2-yl)quinoline-8-carboxamide

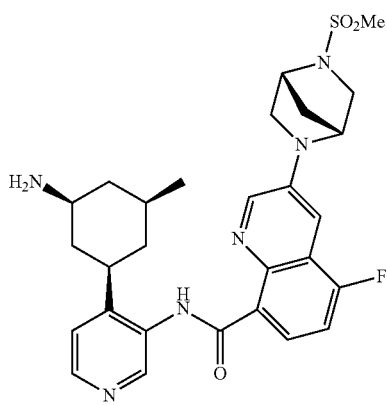 [SMILES: C[C@@H]1C[C@H](N)C[C@H](c2ccncc2NC(=O)c2ccc(F)c3cc(N4C[C@H]5C[C@@H]4CN5S(C)(=O)=O)cnc23)C1]

This compound was synthesized according to the procedures of Example 32, using Intermediate 5. LCMS calculated for $C_{28}H_{34}FN_6O_3S$ $(M+H)^+$ m/z=553.2; found: 553.2.

Intermediate 6. (S)-Methyl 3-methylpiperazine-1-carboxylate (HCl Salt

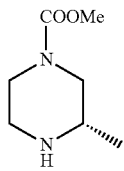

Methyl chloroformate (230 µL, 3 mmol) was slowly added at 0° C. to a solution of tert-butyl (2S)-2-methylpiperazine-1-carboxylate (300 mg, 1.5 mmol) and triethylamine (835 µL, 6 mmol) in methylene chloride (6 mL). After stirring at r.t. for 1 h, reaction mixture was carefully quenched by addition of water and the desired product was extracted with ethyl acetate. The organic phase was washed with brine, dried over sodium sulfate and solvent was evaporated under reduced pressure. Crude material was purified by Biotage Isolera™ to give (S)-1-tert-butyl 4-methyl 2-methylpiperazine-1,4-dicarboxylate (378 mg, 97%). LCMS calculated for $C_7H_{15}N_2O_2$ $(M+H-Boc)^+$ m/z=159.1; found: 159.1.

A 4.0 M solution of hydrogen chloride in dioxane (4 mL, 16 mmol) was added to the (S)-1-tert-butyl 4-methyl 2-methylpiperazine-1,4-dicarboxylate (378 mg, 1.45 mmol). After stirring at r.t. for 1 h, solvent was evaporated under reduced pressure and the product was dried under vacuum for 1 h. LCMS calculated for $C_7H_{15}N_2O_2$ $(M+H)^+$ m/z=159.1; found: 159.1.

Example 88

(S)-Methyl 4-(8-(4-((1R,3S,5S)-3-amino-5-methylcyclohexyl)pyridin-3-ylcarbamoyl)-5-fluoroquinolin-3-yl)-3-methylpiperazine-1-carboxylate

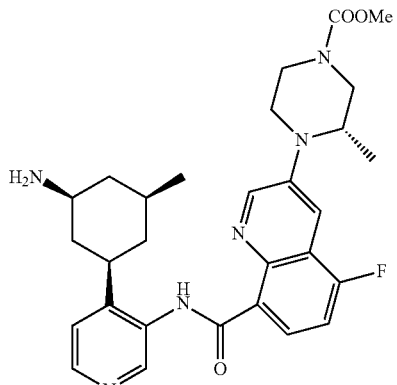

This compound was synthesized according to the procedures of Example 32, using Intermediate 6. LCMS calculated for $C_{29}H_{36}FN_6O_3$ $(M+H)^+$ m/z=535.3; found: 535.2.

Intermediate 7. (R)-Methyl 3-methylpiperazine-1-carboxylate (HCl Salt

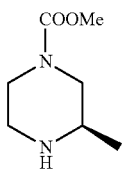

This compound was synthesized according to the procedures of Intermediate 6, using tert-butyl (2R)-2-methylpiperazine-1-carboxylate. LCMS calculated for $C_7H_{15}N_2O_2$ $(M+H)^+$ m/z=159.1; found: 159.1.

Example 89

(R)-Methyl 4-(8-(4-((1R,3S,5S)-3-amino-5-methylcyclohexyl)pyridin-3-ylcarbamoyl)-5-fluoroquinolin-3-yl)-3-methylpiperazine-1-carboxylate

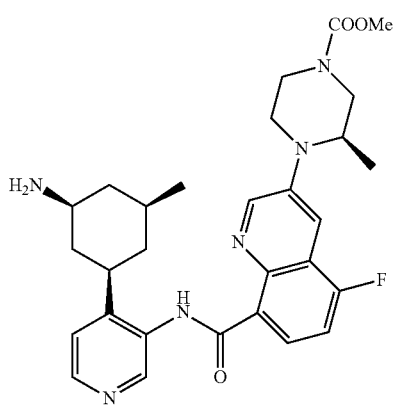 [SMILES: COC(=O)N1CCN(c2cnc3c(C(=O)Nc4cnccc4[C@@H]4C[C@H](C)C[C@H](N)C4)ccc(F)c3c2)[C@H](C)C1]

This compound was synthesized according to the procedures of Example 32, using Intermediate 7. LCMS calculated for $C_{29}H_{36}FN_6O_3$ $(M+H)^+$ m/z=535.3; found: 535.2.

Intermediate 8. (1R,4R)-Methyl 2,5-diazabicyclo[2.2.1]heptane-2-carboxylate (HCl Salt

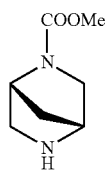 [SMILES: COC(=O)N1C[C@H]2C[C@@H]1CN2]

This compound was synthesized according to the procedures of Intermediate 6, using (1R,4R)-tert-butyl 2,5-diazabicyclo[2.2.1]heptane-2-carboxylate. LCMS calculated for $C_7H_{13}N_2O_2$ (M+H)$^+$ m/z=157.1; found: 157.1.

Example 90

(1R,4R)-Methyl 5-(8-(4-((1R,3S,5S)-3-amino-5-methylcyclohexyl)pyridin-3-ylcarbamoyl)-5-fluoroquinolin-3-yl)-2,5-diazabicyclo[2.2.1]heptane-2-carboxylate

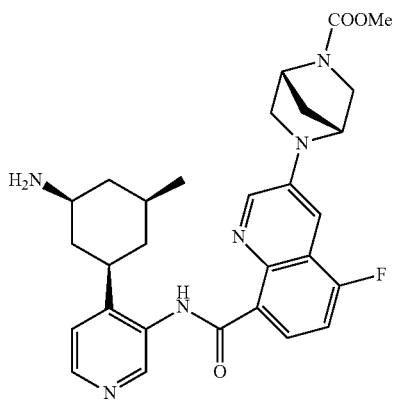 [SMILES: COC(=O)N1C[C@H]2C[C@@H]1CN2c1cnc2c(C(=O)Nc3cnccc3[C@@H]3C[C@H](C)C[C@H](N)C3)ccc(F)c2c1]

This compound was synthesized according to the procedures of Example 32, using Intermediate 8. LCMS calculated for $C_{29}H_{34}FN_6O_3$ (M+H)$^+$ m/z=533.3; found: 533.2.

Example 91

N-{4-[(1R,3S,5S)-3-amino-5-methylcyclohexyl]pyridin-3-yl}-3-(2,6-difluorophenyl)-5-fluorocinnoline-8-carboxamide

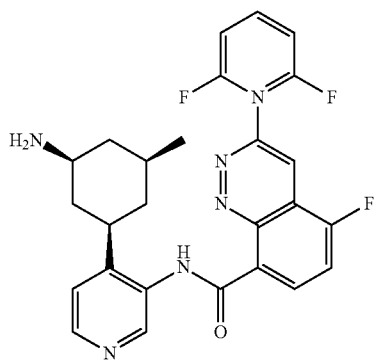

Step 1. 1-(2-Bromo-3-fluorophenyl)-3,3-diethyltriaz-1-ene

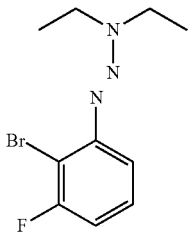

A solution of 2-bromo-3-fluoroaniline (24.2 g, 127 mmol) in THF (122 mL), acetonitrile (122 mL) and water (141 mL) was cooled to −5° C. with a salt/ice bath. Then 12.0 M aqueous hydrogen chloride (84.9 mL, 1020 mmol) was added followed by dropwise addition of a solution of sodium nitrite (17.6 g, 255 mmol) in water (95 mL) and acetonitrile (32 mL). The reaction mixture was stirred at −5° C. for 30 min. The yellow suspension was then transferred slowly via cannula to a stirred solution of N-ethylethanamine (263.5 mL, 2547 mmol) in water (765 mL) and acetonitrile (765 mL) cooled to 0° C. The mixture was stirred at 0° C. for 30 min. The mixture was diluted with 300 mL satd. NaHCO$_3$ and extracted with EtOAc (500 ml). The organic layer was separated, washed with brine, dried over Na$_2$SO$_4$, filtered, and concentrated in vacuo. The crude product was purified with flash chromatography (eluting with a gradient of 0-15% DCM in hexanes) to the obtain the desired product as a red oil (33.9 g, 97%). LCMS calculated for $C_{10}H_{14}BrFN_3$ (M+H)$^+$: m/z=274.0, 276.0; Found: 274.0, 276.0.

Step 2. 3,3-Diethyl-1-{3-fluoro-2-[(trimethylsilyl)ethynyl]phenyl}triaz-1-ene

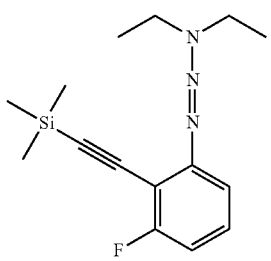 [SMILES: CCN(CC)N=Nc1cccc(F)c1C#C[Si](C)(C)C]

To a round bottom flask was added tetrakis(triphenylphosphine)palladium(0) (7.1 g, 6.2 mmol). The flask was sealed and evacuated under vacuum and refilled by N$_2$. (this process was repeated three times). Pyrrolidine (270 mL, 3200 mmol) was added followed by 1-(2-bromo-3-fluorophenyl)-3,3-diethyltriaz-1-ene (33.9 g, 124 mmol). The (trimethylsilyl)acetylene (28.0 mL, 198 mmol) was added using a syringe pump over 48 h at 95° C. After cooling to room temperature, the solvent was evaporated in vacuo. The residue was dissolved in EtOAc and diluted with water. The organic layer was washed with brine, dried over Na$_2$SO$_4$, filtered and concentrated. The crude product was purified with flash chromatography (eluting with a gradient of 0-15% DCM in hexanes) to give the desired product as a red oil (28.0 g, 78%). LCMS calculated for $C_{15}H_{23}FN_3Si$ (M+H)$^+$: m/z=292.2; Found: 292.2.

Step 3. 3,3-Diethyl-1-(2-ethynyl-3-fluorophenyl)triaz-1-ene

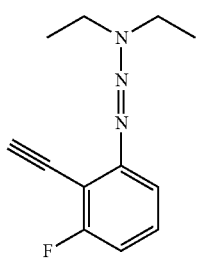 [SMILES: C#Cc1c(F)cccc1N=NN(CC)CC]

To a solution of 3,3-diethyl-1-{3-fluoro-2-[(trimethylsilyl)ethynyl]phenyl}triaz-1-ene (23.6 g, 81.0 mmol) in THF (650 mL) was added 1.0 M tetra-n-butylammonium fluoride in THF (85.0 mL, 85.0 mmol). The resulting mixture was stirred at room temperature for 1 h. The reaction mixture was diluted with ethyl acetate and water. The aqueous layer was extracted with ethyl acetate once. The combined organic layers were washed with brine, dried over $Na_2SO_4$, filtered and concentrated. The crude product was purified with flash chromatography (eluting with a gradient of 0-10% ethyl acetate in hexanes) to give the desired product as a red oil (15.2 g, 86%). LCMS calculated for $C_{12}H_{15}FN_3$ $(M+H)^+$: m/z=220.1; Found: 220.1.

Step 4. 5-Fluorocinnoline

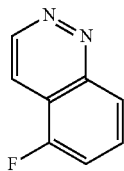

A solution of 3,3-diethyl-1-(2-ethynyl-3-fluorophenyl)triaz-1-ene (1.4 g, 6.2 mmol) in 1,2-dichlorobenzene (14 mL, 120 mmol) was placed in a microwave vial and was sealed. The mixture was heated in the microwave for 55 min at 220° C. The crude product was dissolved in DCM and was purified on a 50 g column (eluting with a gradient of 0-50% ethyl acetate in hexanes) to give the desired product as a solid (0.52 g, 56%). LCMS calculated for $C_8H_6FN_2$ $(M+H)^+$: m/z=149.0; Found: 149.1.

Step 5. 5-Fluoro-8-iodocinnoline and 5-Fluoro-3,8-diiodocinnoline

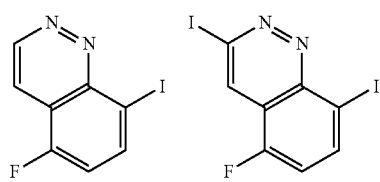 [SMILES: Fc1ccc(I)c2nnccc12 ; Fc1ccc(I)c2nnc(I)cc12]

To a flask was added 5-fluorocinnoline (4.9 g, 33 mmol), tetrahydrofuran (130 mL) and a 1.9 M zinc dichloride in 2-methyltetrahydrofuran solution (17.4 mL, 33.1 mmol) at room temperature, followed by the immediate addition of 1.0 M lithium chloride-chloro(2,2,6,6-tetramethylpiperidin-1-yl)magnesium (1:1) in THF (66.2 mL, 66.2 mmol). The reaction mixture was then heated at 50° C. for 3 h. The reaction mixture was then cooled to 0° C. and cannulated into a solution of iodine (16.8 g, 66.2 mmol) in THF (65 mL) pre-cooled to 0° C. The reaction mixture was stirred at 0° C. for 30 min, then at room temperature for 1 h. The reaction was quenched with a saturated aqueous solution of $Na_2S_2O_3$ (200 mL) and extracted with ethyl acetate (3×) and dried over $Na_2SO_4$, filtered and concentrated. The crude product was purified by flash chromatography (eluting with a gradient of 0-30% ethyl acetate in hexanes) to give 5-fluoro-8-iodocinnoline as yellow solid (3.8 g, 42%). $^1$H NMR (400 MHz, CDCl$_3$) δ 9.51 (d, J=5.9 Hz, 1H), 8.41 (dd, J=8.1, 5.5 Hz, 1H), 8.03 (d, J=5.9 Hz, 1H), 7.25 (m, 1H), LCMS calculated for $C_8H_5FIN_2$ $(M+H)^+$: m/z=274.9; Found: 275.0. 5-Fluoro-3,8-diiodocinnoline was isolated as a brown solid (1.5 g, 12%). LCMS calculated for $C_8H_4FI_2N_2$ $(M+H)^+$: m/z=400.8; Found: 400.8.

Step 6. 5-Fluoro-8-vinylcinnoline

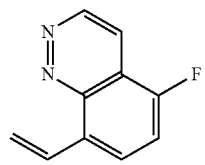

A flask charged with 5-fluoro-8-iodocinnoline (3.80 g, 13.9 mmol), 4,4,5,5-tetramethyl-2-vinyl-1,3,2-dioxaborolane (3.53 mL, 20.8 mmol), dicyclohexyl-(2',4',6'-triisopropylbiphenyl-2-yl)phosphine-(2'-aminobiphenyl-2-yl)(chloro)palladium (1:1) (710 mg, 0.90 mmol) and tripotassium phosphate hydrate (7.03 g, 30.5 mmol) was evacuated and refilled with nitrogen (this process was repeated three times). 1,4-Dioxane (76 mL) and water (25 mL) were added to flask. The resulting mixture was stirred at 70° C. for 1 h. After cooling to room temperature, the reaction mixture was diluted with water and ethyl acetate. The organic layer was washed with brine, dried over $Na_2SO_4$, filtered and concentrated. The residue was purified with flash chromatography (eluting with a gradient of 0-30% ethyl acetate in hexanes) to give the desired product as a yellow solid (1.9 g, 78%). LCMS calculated for $C_{10}H_8FN_2$ $(M+H)^+$: m/z=175.1; Found: 175.1.

Step 7. 5-Fluoro-3-iodo-8-vinylcinnoline

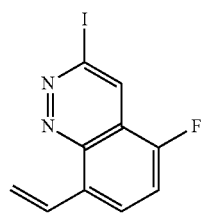

To a solution of 5-fluoro-8-vinylcinnoline (358 mg, 2.06 mmol) in THF (5.4 mL) was added boron trifluoride etherate (286 μL, 2.26 mmol) at 0° C. dropwise. After stirring for 15 min, the solution was cooled to −78° C. and 0.5 M bis(2,2, 6,6-tetramethylpiperidinyl)magnesium, lithium chloride (TMP$_2$Mg 2LiCl) in THF (4.52 mL, 2.26 mmol) was added dropwise. The reaction mixture was stirred for 10 min at −78° C., then was cannulated into a solution of iodine (1.04 g, 4.11 mmol) in THF (3.2 mL) at −78° C. The reaction mixture was allowed to warm to room temperature and stirred overnight. Then the reaction mixture was quenched with aq. Na$_2$S$_2$O$_3$ solution, extracted with ethyl acetate (2×) and dried over Na$_2$SO$_4$, filtered and concentrated. The crude was purified with flash chromatography (eluting with a gradient of 0-80% ethyl acetate in hexanes) to give the desired product as a yellow solid (0.26 g, 41%). $^1$H NMR (400 MHz, CDCl$_3$) δ 8.51 (s, 1H), 8.10 (m, 1H), 7.97 (m, 1H), 7.44 (t, J=8.5 Hz, 1H) 6.09 (d, J=17.7 Hz, 1H), 5.65 (d, J=11.1 Hz, 1H). LCMS calculated for C$_{10}$H$_7$FIN$_2$ (M+H)$^+$: m/z=301.0; Found: 301.0.

Step. 8. 5-Fluoro-3-iodocinnoline-8-carbaldehyde

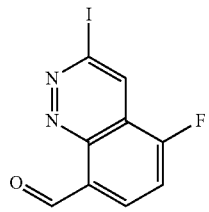 [SMILES: O=Cc1ccc(F)c2cc(I)nnc12]

To a solution of 5-fluoro-3-iodo-8-vinylcinnoline (255 mg, 0.850 mmol) in THF (10 mL) and water (0.8 mL) was added 0.16 M osmium tetraoxide in water (110 μL, 0.017 mmol) and sodium metaperiodate (0.73 g, 3.4 mmol). The resulting mixture was stirred at 60° C. for 1 h. The mixture was filtered through a pad of Celite, and rinsed with THF. The organic layer was concentrated in vacuo. The residue was purified with flash chromatography (eluting with a gradient of 0-30% ethyl acetate in hexanes) to give the desired compound as a yellow powder (143 mg, 56%). $^1$H NMR (400 MHz, CDCl$_3$) δ 11.56 (s, 1H), 8.63 (s, 1H), 8.48 (dd, J=8.1, 5.8 Hz, 1H), 7.60 (t, J=8.3 Hz, 1H). LCMS calculated for C$_9$H$_5$FIN$_2$O (M+H)$^+$: m/z=302.9; Found: 302.9.

Step 9. 5-Fluoro-3-iodocinnoline-8-carboxylic acid

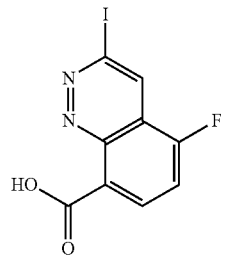

A solution of 5-fluoro-3-iodocinnoline-8-carbaldehyde (142 mg, 0.470 mmol) and sodium dihydrogenphosphate (20.6 mg, 0.172 mmol) in acetonitrile (2.5 mL) and water (0.50 mL) was cooled in an ice bath. Hydrogen peroxide (59 μL, 1.9 mmol) was added followed by solid sodium chlorite (110 mg, 0.96 mmol), and the mixture was stirred for 3 h. The solvent was removed in vacuo. The residue was partitioned between ethyl acetate and water. Then 1 M HCl solution was added to adjust pH to 1. The aqueous layer was extracted with DCM (3×), and the combined organic phases were dried over MgSO$_4$, filtered, and concentrated to give product as a red solid (110 mg, 74%). LCMS calculated for C$_9$H$_5$FIN$_2$O$_2$ (M+H)$^+$: m/z=318.9; Found: 318.9.

Step 10. tert-Butyl [(1S,3R,5S)-3-(3-{[(5-fluoro-3-iodocinnolin-8-yl)carbonyl]amino}pyridin-4-yl)-5-methylcyclohexyl]carbamate

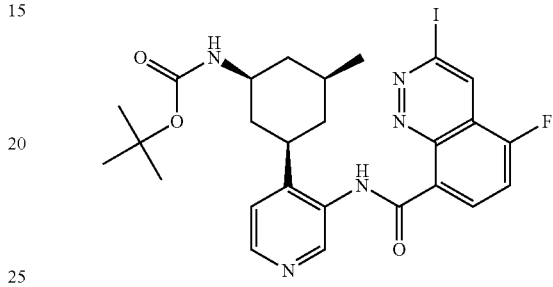

A solution of 5-fluoro-3-iodocinnoline-8-carboxylic acid (120 mg, 0.377 mmol) and tert-butyl [(1S,3R,5S)-3-(3-aminopyridin-4-yl)-5-methylcyclohexyl]carbamate (96.0 mg, 0.314 mmol) in DMF (1.0 mL) was added to N,N,N',N'-tetramethyl-O-(7-azabenzotriazol-1-yl)uronium hexafluorophosphate (174 mg, 0.458 mmol) and N,N-diisopropylethylamine (160 μL, 0.94 mmol). The resulting mixture was stirred at room temperature overnight. The reaction was quenched with water, and the aqueous layer was extracted with DCM once. The combined organic layers were dried over Na$_2$SO$_4$, filtered and concentrated. The residue was purified by flash chromatography (eluting with a gradient of 0-100% ethyl acetate/hexanes) to give the desired product as yellow solid (160 mg, 84%). LCMS calculated for C$_{26}$H$_{30}$FIN$_5$O$_3$ (M+H)$^+$: m/z=606.1; Found: 606.1.

Step 11. tert-Butyl {(1S,3R,5S)-3-[3-({[3-(2,6-difluorophenyl)-5-fluorocinnolin-8-yl]carbonyl}amino)pyridin-4-yl]-5-methylcyclohexyl}carbamate

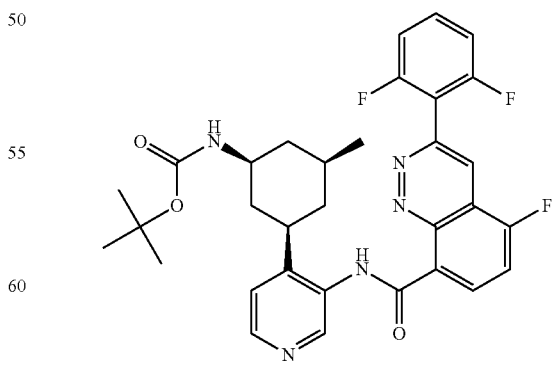

A microwave vial was charged with tert-butyl [(1S,3R, 5S)-3-(3-{[(5-fluoro-3-iodocinnolin-8-yl)carbonyl] amino}pyridin-4-yl)-5-methylcyclohexyl]carbamate (20.2 mg, 0.0334 mmol), 2-(2,6-difluorophenyl)-4,4,5,5-tetramethyl-1,3,2-dioxaborolane (12.8 mg, 0.0534 mmol), dicyclohexyl-(2',4',6'-triisopropylbiphenyl-2-yl)phosphine-(2'-aminobiphenyl-2-yl)(chloro)palladium (1:1) (2.3 mg, 0.0029 mmol) and tripotassium phosphate hydrate (16.9 mg, 0.0735 mmol). The vial was sealed and evacuated under vacuum and refilled with nitrogen (this process was repeated three times), 1,4-dioxane (0.36 mL) and water (0.12 mL) was added. The resulting mixture was stirred at 70° C. for 1 h. After cooling to room temperature, the reaction mixture was diluted with water and DCM. The organic layer was concentrated and purified with flash chromatography (eluting with a gradient of 0-100% ethyl acetate in hexanes) to give the desired product as a yellow oil (10.2 mg, 52%). LCMS calculated for $C_{32}H_{33}F_3N_5O_3$ (M+H)$^+$: m/z=592.3; Found: 592.3.

Step 12. N-{4-[(1R,3S,5S)-3-Amino-5-methylcyclohexyl]pyridin-3-yl}-3-(2,6-difluorophenyl)-5-fluorocinnoline-8-carboxamide The compound from the previous step was treated with 1:1 DCM/TFA (2 mL) for 1 h. The volatiles were removed in vacuo and the residue was dissolved in methanol and purified with prep-LCMS (XBridge C18 column, eluting with a gradient of acetonitrile/water containing 0.1% ammonium hydroxide, at flow rate of 60 mL/min) to give the desired product as a yellow solid (6.2 mg, 73%). LCMS calculated for $C_{27}H_{25}F_3N_5O$ (M+H)$^+$: m/z=492.2; Found: 492.2.

Example 92

N-{4-[(1R,3S,5S)-3-Amino-5-methylcyclohexyl]pyridin-3-yl}-3-ethyl-5-fluorocinnoline-8-carboxamide

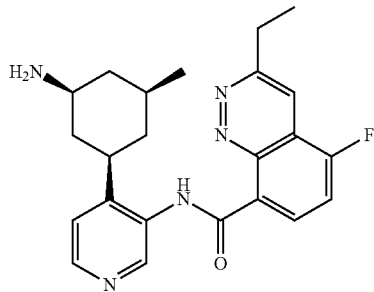 [SMILES: CCc1cc2c(F)ccc(C(=O)Nc3cnccc3[C@@H]3C[C@H](C)C[C@H](N)C3)c2nn1]

Step 1. tert-Butyl [(1S,3R,5S)-3-(3-{[(5-fluoro-3-vinylcinnolin-8-yl)carbonyl]amino}pyridin-4-yl)-5-methylcyclohexyl]carbamate

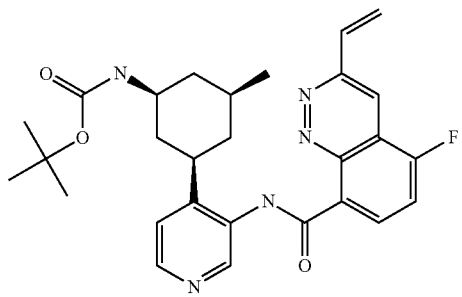 [SMILES: C=Cc1cc2c(F)ccc(C(=O)Nc3cnccc3[C@@H]3C[C@H](C)C[C@H](NC(=O)OC(C)(C)C)C3)c2nn1]

A microwave vial charged with tert-butyl [(1S,3R,5S)-3-(3{[[(5-fluoro-3-iodocinnolin-8-yl)carbonyl]amino}pyridin-4-yl)-5-methylcyclohexyl]carbamate (25.1 mg, 0.0414 mmol), dicyclohexyl-(2',4',6'-triisopropylbiphenyl-2-yl)phosphine-(2'-aminobiphenyl-2-yl)(chloro)palladium (1:1) (2.9 mg, 0.0036 mmol) and tripotassium phosphate hydrate (21.0 mg, 0.0913 mmol) was sealed, evacuated, and refilled with nitrogen (this process was repeated three times). To the vial was added 4,4,5,5-tetramethyl-2-vinyl-1,3,2-dioxaborolane (11.2 μL, 0.0663 mmol), 1,4-dioxane (0.45 mL) and water (0.15 mL). The resulting mixture was stirred at 70° C. for 1 h. After cooling to room temperature, the reaction mixture was diluted with water and DCM. The organic layer was concentrated and purified with flash chromatography (eluting with a gradient of 0-100% ethyl acetate in hexanes) to give the desired product as a yellow oil (13.2 mg, 63%). LCMS calculated for $C_{28}H_{33}FN_5O_3$ (M+H)$^+$: m/z=506.3; Found: 506.2.

Step 2. N-{4-[(1R,3S,5S)-3-Amino-5-methylcyclohexyl]pyridin-3-yl}-3-ethyl-5-fluorocinnoline-8-carboxamide To a solution of tert-butyl [(1S,3R,5S)-3-(3{[[(5-fluoro-3-vinylcinnolin-8-yl)carbonyl]amino}pyridin-4-yl)-5-methylcyclohexyl]carbamate (13.2 mg) in methanol (2 mL) was added 10% palladium on carbon (5 mg). The resulting suspension was stirred under a $H_2$ balloon for 2 h. After filtration and concentration, the residue was treated with 1:1 DCM/TFA (2 mL) for 1 h. The volatiles were removed in vacuo and the residue was dissolved in methanol and purified by prep-LCMS (XBridge C18 column, eluting with a gradient of acetonitrile/water containing 0.1% ammonium hydroxide, at flow rate of 60 mL/min) to give the desired product as yellow solid (4.2 mg, 40%). LCMS calculated for $C_{23}H_{27}FN_5O$ (M+H)$^+$: m/z=408.2; Found: 408.1.

Example 93

N-{4-[(1R,3S,5S)-3-Amino-5-methylcyclohexyl]pyridin-3-yl}-5-fluoro-3-(2-methylpiperidin-1-yl)cinnoline-8-carboxamide

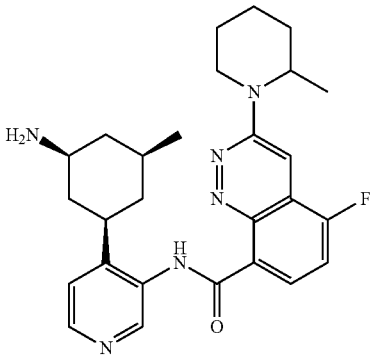 [SMILES: CC1CCCCN1c1cc2c(F)ccc(C(=O)Nc3cnccc3[C@@H]3C[C@H](C)C[C@H](N)C3)c2nn1]

Step 1. tert-Butyl {(1S,3R,5S)-3-[3-({[5-fluoro-3-(2-methylpiperidin-1-yl)cinnolin-8-yl]carbonyl}amino)pyridin-4-yl]-5-methylcyclohexyl}carbamate

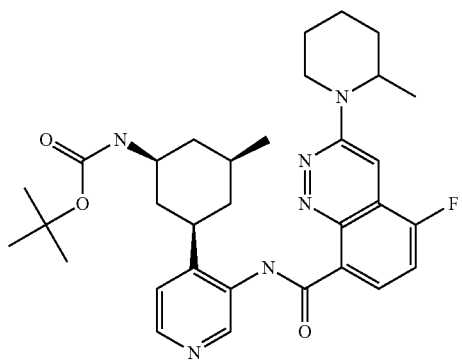 [SMILES: CC1CCCCN1c1cc2c(F)ccc(C(=O)Nc3cnccc3[C@@H]3C[C@H](C)C[C@H](NC(=O)OC(C)(C)C)C3)c2nn1]

To a vial was charged with tert-butyl [(1S,3R,5S)-3-(3-{[(5-fluoro-3-iodocinnolin-8-yl)carbonyl]amino}pyridin-4-yl)-5-methylcyclohexyl]carbamate (21.0 mg, 0.0347 mmol), dicyclohexyl-(2',6'-diisopropoxybiphenyl-2-yl)phosphine-(2'-aminobiphenyl-2-yl)(chloro)palladium (1:1) (2.7 mg, 0.0035 mmol) and cesium carbonate (46.3 mg, 0.142 mmol). The vial was sealed with a teflon screw-cap, evacuated and backfilled with nitrogen (this process was repeated a total of three times). A solution of 2-methylpiperidine (20.4 µL, 0.173 mmol) in anhydrous dioxane (0.4 mL) was added. The mixture was heated at 80° C. overnight. After cooling to room temperature, the reaction mixture was diluted with water and DCM, and the organic layer was separated and concentrated. The crude product was purified with flash chromatography (eluting with a gradient of 0-100% ethyl acetate in hexanes) to give the desired product as a brown oil. LCMS calculated for $C_{32}H_{42}FN_6O_3$ (M+H)$^+$: m/z=577.3; Found: 577.3.

Step 2. N-{4-[(1R,3S,5S)-3-Amino-5-methylcyclohexyl]pyridin-3-yl}-5-fluoro-3-(2-methylpiperidin-1-yl)cinnoline-8-carboxamide The compound from the previous step was treated with 1:1 DCM/TFA (2 mL) for 1 h. The volatiles were removed in vacuo and the residue was dissolved in methanol and purified with prep-LCMS (XBridge C18 column, eluting with a gradient of acetonitrile/water containing 0.1% TFA, at flow rate of 60 mL/min) to give the desired product as a yellow solid (1.2 mg, 7% over 2 steps). LCMS calculated for $C_{27}H_{34}FN_6O$ (M+H)$^+$: m/z=477.3; Found: 477.3.

Example 94

N-{4-[(1R,3S,5S)-3-Amino-5-methylcyclohexyl]pyridin-3-yl}-5-fluoro-3-[(3R)-3-methylmorpholin-4-yl]cinnoline-8-carboxamide

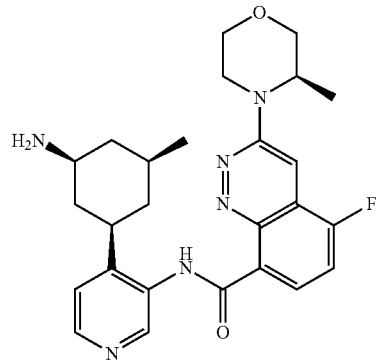 [SMILES: C[C@@H]1C[C@H](N)C[C@H](c2ccncc2NC(=O)c2ccc(F)c3cc(N4CCOC[C@H]4C)nnc23)C1]

This compound was prepared according to the procedure described in Example 93, using (3R)-3-methylmorpholine, instead of 2-methylpiperidine as starting material. LCMS calculated for $C_{26}H_{32}FN_6O_2$ (M+H)$^+$: m/z=479.3; Found: 479.2. $^1$H NMR (600 MHz, DMSO) δ 12.83 (s, 1H), 9.49 (s, 1H), 8.51 (d, J=5.4 Hz, 1H), 8.37 (dd, J=8.0, 5.8 Hz, 1H), 8.00 (m, 2H), 7.66 (m, 1H), 7.62 (s, 1H), 7.58 (d, J=5.4 Hz, 1H), 4.70 (dd, J=6.7, 2.3 Hz, 1H), 4.14-4.05 (m, 2H), 3.87 (d, J=11.3 Hz, 1H), 3.79 (m, 1H), 3.64 (m, 1H), 3.39-3.29 (m, 3H), 2.12 (d, J=11.7 Hz, 1H), 2.03 (m, 2H), 1.90 (d, J=12.6 Hz, 1H), 1.54 (m, 1H), 1.28 (d, J=6.7 Hz, 3H), 1.17 (m, 2H), 1.02 (d, J=6.4 Hz, 3H).

Example 95

N-{4-[(1R,3S,5S)-3-Amino-5-methylcyclohexyl]pyridin-3-yl}-5-fluoro-3-[(2R)-2-methylpyrrolidin-1-yl]cinnoline-8-carboxamide

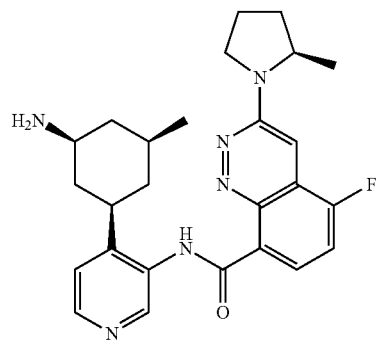 [SMILES: C[C@@H]1C[C@H](N)C[C@H](c2ccncc2NC(=O)c2ccc(F)c3cc(N4CCC[C@H]4C)nnc23)C1]

This compound was prepared according to the procedure described in Example 93, using (2R)-2-methylpyrrolidine, instead of 2-methylpiperidine as starting material. LCMS calculated for $C_{26}H_{32}FN_6O$ (M+H)$^+$: m/z=463.3; Found: 463.3. $^1$H NMR (500 MHz, dmso) δ 13.00 (s, 1H), 9.56 (s, 1H), 8.49 (d, J=5.4 Hz, 1H), 8.29 (dd, J=8.1, 5.9 Hz, 1H), 7.96 (s, 2H), 7.62-7.54 (m, 2H), 7.16 (s, 1H), 4.47-4.40 (m, 1H), 3.70 (t, J=8.3 Hz, 1H), 3.45 (m, 2H), 3.33 (t, J=12.1 Hz, 1H), 2.24-2.03 (m, 7H), 1.91-1.80 (m, 2H), 1.51 (q, J=12.1 Hz, 1H), 1.28 (d, J=6.3 Hz, 3H), 1.16 (m, 2H), 1.01 (d, J=6.5 Hz, 3H).

Example 96

N-(4-((1R,3S,5S)-3-Amino-5-methylcyclohexyl)pyridin-3-yl)-3-(2-azabicyclo[2.2.1]heptan-2-yl)-5-fluoroquinoline-8-carboxamide

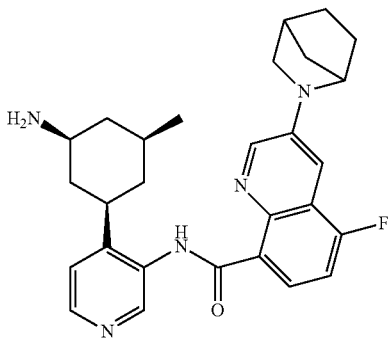 [SMILES: C[C@@H]1C[C@H](N)C[C@H](c2ccncc2NC(=O)c2ccc(F)c3cc(N4CC5CCC4C5)cnc23)C1]

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then 1,4-dioxane (2 mL) and 2-azabicyclo[2.2.1]heptane (6 µL, 0.06 mmol) were added. The reaction was stirred at 80° C. overnight. At this time the reaction was quenched by the addition of water and the product was extracted with ethyl acetate. Combined organic fractions were washed with brine, dried over sodium sulfate and the solvents were evaporated under reduced pressure. Trifluoroacetic acid (1 mL) and dichloromethane (1 mL) were added to the obtained crude product and the reaction mixture was stirred at r.t. for 1 h. After dilution with acetonitrile and neutralization by the addition of the ammonia solution, the desired product was purified by RP-HPLC (water XBridge C18 column, 30 mm×100 mm, 5 µm particle size, eluting with a gradient of acetonitrile/water containing 0.1% NH$_4$OH, at flow rate of 60 mL/min). LCMS calculated for C$_{28}$H$_{33}$FN$_5$O (M+H)$^+$ m/z=474.2; found: 474.2.

Example 97

N-(4-((1R,3S,5S)-3-Amino-5-methylcyclohexyl)pyridin-3-yl)-5-fluoro-3-((2-fluorophenyl)(methyl)amino)quinoline-8-carboxamide

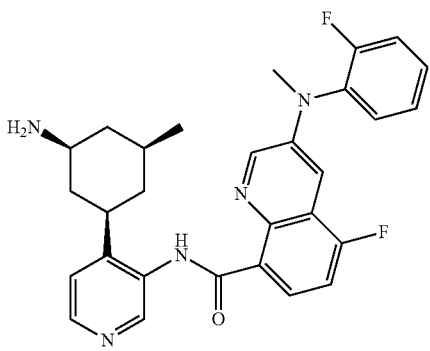 [SMILES: C[C@@H]1C[C@H](N)C[C@H](c2ccncc2NC(=O)c2ccc(F)c3cc(N(C)c4ccccc4F)cnc23)C1]

This compound was synthesized according to the procedures of Example 96, using 2-fluoro-N-methylaniline. LCMS calculated for C$_{29}$H$_{30}$F$_2$N$_5$O (M+H)$^+$ m/z=502.2; found: 502.2.

1H NMR (600 MHz, DMSO-d6) δ 13.10 (s, 1H), 9.35 (s, 1H), 8.51-8.41 (m, 3H), 7.93 (br, 2H), 7.74 (d, J=3.0 Hz, 1H), 7.65-7.57 (m, 2H), 7.54-7.45 (m, 3H), 7.44-7.38 (m, 1H), 3.48 (s, 3H), 3.21-3.08 (m, 1H), 3.02-2.88 (m, 1H), 2.01 (d, J=12.0 Hz, 1H), 1.89 (d, J=12.4 Hz, 1H), 1.80 (d, J=12.8 Hz, 1H), 1.47 (q, J=12.0 Hz, 1H), 1.36-1.22 (m, 1H), 1.14-1.06 (m, 1H), 1.06-0.99 (m, 1H), 0.80 (d, J=6.5 Hz, 3H) ppm.

Example 98

N-(4-((1R,3S,5S)-3-Amino-5-methylcyclohexyl)pyridin-3-yl)-5-fluoro-3-(3-hydroxy-8-azabicyclo[3.2.1]octan-8-yl)quinoline-8-carboxamide

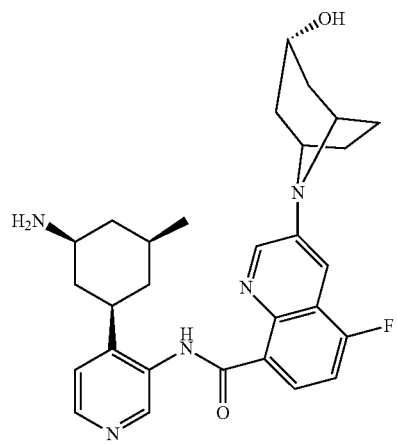

This compound was synthesized according to the procedures of Example 96, using endo-8-azabicyclo[3.2.1]octan-3-ol. LCMS calculated for C$_{29}$H$_{35}$FN$_5$O$_2$ (M+H)$^+$ m/z=504.2; found: 504.2.

Example 99

N-(4-((1R,3S,5S)-3-Amino-5-methylcyclohexyl)pyridin-3-yl)-3-((R)-2,4-dimethyl-5-oxopiperazin-1-yl)-5-fluoroquinoline-8-carboxamide

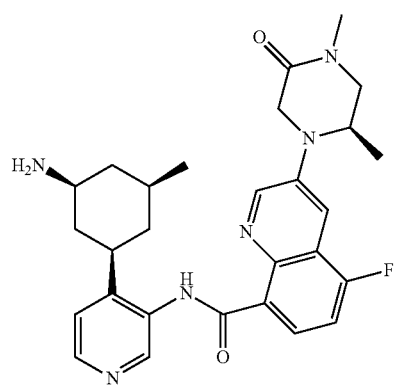 [SMILES: C[C@@H]1C[C@H](N)C[C@H](c2ccncc2NC(=O)c2ccc(F)c3cc(N4CC(=O)N(C)C[C@H]4C)cnc23)C1]

This compound was synthesized according to the procedures of Example 96, using (R)-1,5-dimethylpiperazin-2-one. LCMS calculated for $C_{28}H_{34}FN_6O_2$ (M+H)+ m/z=505.2; found: 505.2.

Example 100

N-(4-((1R,3S,5S)-3-Amino-5-methylcyclohexyl)pyridin-3-yl)-5-fluoro-3-((R)-4-oxodihydro-1H-pyrido[1,2-a]pyrazin-2(6H,7H,8H,9H,9aH)-yl)quinoline-8-carboxamide

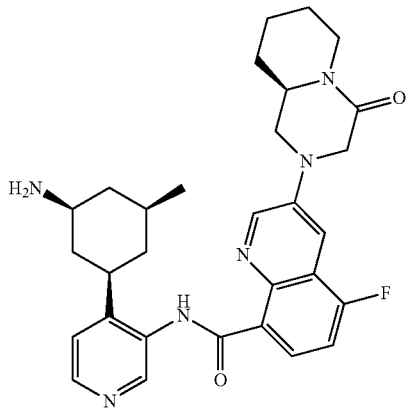 [SMILES: C[C@@H]1C[C@H](N)C[C@H](c2ccncc2NC(=O)c2ccc(F)c3cc(N4CC(=O)N5CCCC[C@@H]5C4)cnc23)C1]

This compound was synthesized according to the procedures of Example 96, using (R)-hexahydro-1H-pyrido[1,2-a]pyrazin-4(6H)-one. LCMS calculated for $C_{30}H_{36}FN_6O_2$ (M+H)+ m/z=531.2; found: 531.3.

1H NMR (600 MHz, DMSO-d6) δ 13.04 (s, 1H), 9.24 (s, 1H), 9.07 (d, J=3.0 Hz, 1H), 8.55 (d, J=5.4 Hz, 1H), 8.46 (dd, J=8.3, 6.2 Hz, 1H), 8.08-7.99 (m, 2H), 7.83 (d, J=3.0 Hz, 1H), 7.63 (d, J=5.5 Hz, 1H), 7.60 (dd, J=9.4, 8.5 Hz, 1H), 4.57-4.50 (m, 1H), 4.25 (d, J=16.6 Hz, 1H), 4.11 (dd, J=13.3, 3.4 Hz, 1H), 4.02 (d, J=16.7 Hz, 1H), 3.63-3.55 (m, 1H), 3.39 (dd, J=13.3, 8.1 Hz, 1H), 3.33-3.16 (m, 2H), 2.54 (td, J=13.1, 2.9 Hz, 1H), 2.14 (d, J=11.8 Hz, 1H), 1.99 (d, J=12.2 Hz, 1H), 1.93-1.80 (m, 4H), 1.80-1.68 (m, 1H), 1.61-1.47 (m, 2H), 1.39-1.26 (m, 2H), 1.18 (q, J=12.2 Hz, 1H), 1.10 (q, J=12.1 Hz, 1H), 0.99 (d, J=6.6 Hz, 3H) ppm.

Example 101

N-(4-((1R,3S,5S)-3-Amino-5-methylcyclohexyl)pyridin-3-yl)-5-fluoro-3-(4-methoxyazepan-1-yl)quinoline-8-carboxamide

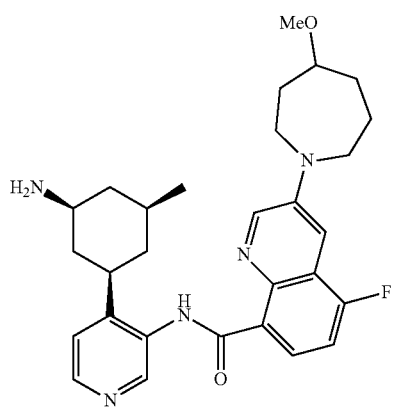 [SMILES: COC1CCCN(c2cnc3c(C(=O)Nc4cnccc4[C@@H]4C[C@H](C)C[C@H](N)C4)ccc(F)c3c2)CC1]

This compound was synthesized according to the procedures of Example 96, using 4-methoxyazepane. LCMS calculated for $C_{29}H_{37}FN_5O_2$ (M+H)+ m/z=506.2; found: 506.2.

Example 102

N-(4-((1R,3S,5S)-3-Amino-5-methylcyclohexyl)pyridin-3-yl)-5-fluoro-3-(1,4-oxazepan-4-yl)quinoline-8-carboxamide

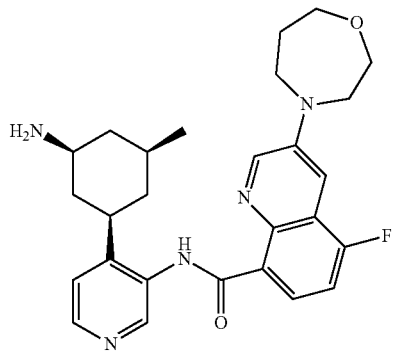 [SMILES: C[C@@H]1C[C@H](N)C[C@H](c2ccncc2NC(=O)c2ccc(F)c3cc(N4CCCOCC4)cnc23)C1]

This compound was synthesized according to the procedures of Example 96, using 1,4-oxazepane. LCMS calculated for $C_{27}H_{33}FN_5O_2$ (M+H)+ m/z=478.2; found: 478.2.

1H NMR (600 MHz, DMSO-d6) δ 13.18 (s, 1H), 9.27 (s, 1H), 8.88 (d, J=3.1 Hz, 1H), 8.52 (s, 1H), 8.36 (dd, J=8.3, 6.2 Hz, 1H), 8.01 (s, 2H), 7.58 (d, J=5.0 Hz, 1H), 7.56-7.49 (m, 2H), 3.86-3.78 (m, 6H), 3.70-3.63 (m, 2H), 3.32-3.14 (m, 2H), 2.12 (d, J=11.9 Hz, 1H), 2.03-1.94 (m, 3H), 1.93 (d, J=12.9 Hz, 1H), 1.80-1.66 (m, 1H), 1.57 (q, J=12.0 Hz, 1H), 1.23-1.06 (m, 2H), 1.00 (d, J=6.6 Hz, 3H) ppm.

Example 103

N-(4-((1R,3S,5S)-3-Amino-5-methylcyclohexyl)pyridin-3-yl)-5-fluoro-3-(6-hydroxy-2-azaspiro[3.3]heptan-2-yl)quinoline-8-carboxamide

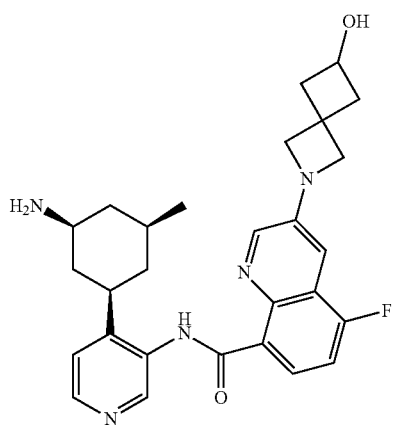 [SMILES: C[C@@H]1C[C@H](N)C[C@H](c2ccncc2NC(=O)c2ccc(F)c3cc(N4CC5(CC(O)C5)C4)cnc23)C1]

This compound was synthesized according to the procedures of Example 96, using 2-azaspiro[3.3]heptan-6-ol. LCMS calculated for $C_{28}H_{33}FN_5O_2$ (M+H)+ m/z=490.2; found: 490.2.

113

Example 104

N-(4-((1R,3S,5S)-3-Amino-5-methylcyclohexyl)pyridin-3-yl)-5-fluoro-3-(4-hydroxyazepan-1-yl)quinoline-8-carboxamide

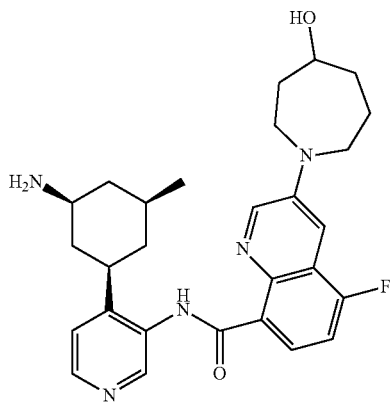 [SMILES: C[C@@H]1C[C@H](N)C[C@H](c2ccncc2NC(=O)c2ccc(F)c3cc(N4CCCC(O)CC4)cnc23)C1]

This compound was synthesized according to the procedures of Example 96, using azepan-4-ol. LCMS calculated for $C_{28}H_{35}FN_5O_2$ (M+H)$^+$ m/z=492.2; found: 492.3.

Example 105

N-(4-((1R,3S,5S)-3-Amino-5-methylcyclohexyl)pyridin-3-yl)-5-fluoro-3-((R)-3-methylpiperidin-1-yl)quinoline-8-carboxamide

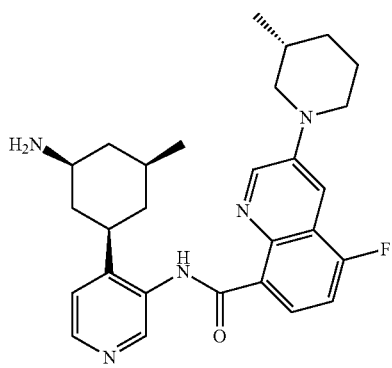 [SMILES: C[C@@H]1C[C@H](N)C[C@H](c2ccncc2NC(=O)c2ccc(F)c3cc(N4CCC[C@@H](C)C4)cnc23)C1]

This compound was synthesized according to the procedures of Example 96, using (R)-3-methylpiperidine. LCMS calculated for $C_{28}H_{35}FN_5O$ (M+H)$^+$ m/z=476.2; found: 476.2.

114

Example 106

N-(4-((1R,3S,5S)-3-Amino-5-methylcyclohexyl)pyridin-3-yl)-3-(3-oxa-9-azabicyclo[3.3.1]nonan-9-yl)-5-fluoroquinoline-8-carboxamide

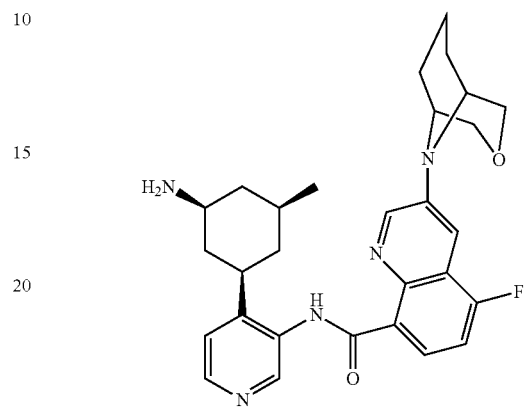

This compound was synthesized according to the procedures of Example 96, using 3-oxa-9-azabicyclo[3.3.1]nonane. LCMS calculated for $C_{29}H_{35}FN_5O_2$ (M+H)$^+$ m/z=504.2; found: 504.2.

Example 107

N-(4-((1R,3S,5S)-3-Amino-5-methylcyclohexyl)pyridin-3-yl)-5-fluoro-3-(2-azaspiro[3.3]heptan-2-yl)quinoline-8-carboxamide

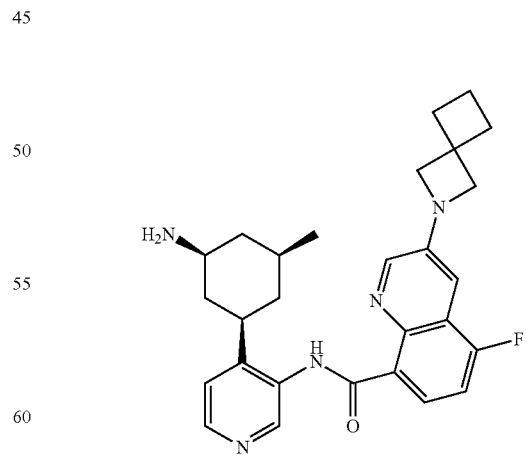

This compound was synthesized according to the procedures of Example 96, using 2-azaspiro[3.3]heptane. LCMS calculated for $C_{28}H_{33}FN_5O$ (M+H)$^+$ m/z=474.2; found: 474.2.

Example 108

N-(4-((1R,3S,5S)-3-Amino-5-methylcyclohexyl)pyridin-3-yl)-5-fluoro-3-((3S,4S)-3-fluoro-4-hydroxypiperidin-1-yl)quinoline-8-carboxamide

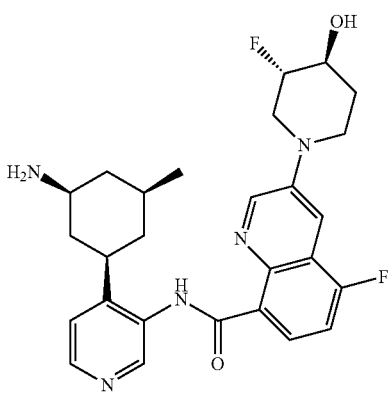 [SMILES: C[C@@H]1C[C@H](N)C[C@H](c2ccncc2NC(=O)c2ccc(F)c3cc(N4CC[C@H](O)[C@@H](F)C4)cnc23)C1]

This compound was synthesized according to the procedures of Example 96, using (3S,4S)-3-fluoropiperidin-4-ol. LCMS calculated for $C_{27}H_{32}F_2N_5O_2$ (M+H)$^+$ m/z=496.2; found: 496.2.

1H NMR (600 MHz, DMSO-d6) δ 12.95 (s, 1H), 9.17 (d, J=3.0 Hz, 1H), 9.08 (s, 1H), 8.44 (dd, J=8.3, 6.2 Hz, 1H), 8.35 (d, J=5.1 Hz, 1H), 7.77 (d, J=3.0 Hz, 1H), 7.59-7.53 (m, 1H), 7.38 (d, J=5.1 Hz, 1H), 5.40 (br, 1H), 4.61-4.41 (m, 1H), 4.09-3.94 (m, 1H), 3.85-3.68 (m, 2H), 3.49-3.41 (m, 1H), 3.37-3.25 (m, 1H), 2.99 (t, J=12.1 Hz, 1H), 2.80-2.65 (m, 1H), 2.13-2.00 (m, 2H), 1.83 (d, J=12.7 Hz, 1H), 1.75 (d, J=12.5 Hz, 1H), 1.70-1.50 (m, 2H), 1.25-1.09 (m, 2H), 0.94 (d, J=6.6 Hz, 3H), 0.81 (q, J=11.9 Hz, 1H) ppm.

Example 109

N-(4-((1R,3S,5S)-3-amino-5-methylcyclohexyl)pyridin-3-yl)-5-fluoro-3-(1,2-oxazinan-2-yl)quinoline-8-carboxamide

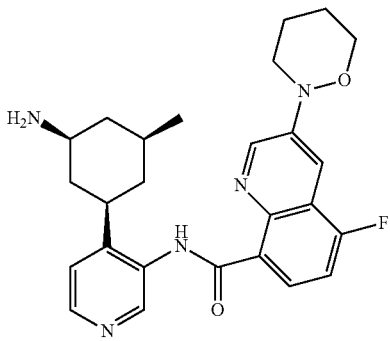 [SMILES: C[C@@H]1C[C@H](N)C[C@H](c2ccncc2NC(=O)c2ccc(F)c3cc(N4CCCCO4)cnc23)C1]

This compound was synthesized according to the procedures of Example 96, using 1,2-oxazinane. LCMS calculated for $C_{26}H_{31}FN_5O_2$ (M+H)$^+$ m/z=464.2; found: 464.3.

Example 110

N-(4-((1R,3S,5S)-3-Amino-5-methylcyclohexyl)pyridin-3-yl)-3-(dihydro-1H-furo[3,4-c]pyrrol-5(3H,6H,6aH)-yl)-5-fluoroquinoline-8-carboxamide

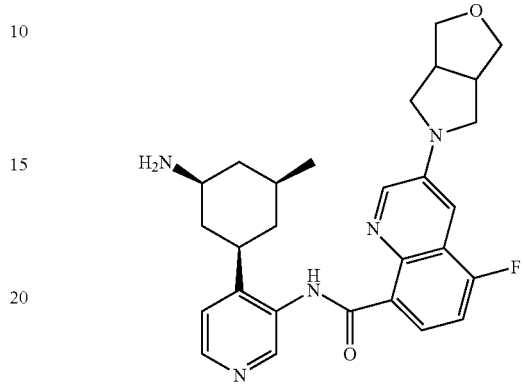

This compound was synthesized according to the procedures of Example 96, using hexahydro-1H-furo[3,4-c]pyrrole. LCMS calculated for $C_{28}H_{33}FN_5O_2$ (M+H)$^+$ m/z=490.2; found: 490.2.

Example 111

N-(4-((1R,3S,5S)-3-Amino-5-methylcyclohexyl)pyridin-3-yl)-5-fluoro-3-(3-methylazetidin-1-yl)quinoline-8-carboxamide

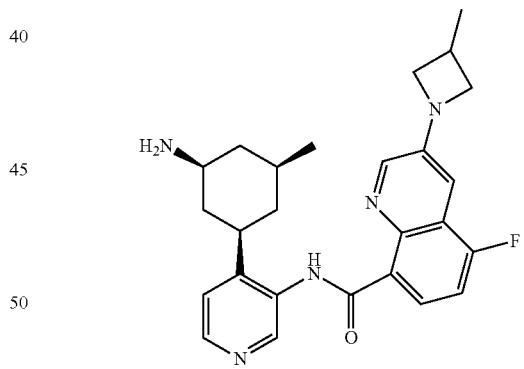

This compound was synthesized according to the procedures of Example 96, using 3-methylazetidine. LCMS calculated for $C_{26}H_{31}FN_5O$ (M+H)$^+$ m/z=448.2; found: 448.2.

1H NMR (600 MHz, DMSO-d6) δ 13.11 (s, 1H), 9.26 (s, 1H), 8.52 (d, J=5.1 Hz, 1H), 8.46 (d, J=2.9 Hz, 1H), 8.37 (dd, J=8.3, 6.3 Hz, 1H), 8.08-7.98 (m, 2H), 7.59 (d, J=5.4 Hz, 1H), 7.56-7.51 (m, 1H), 7.23 (d, J=2.8 Hz, 1H), 4.24 (td, J=7.7, 2.9 Hz, 2H), 3.74-3.68 (m, 2H), 3.27-3.13 (m, 2H), 2.99-2.89 (m, 1H), 2.12 (d, J=11.8 Hz, 1H), 2.01 (d, J=12.2 Hz, 1H), 1.89 (d, J=12.9 Hz, 1H), 1.79-1.68 (m, 1H), 1.56 (q, J=12.1 Hz, 1H), 1.32 (d, J=6.9 Hz, 3H), 1.19 (q, J=12.2 Hz, 1H), 1.11 (q, J=12.1 Hz, 1H), 1.02 (d, J=6.6 Hz, 3H) ppm.

Example 112

N-(4-((1R,3S,5S)-3-Amino-5-methylcyclohexyl)pyridin-3-yl)-3-((S)-2,4-dimethyl-3-oxopiperazin-1-yl)-5-fluoroquinoline-8-carboxamide

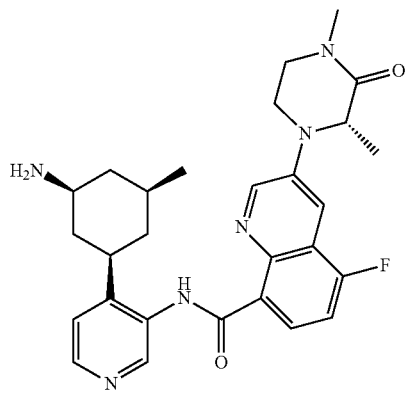 [SMILES: C[C@@H]1C[C@H](N)C[C@H](c2ccncc2NC(=O)c2ccc(F)c3cc(N4CCN(C)C(=O)[C@@H]4C)cnc23)C1]

This compound was synthesized according to the procedures of Example 96, using (S)-1,3-dimethylpiperazin-2-one. LCMS calculated for $C_{28}H_{34}FN_6O_2$ (M+H)$^+$ m/z=505.2; found: 505.2.

Example 113

N-(4-((1R,3S,5S)-3-Amino-5-methylcyclohexyl)pyridin-3-yl)-5-fluoro-3-((S)-3-methylpiperidin-1-yl)quinoline-8-carboxamide

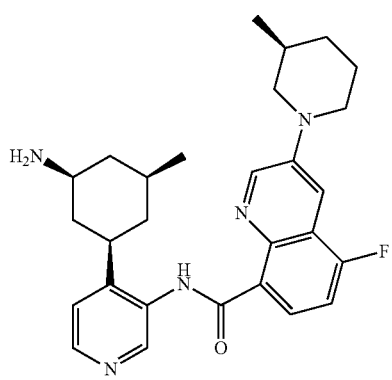 [SMILES: C[C@@H]1C[C@H](N)C[C@H](c2ccncc2NC(=O)c2ccc(F)c3cc(N4CCC[C@H](C)C4)cnc23)C1]

This compound was synthesized according to the procedures of Example 96, using (S)-3-methylpiperidine. LCMS calculated for $C_{28}H_{35}FN_5O$ (M+H)$^+$ m/z=476.2; found: 476.2.

Example 114

N-(4-((1R,3S,5S)-3-Amino-5-methylcyclohexyl)pyridin-3-yl)-3-(4-cyclopropyl-3-oxopiperazin-1-yl)-5-fluoroquinoline-8-carboxamide

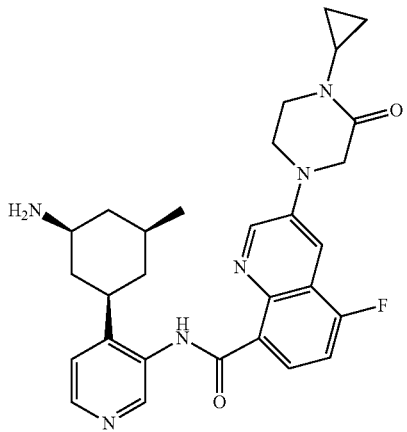 [SMILES: C[C@@H]1C[C@H](N)C[C@H](c2ccncc2NC(=O)c2ccc(F)c3cc(N4CCN(C5CC5)C(=O)C4)cnc23)C1]

This compound was synthesized according to the procedures of Example 96, using 1-cyclopropylpiperazin-2-one. LCMS calculated for $C_{29}H_{34}FN_6O_2$ (M+H)$^+$ m/z=517.2; found: 517.2.

1H NMR (600 MHz, DMSO-d6) δ 13.03 (s, 1H), 9.22 (s, 1H), 9.00 (d, J=3.0 Hz, 1H), 8.54 (d, J=5.3 Hz, 1H), 8.44 (dd, J=8.3, 6.2 Hz, 1H), 8.05-7.98 (m, 2H), 7.72 (d, J=3.0 Hz, 1H), 7.64-7.55 (m, 2H), 4.12 (d, J=1.9 Hz, 2H), 3.81-3.72 (m, 2H), 3.49 (t, J=5.4 Hz, 2H), 3.30-3.10 (m, 2H), 2.87-2.73 (m, 1H), 2.13 (d, J=11.9 Hz, 1H), 1.99 (d, J=12.0 Hz, 1H), 1.90 (d, J=12.8 Hz, 1H), 1.81-1.70 (m, 1H), 1.53 (q, J=12.1 Hz, 1H), 1.20 (q, J=12.2 Hz, 1H), 1.10 (q, J=12.1 Hz, 1H), 1.01 (d, J=6.6 Hz, 3H), 0.83-0.66 (m, 5H) ppm.

Example 115

N-(4-((1R,3S,5S)-3-Amino-5-methylcyclohexyl)pyridin-3-yl)-5-fluoro-3-(4-isopropyl-3-oxopiperazin-1-yl)quinoline-8-carboxamide

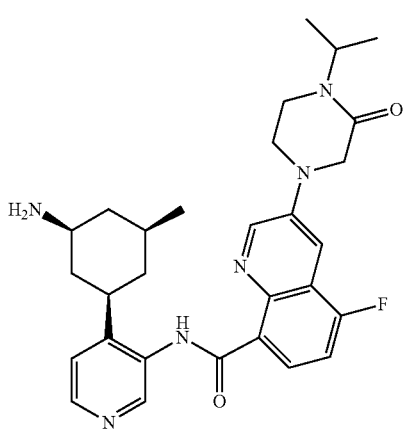 [SMILES: CC(C)N1CCN(c2cnc3c(C(=O)Nc4cnccc4[C@@H]4C[C@H](C)C[C@H](N)C4)ccc(F)c3c2)CC1=O]

119

This compound was synthesized according to the procedures of Example 96, using 1-isopropylpiperazin-2-one. LCMS calculated for $C_{29}H_{36}FN_6O_2$ (M+H)$^+$ m/z=519.2; found: 519.2.

Example 116

N-(4-((1R,3S,5S)-3-Amino-5-methylcyclohexyl)pyridin-3-yl)-3-(3,3-dimethylazetidin-1-yl)-5-fluoro-quinoline-8-carboxamide

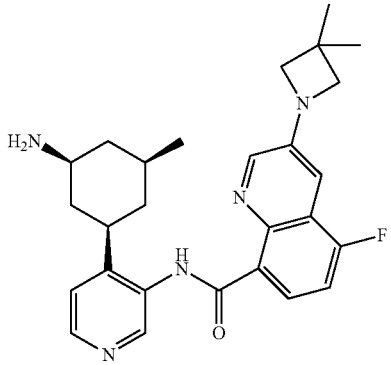 [SMILES: C[C@@H]1C[C@H](N)C[C@H](c2ccncc2NC(=O)c2ccc(F)c3cc(N4CC(C)(C)C4)cnc23)C1]

This compound was synthesized according to the procedures of Example 96, using 3,3-dimethylazetidine. LCMS calculated for $C_{27}H_{33}FN_5O$ (M+H)$^+$ m/z=462.2; found: 462.3.

1H NMR (600 MHz, DMSO-d6) δ 13.08 (s, 1H), 9.24 (s, 1H), 8.51 (d, J=5.3 Hz, 1H), 8.48 (d, J=2.9 Hz, 1H), 8.38 (dd, J=8.3, 6.3 Hz, 1H), 8.01 (br, 2H), 7.59-7.56 (m, 1H), 7.56-7.52 (m, 1H), 7.25 (d, J=2.8 Hz, 1H), 3.84 (d, J=1.8 Hz, 4H), 3.29-3.11 (m, 2H), 2.12 (d, J=11.9 Hz, 1H), 2.01 (d, J=11.9 Hz, 1H), 1.90 (d, J=12.7 Hz, 1H), 1.80-1.68 (m, 1H), 1.56 (q, J=12.0 Hz, 1H), 1.36 (s, 6H), 1.19 (q, J=12.2 Hz, 1H), 1.11 (q, J=12.1 Hz, 1H), 1.02 (d, J=6.6 Hz, 3H) ppm.

Example 117

N-(4-((1R,3S,5S)-3-Amino-5-methylcyclohexyl)pyridin-3-yl)-5-fluoro-3-(4-isobutyl-3-oxopiperazin-1-yl)quinoline-8-carboxamide

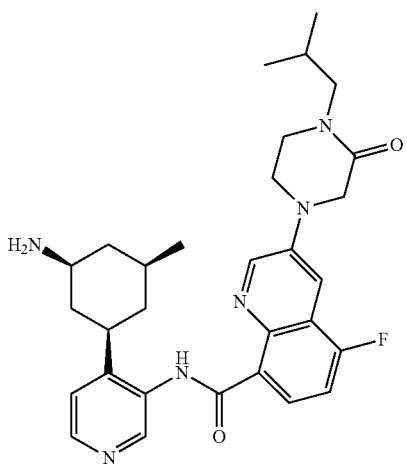 [SMILES: CC(C)CN1CCN(c2cnc3c(C(=O)Nc4cnccc4[C@@H]4C[C@H](C)C[C@H](N)C4)ccc(F)c3c2)CC1=O]

120

This compound was synthesized according to the procedures of Example 96, using 1-isobutylpiperazin-2-one. LCMS calculated for $C_{30}H_{38}FN_6O_2$ (M+H)$^+$ m/z=533.3; found: 533.3.

Example 118

N-(4-((1R,3S,5S)-3-Amino-5-methylcyclohexyl)pyridin-3-yl)-5-fluoro-3-(3-methoxy-3-methylazetidin-1-yl)quinoline-8-carboxamide

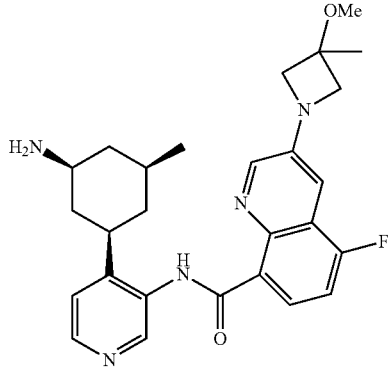 [SMILES: COC1(C)CN(c2cnc3c(C(=O)Nc4cnccc4[C@@H]4C[C@H](C)C[C@H](N)C4)ccc(F)c3c2)C1]

This compound was synthesized according to the procedures of Example 96, using 3-methoxy-3-methylazetidine. LCMS calculated for $C_{27}H_{33}FN_5O_2$ (M+H)$^+$ m/z=478.2; found: 478.2.

1H NMR (600 MHz, DMSO-d6) δ 13.04 (s, 1H), 9.22 (s, 1H), 8.53 (d, J=2.9 Hz, 1H), 8.50 (d, J=5.3 Hz, 1H), 8.39 (dd, J=8.3, 6.3 Hz, 1H), 8.05-7.98 (m, 2H), 7.59-7.52 (m, 2H), 7.33 (d, J=2.8 Hz, 1H), 4.06 (t, J=8.2 Hz, 2H), 3.99 (t, J=8.1 Hz, 2H), 3.26 (s, 3H), 3.24-3.10 (m, 2H), 2.12 (d, J=11.9 Hz, 1H), 2.01 (d, J=12.2 Hz, 1H), 1.89 (d, J=12.7 Hz, 1H), 1.78-1.69 (m, 1H), 1.59-1.49 (m, 4H), 1.20 (q, J=12.2 Hz, 1H), 1.10 (q, J=12.1 Hz, 1H), 1.02 (d, J=6.6 Hz, 3H) ppm.

Example 119

N-(4-((1R,3S,5S)-3-Amino-5-methylcyclohexyl)pyridin-3-yl)-5-fluoro-3-(2-methyl-6,7-dihydro-2H-pyrazolo[4,3-c]pyridin-5(4H)-yl)quinoline-8-carboxamide

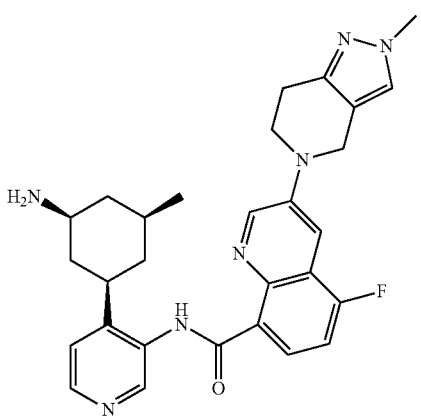 [SMILES: C[C@@H]1C[C@H](N)C[C@H](c2ccncc2NC(=O)c2ccc(F)c3cc(N4CCc5nn(C)cc5C4)cnc23)C1]

121

This compound was synthesized according to the procedures of Example 96, using 2-methyl-4,5,6,7-tetrahydro-2H-pyrazolo[4,3-c]pyridine. LCMS calculated for $C_{29}H_{33}FN_{7O}$ (M+H)+ m/z=514.2; found: 514.2.

Example 120

N-(4-((1R,3S,5S)-3-Amino-5-methylcyclohexyl)pyridin-3-yl)-5-fluoro-3-(5-fluoro-2H-benzo[b][1,4]oxazin-4(3H)-yl)quinoline-8-carboxamide

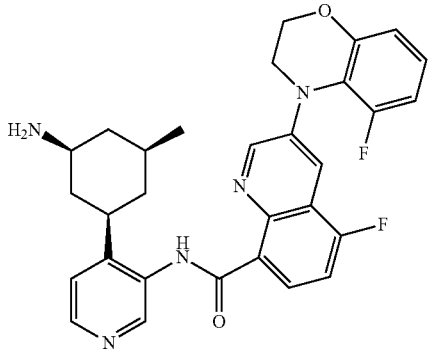 [SMILES: C[C@@H]1C[C@H](N)C[C@H](c2ccncc2NC(=O)c2ccc(F)c3cc(N4CCOc5cccc(F)c54)cnc23)C1]

This compound was synthesized according to the procedures of Example 96, using 5-fluoro-3,4-dihydro-2H-benzo[b][1,4]oxazine. LCMS calculated for $C_{30}H_{30}F_2N_5O_2$ (M+H)+ m/z=530.2; found: 530.3.

Example 121

N-(4-((1R,3S,5S)-3-Amino-5-methylcyclohexyl)pyridin-3-yl)-5-fluoro-3-(7-oxa-2-azaspiro[3.5]nonan-2-yl)quinoline-8-carboxamide

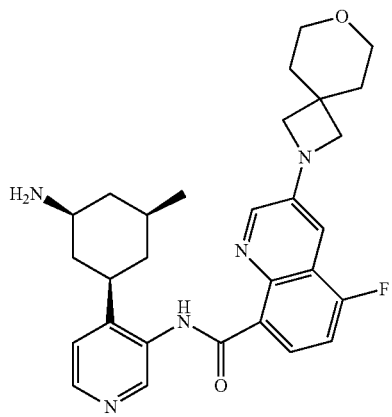 [SMILES: C[C@@H]1C[C@H](N)C[C@H](c2ccncc2NC(=O)c2ccc(F)c3cc(N4CC5(CCOCC5)C4)cnc23)C1]

This compound was synthesized according to the procedures of Example 96, using 7-oxa-2-azaspiro[3.5]nonane. LCMS calculated for $C_{29}H_{35}FN_5O_2$ (M+H)+ m/z=504.2; found: 504.2.

Example 122

N-(4-((1R,3S,5S)-3-Amino-5-methylcyclohexyl)pyridin-3-yl)-3-(3-ethoxyazetidin-1-yl)-5-fluoroquinoline-8-carboxamide

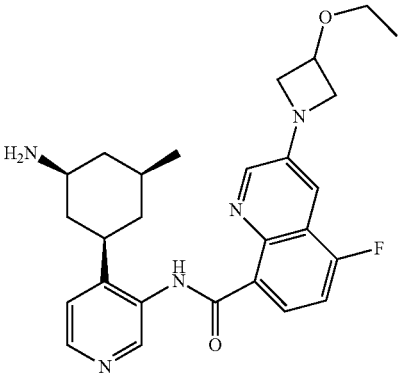 [SMILES: CCOC1CN(c2cnc3c(C(=O)Nc4cnccc4[C@@H]4C[C@H](C)C[C@H](N)C4)ccc(F)c3c2)C1]

This compound was synthesized according to the procedures of Example 96, using 3-ethoxyazetidine. LCMS calculated for $C_{27}H_{33}FN_5O_2$ (M+H)+ m/z=478.2; found: 478.2.

Example 123

N-(4-((1R,3S,5S)-3-Amino-5-methylcyclohexyl)pyridin-3-yl)-5-fluoro-3-((S)-2-(hydroxymethyl)azetidin-1-yl)quinoline-8-carboxamide

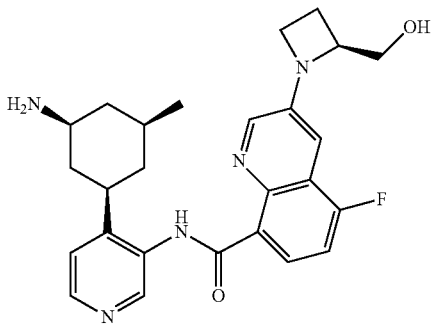 [SMILES: C[C@@H]1C[C@H](N)C[C@H](c2ccncc2NC(=O)c2ccc(F)c3cc(N4CC[C@H]4CO)cnc23)C1]

This compound was synthesized according to the procedures of Example 96, using (S)-azetidin-2-ylmethanol. LCMS calculated for $C_{26}H_{31}FN_5O_2$ (M+H)+ m/z=464.2; found: 464.2.

Example 124

N-(4-((1R,3S,5S)-3-Amino-5-methylcyclohexyl)pyridin-3-yl)-5-fluoro-3-(4-(methylsulfonyl)-1,4-diazepan-1-yl)quinoline-8-carboxamide

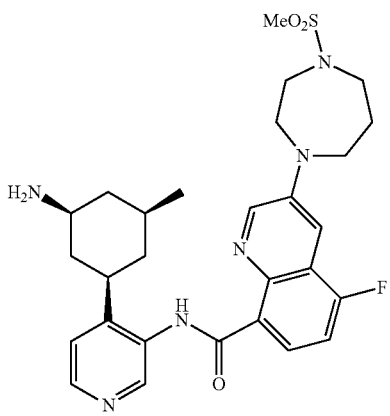 [SMILES: C[C@@H]1C[C@H](N)C[C@H](c2ccncc2NC(=O)c2ccc(F)c3cc(N4CCCN(S(C)(=O)=O)CC4)cnc23)C1]

This compound was synthesized according to the procedures of Example 96, using 1-(methylsulfonyl)-1,4-diazepane. LCMS calculated for $C_{28}H_{36}FN_6O_3S$ $(M+H)^+$ m/z=555.2; found: 555.2.

Example 125

N-(4-((1R,3S,5S)-3-Amino-5-methylcyclohexyl)pyridin-3-yl)-5-fluoro-3-(2-fluorophenylamino)quinoline-8-carboxamide

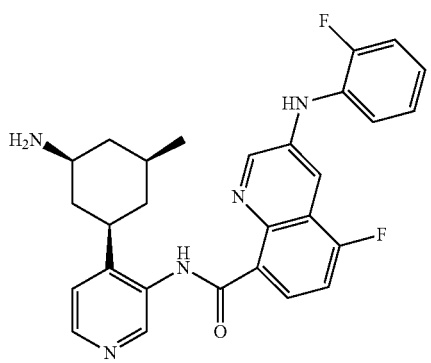 [SMILES: C[C@@H]1C[C@H](N)C[C@H](c2ccncc2NC(=O)c2ccc(F)c3cc(Nc4ccccc4F)cnc23)C1]

This compound was synthesized according to the procedures of Example 96, using 2-fluoroaniline. LCMS calculated for $C_{28}H_{28}F_2N_5O$ $(M+H)^+$ m/z=488.2; found: 488.2.

Example 126

Methyl 4-(8-(4-((1R,3S,5S)-3-amino-5-methylcyclohexyl)pyridin-3-ylcarbamoyl)-5-fluoroquinolin-3-yl)-1,4-diazepane-1-carboxylate

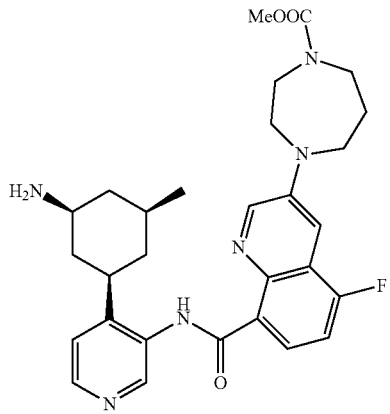 [SMILES: COC(=O)N1CCCN(c2cnc3c(C(=O)Nc4cnccc4[C@@H]4C[C@H](C)C[C@H](N)C4)ccc(F)c3c2)CC1]

This compound was synthesized according to the procedures of Example 96, using methyl 1,4-diazepane-1-carboxylate. LCMS calculated for $C_{29}H_{36}FN_6O_3$ $(M+H)^+$ m/z=535.2; found: 535.3.

Example 127

N-(4-((1R,3S,5S)-3-Amino-5-methylcyclohexyl)pyridin-3-yl)-5-fluoro-3-(1-methyl-4,5-dihydro-1H-pyrazolo[3,4-c]pyridin-6(7H)-yl)quinoline-8-carboxamide

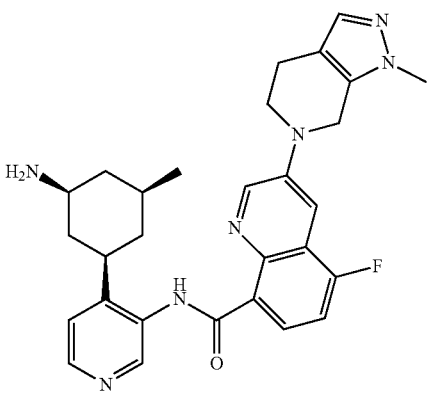 [SMILES: C[C@@H]1C[C@H](N)C[C@H](c2ccncc2NC(=O)c2ccc(F)c3cc(N4CCc5cnn(C)c5C4)cnc23)C1]

This compound was synthesized according to the procedures of Example 96, using 1-methyl-4,5,6,7-tetrahydro-1H-pyrazolo[3,4-c]pyridine. LCMS calculated for $C_{29}H_{33}FN_7O$ $(M+H)^+$ m/z=514.3; found: 514.3.

Example 128

N-(4-((1R,3S,5S)-3-Amino-5-methylcyclohexyl)pyridin-3-yl)-5-fluoro-3-(6-methyl-1,1-dioxido-1,2,6-thiadiazinan-2-yl)quinoline-8-carboxamide

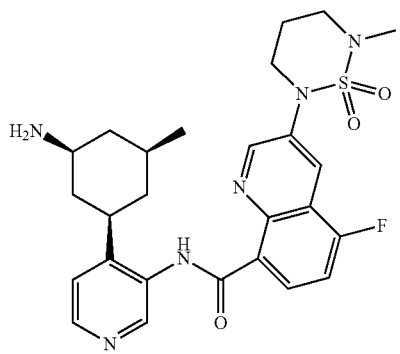 [SMILES: C[C@@H]1C[C@H](N)C[C@H](c2ccncc2NC(=O)c2ccc(F)c3cc(N4CCCN(C)S4(=O)=O)cnc23)C1]

This compound was synthesized according to the procedures of Example 96, using 2-methyl-1,2,6-thiadiazinane 1,1-dioxide. LCMS calculated for $C_{26}H_{32}FN_6O_3S$ (M+H)$^+$ m/z=527.2; found: 527.2.

Example 129

N-(4-((1R,3S,5S)-3-Amino-5-methylcyclohexyl)pyridin-3-yl)-3-(2-cyanophenylamino)-5-fluoroquinoline-8-carboxamide

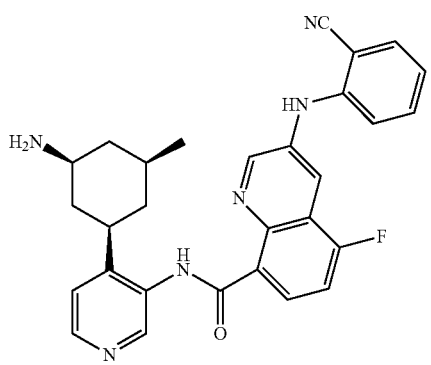 [SMILES: C[C@@H]1C[C@H](N)C[C@H](c2ccncc2NC(=O)c2ccc(F)c3cc(Nc4ccccc4C#N)cnc23)C1]

This compound was synthesized according to the procedures of Example 96, using 2-aminobenzonitrile. LCMS calculated for $C_{29}H_{28}FN_6O$ (M+H)$^+$ m/z=495.2; found: 495.2.

Example 130

N-(4-((1R,3S,5S)-3-Amino-5-methylcyclohexyl)pyridin-3-yl)-5'-fluoro-3,4-dihydro-2H-1,3'-biquinoline-8'-carboxamide

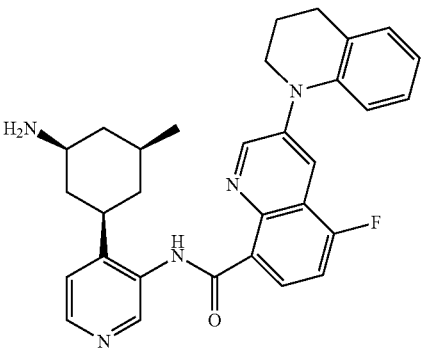 [SMILES: C[C@@H]1C[C@H](N)C[C@H](c2ccncc2NC(=O)c2ccc(F)c3cc(N4CCCc5ccccc54)cnc23)C1]

This compound was synthesized according to the procedures of Example 96, using 1,2,3,4-tetrahydroquinoline. LCMS calculated for $C_{31}H_{33}FN_5O$ (M+H)$^+$ m/z=510.2; found: 510.2.

Example 131

N-(4-((1R,3S,5S)-3-Amino-5-methylcyclohexyl)pyridin-3-yl)-5-fluoro-3-(4-methoxypiperidin-1-yl)quinoline-8-carboxamide

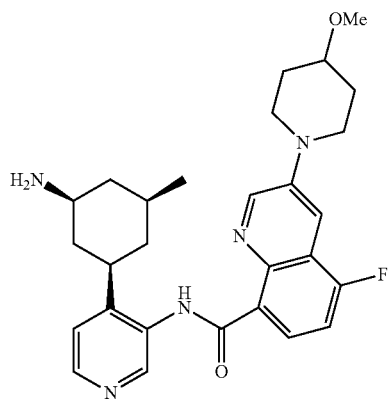

This compound was synthesized according to the procedures of Example 96, using 4-methoxypiperidine. LCMS calculated for $C_{28}H_{35}FN_5O_2$ (M+H)$^+$ m/z=492.2; found: 492.2.

Example 132

N-(4-((1R,3S,5S)-3-Amino-5-methylcyclohexyl)pyridin-3-yl)-5-fluoro-3-(2-(hydroxymethyl)morpholino)quinoline-8-carboxamide

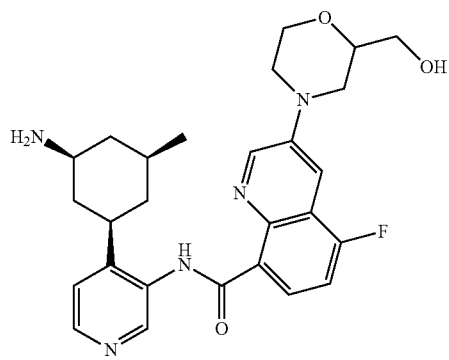 [SMILES: C[C@@H]1C[C@H](N)C[C@H](c2ccncc2NC(=O)c2ccc(F)c3cc(N4CCOC(CO)C4)cnc23)C1]

This compound was synthesized according to the procedures of Example 96, using morpholin-2-ylmethanol. LCMS calculated for $C_{27}H_{33}FN_5O_3$ (M+H)$^+$ m/z=494.2; found: 494.2.

Example 133

N-(4-((1R,3S,5S)-3-Amino-5-methylcyclohexyl)pyridin-3-yl)-5-fluoro-3-(4-(2-methoxyethyl)-3-oxopiperazin-1-yl)quinoline-8-carboxamide

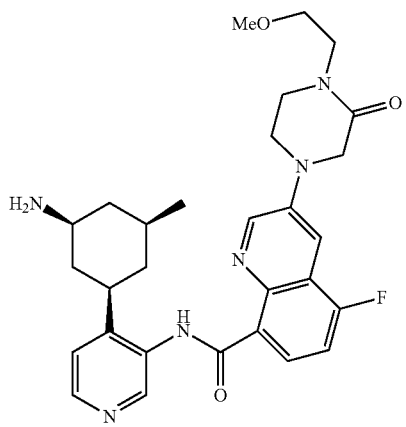 [SMILES: COCCN1CCN(c2cnc3c(C(=O)Nc4cnccc4[C@@H]4C[C@H](C)C[C@H](N)C4)ccc(F)c3c2)CC1=O]

This compound was synthesized according to the procedures of Example 96, using 1-(2-methoxyethyl)piperazin-2-one. LCMS calculated for $C_{29}H_{36}FN_6O_3$ (M+H)$^+$ m/z=535.2; found: 535.2.

Example 134

N-(4-((1R,3S,5S)-3-Amino-5-methylcyclohexyl)pyridin-3-yl)-3-(5,6-dihydro-[1,2,4]triazolo[4,3-a]pyrazin-7(8H)-yl)-5-fluoroquinoline-8-carboxamide

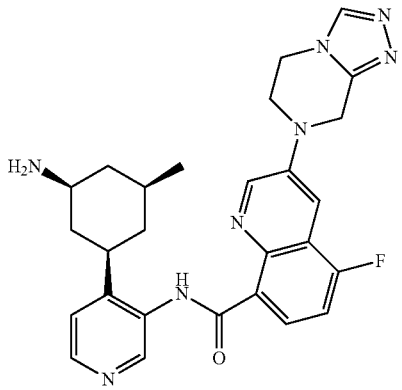 [SMILES: C[C@@H]1C[C@H](N)C[C@H](c2ccncc2NC(=O)c2ccc(F)c3cc(N4CCn5cnnc5C4)cnc23)C1]

This compound was synthesized according to the procedures of Example 96, using 5,6,7,8-tetrahydro-[1,2,4]triazolo[4,3-a]pyrazine. LCMS calculated for $C_{27}H_{30}FN_8O$ (M+H)$^+$ m/z=501.2; found: 501.2.

Example 135

N-(4-((1R,3S,5S)-3-Amino-5-methylcyclohexyl)pyridin-3-yl)-5-fluoro-3-(4-methyl-3-oxo-1,4-diazepan-1-yl)quinoline-8-carboxamide

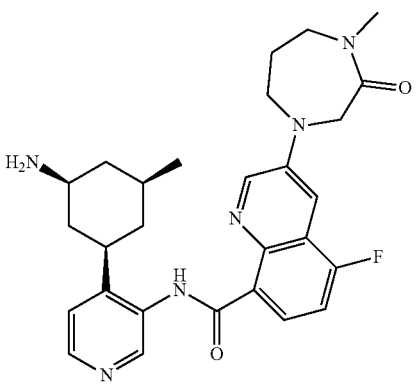 [SMILES: C[C@@H]1C[C@H](N)C[C@H](c2ccncc2NC(=O)c2ccc(F)c3cc(N4CCCN(C)C(=O)C4)cnc23)C1]

This compound was synthesized according to the procedures of Example 96, using 1-methyl-1,4-diazepan-2-one. LCMS calculated for $C_{28}H_{34}FN_6O_2$ (M+H)$^+$ m/z=505.2; found: 505.2.

Example 136

N-(4-((1R,3S,5S)-3-Amino-5-methylcyclohexyl)pyridin-3-yl)-3-(7-azabicyclo[2.2.1]heptan-7-yl)-5-fluoroquinoline-8-carboxamide

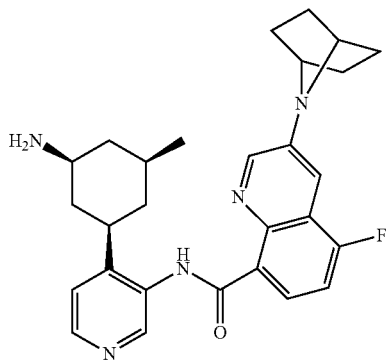 [SMILES: C[C@@H]1C[C@H](N)C[C@H](c2ccncc2NC(=O)c2ccc(F)c3cc(N4C5CCC4CC5)cnc23)C1]

This compound was synthesized according to the procedures of Example 96, using 7-azabicyclo[2.2.1]heptane. LCMS calculated for $C_{28}H_{33}FN_5O$ (M+H)$^+$ m/z=474.2; found: 474.2.

1H NMR (600 MHz, DMSO-d6) δ 13.06 (s, 1H), 9.24 (s, 1H), 8.99 (d, J=2.9 Hz, 1H), 8.53 (d, J=5.3 Hz, 1H), 8.43 (dd, J=8.3, 6.2 Hz, 1H), 8.11-8.00 (m, 2H), 7.86 (d, J=2.8 Hz, 1H), 7.64-7.53 (m, 2H), 4.62 (s, 2H), 3.33-3.14 (m, 2H), 2.14 (d, J=11.9 Hz, 1H), 2.00 (d, J=12.3 Hz, 1H), 1.91 (d, J=12.8 Hz, 1H), 1.82-1.69 (m, 5H), 1.60-1.49 (m, 5H), 1.17 (q, J=12.2 Hz, 1H), 1.10 (q, J=12.1 Hz, 1H), 1.00 (d, J=6.6 Hz, 3H) ppm.

Example 137

N-(4-((1R,3S,5S)-3-Amino-5-methylcyclohexyl)pyridin-3-yl)-5',8-difluoro-3,4-dihydro-2H-1,3'-bi-quinoline-8'-carboxamide

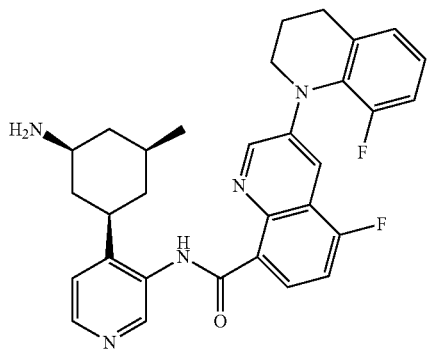 [SMILES: C[C@@H]1C[C@H](N)C[C@H](c2ccncc2NC(=O)c2ccc(F)c3cc(N4CCCc5cccc(F)c54)cnc23)C1]

This compound was synthesized according to the procedures of Example 96, using 8-fluoro-1,2,3,4-tetrahydroquinoline. LCMS calculated for $C_{31}H_{32}F_2N_5O$ (M+H)$^+$ m/z=528.2; found: 528.2.

Example 138

N-(4-((1R,3S,5S)-3-Amino-5-methylcyclohexyl)pyridin-3-yl)-3-(1,1-dioxidoisothiazolidin-2-yl)-5-fluoroquinoline-8-carboxamide

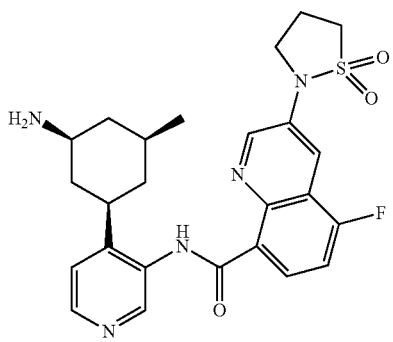 [SMILES: C[C@@H]1C[C@H](N)C[C@H](c2ccncc2NC(=O)c2ccc(F)c3cc(N4CCCS4(=O)=O)cnc23)C1]

This compound was synthesized according to the procedures of Example 96, using isothiazolidine 1,1-dioxide. LCMS calculated for $C_{25}H_{29}FN_5O_3S$ (M+H)$^+$ m/z=498.2; found: 498.2.

Example 139

N-(4-((1R,3S,5S)-3-Amino-5-methylcyclohexyl)pyridin-3-yl)-3-((3-(difluoromethoxy)pyridin-2-yl)(methyl)amino)-5-fluoroquinoline-8-carboxamide

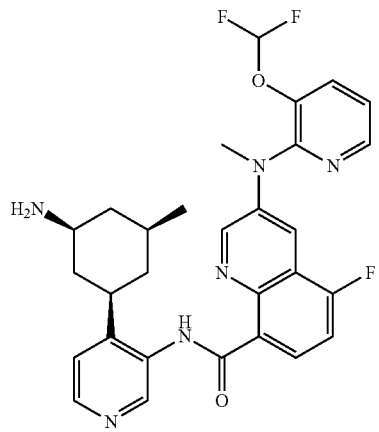 [SMILES: C[C@@H]1C[C@H](N)C[C@H](c2ccncc2NC(=O)c2ccc(F)c3cc(N(C)c4ncccc4OC(F)F)cnc23)C1]

Step 1. Methyl 3-{[3-(difluoromethoxy)pyridin-2-yl]amino}-5-fluoroquinoline-8-carboxylate

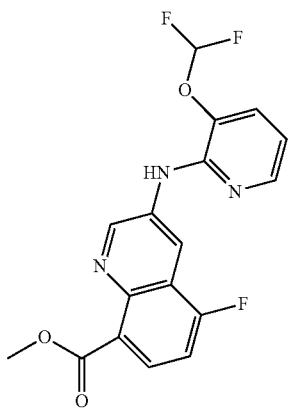 [SMILES: COC(=O)c1ccc(F)c2cc(Nc3ncccc3OC(F)F)cnc12]

Methyl 5-fluoro-3-iodoquinoline-8-carboxylate (200 mg, 0.6 mmol), cesium carbonate (590 mg, 1.8 mmol), 3-(difluoromethoxy)pyridin-2-amine (120 mg, 0.78 mmol), RuPhos Pd G2 (70. mg, 0.09 mmol, Sigma-Aldrich) and a magnet bar were placed in a vial which was then evacuated and backfilled with nitrogen three times. Then 1,4-dioxane (8 mL) was added. The reaction mixture was stirred at 80° C. overnight. At this time the reaction was quenched by the addition of water and the product was extracted with ethyl acetate. Combined organic fractions were washed with brine, dried over sodium sulfate and filtered. The filtrate was concentrated under reduced pressure to give the crude product which was used in the next step without further purification. LCMS calculated for $C_{17}H_{13}F_3N_3O_3$ (M+H)$^+$ m/z=364.1; found: 364.1.

Step 2. Methyl 3-[[3-(difluoromethoxy)pyridin-2-yl](methyl)amino]-5-fluoroquinoline-8-carboxylate

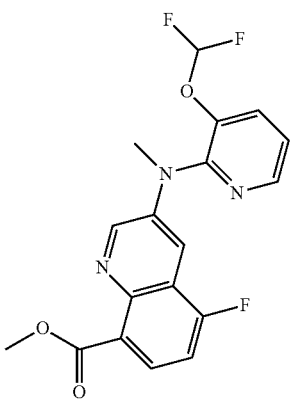 [SMILES: COC(=O)c1ccc(F)c2cc(N(C)c3ncccc3OC(F)F)cnc12]

NaH in mineral oil (29 mg, 0.72 mmol) was slowly added to a mixture of methyl 3-{[3-(difluoromethoxy)pyridin-2-yl]amino}-5-fluoro quino line-8-carboxylate (from previous step) and methyl iodide (0.11 mL, 1.8 mmol) in N,N-dimethylformamide (1.51 mL). After stirring at r.t. for 1 h, the reaction was quenched with water. The mixture was extracted with ethyl acetate. Combined organic fractions were washed with brine, dried over sodium sulfate and filtered. The filtrate was concentrated under reduced pressure. Crude material was purified by Biotage Isolera™ (flash purification system with hexane/ethyl acetate at a ratio from 0 to 100%) to give the desired product (211 mg, 93% over two steps). LCMS calculated for $C_{18}H_{15}F_3N_3O_3$ (M+H)$^+$ m/z=378.1; found: 378.1.

Step 3. 3-[[3-(difluoromethoxy)pyridin-2-yl](methyl)amino]-5-fluoroquinoline-8-carboxylic acid

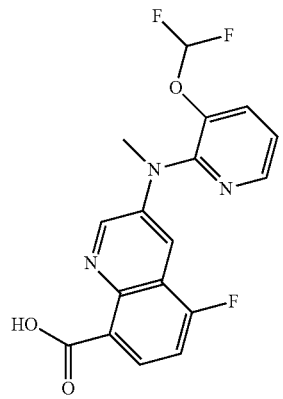 [SMILES: CN(c1cnc2c(C(=O)O)ccc(F)c2c1)c1ncccc1OC(F)F]

A 1 M solution of sodium hydroxide in water (2.2 mL, 2.2 mmol) was added to a solution of methyl 3-[[3-(difluoromethoxy)pyridin-2-yl](methyl)amino]-5-fluoroquinoline-8-carboxylate (211 mg, 0.559 mmol) in tetrahydrofuran (6 mL) and methanol (4 mL). After stirring at r.t. for 2 h, pH was adjusted to 5 by the addition of a 1 M solution of HCl. The product was then extracted with ethyl acetate and the organic phase was washed with brine. The organic phase was dried over sodium sulfate and filtered. The filtrate was concentrated under reduced pressure. The resulting crude product was used directly in the next step without further purification (195 mg, 96%). LCMS calculated for $C_{17}H_{13}F_3N_3O_3$ (M+H)$^+$ m/z=364.1; found 364.1.

Step 4. N-{4-[(1R,3S,5S)-3-Amino-5-methylcyclohexyl]pyridin-3-yl}-3-[[3-(difluoromethoxy)pyridin-2-yl](methyl)amino]-5-fluoroquinoline-8-carboxamide

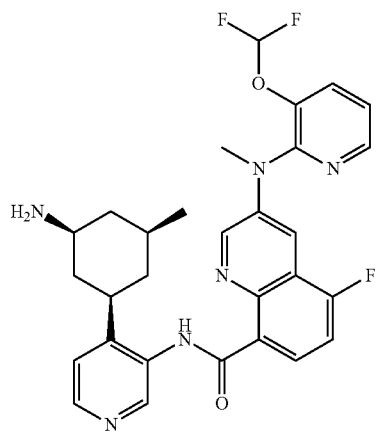 [SMILES: C[C@@H]1C[C@H](N)C[C@H](c2ccncc2NC(=O)c2ccc(F)c3cc(N(C)c4ncccc4OC(F)F)cnc23)C1]

To a mixture of tert-butyl (1S,3R,5S)-3-(3-aminopyridin-4-yl)-5-methylcyclohexylcarbamate (15 mg, 0.049 mmol) and 3-[[3-(difluoromethoxy)pyridin-2-yl](methyl)amino]-5-fluoroquinoline-8-carboxylic acid (17.8 mg, 0.0491 mmol) in N,N-dimethylformamide (1.5 mL) was added N,N-diisopropylethylamine (17 µL, 0.098 mmol) and N,N,N',N'-tetramethyl-O-(7-azabenzotriazol-1-yl)uronium hexafluorophosphate (24 mg, 0.064 mmol). After stirring at r.t. for 2 hours, the reaction was quenched with water. The precipitate was collected by filtration and washed with water twice. Then it was redissolved in ethyl acetate to give a solution which was washed with brine, dried over sodium sulfate and filtered.

After the solvent was evaporated, trifluoroacetic acid (1 mL) and dichloromethane (1 mL) were added to the obtained crude product and the reaction mixture was stirred at r.t. for 1 h. After dilution with acetonitrile and neutralization with the ammonia solution, the desired product was purified by RP-HPLC (water XBridge C18 column, 30 mm×100 mm, 5 µm particle size, eluting with a gradient of acetonitrile/water containing 0.1% $NH_4OH$, at flow rate of 60 mL/min). LCMS calculated for $C_{29}H_{30}F_3N_6O_2$ $(M+H)^+$ m/z=551.2; found: 551.3.

Example 140

N-(4-((1R,3S,5S)-3-Amino-5-methylcyclohexyl)pyridin-3-yl)-3-((2-cyanocyclopentyl)(methyl)amino)-5-fluoroquinoline-8-carboxamide

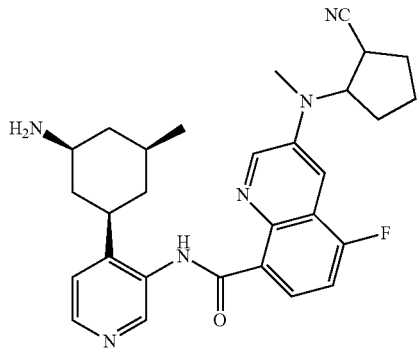 [SMILES: C[C@@H]1C[C@H](N)C[C@H](c2ccncc2NC(=O)c2ccc(F)c3cc(N(C)C4CCCC4C#N)cnc23)C1]

This compound was synthesized according to the procedures of Example 139, using 2-aminocyclopentanecarbonitrile. LCMS calculated for $C_{29}H_{34}FN_6O$ $(M+H)^+$ m/z=501.3; found: 501.3.

Example 141

N-(4-((1R,3S,5S)-3-Amino-5-methylcyclohexyl)pyridin-3-yl)-3-((2,6-dimethylpyridin-3-yl)(methyl)amino)-5-fluoroquinoline-8-carboxamide

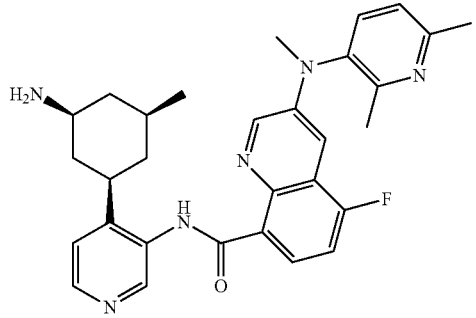 [SMILES: Cc1ccc(N(C)c2cnc3c(C(=O)Nc4cnccc4[C@@H]4C[C@H](C)C[C@H](N)C4)ccc(F)c3c2)c(C)n1]

This compound was synthesized according to the procedures of Example 139, using 2,6-dimethylpyridin-3-amine. LCMS calculated for $C_{30}H_{34}FN_6O$ $(M+H)^+$ m/z=513.3; found: 513.3.

Example 142

N-(4-((1R,3S,5S)-3-Amino-5-methylcyclohexyl)pyridin-3-yl)-5-fluoro-3-((3-fluoropyridin-2-yl)(methyl)amino)quinoline-8-carboxamide

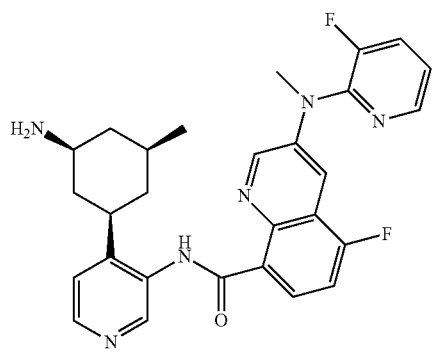 [SMILES: C[C@@H]1C[C@H](N)C[C@H](c2ccncc2NC(=O)c2ccc(F)c3cc(N(C)c4ncccc4F)cnc23)C1]

This compound was synthesized according to the procedures of Example 139, using 3-fluoropyridin-2-amine. LCMS calculated for $C_{28}H_{29}F_2N_6O$ $(M+H)^+$ m/z=503.2; found: 503.2.

Example 143

N-(4-((1R,3S,5S)-3-Amino-5-methylcyclohexyl)pyridin-3-yl)-5-fluoro-3-(methyl(4-(trifluoromethyl)pyridin-3-yl)amino)quinoline-8-carboxamide

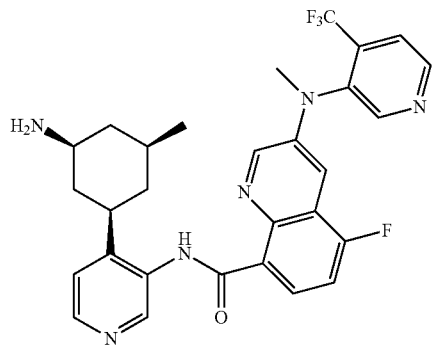 [SMILES: C[C@@H]1C[C@H](N)C[C@H](c2ccncc2NC(=O)c2ccc(F)c3cc(N(C)c4cnccc4C(F)(F)F)cnc23)C1]

This compound was synthesized according to the procedures of Example 139, using 4-(trifluoromethyl)pyridin-3-amine. LCMS calculated for $C_{29}H_{29}F_4N_6O$ $(M+H)^+$ m/z=553.2; found: 553.2.

Example 144

N-(4-((1R,3S,5S)-3-Amino-5-methylcyclohexyl)pyridin-3-yl)-5-fluoro-3-((6-methoxy-2-methylpyridin-3-yl)(methyl)amino)quinoline-8-carboxamide

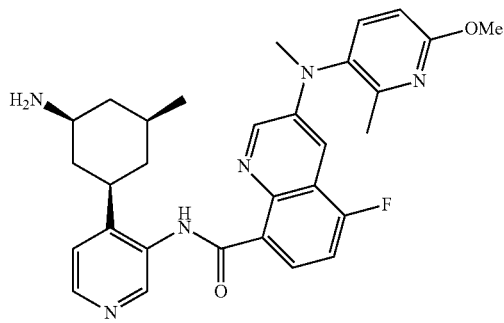 [SMILES: COc1ccc(N(C)c2cnc3c(C(=O)Nc4cnccc4[C@@H]4C[C@H](C)C[C@H](N)C4)ccc(F)c3c2)c(C)n1]

This compound was synthesized according to the procedures of Example 139, using 6-methoxy-2-methylpyridin-3-amine. LCMS calculated for $C_{30}H_{34}FN_6O_2$ $(M+H)^+$ m/z=529.3; found: 529.2.

Example 145

N-(4-((1R,3S,5S)-3-Amino-5-methylcyclohexyl)pyridin-3-yl)-5-fluoro-3-((3-fluoropyridin-4-yl)(methyl)amino)quinoline-8-carboxamide

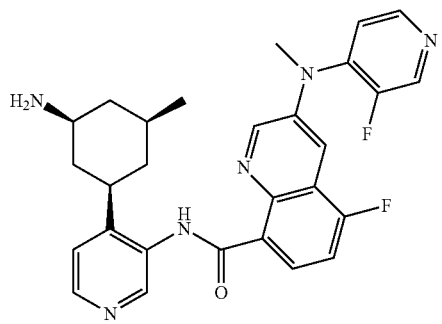 [SMILES: C[C@@H]1C[C@H](N)C[C@H](c2ccncc2NC(=O)c2ccc(F)c3cc(N(C)c4ccncc4F)cnc23)C1]

This compound was synthesized according to the procedures of Example 139, using 3-fluoropyridin-4-amine. LCMS calculated for $C_{28}H_{29}F_2N_6O$ $(M+H)^+$ m/z=503.2; found: 503.2.

Example 146

N-(4-((1R,3S,5S)-3-Amino-5-methylcyclohexyl)pyridin-3-yl)-5-fluoro-3-(methyl(4-methylpyridin-3-yl)amino)quinoline-8-carboxamide

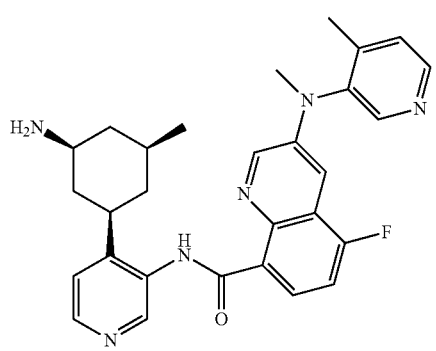 [SMILES: Cc1ccncc1N(C)c1cnc2c(C(=O)Nc3cnccc3[C@@H]3C[C@H](C)C[C@H](N)C3)ccc(F)c2c1]

This compound was synthesized according to the procedures of Example 139, using 4-methylpyridin-3-amine. LCMS calculated for $C_{29}H_{32}FN_6O$ $(M+H)^+$ m/z=499.2; found: 499.2.

Example 147

N-(4-((1R,3S,5S)-3-Amino-5-methylcyclohexyl)pyridin-3-yl)-5-fluoro-3-(methyl(2-methylcyclobutyl)amino)quinoline-8-carboxamide

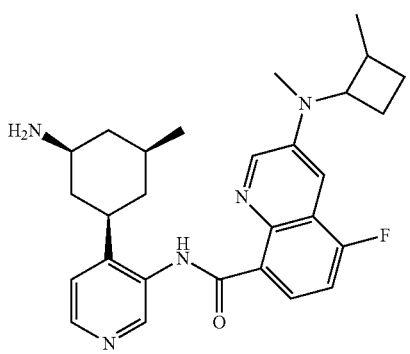 [SMILES: CC1CCC1N(C)c1cnc2c(C(=O)Nc3cnccc3[C@@H]3C[C@H](C)C[C@H](N)C3)ccc(F)c2c1]

This compound was synthesized according to the procedures of Example 139, using 2-methylcyclobutanamine. LCMS calculated for $C_{28}H_{35}FN_5O$ $(M+H)^+$ m/z=476.3; found: 476.3.

Example 148

N-(4-((1R,3S,5S)-3-Amino-5-methylcyclohexyl)pyridin-3-yl)-5-fluoro-3-((4-methoxyphenyl)(methyl)amino)quinoline-8-carboxamide

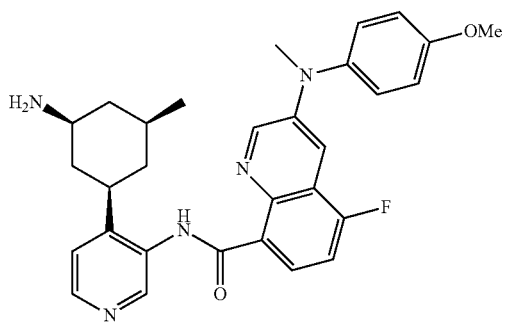 [SMILES: COc1ccc(N(C)c2cnc3c(C(=O)Nc4cnccc4[C@@H]4C[C@H](C)C[C@H](N)C4)ccc(F)c3c2)cc1]

This compound was synthesized according to the procedures of Example 139, using 4-methoxyaniline. LCMS calculated for $C_{30}H_{33}FN_5O_2$ $(M+H)^+$ m/z=514.3; found: 514.3.

Example 149

N-(4-((1R,3S,5S)-3-Amino-5-methylcyclohexyl)pyridin-3-yl)-5-fluoro-3-(methyl(3-methylpyrazin-2-yl)amino)quinoline-8-carboxamide

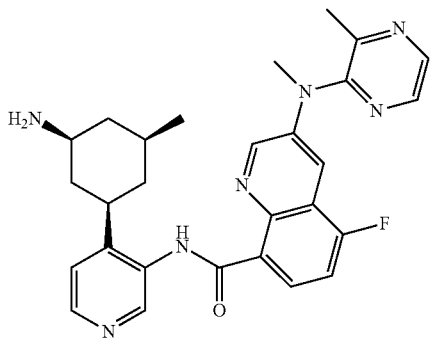 [SMILES: Cc1nccnc1N(C)c1cnc2c(C(=O)Nc3cnccc3[C@@H]3C[C@H](C)C[C@H](N)C3)ccc(F)c2c1]

This compound was synthesized according to the procedures of Example 139, using 3-methylpyrazin-2-amine. LCMS calculated for $C_{28}H_{31}FN_7O$ $(M+H)^+$ m/z=500.3; found: 500.3.

Example 150

N-(4-((1R,3S,5S)-3-Amino-5-methylcyclohexyl)pyridin-3-yl)-5-fluoro-3-((4-methoxypyridin-3-yl)(methyl)amino)quinoline-8-carboxamide

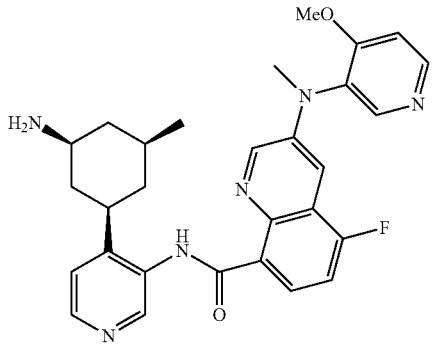 [SMILES: COc1ccncc1N(C)c1cnc2c(C(=O)Nc3cnccc3[C@@H]3C[C@H](C)C[C@H](N)C3)ccc(F)c2c1]

This compound was synthesized according to the procedures of Example 139, using 4-methoxypyridin-3-amine. LCMS calculated for $C_{29}H_{32}FN_6O_2$ $(M+H)^+$ m/z=515.3; found: 515.3.

Example 151

N-(4-((1R,3S,5S)-3-Amino-5-methylcyclohexyl)pyridin-3-yl)-5-fluoro-3-(methyl(tetrahydro-2H-pyran-3-yl)amino)quinoline-8-carboxamide

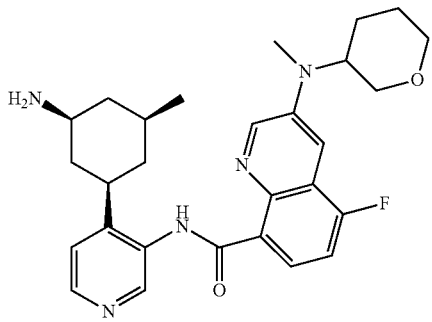 [SMILES: C[C@@H]1C[C@H](N)C[C@H](c2ccncc2NC(=O)c2ccc(F)c3cc(N(C)C4CCCOC4)cnc23)C1]

This compound was synthesized according to the procedures of Example 139, using tetrahydro-2H-pyran-3-amine. LCMS calculated for $C_{28}H_{35}FN_5O_2$ $(M+H)^+$ m/z=492.3; found: 492.3.

Example 152

N-(4-((1R,3S,5S)-3-Amino-5-methylcyclohexyl)pyridin-3-yl)-5-fluoro-3-((2-methoxyphenyl)(methyl)amino)quinoline-8-carboxamide

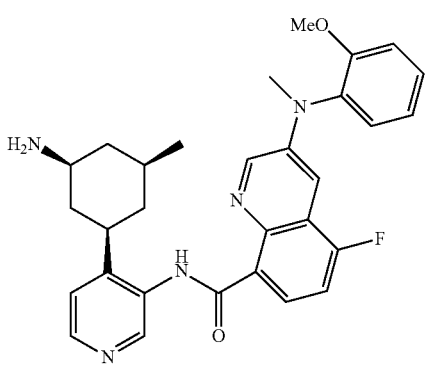 [SMILES: COc1ccccc1N(C)c1cnc2c(C(=O)Nc3cnccc3[C@@H]3C[C@H](C)C[C@H](N)C3)ccc(F)c2c1]

This compound was synthesized according to the procedures of Example 139, using 2-methoxyaniline. LCMS calculated for $C_{30}H_{33}FN_5O_2$ $(M+H)^+$ m/z=514.3; found: 514.3.

Example 153

N-(4-((1R,3S,5S)-3-Amino-5-methylcyclohexyl)pyridin-3-yl)-5-fluoro-3-(imidazo[1,2-a]pyridin-6-yl(methyl)amino)quinoline-8-carboxamide

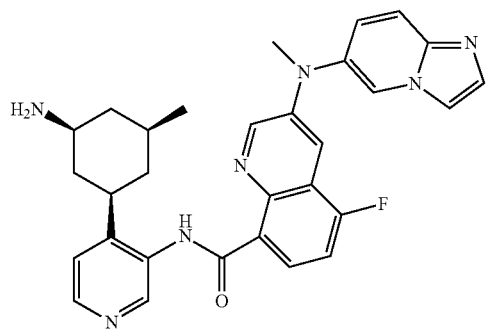 [SMILES: C[C@@H]1C[C@H](N)C[C@H](c2ccncc2NC(=O)c2ccc(F)c3cc(N(C)c4ccc5nccn5c4)cnc23)C1]

This compound was synthesized according to the procedures of Example 139, using imidazo[1,2-a]pyridin-6-amine. LCMS calculated for $C_{30}H_{31}FN_7O$ $(M+H)^+$ m/z=524.3; found: 524.2.

Example 154

N-(4-((1R,3S,5S)-3-Amino-5-methylcyclohexyl) pyridin-3-yl)-5-fluoro-3-(methyl((R)-tetrahydro-furan-3-yl)amino)quinoline-8-carboxamide

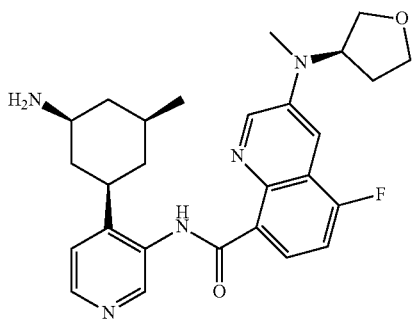 [SMILES: C[C@@H]1C[C@H](N)C[C@H](c2ccncc2NC(=O)c2ccc(F)c3cc(N(C)[C@@H]4CCOC4)cnc23)C1]

This compound was synthesized according to the procedures of Example 139, using (R)-tetrahydrofuran-3-amine. LCMS calculated for $C_{27}H_{33}FN_5O_2$ $(M+H)^+$ m/z=478.3; found: 478.2.

Example 155

N-(4-((1R,3S,5S)-3-Amino-5-methylcyclohexyl] pyridin-3-yl}-5-fluoro-3-[(2S,4R)-4-methoxy-2-methylpyrrolidin-1-yl]quinoline-8-carboxamide

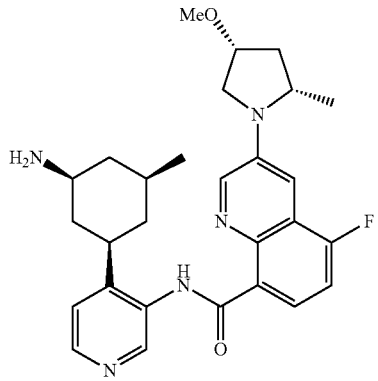 [SMILES: CO[C@@H]1C[C@H](C)N(c2cnc3c(C(=O)Nc4cnccc4[C@@H]4C[C@H](C)C[C@H](N)C4)ccc(F)c3c2)C1]

Step 1. tert-Butyl (2S,4R)-4-methoxy-2-methylpyrrolidine-1-carboxylate

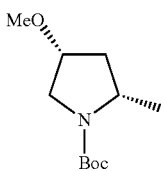

NaH in mineral oil (43 mg, 1.8 mmol) was slowly added to a mixture of tert-butyl (2S,4R)-4-hydroxy-2-methylpyrrolidine-1-carboxylate (300 mg, 1.5 mmol) and methyl iodide (280 µL, 4.5 mmol) in N,N-dimethylformamide (5 mL). After stirring at r.t. for 1 h, the reaction was quenched with water. The mixture was extracted with ethyl acetate. Combined organic fractions were washed with brine, dried over sodium sulfate and filtered. The filtrate was concentrated under reduced pressure. Crude material was purified by Biotage Isolera™ (flash purification system with hexane/ethyl acetate at a ratio from 0 to 100%) to give the desired product (297 mg, 92%). LCMS calculated for $C_7H_{14}NO_3$ $(M-tBu+H)^+$ m/z=160.1; found: 160.1.

Step 2. (2S,4R)-4-Methoxy-2-methylpyrrolidine hydrochloride

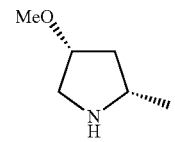

A 4.0M solution of hydrogen chloride in dioxane (3 mL, 10 mmol) was added to a solution of tert-butyl (2S,4R)-4-methoxy-2-methylpyrrolidine-1-carboxylate (297 mg, 1.4 mmol) in methanol (2 mL). After stirring at r.t. for 1 h, the reaction was concentrated under reduced pressure to give the HCl salt of the desired product which was used directly in the next step without further purification. LCMS calculated for $C_6H_{14}NO$ $(M+H)^+$ m/z=116.1; found: 116.1.

Step 3. N-{4-[(1R,3S,5S)-3-Amino-5-methylcyclohexyl]pyridin-3-yl}-5-fluoro-3-[(2S,4R)-4-methoxy-2-methylpyrrolidin-1-yl]quinoline-8-carboxamide

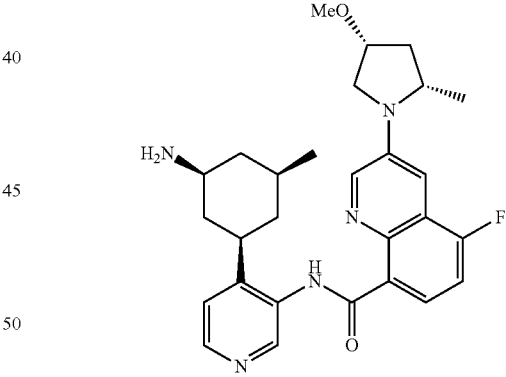

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), (2S,4R)-4-methoxy-2-methylpyrrolidine hydrochloride (10 mg, 0.06 mmol), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then 1,4-dioxane (2 mL) was added. The reaction was stirred at 80° C. overnight. After cooling to room temperature, the reaction was quenched with water. The mixture was extracted with ethyl acetate. Combined organic fractions were washed with brine, dried over sodium sulfate and filtered. The filtrate was concentrated under reduced pressure. Trifluoroacetic acid (1 mL) and dichloromethane (1 mL) were added to the obtained crude product and the reaction mixture was stirred at r.t. for 1 h. After dilution with acetonitrile and neutralization with ammonia solution, the desired product was purified by RP-HPLC (water XBridge C18 column, 30 mm×100 mm, 5 μm particle size, eluting with a gradient of acetonitrile/water containing 0.1% NH$_4$OH, at flow rate of 60 mL/min). LCMS calculated for C$_{28}$H$_{35}$FN$_5$O$_2$ (M+H)$^+$ m/z=492.3; found: 492.2.

$^1$H NMR (600 MHz, DMSO-d6) δ 13.17 (s, 1H), 9.28 (s, 1H), 8.73 (d, J=2.9 Hz, 1H), 8.50 (d, J=5.3 Hz, 1H), 8.36 (dd, J=8.2, 6.2 Hz, 1H), 7.96 (br, 2H), 7.60-7.46 (m, 2H), 7.33 (d, J=2.9 Hz, 1H), 4.25 (p, J=6.5 Hz, 1H), 4.18 (t, J=5.1 Hz, 1H), 3.70 (d, J=11.2 Hz, 1H), 3.61 (dd, J=11.2, 5.1 Hz, 1H), 3.35 (s, 3H), 3.32-3.19 (m, 2H), 2.34-2.25 (m, 1H), 2.12 (d, J=11.9 Hz, 1H), 2.06-1.98 (m, 2H), 1.94 (d, J=12.7 Hz, 1H), 1.85-1.72 (m, 1H), 1.59 (q, J=12.0 Hz, 1H), 1.34 (d, J=6.3 Hz, 3H), 1.21-1.13 (m, 1H), 1.13-1.06 (m, 1H), 1.01 (d, J=6.6 Hz, 3H) ppm.

Example 156

N-(4-((1R,3S,5S)-3-Amino-5-methylcyclohexyl)pyridin-3-yl)-5-fluoro-3-((2R,4R)-4-methoxy-2-methylpyrrolidin-1-yl)quinoline-8-carboxamide

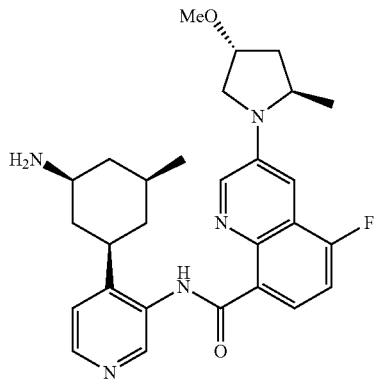 [SMILES: CO[C@@H]1C[C@@H](C)N(c2cnc3c(C(=O)Nc4cnccc4[C@@H]4C[C@H](C)C[C@H](N)C4)ccc(F)c3c2)C1]

This compound was synthesized according to the procedures of Example 155, using (2R,4R)-tert-butyl 4-hydroxy-2-methylpyrrolidine-1-carboxylate. LCMS calculated for C$_{28}$H$_{35}$FN$_5$O$_2$ (M+H)$^+$ m/z=492.3; found: 492.3.

Example 157

N-(4-((1R,3S,5S)-3-Amino-5-methylcyclohexyl)pyridin-3-yl)-5-fluoro-3-((2S,4S)-4-methoxy-2-methylpyrrolidin-1-yl)quinoline-8-carboxamide

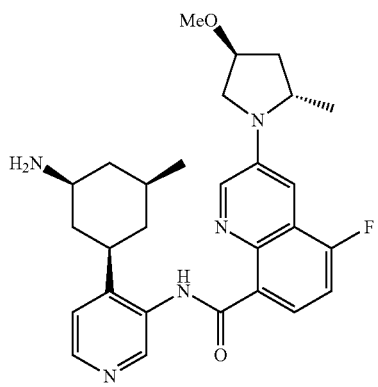 [SMILES: CO[C@H]1C[C@H](C)N(c2cnc3c(C(=O)Nc4cnccc4[C@@H]4C[C@H](C)C[C@H](N)C4)ccc(F)c3c2)C1]

This compound was synthesized according to the procedures of Example 155, using (2S,4S)-tert-butyl 4-hydroxy-2-methylpyrrolidine-1-carboxylate. LCMS calculated for C$_{28}$H$_{35}$FN$_5$O$_2$ (M+H)$^+$ m/z=492.3; found: 492.3.

Example 158

N-(4-((1R,3S,5S)-3-Amino-5-methylcyclohexyl)pyridin-3-yl)-5-fluoro-3-((2R,4S)-4-methoxy-2-methylpyrrolidin-1-yl)quinoline-8-carboxamide

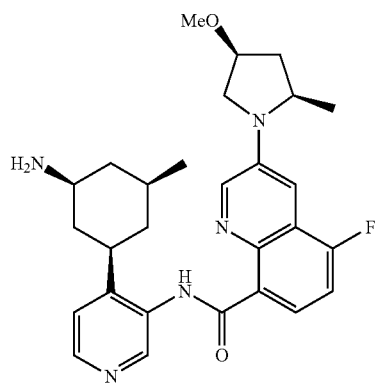 [SMILES: CO[C@H]1C[C@@H](C)N(c2cnc3c(C(=O)Nc4cnccc4[C@@H]4C[C@H](C)C[C@H](N)C4)ccc(F)c3c2)C1]

This compound was synthesized according to the procedures of Example 155, using (2R,4S)-tert-butyl 4-hydroxy-2-methylpyrrolidine-1-carboxylate. LCMS calculated for C$_{28}$H$_{35}$FN$_5$O$_2$ (M+H)$^+$ m/z=492.3; found: 492.3.

1H NMR (600 MHz, DMSO-d6) δ 13.25 (s, 1H), 9.32 (s, 1H), 8.67 (d, J=3.0 Hz, 1H), 8.58-8.47 (m, 1H), 8.34 (dd, J=8.2, 6.2 Hz, 1H), 8.02 (br, 2H), 7.61 (d, J=5.3 Hz, 1H), 7.51 (dd, J=9.6, 8.4 Hz, 1H), 7.28 (d, J=2.9 Hz, 1H), 4.24 (p, J=6.7 Hz, 1H), 4.18 (t, J=5.1 Hz, 1H), 3.69 (d, J=11.2 Hz, 1H), 3.57 (dd, J=11.3, 5.1 Hz, 1H), 3.34 (s, 3H), 3.28-3.12 (m, 2H), 2.33-2.25 (m, 1H), 2.11 (d, J=11.9 Hz, 1H), 2.04 (d, J=13.2 Hz, 1H), 2.00 (d, J=12.4 Hz, 1H), 1.94 (d, J=12.7 Hz, 1H), 1.83-1.73 (m, 1H), 1.55 (q, J=12.0 Hz, 1H), 1.34 (d, J=6.3 Hz, 3H), 1.21 (q, J=12.1 Hz, 1H), 1.12 (q, J=12.1 Hz, 1H), 1.05 (d, J=6.5 Hz, 3H) ppm.

Example 159

N-(4-((1R,3S,5S)-3-Amino-5-methylcyclohexyl)pyridin-3-yl)-5-fluoro-3-((2R,4S)-4-methoxy-2-methylpiperidin-1-yl)quinoline-8-carboxamide

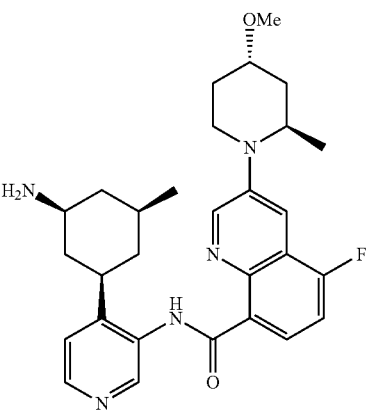 [SMILES: CO[C@H]1CCN(c2cnc3c(C(=O)Nc4cnccc4[C@@H]4C[C@H](C)C[C@H](N)C4)ccc(F)c3c2)[C@H](C)C1]

This compound was synthesized according to the procedures of Example 155, using (2R,4S)-tert-butyl 4-hydroxy-2-methylpiperidine-1-carboxylate. LCMS calculated for $C_{29}H_{37}FN_5O_2$ (M+H)$^+$ m/z=506.3; found: 506.3.

1H NMR (600 MHz, DMSO-d6) δ 13.17 (s, 1H), 9.25 (s, 1H), 9.05 (d, J=3.0 Hz, 1H), 8.55 (d, J=5.5 Hz, 1H), 8.40 (dd, J=8.3, 6.2 Hz, 1H), 8.17-8.07 (m, 2H), 7.70-7.63 (m, 2H), 7.55 (dd, J=9.5, 8.5 Hz, 1H), 4.67-4.57 (m, 1H), 3.88-3.77 (m, 1H), 3.70-3.56 (m, 1H), 3.30 (s, 3H), 3.26-3.16 (m, 2H), 3.13 (td, J=12.8, 2.9 Hz, 1H), 2.23-2.17 (m, 1H), 2.14 (d, J=11.7 Hz, 1H), 2.07-2.02 (m, 1H), 1.98 (d, J=12.4 Hz, 1H), 1.90 (d, J=12.8 Hz, 1H), 1.77-1.67 (m, 1H), 1.62 (td, J=12.2, 5.3 Hz, 1H), 1.56 (q, J=12.0 Hz, 1H), 1.41 (qd, J=12.4, 4.8 Hz, 1H), 1.18 (q, J=12.2 Hz, 1H), 1.13 (d, J=6.9 Hz, 3H), 1.12-1.06 (m, 1H), 0.99 (d, J=6.6 Hz, 3H) ppm.

Example 160

N-(4-((1R,3S,5S)-3-Amino-5-methylcyclohexyl)pyridin-3-yl)-5-fluoro-3-((2S,4R)-4-methoxy-2-methylpiperidin-1-yl)quinoline-8-carboxamide

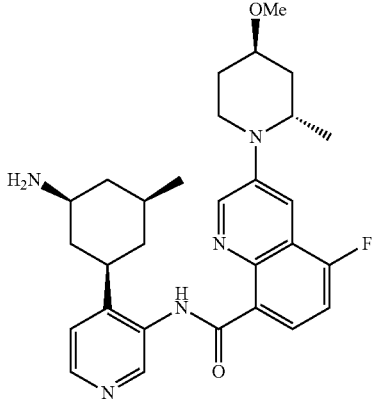 [SMILES: CO[C@@H]1CCN(c2cnc3c(C(=O)Nc4cnccc4[C@@H]4C[C@H](C)C[C@H](N)C4)ccc(F)c3c2)[C@@H](C)C1]

This compound was synthesized according to the procedures of Example 155, using (2S,4R)-tert-butyl 4-hydroxy-2-methylpiperidine-1-carboxylate. LCMS calculated for $C_{29}H_{37}FN_5O_2$ (M+H)$^+$ m/z=506.3; found: 506.3.

Example 161

N-(4-((1R,3S,5S)-3-Amino-5-methylcyclohexyl)pyridin-3-yl)-5-fluoro-3-((2R,4R)-4-methoxy-2-methylpiperidin-1-yl)quinoline-8-carboxamide

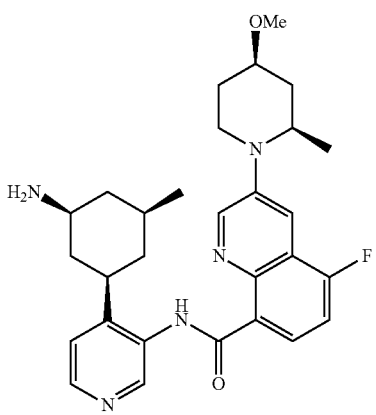 [SMILES: CO[C@@H]1CCN(c2cnc3c(C(=O)Nc4cnccc4[C@@H]4C[C@H](C)C[C@H](N)C4)ccc(F)c3c2)[C@H](C)C1]

This compound was synthesized according to the procedures of Example 155, using (2R,4R)-tert-butyl 4-hydroxy-2-methylpiperidine-1-carboxylate. LCMS calculated for $C_{29}H_{37}FN_5O_2$ (M+H)$^+$ m/z=506.3; found: 506.3.

1H NMR (500 MHz, dmso-d6) δ 13.23 (s, 1H), 9.32 (s, 1H), 8.97 (d, J=2.9 Hz, 1H), 8.58 (d, J=5.5 Hz, 1H), 8.42 (dd, J=8.3, 6.2 Hz, 1H), 8.04 (br, 2H), 7.78-7.66 (m, 2H), 7.55 (dd, J=9.5, 8.5 Hz, 1H), 4.28-4.17 (m, 1H), 3.58 (p, J=4.0 Hz, 1H), 3.51 (dt, J=12.5, 4.3 Hz, 2H), 3.31 (s, 3H), 3.29-3.12 (m, 2H), 2.12 (d, J=12.1 Hz, 1H), 2.03-1.82 (m, 6H), 1.79-1.68 (m, 1H), 1.57 (q, J=12.0 Hz, 1H), 1.22 (d, J=6.7 Hz, 3H), 1.20-1.15 (m, 1H), 1.11 (q, J=12.1 Hz, 1H), 1.00 (d, J=6.6 Hz, 3H) ppm.

Example 162

N-(4-((1R,3S,5S)-3-Amino-5-methylcyclohexyl)pyridin-3-yl)-5-fluoro-3-((3R,4R)-3-fluoro-4-methoxypiperidin-1-yl)quinoline-8-carboxamide

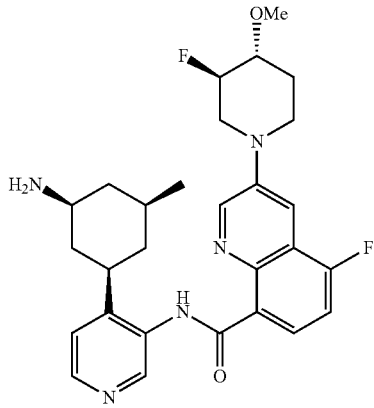 [SMILES: CO[C@@H]1CCN(c2cnc3c(C(=O)Nc4cnccc4[C@@H]4C[C@H](C)C[C@H](N)C4)ccc(F)c3c2)C[C@H]1F]

This compound was synthesized according to the procedures of Example 155, using (3R,4R)-tert-butyl 3-fluoro-4-hydroxypiperidine-1-carboxylate. LCMS calculated for $C_{28}H_{34}F_2N_5O_2$ (M+H)$^+$ m/z=510.3; found: 510.2.

Example 163

N-(4-((1R,3S,5S)-3-Amino-5-methylcyclohexyl)pyridin-3-yl)-5-fluoro-3-((3S,4S)-3-fluoro-4-(2-methoxyethoxy)piperidin-1-yl)quinoline-8-carboxamide

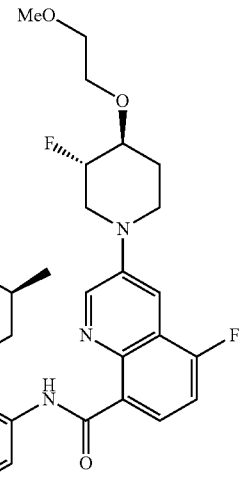

This compound was synthesized according to the procedures of Example 155, using (3S,4S)-tert-butyl 3-fluoro-4-hydroxypiperidine-1-carboxylate and 1-iodo-2-methoxyethane. LCMS calculated for $C_{30}H_{38}F_2N_5O_3$ (M+H)⁺ m/z=554.3; found: 554.2.

1H NMR (600 MHz, DMSO-d6) δ 12.95 (s, 1H), 9.13 (s, 1H), 9.08 (d, J=3.0 Hz, 1H), 8.50 (d, J=5.3 Hz, 1H), 8.44 (dd, J=8.3, 6.2 Hz, 1H), 7.89 (br, 2H), 7.82 (d, J=3.0 Hz, 1H), 7.63-7.55 (m, 1H), 7.52 (d, J=5.4 Hz, 1H), 4.79-4.61 (m, 1H), 4.04-3.94 (m, 1H), 3.78-3.66 (m, 4H), 3.55-3.46 (m, 3H), 3.37-3.30 (m, 1H), 3.28 (s, 3H), 3.25-3.14 (m, 2H), 2.18-2.08 (m, 2H), 1.97 (d, J=12.0 Hz, 1H), 1.91 (d, J=12.7 Hz, 1H), 1.79-1.65 (m, 2H), 1.51 (q, J=12.0 Hz, 1H), 1.18 (q, J=12.2 Hz, 1H), 1.08 (q, J=12.0 Hz, 1H), 1.01 (d, J=6.6 Hz, 3H) ppm.

Example 164

N-(4-((1R,3S,5S)-3-Amino-5-methylcyclohexyl]pyridin-3-yl}-5-fluoro-3-[(2R,4S)-4-hydroxy-2-methylpyrrolidin-1-yl]quinoline-8-carboxamide

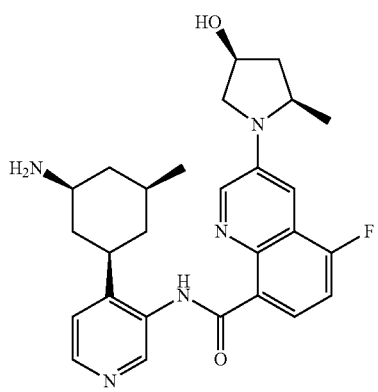 [SMILES: C[C@@H]1C[C@H](N)C[C@H](c2ccncc2NC(=O)c2ccc(F)c3cc(N4C[C@@H](O)C[C@H]4C)cnc23)C1]

Step 1. (3S,5R)-5-Methylpyrrolidin-3-ol hydrochloride

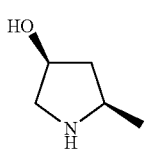

A 4.0M solution of hydrogen chloride in dioxane (3 mL, 10 mmol) was added to a solution of tert-butyl (2R,4S)-4-hydroxy-2-methylpyrrolidine-1-carboxylate (0.30 g, 1.5 mmol) in methanol (2 mL). After stirring at r.t. for 1 h, the reaction was concentrated under reduced pressure to give the HCl salt of the desired product which was used directly in the next step without further purification. LCMS calculated for $C_5H_{12}NO$ (M+H)⁺ m/z=102.1; found: 102.1.

Step 2. N-{4-[(1R,3S,5S)-3-Amino-5-methylcyclohexyl]pyridin-3-yl}-5-fluoro-3-[(2R,4S)-4-hydroxy-2-methylpyrrolidin-1-yl]quinoline-8-carboxamide

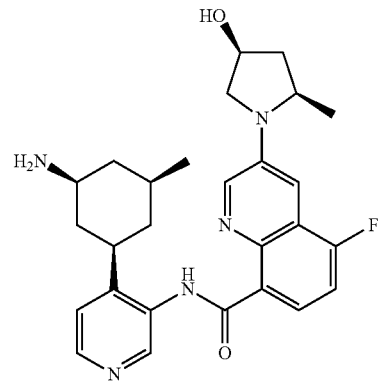 [SMILES: C[C@@H]1C[C@H](N)C[C@H](c2ccncc2NC(=O)c2ccc(F)c3cc(N4C[C@@H](O)C[C@H]4C)cnc23)C1]

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), (3S,5R)-5-methylpyrrolidin-3-ol hydrochloride (8 mg, 0.06 mmol), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then 1,4-dioxane (2 mL) was added. The reaction was stirred at 80° C. overnight. After cooling to room temperature, the reaction was quenched with water. The mixture was extracted with ethyl acetate. Combined organic fractions were washed with brine, dried over sodium sulfate and filtered. The filtrate was concentrated under reduced pressure. Trifluoroacetic acid (1 mL) and dichloromethane (1 mL) were added to the obtained crude product and the reaction mixture was stirred at r.t. for 1 h. After dilution with acetonitrile and neutralization with ammonia solution, the desired product was purified by RP-HPLC (water XBridge C18 column, 30 mm×100 mm, 5 μm particle size, eluting with a gradient of acetonitrile/water containing 0.1% NH₄OH, at flow rate of 60 mL/min). LCMS calculated for $C_{27}H_{33}FN_5O_2$ (M+H)⁺ m/z=478.3; found: 478.3.

Example 165

N-(4-((1R,3S,5S)-3-Amino-5-methylcyclohexyl)pyridin-3-yl)-5-fluoro-3-((2S,4S)-4-hydroxy-2-methylpyrrolidin-1-yl)quinoline-8-carboxamide

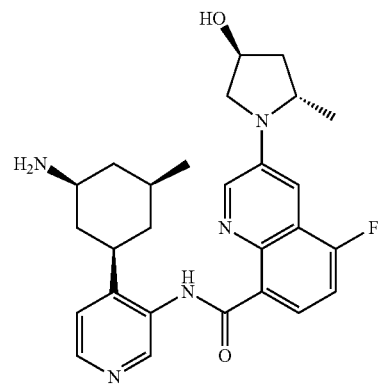 [SMILES: C[C@@H]1C[C@H](N)C[C@H](c2ccncc2NC(=O)c2ccc(F)c3cc(N4C[C@@H](O)C[C@@H]4C)cnc23)C1]

This compound was synthesized according to the procedures of Example 164, using (2S,4S)-tert-butyl 4-hydroxy-2-methylpyrrolidine-1-carboxylate. LCMS calculated for $C_{27}H_{33}FN_5O_2$ (M+H)$^+$ m/z=478.3; found: 478.3.

Example 166

N-(4-((1R,3S,5S)-3-Amino-5-methylcyclohexyl)pyridin-3-yl)-5-fluoro-3-((S)-2-methylazetidin-1-yl)quinoline-8-carboxamide

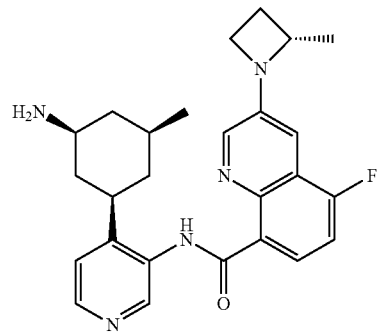 [SMILES: C[C@@H]1C[C@H](N)C[C@H](c2ccncc2NC(=O)c2ccc(F)c3cc(N4CC[C@@H]4C)cnc23)C1]

Step 1. (R)-tert-Butyl 2-((methylsulfonyloxy)methyl)azetidine-1-carboxylate

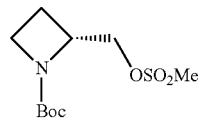

Methanesulfonyl chloride (1.0 mL, 13 mmol) was slowly added at 0° C. to a mixture of tert-butyl (2R)-2-(hydroxymethyl)azetidine-1-carboxylate (2.0 g, 11 mmol) and triethylamine (2.1 mL, 15 mmol) in methylene chloride (10 mL). After stirring at r.t. overnight, the reaction was quenched with a saturated solution of sodium bicarbonate. The mixture was extracted with DCM. Combined organic fractions were washed with brine, dried over sodium sulfate and filtered. The filtrate was concentrated under reduced pressure. The resulting residue was purified by Biotage Isolera™ (flash purification system with hexane/ethyl acetate at a ratio from 0 to 100%) to give the desired product (2.6 g, 90%). LCMS calculated for $C_6H_{12}NO_5S$ (M-tBu+H)$^+$ m/z=210.0; found: 210.1.

Step 2. (9-tert-Butyl 2-methylazetidine-1-carboxylate

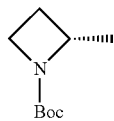

A 1.0 M solution of lithium triethylborohydride in THF (37 mL, 37 mmol) was added dropwise at 0° C. to a solution of tert-butyl (2R)-2-{[(methylsulfonyl)oxy]methyl}azetidine-1-carboxylate (2.6 g, 9.8 mmol) in tetrahydrofuran (20 mL). After stirring at r.t. for 1 h, the reaction was quenched with a saturated solution of sodium bicarbonate and the mixture was extracted with DCM. Combined organic fractions were washed with brine, dried over sodium sulfate and filtered. The filtrate was concentrated under reduced pressure. The resulting residue was purified by Biotage Isolera™ (flash purification system with hexane/ethyl acetate at a ratio from 0 to 100%) to give the desired product (0.8 g, 48%). LCMS calculated for $C_5H_{10}NO_2$ (M-tBu+H)$^+$ m/z=116.1; found: 116.1.

Step 3. (S)-2-Methylazetidine

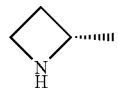

A 4.0M solution of hydrogen chloride in dioxane (5 mL, 20 mmol) was added to a solution of tert-butyl (2S)-2-methylazetidine-1-carboxylate (0.80 g, 4.7 mmol) in methanol (5 mL). After stirring at r.t. for 1 h, the reaction was concentrated under reduced pressure to give the HCl salt of the desired product which was used in the next step without further purification. LCMS calculated for $C_4H_{10}N$ (M+H)$^+$ m/z=72.1; found: 72.1.

Step 4. N-(4-((1R,3S,5S)-3-Amino-5-methylcyclohexyl)pyridin-3-yl)-5-fluoro-3-((S)-2-methylazetidin-1-yl)quinoline-8-carboxamide

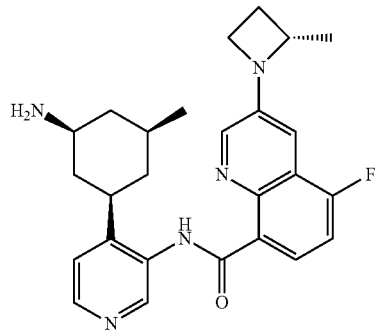 [SMILES: C[C@@H]1C[C@H](N)C[C@H](c2ccncc2NC(=O)c2ccc(F)c3cc(N4CC[C@@H]4C)cnc23)C1]

tert-Butyl (1S,3R,5S)-3-(3-(5-fluoro-3-iodoquinoline-8-carboxamido)pyridin-4-yl)-5-methylcyclohexylcarbamate (20 mg, 0.03 mmol, Intermediate 1), (2S)-2-methylazetidine hydrochloride (7 mg, 0.06 mmol), cesium carbonate (29 mg, 0.09 mmol), RuPhos Pd G2 (5 mg, 0.006 mmol, Sigma-Aldrich) and a magnet bar were placed in a vial which was then evacuated and backfilled with nitrogen three times. Then 1,4-dioxane (2 mL) was added. The reaction was stirred at 80° C. overnight. After cooling to room temperature, the reaction was quenched with water and the mixture was extracted with ethyl acetate. Combined organic fractions were washed with brine, dried over sodium sulfate and filtered. The filtrate was concentrated under reduced pressure. Trifluoroacetic acid (1 mL) and dichloromethane (1 mL) were added to the obtained crude product and the reaction mixture was stirred at r.t. for 1 h. After dilution with acetonitrile and neutralization with ammonia solution, the desired product was purified by RP-HPLC (water XBridge C18 column, 30 mm×100 mm, 5 µm particle size, eluting with a gradient of acetonitrile/water containing 0.1% NH₄OH, at flow rate of 60 mL/min). LCMS calculated for $C_{26}H_{31}FN_5O$ (M+H)⁺ m/z=448.2; found: 448.2.

Example 167

N-(4-((1R,3S,5S)-3-Amino-5-methylcyclohexyl) pyridin-3-yl)-5-fluoro-3-((R)-2-methylazetidin-1-yl) quinoline-8-carboxamide

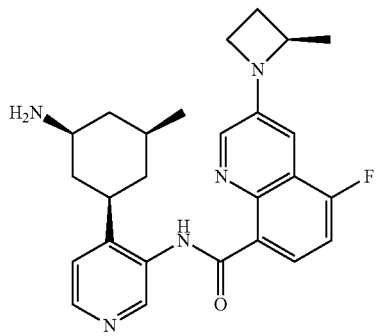 [SMILES: C[C@@H]1C[C@H](N)C[C@H](c2ccncc2NC(=O)c2ccc(F)c3cc(N4CC[C@H]4C)cnc23)C1]

This compound was synthesized according to the procedures of Example 166, using
(S)-tert-butyl 2-(hydroxymethyl)azetidine-1-carboxylate. LCMS calculated for $C_{26}H_{31}FN_5O$ (M+H)⁺ m/z=448.2; found: 448.2.

Example 168

Ethyl 4-(8-(4-((1R,3S,5S)-3-amino-5-methylcyclohexyl)pyridin-3-ylcarbamoyl)-5-fluoroquinolin-3-yl) piperazine-1-carboxylate

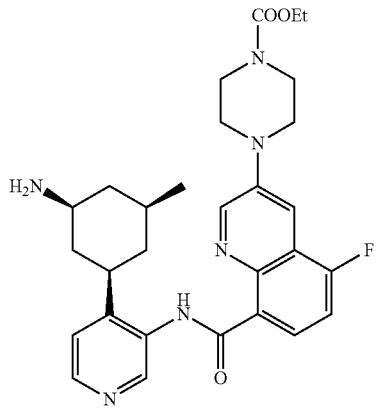 [SMILES: CCOC(=O)N1CCN(c2cnc3c(C(=O)Nc4cnccc4[C@@H]4C[C@H](C)C[C@H](N)C4)ccc(F)c3c2)CC1]

This compound was synthesized according to the procedures of Example 96, using ethyl piperazine-1-carboxylate. LCMS calculated for $C_{29}H_{36}FN_6O_3$ (M+H)⁺ m/z=535.3; found: 535.3.

1H NMR (600 MHz, DMSO-d6) δ 12.97 (s, 1H), 9.16 (s, 1H), 9.08 (d, J=3.0 Hz, 1H), 8.51 (d, J=4.8 Hz, 1H), 8.46 (dd, J=8.3, 6.2 Hz, 1H), 7.92 (br, 2H), 7.79 (d, J=2.9 Hz, 1H), 7.65-7.58 (m, 1H), 7.58-7.54 (m, 1H), 4.10 (q, J=7.1 Hz, 2H), 3.68-3.58 (m, 4H), 3.52-3.40 (m, 4H), 3.25-3.12 (m, 2H), 2.13 (d, J=12.3 Hz, 1H), 1.98 (d, J=12.2 Hz, 1H), 1.89 (d, J=12.8 Hz, 1H), 1.79-1.65 (m, 1H), 1.50 (q, J=12.1 Hz, 1H), 1.23 (t, J=7.1 Hz, 3H), 1.21-1.16 (m, 1H), 1.08 (q, J=12.0 Hz, 1H), 1.00 (d, J=6.6 Hz, 3H) ppm.

Example 169

N-(4-((1R,3S,5S)-3-Amino-5-methylcyclohexyl) pyridin-3-yl)-5-fluoro-3-((R)-2-methylpiperidin-1-yl)quinoline-8-carboxamide

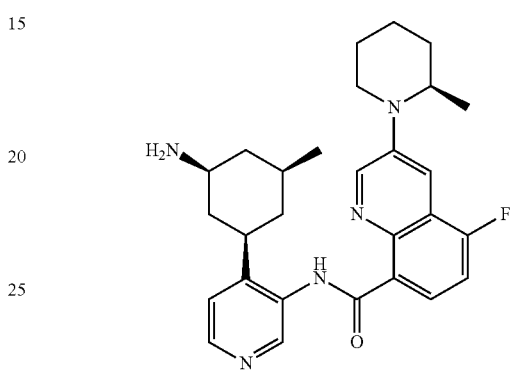

This compound was synthesized according to the procedures of Example 96, using (R)-2-methylpiperidine. LCMS calculated for $C_{28}H_{35}FN_5O$ (M+H)⁺ m/z=476.3; found: 476.2.

1H NMR (600 MHz, DMSO-d6) δ 13.15 (s, 1H), 9.22 (s, 1H), 9.02 (d, J=3.0 Hz, 1H), 8.54 (d, J=5.4 Hz, 1H), 8.41 (dd, J=8.3, 6.2 Hz, 1H), 7.99 (s, 2H), 7.65 (d, J=3.0 Hz, 1H), 7.61 (d, J=5.4 Hz, 1H), 7.56 (dd, J=9.5, 8.4 Hz, 1H), 4.53-4.40 (m, 1H), 3.72-3.62 (m, 1H), 3.29-3.16 (m, 2H), 3.08 (td, J=12.2, 3.0 Hz, 1H), 2.11 (d, J=11.9 Hz, 1H), 1.98 (d, J=12.2 Hz, 1H), 1.93 (d, J=12.9 Hz, 1H), 1.90-1.80 (m, 2H), 1.78-1.65 (m, 3H), 1.65-1.50 (m, 3H), 1.18 (q, J=12.1 Hz, 1H), 1.13 (d, J=6.7 Hz, 3H), 1.10-1.05 (m, 1H), 1.01 (d, J=6.6 Hz, 3H) ppm.

Example 170

N-(4-((1R,3S,5S)-3-Amino-5-methylcyclohexyl) pyridin-3-yl)-5-fluoro-3-((S)-2-methylpiperidin-1-yl) quinoline-8-carboxamide

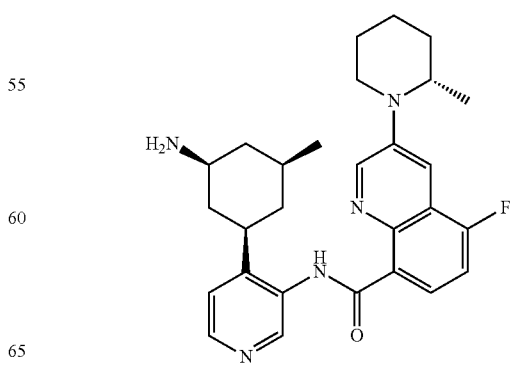

This compound was synthesized according to the procedures of Example 96, using (S)-2-methylpiperidine. LCMS calculated for $C_{28}H_{35}FN_5O$ (M+H)$^+$ m/z=476.3; found: 476.2.

Example A. Pim Enzyme Assays

Pim-1 and Pim-3 kinase assays-20 μL reactions were run in white 384 well polystyrene plates dotted with 0.8 μL compound/DMSO in the assay buffer (50 mM Tris, pH 7.5, 0.01% Tween-20, 5 mM mgCl$_2$, 0.01% BSA, 5 mM DTT), containing 0.05 μM Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA,) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 mL each. Supplementation of the STOP buffer with beads and stopping the reactions were done under reduced light. Prior to the stopping reactions STOP buffer with beads was preincubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay-20 μL reactions were run in white 384 well polystyrene plates dotted with 0.8 μL compound/DMSO in the assay buffer (50 mM Tris, pH 7.5, 0.01% Tween-20, 5 mM mgCl$_2$, 0.01% BSA, 5 mM DTT), containing 0.05 μM Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an IC$_{50}$ of 2 μM or less when tested for PIM kinase activity under the assay conditions disclosed above are considered active.

Although the above in vitro assays are conducted at 1 mM ATP compounds can also be evaluated for potency and in vitro activity against PIM targets utilizing K$_m$ conditions, where the concentration of ATP is set to the K$_m$ value and the assay is more sensitive to PIM inhibition activity.

Data obtained for the Example compounds using the methods described in Example A, is provided in Table 1.

TABLE 1

| Example | PIM1 IC$_{50}$ (nM)$^a$ | PIM2 IC$_{50}$ (nM)$^b$ | PIM3 IC$_{50}$ (nM)$^a$ |
|---|---|---|---|
| 1 | * | ++ | * |
| 2 | * | + | * |
| 3 | * | ++ | ** |
| 4 | * | ++ | ** |
| 5 | * | + | * |
| 6 | * | + | * |
| 7 | * | + | * |
| 8 | * | + | * |
| 9 | * | ++ | * |
| 10 | * | ++ | * |
| 11 | * | ++ | * |
| 12 | * | ++ | * |
| 13 | * | + | * |
| 14 | * | ++ | * |
| 15 | * | + | * |
| 16 | * | + | * |
| 17 | * | ++ | * |
| 18 | * | + | * |
| 19 | * | ++ | * |
| 20 | * | + | * |
| 21 | * | + | * |
| 22 | * | + | * |
| 23 | * | ++ | * |
| 24 | * | ++ | * |
| 25 | * | + | * |
| 26 | * | + | * |
| 27 | * | + | * |
| 28 | * | + | * |
| 29 | * | + | * |
| 30 | * | ++ | * |
| 31 | * | ++ | * |
| 32 | * | + | * |
| 33 | * | + | * |
| 34 | * | + | * |
| 35 | * | +++ | ** |
| 36 | * | ++ | ** |
| 37 | * | +++ | ** |
| 38 | * | ++ | ** |
| 39 | * | + | ** |
| 40 | * | ++ | * |
| 41 | ** | ++ | ** |
| 42 | * | + | * |
| 43 | * | + | * |
| 44 | * | ++ | * |
| 45 | * | ++ | ** |
| 46 | * | ++ | * |
| 47 | * | + | * |
| 48 | * | ++ | * |
| 49 | * | ++ | * |
| 50 | * | + | * |
| 51 | * | ++ | * |
| 52 | * | +++ | ** |
| 53 | * | ++ | * |
| 54 | * | ++ | * |
| 55 | * | + | * |
| 56 | * | + | * |
| 57 | * | + | ** |
| 58 | * | + | * |
| 59 | * | +++ | ** |
| 60 | * | +++ | ** |
| 61 | * | +++ | ** |
| 62 | * | ++ | * |
| 63 | * | ++ | * |
| 64 | * | ++ | * |
| 65 | * | ++ | * |
| 66 | * | ++ | * |
| 67 | * | + | * |
| 68 | * | + | * |
| 69 | * | + | * |
| 70 | * | ++ | * |
| 71 | * | ++ | * |
| 72 | * | ++ | * |
| 73 | * | + | * |
| 74 | * | ++ | * |
| 75 | * | + | * |
| 76 | * | + | * |
| 77 | * | + | * |
| 78 | * | ++ | * |
| 79 | * | ++ | * |
| 80 | * | + | * |
| 81 | * | + | * |
| 82 | * | ++ | * |
| 83 | * | + | * |
| 84 | * | ++ | * |
| 85 | * | ++ | * |
| 86 | * | + | * |
| 87 | * | ++ | * |
| 88 | * | + | * |
| 89 | * | + | * |
| 90 | * | + | * |
| 91 | * | +++ | ** |

TABLE 1-continued

| Example | PIM1 IC$_{50}$ (nM)$^a$ | PIM2 IC$_{50}$ (nM)$^b$ | PIM3 IC$_{50}$ (nM)$^a$ |
|---|---|---|---|
| 92 | * | +++ | ** |
| 93 | * | + | * |
| 94 | * | + | * |
| 95 | * | + | * |
| 96 | * | + | * |
| 97 | * | + | * |
| 98 | * | + | * |
| 99 | * | + | * |
| 100 | * | + | * |
| 101 | * | + | * |
| 102 | * | + | * |
| 103 | * | + | * |
| 104 | * | + | * |
| 105 | * | + | * |
| 106 | * | + | * |
| 107 | * | + | * |
| 108 | * | + | * |
| 109 | * | + | * |
| 110 | * | + | * |
| 111 | * | + | * |
| 112 | * | + | * |
| 113 | * | + | * |
| 114 | * | + | * |
| 115 | * | + | * |
| 116 | * | + | * |
| 117 | * | + | * |
| 118 | * | + | * |
| 119 | * | + | * |
| 120 | * | + | * |
| 121 | * | + | * |
| 122 | * | + | * |
| 123 | * | + | * |
| 124 | * | + | * |
| 125 | * | + | * |
| 126 | * | + | * |
| 127 | * | + | * |
| 128 | * | + | * |
| 129 | * | ++ | * |
| 130 | * | ++ | * |
| 131 | * | ++ | * |
| 132 | * | ++ | * |
| 133 | * | ++ | * |
| 134 | * | ++ | * |
| 135 | * | ++ | * |
| 136 | * | + | * |
| 137 | * | + | * |
| 138 | * | ++ | * |
| 139 | * | + | * |
| 140 | * | + | * |
| 141 | * | + | * |
| 142 | * | + | * |
| 143 | * | + | * |
| 144 | * | + | * |
| 145 | * | + | * |
| 146 | * | + | * |
| 147 | * | + | * |
| 148 | * | + | * |
| 149 | * | + | * |
| 150 | * | + | * |
| 151 | * | + | * |
| 152 | * | + | * |
| 153 | * | ++ | * |
| 154 | * | ++ | * |
| 155 | * | + | * |
| 156 | * | + | * |
| 157 | * | + | * |
| 158 | * | + | * |
| 159 | * | + | * |
| 160 | * | + | * |
| 161 | * | + | * |
| 162 | * | + | * |
| 163 | * | + | * |
| 164 | * | + | * |
| 165 | * | + | * |
| 166 | * | + | * |
| 167 | * | + | * |
| 168 | * | ++ | * |
| 169 | * | + | * |
| 170 | * | ++ | ** |

$^a$IC$_{50}$ ≤ 10 nM: *; 10 nM < IC$_{50}$ ≤ 50 nM: ; 50 nM < IC$_{50}$ ≤ 500 nM: *; 500 nM < IC$_{50}$ ≤ 2000 nM: ****.
$^b$IC$_{50}$ ≤ 100 nM: +; 100 nM < IC$_{50}$ ≤ 1000 nM: ++; 1000 nM < IC$_{50}$ ≤ 10000 nM: +++.

Example B. Pim Cellular Assays

One or more compounds of the invention were tested for inhibitory activity of PIM according to at least one of the following cellular assays. Compounds of the invention having an IC$_{50}$ of 10 μM or less when tested for PIM kinase activity under the cellular assay conditions disclosed below would be and were considered active.

Pim Cell Proliferation Assay

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the anti-proliferation activity of test compounds, both cell lines are plated with the culture medium (2×10$^3$ cells/well/in 200 μL) into 96-well polystyrene ultralow binding (Costar,) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim Cell Proliferation Assay

MOLM-16 cells are purchased from DSMZ (Germany) and maintained in the culture medium recommended, RPMI, 20% FBS. To measure the anti-proliferation activity of test compounds, the cells are plated with the RPMI, 10% FBS (1×10$^4$ cells/well/in 200 μL) into 96-well polystyrene ultralow binding plates (Costar) in the presence or absence of a concentration range of test compounds. After 4 days, [$^3$H]-thymidine, 1 μCi/10 μL/well (PerkinElmer, Boston, Mass.) in RPMI, 10% FBS is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim pBAD Signaling Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1\times10^6$/well/100 μL for KG1A and $4\times10^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA kit (Cell Signaling Path Scan phosphor pBAD ELISA) is utilized. 50 μL of the lysate is tested per the ELISA protocol and the data analysis is performed by software on a SpectrMax5 plate reader (Molecular Devices, Sunnyvale, Calif.). $IC_{50}$ determination is performed by fitting the curve of percent inhibition versus the log of the inhibitor concentration using the GraphPad Prism 5.0 software.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of treating a myeloproliferative disorder, comprising administering to a patient in need thereof a therapeutically effective amount of a compound selected from:

N-{4-[(1R,3S,5S)-3-Amino-5-methylcyclohexyl]pyridin-3-yl}-5-fluoroquinoline-8-carboxamide;

N-{4-[(1R,3S,5S)-3-Amino-5-methylcyclohexyl]pyridin-3-yl}-5-fluoro-3-[(3R)-3-fluoropiperidin-1-yl]quinoline-8-carboxamide;

N-{4-[(1R,3S,5S)-3-Amino-5-methylcyclohexyl]pyridin-3-yl}-5-fluoro-3-pyrrolidin-1-ylquinoline-8-carboxamide;

N-{4-[(1R,3S,5S)-3-Amino-5-methylcyclohexyl]pyridin-3-yl}-3-azetidin-1-yl-5-fluoroquinoline-8-carboxamide;

N-{4-[(1R,3S,5S)-3-Amino-5-methylcyclohexyl]pyridin-3-yl}-5-fluoro-3-[(3S)-3-fluoropyrrolidin-1-yl]quinoline-8-carboxamide;

N-{4-[(1R,3S,5S)-3-Amino-5-methylcyclohexyl]pyridin-3-yl}-5-fluoro-3-[(3R)-3-fluoropyrrolidin-1-yl]quinoline-8-carboxamide;

N-{4-[(1R,3S,5S)-3-Amino-5-methylcyclohexyl]pyridin-3-yl}-3-[(3S)-3-cyanopyrrolidin-1-yl]-5-fluoroquinoline-8-carboxamide;

N-{4-[(1R,3S,5S)-3-Amino-5-methylcyclohexyl]pyridin-3-yl}-3-[(3R)-3-cyanopyrrolidin-1-yl]-5-fluoroquinoline-8-carboxamide;

N-{4-[(1R,3S,5S)-3-Amino-5-methylcyclohexyl]pyridin-3-yl}-5-fluoro-3-(3-fluoroazetidin-1-yl)quinoline-8-carboxamide;

N-{4-[(1R,3S,5S)-3-Amino-5-methylcyclohexyl]pyridin-3-yl}-5-fluoro-3-morpholin-4-ylquinoline-8-carboxamide;

N-{4-[(1R,3S,5S)-3-Amino-5-methylcyclohexyl]pyridin-3-yl}-5-fluoro-3-[(3S)-3-methoxypiperidin-1-yl]quinoline-8-carboxamide;

N-{4-[(1R,3S,5S)-3-Amino-5-methylcyclohexyl]pyridin-3-yl}-5-fluoro-3-[(3S)-3-methoxypiperidin-1-yl]quinoline-8-carboxamide;

N-{4-[(1R,3S,5S)-3-Amino-5-methylcyclohexyl]pyridin-3-yl}-3-cyclopropyl-5-fluoroquinoline-8-carboxamide;

N-{4-[(1R,3S,5S)-3-Amino-5-methylcyclohexyl]pyridin-3-yl}-3-(cyclopropylethynyl)-5-fluoroquinoline-8-carboxamide;

N-{4-[(1R,3S,5S)-3-Amino-5-methylcyclohexyl]pyridin-3-yl}-3-(2-cyano-6-fluorophenyl)-5-fluoroquinoline-8-carboxamide;

tert-Butyl {(1S,3R,5S)-3-[3-({[3-(2,6-difluorophenyl)-5-fluoroquinolin-8-yl]carbonyl}amino)pyridin-4-yl]-5-methylcyclohexyl}carbamate;

N-{4-[(1R,3S,5S)-3-Amino-methylcyclohexyl]pyridin-3-yl}-3-(2-cyanophenyl)-5-fluoroquinoline-8-carboxamide;

N-{4-[(1R,3S,5S)-3-Amino-methylcyclohexyl]pyridin-3-yl}-3-(2,6-difluoro-4-hydroxyphenyl)-5-fluoroquinoline-8-carboxamide;

N-{4-[(1R,3S,5S)-3-Amino-5-methylcyclohexyl]pyridin-3-yl}-3-[cyclopropylmethyl)(methyl)amino]-5-fluoroquinoline-8-carboxamide;

N-(4-((1R,3S,5S)-3-Amino-5-methylcyclohexyl)pyridin-3-yl)-3-(ethyl(methyl)amino)-5-fluoroquinoline-8-carboxamide;

N-{4-[(1R,3S,5S)-3-Amino-5-methylcyclohexyl]pyridin-3-yl}-5-fluoro-3-[methyl(2,2,2-trifluoroethyl)amino]quinoline-8-carboxamide;

N-{4-[(1R,3S,5S)-3-Amino-5-methylcyclohexyl]pyridin-3-yl}-5-fluoro-3-[(2-fluoroethyl)(methyl)amino]quinoline-8-carboxamide;

N-{4-[(1R,3S,5S)-3-Amino-5-methylcyclohexyl]pyridin-3-yl}-5-fluoro-3-[methyl(tetrahydrofuran-3-yl)amino]quinoline-8-carboxamide;

N-{4-[(1R,3S,5S)-3-Amino-5-methylcyclohexyl]pyridin-3-yl}-3-[cyclobutyl(methyl)amino]-5-fluoroquinoline-8-carboxamide;

N-{4-[(1R,3S,5S)-3-Amino-5-methylcyclohexyl]pyridin-3-yl}-3-(dimethylamino)-5-fluoroquinoline-8-carboxamide;

N-{4-[(1R,3S,5S)-3-Amino-5-methylcyclohexyl]pyridin-3-yl}-5-fluoro-3-[(2-fluoroethyl)amino]quinoline-8-carboxamide;

N-{4-[(1R,3S,5S)-3-Amino-5-methylcyclohexyl]pyridin-3-yl}-3-[(2,2-difluoroethyl)amino]-5-fluoroquinoline-8-carboxamide;

N-{4-[(1R,3S,5S)-3-Amino-5-methylcyclohexyl]pyridin-3-yl}-3-(3,3-difluoropiperidin-1-yl)-5-fluoroquinoline-8-carboxamide;

N-{4-[(1R,3S,5S)-3-Amino-5-methylcyclohexyl]pyridin-3-yl}-5-fluoro-3-[(3S,4S)-3-fluoro-4-hydroxypiperidin-1-yl]quinoline-8-carboxamide;

N-{4-[(1R,3S,5S)-3-Amino-5-methylcyclohexyl]pyridin-3-yl}-5-fluoro-3-(4-methylpiperazin-1-yl)quinoline-8-carboxamide;

N-{4-[(1R,3S,5S)-3-Amino-5-methylcyclohexyl]pyridin-3-yl}-5-fluoro-3-(tetrahydro-2H-pyran-4-yl)quinoline-8-carboxamide;

N-{4-[(1R,3S,5S)-3-Amino-5-methylcyclohexyl]pyridin-3-yl}-5-fluoro-3-((R)-3-methylmorpholino)quinoline-8-carboxamide;

N-(4-((1R,3S,5S)-3-Amino-5-methylcyclohexyl)pyridin-3-yl)-5-fluoro-3-((S)-3-methylmorpholino)quinoline-8-carboxamide;

N-(4-((1R,3S,5S)-3-Amino-5-methylcyclohexyl)pyridin-3-yl)-5-fluoro-3-((R)-2-methylpyrrolidin-1-yl)quinoline-8-carboxamide;
N-(4-((1R,3S,5S)-3-Amino-5-methylcyclohexyl)pyridin-3-yl)-3-(2,5-dimethylmorpholino)-5-fluoroquinoline-8-carboxamide;
N-(4-((1R,3S,5S)-3-Amino-5-methylcyclohexyl)pyridin-3-yl)-3-(2,5-dimethylpyrrolidin-1-yl)-5-fluoroquinoline-8-carboxamide;
N-(4-((1R,3S,5S)-3-Amino-5-methylcyclohexyl)pyridin-3-yl)-3-(2,6-dimethylmorpholino)-5-fluoroquinoline-8-carboxamide;
N-(4-((1R,3S,5S)-3-Amino-5-methylcyclohexyl)pyridin-3-yl)-5-fluoro-3-((S)-2-methylmorpholino)quinoline-8-carboxamide;
N-(4-((1R,3S,5S)-3-Amino-5-methylcyclohexyl)pyridin-3-yl)-5-fluoro-3-((S)-2-methylpyrrolidin-1-yl)quinoline-8-carboxamide;
N-(4-((1R,3S,5S)-3-Amino-5-methylcyclohexyl)pyridin-3-yl)-3-(4,4-difluoropiperidin-1-yl)-5-fluoroquinoline-8-carboxamide;
N-(4-((1R,3S,5S)-3-Amino-5-methylcyclohexyl)pyridin-3-yl)-5-fluoro-3-(4-hydroxy-4-methylpiperidin-1-yl)quinoline-8-carboxamide;
N-(4-((1R,3S,5S)-3-Amino-5-methylcyclohexyl)pyridin-3-yl)-3-((2,2-difluoroethyl)(methyl)amino)-5-fluoroquinoline-8-carboxamide;
N-(4-((1R,3S,5S)-3-Amino-5-methylcyclohexyl)pyridin-3-yl)-5-fluoro-3-(2-methylpiperidin-1-yl)quinoline-8-carboxamide;
N-(4-((1R,3S,5S)-3-Amino-5-methylcyclohexyl)pyridin-3-yl)-5-fluoro-3-(4-hydroxypiperidin-1-yl)quinoline-8-carboxamide;
N-(4-((1R,3S,5S)-3-Amino-5-methylcyclohexyl)pyridin-3-yl)-3-(4-cyanopiperidin-1-yl)-5-fluoroquinoline-8-carboxamide;
N-(4-((1R,3S,5S)-3-Amino-5-methylcyclohexyl)pyridin-3-yl)-5-fluoro-3-(4-methylpiperidin-1-yl)quinoline-8-carboxamide;
N-(4-((1R,3S,5S)-3-Amino-5-methylcyclohexyl)pyridin-3-yl)-5-fluoro-3-((R)-2-(methoxymethyl)pyrrolidin-1-yl)quinoline-8-carboxamide;
N-(4-((1R,3S,5S)-3-Amino-5-methylcyclohexyl)pyridin-3-yl)-5-fluoro-3-((S)-2-(methoxymethyl)pyrrolidin-1-yl)quinoline-8-carboxamide;
N-(4-((1R,3S,5S)-3-Amino-5-methylcyclohexyl)pyridin-3-yl)-5-fluoro-3-((R)-3-methoxypyrrolidin-1-yl)quinoline-8-carboxamide;
N-(4-((1R,3S,5S)-3-Amino-5-methylcyclohexyl)pyridin-3-yl)-5-fluoro-3-((S)-3-methoxypyrrolidin-1-yl)quinoline-8-carboxamide;
N-(4-((1R,3S,5S)-3-Amino-5-methylcyclohexyl)pyridin-3-yl)-5-fluoro-3-((2-methoxymethyl)(methyl)amino)quinoline-8-carboxamide;
N-(4-((1R,3S,5S)-3-Amino-5-methylcyclohexyl)pyridin-3-yl)-3-((S)-1-cyclopropylethylamino)-5-fluoroquinoline-8-carboxamide;
N-(4-((1R,3S,5S)-3-Amino-5-methylcyclohexyl)pyridin-3-yl)-5-fluoro-3-((S)-3-methylbutan-2-ylamino)quinoline-8-carboxamide;
N-(4-((1R,3S,5S)-3-amino-5-methylcyclohexyl)pyridin-3-yl)-5-fluoro-3-((R)-3-methylbutan-2-ylamino)quinoline-8-carboxamide;
N-(4-((1R,3S,5S)-3-Amino-5-methylcyclohexyl)pyridin-3-yl)-5-fluoro-3-(methyl(propyl)amino)quinoline-8-carboxamide;
N-(4-((1R,3S,5S)-3-Amino-5-methylcyclohexyl)pyridin-3-yl)-5-fluoro-3-isopropyl(methyl)amino)quinoline-8-carboxamide;
N-(4-((1R,3S,5S)-3-Amino-5-methylcyclohexyl)pyridin-3-yl)-3-(2-ethylpiperidin-1-yl)-5-fluoroquinoline-8-carboxamide;
N-(4-((1R,3S,5S)-3-Amino-5-methylcyclohexyl)pyridin-3-yl)-3-(2-(difluoromethyl)piperidin-1-yl)-5-fluoroquinoline-8-carboxamide;
N-(4-((1R,3S,5S)-3-Amino-5-methylcyclohexyl)pyridin-3-yl)-5,6'-difluoro-3,8'-biquinoline-8-carboxamide;
N-(4-((1R,3S,5S)-3-Amino-5-methylcyclohexyl)pyridin-3-yl)-5,5'-difluoro-3,8'-biquinoline-8-carboxamide;
N-(4-((1R,3S,5S)-3-Amino-5-methylcyclohexyl)pyridin-3-yl)-5-fluoro-3-(6-(trifluoromethyl)pyridin-3-yl)quinoline-8-carboxamide;
N-(4-((1R,3S,5S)-3-Amino-5-methylcyclohexyl)pyridin-3-yl)-3-(1-ethyl-1H-pyrazol-4-yl)-5-fluoroquinoline-8-carboxamide;
N-(4-((1R,3S,5S)-3-Amino-5-methylcyclohexyl)pyridin-3-yl)-3-(1,3-dimethyl-1H-pyrazol-4-yl)-5-fluoroquinoline-8-carboxamide;
N-(4-((1R,3S,5S)-3-Amino-5-methylcyclohexyl)pyridin-3-yl)-5-fluoro-3-(1-methyl-1H-pyrazol-4-yl)quinoline-8-carboxamide;
N-(4-((1R,3S,5S)-3-amino-5-methylcyclohexyl)pyridin-3-yl)-5-fluoro-3-(3-methyl-1H-pyrazol-4-yl)quinoline-8-carboxamide;
N-(4-((1R,3S,5S)-3-amino-5-methylcyclohexyl)pyridin-3-yl)-5-fluoro-3-(1H-pyrazol-4-yl)quinoline-8-carboxamide;
N-(4-((1R,3S,5S)-3-Amino-5-methylcyclohexyl)pyridin-3-yl)-3-((R)-3-methylmorpholino)quinoline-8-carboxamide;
N-(4-((1R,3S,5S)-3-Amino-5-methylcyclohexyl)pyridin-3-yl)-3-((R)-2-methylpyrrolidin-1-yl)quinoline-8-carboxamide;
N-(4-((1R,3S,5S)-3-Amino-5-methylcyclohexyl)pyridin-3-yl)-3-((S)-2-methylpyrrolidin-1-yl)quinoline-8-carboxamide;
N-(4-((1R,3S,5S)-3-Amino-5-methylcyclohexyl)pyridin-3-yl)-3-(2-methylpiperidin-1-yl)quinoline-8-carboxamide;
N-(4-((1R,3S,5S)-3-Amino-5-methylcyclohexyl)pyridin-3-yl)-3-(2-(difluoromethyl)piperidin-1-yl)quinoline-8-carboxamide;
N-(4-((1R,3S,5S)-3-Amino-5-methylcyclohexyl)pyridin-3-yl)-3-((2,2-difluoroethyl)(methyl)amino)quinoline-8-carboxamide;
N-(4-((1R,3S,5S)-3-Amino-5-methylcyclohexyl)pyridin-3-yl)-5-fluoro-3-thiomorpholinoquinoline-8-carboxamide;
N-(4-((1R,3S,5S)-3-Amino-5-methylcyclohexyl)pyridin-3-yl)-3-(4-(N,N-dimethylsulfamoyl)piperazin-1-yl)-5-fluoroquinoline-8-carboxamide;
N-(4-((1R,3S,5S)-3-Amino-5-methylcyclohexyl)pyridin-3-yl)-5-fluoro-3-(4-methyl-3-oxopiperazin-1-yl)quinoline-8-carboxamide;
N-(4-((1R,3S,5S)-3-Amino-5-methylcyclohexyl)pyridin-3-yl)-3-(azepan-1-yl)-5-fluoroquinoline-8-carboxamide;
N-(4-((1R,3S,5S)-3-Amino-5-methylcyclohexyl)pyridin-3-yl)-3-(3-oxa-8-azabicyclo[3,2,1]octan-8-yl)-5-fluoroquinoline-8-carboxamide;
N-(4-((1R,3S,5S)-3-Amino-5-methylcyclohexyl)pyridin-3-yl)-5-fluoro-3-(2-oxopyrrolidin-1-yl)quinoline-8-carboxamide;

N-(4-((1R,3S,5S)-3-Amino-5-methylcyclohexyl)pyridin-3-yl)-5-fluoro-3-(indolin-1-yl)quinoline-8-carboxamide;

N-(4-((1R,3S,5S)-3-Amino-5-methylcyclohexyl)pyridin-3-yl)-3-((1R,4R)-2-oxa-5-azabicyclo[2,2,1]heptan-5-yl)-5-fluoroquinoline-8-carboxamide;

N-(4-((1R,3S,5S)-3-Amino-5-methylcyclohexyl)pyridin-3-yl)-3-(6-oxa-3-azabicyclo[3,1,1]heptan-3-yl)-5-fluoroquinoline-8-carboxamide;

N-(4-((1R,3S,5S)-3-Amino-5-methylcyclohexyl)pyridin-3-yl)-3-(4-(dimethylcarbamoyl)piperazin-1-yl)-5-fluoroquinoline-8-carboxamide;

N-(4-((1R,3S,5S)-3-Amino-5-methylcyclohexyl)pyridin-3-yl)-5-fluoro-3-(methyl(phenyl)amino)quinoline-8-carboxamide;

N-(4-((1R,3S,5S)-3-Amino-5-methylcyclohexyl)pyridin-3-yl)-5-fluoro-3-(6-oxohexahydropyrrolo[1,2-a]pyrazin-2(1H)-yl)quinoline-8-carboxamide;

N-(4-((1R,3S,5S)-3-Amino-5-methylcyclohexyl)pyridin-3-yl)-5-fluoro-3-((S)-2-methyl-4-methylsulfonyl)piperazin-1-yl)quinoline-8-carboxamide;

N-(4-((1R,3S,5S)-3-Amino-5-methylcyclohexyl)pyridin-3-yl)-5-fluoro-3-((R)-2-methyl-4-(methylsulfonyl)piperazin-1-yl)quinoline-8-carboxamide;

N-(4-((1R,3S,5S)-3-Amino-5-methylcyclohexyl)pyridin-3-yl)-5-fluoro-3-((1R,4R)-5-(methylsulfonyl)-2,5-diazabicyclo[2,2,1]heptan-2-yl)quinoline-8-carboxamide;

(S)-Methyl 4-(8-(4-((1R,3S,5S)-3-amino-5-methylcyclohexyl)pyridin-3-ylcarbamoyl)-5-fluoroquinolin-3-yl-3-methylpiperazine-1-carboxylate;

(R)-Methyl 4-(8-(4-((1R,3S,5S)-3-amino-5-methylcyclohexyl)pyridin-3-ylcarbamoyl)-5-fluoroquinolin-3-yl)-3-methylpiperazine-1-carboxylate;

(1R,4R)-Methyl 5-(8-(4-((1R,3S,5S)-3-amino-5-methylcyclohexyl)pyridin-3-ylcarbamoyl)-5-fluoroquinolin-3-yl)-2,5-diazabicyclo[2,2,1]heptane-2-carboxylate;

N-{4-[(1R,3S,5S)-3-amino-5-methylcyclohexyl]pyridin-3-yl}-3-(2,6-difluorophenyl)-5-fluorocinnoline-8-carboxamide;

N-{4-[(1R,3S,5S)-3-Amino-5-methylcyclohexyl]pyridin-3-yl}-3-ethyl-5-fluorocinnoline-8-carboxamide;

N-{4-[(1R,3S,5S)-3-Amino-5-methylcyclohexyl]pyridin-3-yl}-5-fluoro-3-(2-methylpiperidin-1-yl)cinnoline-8-carboxamide;

N-{4-[(1R,3S,5S)-3-Amino-5-methylcyclohexyl]pyridin-3-yl}-5-fluoro-3-[(3R)-3-methylmorpholin-4-yl]cinnoline-8-carboxamide;

N-{4-[(1R,3S,5S)-3-Amino-5-methylcyclohexyl]pyridin-3-yl}-5-fluoro-3-[(2R)-2-methylpyrrolidin-1-yl]cinnoline-8-carboxamide;

N-(4-((1R,3S,5S)-3-Amino-5-methylcyclohexyl)pyridin-3-yl)-3-(2-azabicyclo[2,2,1]heptan-2-yl)-5-fluoroquinoline-8-carboxamide;

N-(4-((1R,3S,5S)-3-Amino-5-methylcyclohexyl)pyridin-3-yl)-5-fluoro-3-((2-fluorophenyl)(methyl)amino)quinoline-8-carboxamide;

N-(4-((1R,3S,5S)-3-Amino-5-methylcyclohexyl)pyridin-3-yl)-5-fluoro-3-(3-hydroxy-8-azabicyclo[3,2,1]octan-8-yl)quinoline-8-carboxamide;

N-(4-((1R,3S,5S)-3-Amino-5-methylcyclohexyl)pyridin-3-yl)-3-((R)-2,4-dimethyl-5-oxopiperazin-1-yl)-5-fluoroquinoline-8-carboxamide;

N-(4-((1R,3S,5S)-3-Amino-5-methylcyclohexyl)pyridin-3-yl)-5-fluoro-3-((R)-4-oxodihydro-1H-pyrido[1,2-a]pyrazin-2(6H,7H,8H,9H)-yl)quinoline-8-carboxamide;

N-(4-((1R,3S,5S)-3-Amino-5-methylcyclohexyl)pyridin-3-yl)-5-fluoro-3-(4-methoxyazepan-1-yl)quinoline-8-carboxamide;

N-(4-((1R,3S,5S)-3-Amino-5-methylcyclohexyl)pyridin-3-yl)-5-fluoro-3-(1,4-oxazepan-4-yl)quinoline-8-carboxamide;

N-(4-((1R,3S,5S)-3-Amino-5-methylcyclohexyl)pyridin-3-yl)-5-fluoro-3-(6-hydroxy-2-azaspiro[3,3]heptan-2-yl)quinoline-8-carboxamide;

N-(4-((1R,3S,5S)-3-Amino-5-methylcyclohexyl)pyridin-3-yl)-5-fluoro-3-(4-hydroxyazepan-1-yl)quinoline-8-carboxamide;

N-(4-((1R,3S,5S)-3-Amino-5-methylcyclohexyl)pyridin-3-yl)-5-fluoro-3-((R)-3-methylpiperidin-1-yl)quinoline-8-carboxamide;

N-(4-((1R,3S,5S)-3-Amino-5-methylcyclohexyl)pyridin-3-yl)-3-(3-oxa-9-azabicyclo[3,3,1]nonan-9-yl)-5-fluoroquinoline-8-carboxamide;

N-(4-((1R,3S,5S)-3-Amino-5-methylcyclohexyl)pyridin-3-yl)-5-fluoro-3-(2-azaspiro[3,3]heptan-2-yl)quinoline-8-carboxamide;

N-(4-((1R,3S,5S)-3-Amino-5-methylcyclohexyl)pyridin-3-yl)-5-fluoro-3-((3S,4S)-3-fluoro-4-hydroxypiperidin-1-yl)quinoline-8-carboxamide;

N-(4-((1R,3S,5S)-3-Amino-5-methylcyclohexyl)pyridin-3-yl)-5-fluoro-3-(1,2-oxazinan-2-yl)quinoline-8-carboxamide;

N-(4-((1R,3S,5S)-3-Amino-5-methylcyclohexyl)pyridin-3-yl)-3-(dihydro-1H-furo[3,4-c]pyrrol-5(3H,6H,6aH)-yl)-5-fluoroquinoline-8-carboxamide;

N-(4-((1R,3S,5S)-3-Amino-5-methylcyclohexyl)pyridin-3-yl)-5-fluoro-3-(3-methylazetidin-1-yl)quinoline-8-carboxamide;

N-(4-((1R,3S,5S)-3-Amino-5-methylcyclohexyl)pyridin-3-yl)-3-((S)-2,4-dimethyl-3-oxopiperazin-1-yl)-5-fluoroquinoline-8-carboxamide;

N-(4-((1R,3S,5S)-3-Amino-5-methylcyclohexyl)pyridin-3-yl)-5-fluoro-3-((S)-3-methylpiperidin-1-yl)quinoline-8-carboxamide;

N-(4-((1R,3S,5S)-3-Amino-5-methylcyclohexyl)pyridin-3-yl)-3-(4-cyclopropyl-3-oxopiperazin-1-yl)-5-fluoroquinoline-8-carboxamide;

N-(4-((1R,3S,5S)-3-Amino-5-methylcyclohexyl)pyridin-3-yl)-5-fluoro-3-(4-isopropyl-3-oxopiperazin-1-yl)quinoline-8-carboxamide;

N-(4-((1R,3S,5S)-3-Amino-5-methylcyclohexyl)pyridin-3-yl)-3-(3,3-dimethylazetidin-1-yl)-5-fluoroquinoline-8-carboxamide;

N-(4-((1R,3S,5S)-3-Amino-5-methylcyclohexyl)pyridin-3-yl)-5-fluoro-3-(4-isobutyl-3-oxopiperazin-1-yl)quinoline-8-carboxamide;

N-(4-((1R,3S,5S)-3-Amino-5-methylcyclohexyl)pyridin-3-yl)-5-fluoro-3-(3-methoxy-3-methylazetidin-1-yl)quinoline-8-carboxamide;

N-(4-((1R,3S,5S)-3-Amino-5-methylcyclohexyl)pyridin-3-yl)-5-fluoro-3-(2-methyl-6,7-dihydro-2H-pyrazolo[4,3-c]pyridin-5(4H)-yl)quinoline-8-carboxamide;

N-(4-((1R,3S,5S)-3-Amino-5-methylcyclohexyl)pyridin-3-yl)-5-fluoro-3-(5-fluoro-2H-benzo[b][1,4]oxazin-4(3H)-yl)quinoline-8-carboxamide;

N-(4-((1R,3S,5S)-3-Amino-5-methylcyclohexyl)pyridin-3-yl)-5-fluoro-3-(7-oxa-2-azaspiro[3,5]nonan-2-yl)quinoline-8-carboxamide;

N-(4-((1R,3S,5S)-3-Amino-5-methylcyclohexyl)pyridin-3-yl)-3-(3-ethoxyazetidin-1-yl)-5-fluoroquinoline-8-carboxamide;

N-(4-((1R,3S,5S)-3-Amino-5-methylcyclohexyl)pyridin-3-yl)-5-fluoro-3-((S)-2-(hydroxymethyl)azetidin-1-yl)quinoline-8-carboxamide;
N-(4-((1R,3S,5S)-3-Amino-5-methylcyclohexyl)pyridin-3-yl)-5-fluoro-3-(4-methylsulfonyl)-1,4-diazepan-1-yl)quinoline-8-carboxamide;
N-(4-((1R,3S,5S)-3-Amino-5-methylcyclohexyl)pyridin-3-yl)-5-fluoro-3-((2-fluorophenylamino)quinoline-8-carboxamide;
Methyl 4-(8-(4-(((1R,3S,5S)-3-amino-5-methylcyclohexyl)pyridin-3-ylcarbamoyl)-5-fluoroquinolone-3-yl)-1,4-diazepane-1-carboxylate;
N-(4-((1R,3S,5S)-3-Amino-5-methylcyclohexyl)pyridin-3-yl)-5-fluoro-3-(1-methyl-4,5-dihydro-1H-pyrazolo[3,4-c]pyridin-6(7H)-yl)quinoline-8-carboxamide;
N-(4-((1R,3S,5S)-3-Amino-5-methylcyclohexyl)pyridin-3-yl)-5-fluoro-3-(6-methyl-1,1-dioxido-1,2,6-thiadiazinan-2-yl)quinoline-8-carboxamide;
N-(4-((1R,3S,5S)-3-Amino-5-methylcyclohexyl)pyridin-3-yl)-3-(2-cyanophenylamino)-5-fluoroquinoline-8-carboxamide;
N-(4-((1R,3S,5S)-3-Amino-5-methylcyclohexyl)pyridin-3-yl)-5'-fluoro-3,4-dihydro-2H-1,3'-biquinoline-8'-carboxamide;
N-(4-((1R,3S,5S)-3-Amino-5-methylcyclohexyl)pyridin-3-yl)-5-fluoro-3-(4-methoxypiperidin-1-yl)quinoline-8-carboxamide;
N-(4-((1R,3S,5S)-3-Amino-5-methylcyclohexyl)pyridin-3-yl)-5-fluoro-3-(2-(hydroxymethyl)morpholino)quinoline-8-carboxamide;
N-(4-((1R,3S,5S)-3-Amino-5-methylcyclohexyl)pyridin-3-yl)-5-fluoro-3-(4-(2-methoxyethyl)-3-oxopiperazin-1-yl)quinoline-8-carboxamide;
N-(4-((1R,3S,5S)-3-Amino-5-methylcyclohexyl)pyridin-3-yl)-3-(5,6-dihydro-[1,2,4]triazolo[4,3-a]pyrazin-7(8H)-yl-5-fluoroquinoline-8-carboxamide;
N-(4-((1R,3S,5S)-3-Amino-5-methylcyclohexyl)pyridin-3-yl)-5-fluoro-3-(4-methyl-3-oxo-1,4-diazepan-1-yl)quinoline-8-carboxamide;
N-(4-((1R,3S,5S)-3-Amino-5-methylcyclohexyl)pyridin-3-yl)-3-(7-azabicyclo[2,2,1]heptan-7-yl)-5-fluoroquinoline-8-carboxamide;
N-(4-((1R,3S,5S)-3-Amino-5-methylcyclohexyl)pyridin-3-yl)-5',8-difluoro-3,4-dihydro-2H-1,3'-biquinoline-8'-carboxamide;
N-(4-((1R,3S,5S)-3-Amino-5-methylcyclohexyl)pyridin-3-yl)-3-(1,1-dioxidoisothiazolidin-2-yl)-5-fluoroquinoline-8-carboxamide;
N-(4-((1R,3S,5S)-3-Amino-5-methylcyclohexyl)pyridin-3-yl)-3-((3-(difluoromethoxy)pyridin-2-yl)(methyl)amino)-5-fluoroquinoline-8-carboxamide;
N-(4-((1R,3S,5S)-3-Amino-5-methylcyclohexyl)pyridin-3-yl)-3-((2-cyanocyclopentyl)(methyl)amino)-5-fluoroquinoline-8-carboxamide;
N-(4-((1R,3S,5S)-3-Amino-5-methylcyclohexyl)pyridin-3-yl)-3-((2,6-dimethylpyridin-3-yl)(methyl)amino)-5-fluoroquinoline-8-carboxamide;
-(4-((1R,3S,5S)-3-Amino-5-methylcyclohexyl)pyridin-3-yl)-5-fluoro-3-((3-fluoropyridin-2-yl)(methyl)amino)quinoline-8-carboxamide;
N-(4-((1R,3S,5S)-3-Amino-5-methylcyclohexyl)pyridin-3-yl)-5-fluoro-3-(methyl-(4-trifluoromethyl)pyridin-3-yl)amino)quinoline-8-carboxamide;
N-(4-((1R,3S,5S)-3-Amino-5-methylcyclohexyl)pyridin-3-yl)-5-fluoro-3-((6-methoxy-2-methylpyridin-3-yl)(methyl)amino)quinoline-8-carboxamide;
N-(4-((1R,3S,5S)-3-Amino-5-methylcyclohexyl)pyridin-3-yl)-5-fluoro-3-(3-fluoropyridin-4-yl)(methyl)amino)quinoline-8-carboxamide;
N-(4-((1R,3S,5S)-3-Amino-5-methylcyclohexyl)pyridin-3-yl)-5-fluoro-3-(methyl(4-methylpyridin-3-yl)amino)quinoline-8-carboxamide;
N-(4-((1R,3S,5S)-3-Amino-5-methylcyclohexyl)pyridin-3-yl)-5-fluoro-3-(methyl(2-methylcyclobutyl)amino)quinoline-8-carboxamide;
N-(4-((1R,3S,5S)-3-Amino-5-methylcyclohexyl)pyridin-3-yl)-5-fluoro-3-((4-methoxyphenyl)(methyl)amino)quinoline-8-carboxamide;
N-(4-((1R,3S,5S)-3-Amino-5-methylcyclohexyl)pyridin-3-yl)-5-fluoro-3-(methyl(3-methylpyrazin-2-yl)amino)quinoline-8-carboxamide;
N-(4-((1R,3S,5S)-3-Amino-5-methylcyclohexyl)pyridin-3-yl)-5-fluoro-3-((4-methoxypyridin-3-yl)(methyl)amino)quinoline-8-carboxamide;
N-(4-((1R,3S,5S)-3-Amino-5-methylcyclohexyl)pyridin-3-yl)-5-fluoro-3-(methyl(tetrahyrdo-2H-pyran-3-yl)amino)quinoline-8-carboxamide;
N-(4-((1R,3S,5S)-3-Amino-5-methylcyclohexyl)pyridin-3-yl)-5-fluoro-3-((2-methoxyphenyl)(methyl)amino)quinoline-8-carboxamide;
N-(4-((1R,3S,5S)-3-Amino-5-methylcyclohexyl)pyridin-3-yl)-5-fluoro-3-(imidazo[1,2-α]pyridin-6-yl(methyl)amino)quinoline-8-carboxamide;
N-(4-((1R,3S,5S)-3-Amino-5-methylcyclohexyl)pyridin-3-yl)-5-fluoro-3-(methyl((R)-tetrahydrofuran-3-yl)amino)quinoline-8-carboxamide;
N-(4-((1R,3S,5S)-3-Amino-5-methylcyclohexyl)pyridin-3-yl)-5-fluoro-3-[(2S,4R)-2-methoxy-2-methylpyrrolidin-1-yl]quinoline-8-carboxamide;
N-(4-((1R,3S,5S)-3-Amino-5-methylcyclohexyl)pyridin-3-yl)-5-fluoro-3-(2R,4R)-4-methoxy-2-methylpyrrolidin-1-yl)quinoline-8-carboxamide;
N-(4-((1R,3S,5S)-3-Amino-5-methylcyclohexyl)pyridin-3-yl)-5-fluoro-3-(2S,4S)-4-methoxy-2-methylpyrrolidin-1-yl)quinoline-8-carboxamide;
N-(4-((1R,3S,5S)-3-Amino-5-methylcyclohexyl)pyridin-3-yl)-5-fluoro-3-(2R,4S)-4-methoxy-2-methylpyrrolidin-1-yl)quinoline-8-carboxamide;
N-(4-((1R,3S,5S)-3-Amino-5-methylcyclohexyl)pyridin-3-yl)-5-fluoro-3-(2S,4R)-4-methoxy-2-methylpiperidin-1-yl)quinoline-8-carboxamide;
N-(4-((1R,3S,5S)-3-Amino-5-methylcyclohexyl)pyridin-3-yl)-5-fluoro-3-((2R,4R)-4-methoxy-2-methylpiperidin-1-yl)quinoline-8-carboxamide;
N-(4-((1R,3S,5S)-3-Amino-5-methylcyclohexyl)pyridin-3-yl)-5-fluoro-3-((3R,4R)-3-fluoro-1-methoxypiperidin-1-yl)quinoline-8-carboxamide;
N-(4-((1R,3S,5S)-3-Amino-5-methylcyclohexyl)pyridin-3-yl)-5-fluoro-3-((3S,4S)-3-fluoro-4-(2-methoxyethoxy)piperidin-1-yl)quinoline-8-carboxamide;
N-(4-((1R,3S,5S)-3-Amino-5-methylcyclohexyl)pyridin-3-yl)-5-fluoro-3-((2R,4S)-4-hydroxy-2-methylpyrrolidin-1-yl)quinoline-8-carboxamide;
N-(4-((1R,3S,5S)-3-Amino-5-methylcyclohexyl)pyridin-3-yl)-5-fluoro-3-((2S,4S)-4-hydroxy-2-methyl)pyrrolidin-1-yl)quinoline-8-carboxamide;
N-(4-((1R,3S,5S)-3-Amino-5-methylcyclohexyl)pyridin-3-yl)-5-fluoro-3-((S)-2-methylazetidin-1-yl)quinoline-8-carboxamide;

N-(4-((1R,3S,5S)-3-Amino-5-methylcyclohexyl)pyridin-3-yl)-5-fluoro-3-((R)-2-methylazetidin-1-yl)quinoline-8-carboxamide;

Ethyl 4-(8-(4-((1R,3S,5S)-3-amino-5-methylcyclohexyl)pyridin-3-ylcarbamoyl)-5-fluoroquinolin-3-yl)piperazine-1-carboxylate;

N-(4-((1R,3S,5S)-3-Amino-5-methylcyclohexyl)pyridin-3-yl)-5-fluoro-3-((R)-2-methylpiperidin-1-yl)quinoline-8-carboxamide; and N-(4-((1R,3S,5S)-3-Amino-5-methylcyclohexyl)pyridin-3-yl)-5-fluoro-3-((S)-2-methylpiperidin-1-yl)quinoline-8-carboxamide;

or a pharmaceutically acceptable salt thereof;
wherein the myeloproliferative disorder is selected from polycythemia vera, essential thrombocythemia, myelogenous leukemia, myelofibrosis, primary myelofibrosis, post-polycythemia vera/essential thrombocythemia myelofibrosis, post-essential thrombocythemia myelofibrosis, and post-polycythemia vera myelofibrosis.

2. The method of claim 1, wherein the myeloproliferative disorder is polycythemia vera.

3. The method of claim 1, wherein the myeloproliferative disorder is essential thrombocythemia.

4. The method of claim 1, wherein the myeloproliferative disorder is chronic myelogenous leukemia.

5. The method of claim 1, the myeloproliferative disorder is myelofibrosis.

6. The method of claim 1, wherein the myeloproliferative disorder is primary myelofibrosis.

7. The method of claim 1, wherein the myeloproliferative disorder is post-polycythemia vera/essential thrombocythemia myelofibrosis.

8. The method of claim 1, wherein the myeloproliferative disorder is post-essential thrombocythemia myelofibrosis.

9. The method of claim 1, wherein the myeloproliferative disorder is post-polycythemia vera myelofibrosis.

10. The method of claim 1, wherein the compound is selected from:

N-{4-[(1R,3S,5S)-3-Amino-5-methylcyclohexyl]pyridin-3-yl}-5-fluoro-3-[(3R)-3-fluoropiperidin-1-yl]quinoline-8-carboxamide;

N-{4-[(1R,3S,5S)-3-Amino-5-methylcyclohexyl]pyridin-3-yl}-3-(2-cyano-6-fluorophenyl)-5-fluoroquinoline-8-carboxamide;

N-(4-((1R,3S,5S)-3-Amino-5-methylcyclohexyl)pyridin-3-yl)-5-fluoro-3-((R)-3-methylmorpholino)quinoline-8-carboxamide;

N-(4-((1R,3S,5S)-3-Amino-5-methylcyclohexyl)pyridin-3-yl)-5-fluoro-3-((S)-3-methylmorpholino)quinoline-8-carboxamide;

N-{4-[(1R,3S,5S)-3-Amino-5-methylcyclohexyl]pyridin-3-yl}-5-fluoro-3-[(3R)-3-methylmorpholin-4-yl]cinnoline-8-carboxamide; and N-{4-[(1R,3S,5S)-3-Amino-5-methylcyclohexyl]pyridin-3-yl}-5-fluoro-3-[(2R)-2-methylpyrrolidin-1-yl]cinnoline-8-carboxamide;

or a pharmaceutically acceptable salt thereof.

11. The method of claim 1, wherein the compound is selected from:

N-(4-((1R,3S,5S)-3-Amino-5-methylcyclohexyl)pyridin-3-yl)-5-fluoro-3-((2-fluorophenyl)(methyl)amino)quinoline-8-carboxamide;

N-(4-((1R,3S,5S)-3-Amino-5-methylcyclohexyl)pyridin-3-yl)-5-fluoro-3-((R)-4-oxodihydro-1H-pyrido[1,2-a]pyrazin-2(6H,7H,8H,9H,9aH)-yl)quinoline-8-carboxamide;

N-(4-((1R,3S,5S)-3-Amino-5-methylcyclohexyl)pyridin-3-yl)-5-fluoro-3-(1,4-oxazepan-4-yl)quinoline-8-carboxamide;

N-(4-((1R,3S,5S)-3-Amino-5-methylcyclohexyl)pyridin-3-yl)-5-fluoro-3-((3S,4S)-3-fluoro-4-hydroxypiperidin-1-yl)quinoline-8-carboxamide;

N-(4-((1R,3S,5S)-3-Amino-5-methylcyclohexyl)pyridin-3-yl)-5-fluoro-3-(3-methylazetidin-1-yl)quinoline-8-carboxamide;

N-(4-((1R,3S,5S)-3-Amino-5-methylcyclohexyl)pyridin-3-yl)-3-(4-cyclopropyl-3-oxopiperazin-1-yl)-5-fluoroquinoline-8-carboxamide;

N-(4-((1R,3S,5S)-3-Amino-5-methylcyclohexyl)pyridin-3-yl)-3-(3,3-dimethylazetidin-1-yl)-5-fluoroquinoline-8-carboxamide;

N-(4-((1R,3S,5S)-3-Amino-5-methylcyclohexyl)pyridin-3-yl)-3-(7-azabicyclo[2.2.1]heptan-7-yl)-5-fluoroquinoline-8-carboxamide;

N-(4-((1R,3S,5S)-3-Amino-5-methylcyclohexyl]pyridin-3-yl}-5-fluoro-3-[(2S,4R)-4-methoxy-2-methylpyrrolidin-1-yl]quinoline-8-carboxamide;

N-(4-((1R,3S,5S)-3-Amino-5-methylcyclohexyl)pyridin-3-yl)-5-fluoro-3-[(2R,4S)]-4-methoxy-2-methylpyrrolidin-1-yl)quinoline-8-carboxamide;

N-(4-((1R,3S,5S)-3-Amino-5-methylcyclohexyl)pyridin-3-yl)-5-fluoro-3-[(2R,4S)]-4-methoxy-2-methylpiperidin-1-yl)quinoline-8-carboxamide;

N-(4-((1R,3S,5S)-3-Amino-5-methylcyclohexyl)pyridin-3-yl)-5-fluoro-3-[(2R,4R)]-4-methoxy-2-methylpiperidin-1-yl)quinoline-8-carboxamide;

N-(4-((1R,3S,5S)-3-Amino-5-methylcyclohexyl)pyridin-3-yl)-5-fluoro-3-[(3S,4S)]-3-fluoro-4-(2-methoxyethoxy)piperidin-1-yl)quinoline-8-carboxamide;

Ethyl 4-(8-(4-((1R,3S,5S)-3-amino-5-methylcyclohexyl)pyridin-3-ylcarbamoyl)-5-fluoroquinolin-3-yl)piperazine-1-carboxylate; and N-(4-((1R,3S,5S)-3-Amino-5-methylcyclohexyl)pyridin-3-yl)-5-fluoro-3-((R)-2-methylpiperidin-1-yl)quinoline-8-carboxamide;

or a pharmaceutically acceptable salt thereof.

12. The method of claim 1, wherein the myeloproliferative disorder is a Pim kinase-associated disease.

* * * * *